US011786598B2

(12) United States Patent
Yaworski et al.

(10) Patent No.: US 11,786,598 B2
(45) Date of Patent: *Oct. 17, 2023

(54) LIPID FORMULATIONS FOR DELIVERY OF THERAPEUTIC AGENTS

(71) Applicant: ARBUTUS BIOPHARMA CORPORATION, Vancouver (CA)

(72) Inventors: Ed Yaworski, Maple Ridge (CA); Stephen Reid, Surrey (CA); James Heyes, Vancouver (CA); Adam Judge, Vancouver (CA); Ian MacLachlan, Mission (CA)

(73) Assignee: ARBUTUS BIOPHARMA CORPORATION, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/872,504

(22) Filed: Jul. 25, 2022

(65) Prior Publication Data

US 2023/0248831 A1 Aug. 10, 2023

Related U.S. Application Data

(63) Continuation of application No. 16/109,130, filed on Aug. 22, 2018, now Pat. No. 11,446,383, which is a continuation of application No. 15/818,064, filed on Nov. 20, 2017, now abandoned, which is a continuation of application No. 14/606,905, filed on Jan. 27, 2015, now Pat. No. 9,878,042, which is a continuation of application No. 13/566,952, filed on Aug. 3, 2012, now abandoned, which is a continuation of application No. 12/828,189, filed on Jun. 30, 2010, now Pat. No. 8,283,333.

(60) Provisional application No. 61/295,134, filed on Jan. 14, 2010, provisional application No. 61/222,469, filed on Jul. 1, 2009.

(51) Int. Cl.
| | |
|---|---|
| *C07H 21/02* | (2006.01) |
| *A61K 47/44* | (2017.01) |
| *A61K 9/00* | (2006.01) |
| *A61K 9/127* | (2006.01) |
| *A61K 31/713* | (2006.01) |
| *C12N 15/11* | (2006.01) |
| *C12N 15/88* | (2006.01) |
| *A61K 47/54* | (2017.01) |
| *C12N 15/113* | (2010.01) |

(52) U.S. Cl.
CPC ............ *A61K 47/44* (2013.01); *A61K 9/0019* (2013.01); *A61K 9/1272* (2013.01); *A61K 31/713* (2013.01); *A61K 47/543* (2017.08); *C12N 15/111* (2013.01); *C12N 15/1137* (2013.01); *C12N 15/88* (2013.01); *C12N 2310/14* (2013.01); *C12N 2310/321* (2013.01); *C12N 2310/344* (2013.01); *C12N 2320/30* (2013.01); *C12N 2320/32* (2013.01)

(58) Field of Classification Search
CPC ... A61K 47/60; C12N 2310/14; C12N 15/113
See application file for complete search history.

(56) References Cited

U.S. PATENT DOCUMENTS

| | | | |
|---|---|---|---|
| 4,394,448 A | 7/1983 | Szoka, Jr. et al. |
| 4,438,052 A | 3/1984 | Weder et al. |
| 4,515,736 A | 5/1985 | Deamer |
| 4,598,051 A | 7/1986 | Papahadjopoulos et al. |
| 4,897,355 A | 1/1990 | Eppstein et al. |
| 5,013,556 A | 5/1991 | Woodle et al. |
| 5,171,678 A | 12/1992 | Behr et al. |
| 5,208,036 A | 5/1993 | Eppstein et al. |
| 5,225,212 A | 7/1993 | Martin et al. |
| 5,264,618 A | 11/1993 | Felgner et al. |
| 5,279,833 A | 1/1994 | Rose |
| 5,283,185 A | 2/1994 | Epand et al. |
| 5,320,906 A | 6/1994 | Eley et al. |
| 5,334,761 A | 8/1994 | Gebeyehu et al. |

(Continued)

FOREIGN PATENT DOCUMENTS

| | | |
|---|---|---|
| CA | 2309727 | 4/1999 |
| CA | 2271582 | 11/1999 |

(Continued)

OTHER PUBLICATIONS

Ahmad, A. et al., "New multivalent cationic lipids reveal bell curve for transfection efficiency versus membrane charge density: lipid-DNA complexes for gene delivery," J. Gene Med., 7(6):739-48, 2005.

(Continued)

*Primary Examiner* — Amy H Bowman
(74) *Attorney, Agent, or Firm* — Kilpatrick Townsend & Stockton LLP

(57) ABSTRACT

The present invention provides novel, serum-stable lipid particles comprising one or more active agents or therapeutic agents, methods of making the lipid particles, and methods of delivering and/or administering the lipid particles. More particularly, the present invention provides serum-stable nucleic acid-lipid particles (SNALP) comprising a nucleic acid (e.g., one or more interfering RNA molecules), methods of making the SNALP, and methods of delivering and/or administering the SNALP (e.g., for the treatment of cancer). In particular embodiments, the present invention provides tumor-directed lipid particles that preferentially target solid tumors. The tumor-directed formulations of the present invention are capable of preferentially delivering a payload such as a nucleic acid to cells of solid tumors compared to non-cancerous cells.

17 Claims, 13 Drawing Sheets

Specification includes a Sequence Listing.

(56) References Cited

U.S. PATENT DOCUMENTS

| | | |
|---|---|---|
| 5,545,412 A | 8/1996 | Eppstein et al. |
| 5,578,475 A | 11/1996 | Jessee |
| 5,627,159 A | 5/1997 | Shih et al. |
| 5,641,662 A | 6/1997 | Debs et al. |
| 5,656,743 A | 8/1997 | Busch et al. |
| 5,674,908 A | 10/1997 | Haces et al. |
| 5,703,055 A | 12/1997 | Felgner et al. |
| 5,705,385 A | 1/1998 | Bally et al. |
| 5,736,392 A | 4/1998 | Hawley-Nelson et al. |
| 5,753,613 A | 5/1998 | Ansell et al. |
| 5,820,873 A | 10/1998 | Choi et al. |
| 5,877,220 A | 3/1999 | Schwartz et al. |
| 5,885,613 A | 3/1999 | Holland et al. |
| 5,958,901 A | 9/1999 | Dwyer et al. |
| 5,976,567 A | 11/1999 | Wheeler et al. |
| 5,981,501 A | 11/1999 | Wheeler et al. |
| 6,020,202 A | 2/2000 | Jessee |
| 6,020,526 A | 2/2000 | Schwartz et al. |
| 6,034,135 A | 3/2000 | Schwartz et al. |
| 6,051,429 A | 4/2000 | Hawley-Nelson et al. |
| 6,075,012 A | 6/2000 | Gebeyehu et al. |
| 6,165,501 A | 12/2000 | Tirosh et al. |
| 6,172,049 B1 | 1/2001 | Dwyer et al. |
| 6,251,939 B1 | 6/2001 | Schwartz et al. |
| 6,284,267 B1 | 9/2001 | Aneja |
| 6,287,591 B1 | 9/2001 | Semple et al. |
| 6,339,173 B1 | 1/2002 | Schwartz et al. |
| 6,376,248 B1 | 4/2002 | Hawley-Nelson et al. |
| 6,534,484 B1 | 3/2003 | Wheeler et al. |
| 6,586,410 B1 | 7/2003 | Wheeler et al. |
| 6,638,529 B2 | 10/2003 | Schwartz et al. |
| 6,649,780 B1 | 11/2003 | Eibl et al. |
| 6,671,393 B2 | 12/2003 | Hays et al. |
| 6,696,424 B1 | 2/2004 | Wheeler et al. |
| 6,815,432 B2 | 11/2004 | Wheeler et al. |
| 6,858,224 B2 | 2/2005 | Wheeler et al. |
| 7,166,745 B1 | 1/2007 | Chu et al. |
| 7,422,902 B1 | 9/2008 | Wheeler et al. |
| 7,479,573 B2 | 1/2009 | Chu et al. |
| 7,491,409 B1 | 2/2009 | Meers et al. |
| 7,507,811 B2 | 3/2009 | Khvorova et al. |
| 7,598,370 B2 | 10/2009 | Khvorova et al. |
| 7,601,872 B2 | 10/2009 | Chu et al. |
| 7,687,070 B2 | 3/2010 | Gebeyehu et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,807,815 B2 | 10/2010 | MacLachlan et al. |
| 7,838,658 B2 | 11/2010 | MacLachlan et al. |
| 7,901,708 B2 | 3/2011 | MacLachlan et al. |
| 7,915,450 B2 | 3/2011 | Chu et al. |
| 7,939,505 B2 | 5/2011 | Quay et al. |
| 7,982,027 B2 | 7/2011 | MacLachlan et al. |
| 8,058,068 B2 | 11/2011 | Hawley-Nelson et al. |
| 8,058,069 B2 | 11/2011 | Yaworski et al. |
| 8,101,741 B2 | 1/2012 | MacLachlan et al. |
| 8,158,601 B2 | 4/2012 | Chen et al. |
| 8,158,827 B2 | 4/2012 | Chu et al. |
| 8,188,263 B2 | 5/2012 | MacLachlan et al. |
| 8,227,443 B2 | 7/2012 | MacLachlan et al. |
| 8,236,943 B2 | 8/2012 | Lee et al. |
| 8,283,333 B2 | 10/2012 | Yaworski et al. |
| 8,455,455 B1 | 6/2013 | Robbins et al. |
| 8,466,122 B2 | 6/2013 | Heyes et al. |
| 8,492,359 B2 | 7/2013 | Yaworski et al. |
| 8,513,403 B2 | 8/2013 | MacLachlan et al. |
| 8,569,256 B2 | 10/2013 | Heyes et al. |
| 8,598,333 B2 | 12/2013 | MacLachlan et al. |
| 8,716,464 B2 | 5/2014 | Geisbert et al. |
| 8,822,668 B2 | 9/2014 | Yaworski et al. |
| 8,865,675 B2 | 10/2014 | Heyes et al. |
| 8,999,950 B2 | 4/2015 | MacLachlan et al. |
| 9,006,191 B2 | 4/2015 | MacLachlan et al. |
| 9,006,193 B2 | 4/2015 | Stayton et al. |
| 9,006,417 B2 | 4/2015 | Yaworski et al. |
| 9,018,187 B2 | 4/2015 | Heyes et al. |
| 9,035,039 B2 | 5/2015 | Dhillon et al. |
| 9,126,966 B2 | 9/2015 | Martin et al. |
| 9,139,554 B2 | 9/2015 | Hope et al. |
| 9,187,748 B2 | 11/2015 | Geisbert et al. |
| 9,364,435 B2 | 6/2016 | Yaworski et al. |
| 9,404,127 B2 | 8/2016 | Yaworski et al. |
| 9,504,651 B2 | 11/2016 | MacLachlan et al. |
| 9,518,272 B2 | 12/2016 | Yaworski et al. |
| 9,878,042 B2 | 1/2018 | Yaworski et al. |
| 10,053,689 B2 | 8/2018 | Fitzgerald et al. |
| 10,077,232 B2 | 9/2018 | Heyes et al. |
| 10,415,037 B2 | 9/2019 | Cross et al. |
| 11,141,378 B2 | 10/2021 | Yaworski et al. |
| 11,446,383 B2 | 9/2022 | Yaworski et al. |
| 2001/0048940 A1 | 12/2001 | Tousignant et al. |
| 2003/0069173 A1 | 4/2003 | Hawley-Nelson et al. |
| 2003/0072794 A1 | 4/2003 | Boulikas |
| 2003/0077829 A1 | 4/2003 | MacLachlan |
| 2003/0143732 A1 | 7/2003 | Fosnaugh et al. |
| 2004/0063654 A1 | 4/2004 | Davis et al. |
| 2004/0142892 A1 | 7/2004 | Finn et al. |
| 2004/0253723 A1 | 12/2004 | Tachas et al. |
| 2004/0259247 A1 | 12/2004 | Tuschl et al. |
| 2005/0064595 A1 | 3/2005 | MacLachlan et al. |
| 2005/0107316 A1 | 5/2005 | Strebhardt et al. |
| 2005/0118253 A1 | 6/2005 | MacLachlan et al. |
| 2005/0164974 A1 | 7/2005 | Gold et al. |
| 2005/0255487 A1 | 11/2005 | Khvorova et al. |
| 2005/0260757 A1 | 11/2005 | Gebeyehu et al. |
| 2005/0282188 A1 | 12/2005 | Haeberli et al. |
| 2006/0008910 A1 | 1/2006 | MacLachlan et al. |
| 2006/0025366 A1 | 2/2006 | MacLachlan et al. |
| 2006/0134189 A1 | 6/2006 | MacLachlan et al. |
| 2006/0147514 A1 | 7/2006 | Gebeyehu et al. |
| 2006/0228406 A1 | 10/2006 | Chiou et al. |
| 2006/0240093 A1 | 10/2006 | MacLachlan et al. |
| 2006/0240554 A1 | 10/2006 | Chen et al. |
| 2007/0031844 A1 | 2/2007 | Khvorova et al. |
| 2007/0042031 A1 | 2/2007 | MacLachlan et al. |
| 2007/0054873 A1 | 3/2007 | MacLachlan et al. |
| 2007/0135370 A1 | 6/2007 | MacLachlan et al. |
| 2007/0135372 A1 | 6/2007 | MacLachlan et al. |
| 2007/0202598 A1 | 8/2007 | Chu et al. |
| 2007/0202600 A1 | 8/2007 | Chu et al. |
| 2007/0265438 A1 | 11/2007 | Khvorova et al. |
| 2008/0020058 A1 | 1/2008 | Chen et al. |
| 2008/0249046 A1 | 10/2008 | MacLachlan et al. |
| 2008/0311040 A1 | 12/2008 | Berry et al. |
| 2008/0317839 A1 | 12/2008 | Quay et al. |
| 2009/0143583 A1 | 6/2009 | Chu et al. |
| 2009/0149403 A1 | 6/2009 | MacLachlan et al. |
| 2009/0264511 A1 | 10/2009 | de Fougerolles et al. |
| 2009/0270481 A1 | 10/2009 | MacLachlan et al. |
| 2009/0291131 A1 | 11/2009 | MacLachlan et al. |
| 2010/0105933 A1 | 4/2010 | Chen et al. |
| 2010/0130588 A1 | 5/2010 | Yaworski |
| 2010/0159593 A1 | 6/2010 | Chu et al. |
| 2011/0060032 A1 | 3/2011 | MacLachlan et al. |
| 2011/0076335 A1 | 3/2011 | Yaworski et al. |
| 2011/0091525 A1 | 4/2011 | Heyes et al. |
| 2011/0262527 A1 | 10/2011 | Heyes et al. |
| 2012/0058188 A1 | 3/2012 | MacLachlan et al. |
| 2012/0136073 A1 | 5/2012 | Zhiwei et al. |
| 2012/0183581 A1 | 7/2012 | Yaworski et al. |
| 2012/0238747 A1 | 9/2012 | Chu et al. |
| 2013/0116307 A1 | 5/2013 | Heyes et al. |
| 2013/0122104 A1 | 5/2013 | Yaworski et al. |
| 2013/0303587 A1 | 11/2013 | Yaworski et al. |
| 2014/0065228 A1 | 3/2014 | Yaworski et al. |
| 2014/0134260 A1 | 5/2014 | Heyes et al. |
| 2014/0161894 A1 | 6/2014 | MacLachlan et al. |
| 2014/0179756 A1 | 6/2014 | MacLachlan et al. |
| 2014/0294937 A1 | 10/2014 | MacLachlan et al. |
| 2015/0164799 A1 | 6/2015 | Yaworski et al. |
| 2015/0374834 A1 | 12/2015 | Yaworski et al. |
| 2016/0032320 A1 | 2/2016 | Yaworski et al. |
| 2016/0115483 A1 | 4/2016 | MacLachlan et al. |
| 2016/0251681 A1 | 9/2016 | Yaworski et al. |

(56) References Cited

U.S. PATENT DOCUMENTS

| | | |
|---|---|---|
| 2017/0042814 A1 | 2/2017 | Yaworski et al. |
| 2017/0260523 A1 | 9/2017 | Yaworski et al. |
| 2017/0307608 A1 | 10/2017 | Bettencourt |
| 2018/0071397 A1 | 3/2018 | Yaworski et al. |
| 2018/0085312 A1 | 3/2018 | Yaworski et al. |
| 2018/0092848 A1 | 4/2018 | Yaworski et al. |
| 2019/0032051 A1 | 1/2019 | Yaworski et al. |
| 2019/0240339 A1 | 8/2019 | Yaworski et al. |
| 2020/0113832 A1 | 4/2020 | Yaworski et al. |
| 2021/0207140 A1 | 7/2021 | Yaworski et al. |
| 2021/0220274 A1 | 7/2021 | Yaworski et al. |
| 2021/0267895 A1 | 9/2021 | Yaworski et al. |

FOREIGN PATENT DOCUMENTS

| | | |
|---|---|---|
| CA | 2330741 | 11/1999 |
| CA | 2397016 | 7/2001 |
| CA | 2513623 | 8/2004 |
| CA | 2637931 | 7/2007 |
| CA | 2710713 | 9/2017 |
| CN | 1651450 A | 8/2005 |
| EP | 1 648 519 B1 | 10/2014 |
| EP | 2 567 693 B1 | 10/2015 |
| JP | 03-126211 | 5/1991 |
| JP | 05-202085 | 8/1993 |
| JP | 06-080560 | 3/1994 |
| JP | 2002-525063 | 8/2002 |
| JP | 2003-505401 | 2/2003 |
| JP | 2007-524349 | 8/2007 |
| JP | 2007-528863 | 10/2007 |
| WO | 91/16024 A1 | 10/1991 |
| WO | 93/05162 A1 | 3/1993 |
| WO | 93/12240 A1 | 6/1993 |
| WO | 93/12756 A2 | 7/1993 |
| WO | 93/24640 A2 | 12/1993 |
| WO | 93/25673 A1 | 12/1993 |
| WO | 94/03198 A1 | 2/1994 |
| WO | 95/02698 A1 | 1/1995 |
| WO | 95/18863 A1 | 7/1995 |
| WO | 95/35301 A1 | 12/1995 |
| WO | 96/02655 A1 | 2/1996 |
| WO | 96/10390 A1 | 4/1996 |
| WO | 96/40964 A2 | 12/1996 |
| WO | 96/41873 A1 | 12/1996 |
| WO | 98/51285 A2 | 11/1998 |
| WO | 00/03683 A2 | 1/2000 |
| WO | 00/15820 A1 | 3/2000 |
| WO | 00/62813 A2 | 10/2000 |
| WO | 01/05374 A1 | 1/2001 |
| WO | 01/05873 A1 | 1/2001 |
| WO | 01/075164 A2 | 10/2001 |
| WO | 01/093836 | 12/2001 |
| WO | 02/034236 A2 | 5/2002 |
| WO | 02/087541 A1 | 11/2002 |
| WO | 03/097805 A2 | 11/2003 |
| WO | 2004/045543 A2 | 6/2004 |
| WO | 2004/065546 A2 | 8/2004 |
| WO | 2004/110499 A1 | 12/2004 |
| WO | 2005/007196 A2 | 1/2005 |
| WO | 2005/026372 A1 | 3/2005 |
| WO | 2005/035764 A1 | 4/2005 |
| WO | 2005/120152 A2 | 12/2005 |
| WO | 2006/002538 A1 | 1/2006 |
| WO | 2006/006948 A2 | 1/2006 |
| WO | 2006/035515 | 4/2006 |
| WO | 2006/053430 A1 | 5/2006 |
| WO | 2007/051303 A1 | 5/2007 |
| WO | 2007/056861 A1 | 5/2007 |
| WO | 2009/086558 A1 | 7/2009 |
| WO | 2009/111658 A2 | 9/2009 |
| WO | 2010/042877 A1 | 4/2010 |
| WO | 2010/048228 A2 | 4/2010 |
| WO | 2010/088537 A2 | 8/2010 |
| WO | 2010/105209 A1 | 9/2010 |
| WO | 2011/057003 A2 | 5/2011 |
| WO | 2013/090648 A1 | 6/2013 |
| WO | 2017/223135 A1 | 12/2017 |
| WO | 2018/232357 A1 | 12/2018 |

OTHER PUBLICATIONS

Ahmad, N. "Polo-like kinase (Plk) 1: a novel target for the treatment of prostate cancer," The FASEB Journal, 2004, vol. 18, No. 1, pp. 5-7.

Ahonen et al., "Polo-like kinase 1 creates the tension-sensing 3F3/2 phosphoepitope and modulates the association of spindle-checkpoint proteins at kinetochores," Current Biology, Current Science, London GB, Jun. 21, 2005, vol. 15, No. 12, pp. 1078-1089.

Akinc, A. et al., "The Onpattro story and the clinical translation of nanomedicines containing nucleic acid-based drugs," Nature Nanotechnology, 14:1084-1087, 2019.

Alnylam Pharmaceuticals, Inc., ONPATTRO Label, Revised Aug. 2018, 14 pages.

Ambegia, E. et al., "Stabilized plasmid-lipid particles containing PEG-diacylglycerols exhibit extended circulation lifetimes and tumor selective gene expression," Biochimica et Biophysica Acta, 1669:155-163, 2005.

Arbutus Biopharma Corporation, "Arbutus' LNP Licensee Alnylam Announces FDA Approval of ONPATTRO™ (patisiran), for the Treatment of ATTR Amyloidosis," Press Release, https://investor.arbutusbio.com/news-releases/news-release-details/arbutus-lnp-licensee-alnylam-announces-fda-approval-onpattrotm, Aug. 13, 2018, 2 pages.

Arima, Y. et al., "Complement activation on surfaces modified with ethylene glycol units," Biomaterials, 29:551-560, 2008.

Arpicco, et al., "Preparation and characterization of novel cationic lipids developed for gene transfection," Proceed. Int'l Symp. Control. Rel. Bioact. Mater. (Controlled Release Society, Inc.), 1999, vol. 26, pp. 759-760.

Arpicco, et al., "Synthesis, characterization and transfection activity of new saturated and unsaturated cationic lipids," IL Farmaco, 2004, vol. 59, pp. 869-878.

Bahl, K. et al., "Preclinical and Clinical Demonstration of Immunogenicity by mRNA Vaccines against H10N8 and H7N9 Influenza Viruses," Molecular Therapy, 25(6):1316-1327, 2017.

Ballas, et al., "Liposomes bearing a quaternary ammonium detergent as an efficient vehicle for functional transfer of TMV-RNA into plant protoplasts," Biochimica et Biophysica Acta, 1988, vol. 939, pp. 8-18.

Barinaga, M., "Step taken toward improved vectors for gene transfer," Science, 1994, vol. 266, p. 1326.

Basarkar, A. and J. Singh, "Nanoparticulate systems for polynucleotide delivery," Int. J. Nanomedicine, 2(3):353-360, 2007.

Bass, "The Short Answer," Nature, 2001, vol. 411, pp. 428-429.

Beale, et al., "Gene silencing nucleic acids designed by scanning arrays: Anti-EGFR activity of siRNA, ribozyme and DNA enzymes targeting a single hybridization-accessible region using the same delivery system," Journal of Drug Targeting, 2003, vol. 11, No. 7, pp. 449-456.

Behr, "Synthetic gene-transfer vectors," Acc. Chem. Res., 1993, vol. 26, pp. 274-278.

Bennett, M. et al., "Cholesterol enhances cationic liposome-mediated DNA transfection of human respiratory epithelial cells," Bioscience Reports, 15:47-53, 1995.

Brigham, et al., "Rapid communication: In vivo transfection of murine lungs with a functioning prokaryotic gene using a liposome vehicle," The American Journal of the Medical Sciences, vol. 298, No. 4, pp. 278-281.

Brummelkamp, et al., "A system for stable expression of short interfering RNAs in mammalian cells," Science, 2002, vol. 296. pp. 550-553.

Cekaite et al. "Gene expression analysis in blood cells in response to unmodified and 2'-modified siRNAs reveals TLR-dependent and independent effects," J. Mol. Biol. 2007, vol. 365, pp. 90-108.

Cevc, G., "How membrane chain-melting phase-transition temperature is affected by the lipid chain asymmetry and degree of unsaturation: an effective chain-length model," Biochemistry, 1991, vol. 30, pp. 7186-7193.

(56) References Cited

OTHER PUBLICATIONS

Check, E., "RNA to the Rescue? Disease therapies based on a technique for gene silencing called RNA interference are racing towards the clinic. Erika Check investigates molecular medicine's next big thing," Nature, 425:10-12, 2003.
Chen et al., "Tumor-targeted delivery of siRNA by non-viral vector: safe and effective cancer therapy," Expert Opinion on Drug Delivery, 2008, 5:1301-1311.
Chonn et al., "Recent advances in liposomal drug-delivery systems," Current Opinion in Biotechnology, 1995, vol. 6, pp. 698-708.
Cortesi, R., et al., "Effect of cationic liposome composition on in vitro cytotoxicity and protective effect on carried DNA," International Journal of Pharmaceutics, 1996, vol. 139, pp. 69-78.
Crystal, R., "Transfer of genes to humans: early lessons and obstacles to success," Science, 1995, vol. 270, pp. 404-410.
Culver K., "The first human gene therapy experiment," Gene Therapy: A Handbook for Physicians, 1994, pp. 33-40.
Duzgunes, N., "Membrane fusion," Subcellular Biochemistry, 1985, vol. 11, pp. 195-286.
Dwarki, et al., "Cationic liposome-mediated RNA transfection," Methods in Enzymology, 1993, vol. 217, pp. 644-654.
Elbashir et al., "Duplexes of 21-nucleotide RNAs mediate RNA interference in cultured mammalian cells," Nature, May 2001, vol. 411, pp. 494-498.
Enoch, et al., "Formation and properties of 1000-Å-diameter, single-bilayer phospholipid vesicles," Proc. Natl. Acad. Sci. USA, 1979, vol. 76, No. 1, pp. 145-149.
European Medicines Agency, "New Medicine for Hereditary Rare Disease," Press Release, https://www.ema.europa.eu/en/news/new-medicine-hereditary-rare-disease, Jul. 27, 2018, 2 pages.
Felgner, et al., "Cationic lipid-mediated transfection in mammalian cells: 'Lipofection,'" J. Tiss. Cult. Meth., 1993, vol. 15, pp. 63-68.
Felgner, et al., "Cationic liposome mediated transfection," Proc. West. Pharmacol. Soc., 1989, vol. 32, pp. 115-121.
Felgner, et al., "Enhanced gene delivery and mechanism studies with a novel series of cationic lipid formulations," The Journal of Biological Chemistry, 1994, vol. 269, No. 4, pp. 2550-2561.
Felgner, et al., "Lipofection: A highly efficient, lipid-mediated DNA-transfection procedure," Proc. Natl. Acad. Sci. USA, 1987, vol. 84, pp. 7413-7417.
Filion, M.C. and Phillips, N.C., "Toxicity and immunomodulatory activity of liposomal vectors formulated with cationic lipids towards immune effector cells," Biochim. Biophys. Acta., 1329(2):345-356, 1997.
Gallie, D., "Introduction of mRNA to plant protoplasts using polyethylene glycol," Plant Cell Reports, 13:119-122, 1993.
Gao, et al., "A novel cationic liposome reagent for efficient transfection of mammalian cells," Biochem. Biophys. Res. Comm., 1991, vol. 179, No. 1, pp. 280-285.
Gao, X. et al., "Nonviral gene delivery: What we know and what is next," AAPS Journal, 9(1):E92-104, 2007.
GenBank BC014846, 2006: Strausberg, R. et al., "*Homo sapiens* polo-like kinase 1 (*Drosophila*), mRNA (cDNA clone MGC:9748 IMAGE:3854860), complete cds," PNAS, 99(26):16899-16903, 2002; 3 pages.
Gershon, H., et al., "Mode of formation and structural feature of DNA-cationic liposome complexes used for transfection," Biochemistry, 1993, vol. 32, pp. 7143-7151.
Global Newswire, retrieved from http://globalnewswire.com on Feb. 27, 2013, Tekmira sues Alnylam Pharmaceuticals for repeated misuse of tradesecrets and confidential information, Mar. 16, 2011, pp. 1-3.
Guy-Caffey, et al., "Novel polyaminolipids enhance the cellular uptake of oligonucleotides," The Journal of Biological Chemistry, 1995, vol. 270, No. 52, p. 31391-31396.
Hausseker, D., "The Business of RNAi Therapeutics in 2012," Molecular Therapy-Nucleic Acids, 2:e8, 2012, 12 pages.
Hawley-Nelson, et al., "LipofectAmine™ reagent: a new, higher efficiency polycationic liposome transfection reagent," Focus, 1993, vol. 15, No. 3, pp. 73-80.

Heyes et al., "Cationic lipid saturation influences intracellular delivery of encapsulated nucleic acids," Journal of Controlled Release, 2005, vol. 107, pp. 276-287.
Heyes et al., "Synthesis and characterization of novel poly(ethylene glycol)-lipid conjugates suitable for use in drug delivery," Journal of Controlled Release, Elsevier, Amsterdam NL, May 15, 2006, vol. 112, No. 2, pp. 280-290.
Heyes et al., "Synthesis of novel cationic lipids: effect of structural modification on the efficiency of gene transfer," J. Med. Chem., 2002, vol. 45, pp. 99-114.
Huang, L. et al., "Liposomal Gene Delivery: A Complex Package," Nature Biotechnology, 15:620-621, 1997.
Hyde, et al., "Correction of the ion transport defect in cystic fibrosis transgenic mice by gene therapy," Nature, 1993, vol. 362, pp. 250-255.
Jiang, et al., "Comparison of protein precipitation methods for sample preparation prior to proteomic analysis," Journal of Chromatography A, 2004, vol. 1023, pp. 317-320.
Judge et al. "Design of noninflammatory synthetic siRNA mediating potent gene silencing in vivo," Molecular Therapy, 2006, vol. 13, No. 3, pp. 494-505.
Judge, A. et al., "Hypersensitivity and loss of disease site targeting caused by antibody responses to PEGylated liposomes," Mol Ther, Feb. 2006; vol. 13, No. 2, pp. 328-337.
Judge, A. et al., "Overcoming the innate immune response to small interfering RNA," Hum Gene Ther, Feb. 2008; 19(2):111-124.
Judge, A. et al., "Sequence-dependent stimulation of the mammalian innate immune response by synthetic siRNA," Nature Biotechnology, 2005, vol. 23, pp. 457-462.
Juliano, et al., "The effect of particle size and charge on the clearance rates of liposomes and liposome encapsulated drugs," Biochem. Biophys. Res. Commun., 1975, vol. 63, No. 3, pp. 651-658.
Kauffman, K. et al., "Optimization of Lipid Nanoparticle Formulations for mRNA Delivery in Vivo with Fractional Factorial and Definitive Screening Designs," Nano Lett. 15(11):7300-7306, 2015.
Keough, K., "Influence of chain unsaturation and chain position on thermotropism and intermolecular interactions in membranes," Biochem. Soc. Transactions, 1990, vol. 18, No. 5, pp. 835-837.
Krichevsky, A. et al., "RNAi functions in cultured mammalian neurons," PNAS, 2002, vol. 99, No. 18, pp. 11926-11929.
Lawrence et al. "The formation, characterization and stability of non-ionic surfactant vesicles," S.T.P. Pharma Sciences, 1996, vol. 6, No. 1, pp. 49-60.
Lawrence et al., "Synthesis and aggregation properties of dialkyl polyoxyethylene glycerol ethers," Chemistry and Physics of Lipids, 1996, 82(2):89-100.
Ledford, H., "Gene-Silencing Drug Approved: US Government Okays First RNA-Interference Drug—After a 20-Year Wait," Nature 560:291-292, 2018.
Legendre, J.-Y. et al., "Delivery of plasmid DNA into mammalian cell lines using pH-sensitive liposomes: comparison with cationic liposomes," Pharm. Res., 1992, vol. 9, No. 10, pp. 1235-1242.
Leventis, R., et al., "Interactions of mammalian cells with lipid dispersions containing novel metabolizable cationic amphiphiles," Biochem. Biophys. Acta, 1990, vol. 1023, pp. 124-132.
Li, H. et al., "The role of the transferrin-transferrin-receptor system in drug delivery and targeting," Trends in Pharmacological Sciences, 23(5):206-209, 2002.
Li, W. and Szoka, F., "Lipid-based nanoparticles for nucleic acid delivery," Pharmaceutical Research, 24(3):438-449, 2007.
Lin, A.J. et al., "Three-dimensional imaging of lipid gene-carriers: Membrane charge density controls universal transfection behavior in lamellar cationic liposome-DNA complexes," Biophys. J., 84(5):3307-16, 2003.
Liu et al. "Activation of Cdc2/cyclin B and inhibition of centrosome amplification in cells depleted of Plk1 by siRNA," PNAS, 2002, vol. 99, No. 13, pp. 8672-8676.
Liu et al. "Normal cells, but not cancer cells, survive severe Plk1 depletion," Molecular and Cellular Biology, 2006, vol. 26, No. 6, pp. 2093-2108.
Liu et al. "Polo-like kinase (Plk)1 depletion induces apoptosis in cancer cells," PNAS, 2003, vol. 100, No. 10, pp. 5789-5794.

(56) References Cited

OTHER PUBLICATIONS

Liu, et al., "Cationic liposome-mediated intravenous gene delivery", J. Biol. Chem., 1995, vol. 270, pp. 24864-24870.
MacLachlan, I. and Cullis, P., "Diffusible-PEG-Lipid Stabilized Plasmid Lipid Particles," Advances in Genetics, 53:157-188, 2005.
MacLachlan, I., "Liposomal Formulations for Nucleic Acid Delivery," Antisense Drug Technologies, Second Edition; 2007; pp. 237-270.
Manickam, D. and D. Oupicky, "Polyplex gene delivery modulated by redox potential gradiants," Journal of Drug Targeting, 14(8):519-526, 2006.
Marshall, E., "Gene therapy's growing pains," Science, 1995, vol. 269, pp. 1050-1055.
Middaugh, C. and Ramsey, C., "Analysis of Cationic-Lipid-Plasmid-DNA Complexes," Analytical Chemistry, American Chemical Society, pp. 7240-7248, 2007.
Moghimi, S. et al., "Methylation of the phosphate oxygen moiety of phospholipid-methoxy(polyethylene glycol) conjugate prevents PEGylated liposome-mediated complement activation and anaphylatoxin production," The FASEB Journal, 20:E2057-E2593, 2006.
Murahashi et al., "Synthesis and evaluation of neoglycolipid for liposome modification," Biol. Pharm. Bull., 1997, 20(6):704-707.
Nogawa et al. "Intravesical administration of small interfering RNA targeting PLK-1 successfully prevents the growth of bladder cancer," The Journal of Clinical Investigation, 2005, vol. 115, No. 4, pp. 978-985.
Orkin, et al., NIH Report, Report and Recommendations of the Panel to Assess the NIH Investment in Research on Gene Therapy, 1995, 41 pages.
Ortho Biotech Products, LP, "Doxil® Label—Product Insert, Revised May 2007," https://www.accessdata.fda.gov/drugsatfda_docs/label/2007/ 050718s029lbl.pdf, 33 pages.
Pak, C. et al., "Elastase-activated liposomal delivery to nucleated cells," Biochimica et Biophysica Acta, 1419:111-126, 1999.
Parr et al., Factors influencing the retention and chemical stability of poly(ethylene glycol)-lipid conjugates incorporated into large unilamellar vesicles, Biochimica et Biophysica Acta, 1994, 1195:21-30.
Paul, et al., "Effective expression of small interfering RNA in human cells," Nature Biotech., 2002, vol. 20, pp. 505-508.
Puyal, C., et al., "A new cationic liposome encapsulating genetic material: A potential delivery system for polynucleotides," Eur. J. Biochem., 1995, vol. 228, pp. 697-703.
Robbins, Marjorie et al., "siRNA and innate immunity," Oligonucleotides, May 19, 2009, vol. 19, No. 2, pp. 89-101.
Sawada et al., "Microemulsions in supercritical CO2 utilizing the polyethyleneglycol dialkylglycerol and their use for the solubilization of hydrophiles," Dyes and Pigments, 2005, vol. 65, pp. 64-74.
Schmidt, C., "Therapeutic Interference: Small RNA Molecules Act as Blockers of Disease Metabolism," Modern Drug Discovery, American Chemical Society, pp. 37-42, 2003.
Sedic. M. et al., "Safety Evaluation of Lipid Nanoparticle-Formulated Modified mRNA in the Sprague-Dawley Rat and Cynomolgus Monkey," Veterinary Pathology, 2017:1-14, 2017.
Semple, S. et al., "Influence of cholesterol on the association of plasma proteins with liposomes," Biochemistry, 35:2521-2525, 1996.
Semple, S. et al., "Immunogenicity and Rapid Blood Clearance of Liposomes Containing Polyethylene Glycol-Lipid Conjugates and Nucleic Acid," The Journal Of Pharmacology and Experimental Therapeutics, 312(3):1020-1026, 2006.
Semple, S. et al., "Rational Design of Cationic Lipids for siRNA Delivery," Nature Biotechnology, 28(2):172-176, 2010.
Semple, S. et al., "Supplementary Text and Figures, Supplementary Fig. 1, Supplementary Tables 1-4 and Supplementary Syntheses 1 and 2 to Rational Design of Cationic Lipids for SiRNA Delivery," Nature Biotechnology, 28(2):172-176, 2010, published online at https://www.nature.com/articles/nbt.1602?draft= collection#supplementary-information, last visited on Nov. 14, 2019, 19 pages.

Sequence Alignment Data for SEQ ID No. 57, 3pp.
Shimada, K. et al., "Determination of incorporated amounts of poly(ethylene glycol)-derivatized lipids in liposomes for the physicochemical characterization of stealth liposomes," International Journal of Pharmaceutics, 203:255-263, 2000.
Shin, J. et al. "Acid-triggered release via dePEGylation of DOPE liposomes containing acid-labile vinyl ether PEG-lipids," Journal of Controlled Release, 2003, 91:187-200.
Song, L. et al., "Characterization of the inhibitory effect of PEG-lipid conjugates on the intracellular delivery of plasmid and antisense DNA mediated by cationic lipid liposomes," Biochimica et Biophysica Acta, 2002, 1558:1-13.
Sorensen, D. et al., "Gene silencing by systemic delivery of synthetic siRNAs in adult mice", J. Biol. Chem., 2003, 327:761-766.
Spagnou, S. et al., "Lipidic carriers of siRNA: differences in the formulation, cellular uptake, and delivery with plasmid DNA," Biochemistry, 2004, 43:13348-56.
Spänkuch-Schmitt, B. et al. "Effect of RNA silencing of Polo-Like Kinase-1 (PLK1) on apoptosis and spindle formation in human cancer cells," Journal of the National Cancer Institute, 2002, 94(24):1863-77.
Stamatatos, L. et al., "Interactions of cationic lipid vesicles with negatively charged phospholipid vesicles and biological membranes," Biochemistry, 1988, 27:3917-3925.
Szoka, F. et al., "Comparative properties and methods of preparation of lipid vesicles (liposomes)," Ann. Rev. Biophys. Bioeng., 1980, 9:467-508.
Szoka, F. et al., "Procedure for preparation of liposomes with large internal aqueous space and high capture by reverse-phase evaporation," Proc. Natl. Acad. Sci. USA, 1978, 75(9):4194-98.
Tam P. et al., "Stabilized plasmid-lipid particles for systemic gene therapy," Gene Therapy, 7:1867-74, 2000.
Templeton, N., "Cationic liposome-mediated gene delivery in vivo", Bioscience Reports, 2002, 22(2):283-295.
Timmerman, L. "Merck's Alan Sachs, on RNAi's Big Challenge: Delivery, Delivery, Delivery," Xconomy, Inc., https://xconomy.com/national/2010/01/21/mercks-alan-sachs-on-rnais-big-challenge-delivery-delivery-delivery/ -2016-, last visited on Jan. 21, 2010, 9 pages.
Translation of CN 1651450, Ding, J., Aug. 2005.
U.S. Department of Health and Human Services, "Liposome Drug Products: Chemistry, Manufacturing, and Controls; Human Pharmacokinetics and Bioavailability; and Labeling Documentation, Guidance for Industry," Food and Drug Administration, Center for Drug Evaluation and Research (CDER), Apr. 2018, 18 pages.
U.S. Food and Drug Administration, "FDA Approves First-of-its Kind Targeted RNA-based Therapy to Treat a Rare Disease," Press Announcement, https://www.fda.gov/newsevents/newsroom/pressannouncements/ucm616518.htm, Aug. 10, 2018, 3 pages.
U.S. Food and Drug Administration, "Orange Book: Approved Drug Products with Therapeutic Equivalence Evaluations, Patent and Exclusivity for: N210922," available at https://www.accessdata.fda.gov/scripts/cder/ob/patent_info.cfm?Product_No=001&Appl_No=210922&Appl_type=N, last visited Dec. 19, 2018, 3 pages.
Uyechi-O'Brien, L. and Szoka, F., "Mechanisms for Cationic Lipids in Gene Transfer," Pharmaceutical Gene Delivery Systems, Marcel Dekker, Inc., vol. 131, pp. 79-108, 2003.
Van Der Woude, I. et al., "Parameters influencing the introduction of plasmid DNA into cells by the use of synthetic amphiphiles as a carrier system," Biochimica et Biophysica Acta, 1995, 1240:34-40.
Wheeler, J. et al., "Stabilized plasmid-lipid particles: constructions and characterization," Gene Therapy, 1999, 6:271-281.
Wilson, R. et al., "Counterion-induced condensation of deoxyribonucleic acid, A Light-Scattering Study," Biochemistry, 1979, 18(11):2192-96.
Woodle, M. et al., "Versatility in lipid compositions showing prolonged circulation with sterically stabilized liposomes," Biochimica et Biophysica Acta, 1992, 1105:193-200.
Yew, N.S. and Scheule, R.K., "Toxicity of cationic lipid-DNA complexes," Advances in Genetics, 53:189-214, 2005.
Zhang, P. et al., "Use of small RNA as antiaging cosmeceuticals," J. Cosmetic Sci., 64(6):455-68, 2013 (Abstract only).

(56) References Cited

OTHER PUBLICATIONS

Zhu, N. et al., "Systemic gene expression after intravenous DNA delivery into adult mice," Science, 1993, 261:209-211.
Zimmerman, T. et al, "RNA1-mediated gene silencing in non-human primates," Nature, Nature Publishing Group, London, GB, 2006, 441(7089):111-114.

```
                              SEQUENCE LISTING

Sequence total quantity: 149
SEQ ID NO: 1            moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) sense strand S-1
modified_base           4
                        mod_base = um
modified_base           10
                        mod_base = um
modified_base           14
                        mod_base = um
source                  1..21
                        mol_type = other RNA
                        organism = synthetic construct
SEQUENCE: 1
agatcaccct ccttaaatat t                                                    21

SEQ ID NO: 2            moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) sense strand S-2
modified_base           4
                        mod_base = um
modified_base           10
                        mod_base = um
modified_base           14
                        mod_base = um
modified_base           18
                        mod_base = um
source                  1..21
                        mol_type = other RNA
                        organism = synthetic construct
SEQUENCE: 2
agatcaccct ccttaaatat t                                                    21

SEQ ID NO: 3            moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) sense strand S-3
modified_base           4
                        mod_base = um
modified_base           10
                        mod_base = um
modified_base           14
                        mod_base = um
modified_base           20
                        mod_base = um
source                  1..21
                        mol_type = other RNA
                        organism = synthetic construct
SEQUENCE: 3
agatcaccct ccttaaatat t                                                    21

SEQ ID NO: 4            moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) sense strand S-4
```

```
modified_base         4
                      mod_base = um
modified_base         14
                      mod_base = um
modified_base         10
                      mod_base = um
modified_base         21
                      mod_base = um
source                1..21
                      mol_type = other RNA
                      organism = synthetic construct
SEQUENCE: 4
agatcaccct ccttaaatat t                                              21

SEQ ID NO: 5          moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) sense strand S-5
modified_base         4
                      mod_base = um
modified_base         20
                      mod_base = um
source                1..21
                      mol_type = other RNA
                      organism = synthetic construct
SEQUENCE: 5
agatcaccct ccttaaatat t                                              21

SEQ ID NO: 6          moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) sense strand S-6
modified_base         2
                      mod_base = gm
modified_base         4
                      mod_base = um
modified_base         14
                      mod_base = um
modified_base         10
                      mod_base = um
modified_base         20
                      mod_base = um
source                1..21
                      mol_type = other RNA
                      organism = synthetic construct
SEQUENCE: 6
agatcaccct ccttaaatat t                                              21

SEQ ID NO: 7          moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) sense strand S-7
modified_base         4
                      mod_base = um
modified_base         21
                      mod_base = um
source                1..21
                      mol_type = other RNA
                      organism = synthetic construct
SEQUENCE: 7
agatcaccct ccttaaatat t                                              21

SEQ ID NO: 8          moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) sense strand S-8
```

```
modified_base          2
                       mod_base = gm
modified_base          4
                       mod_base = um
modified_base          21
                       mod_base = um
modified_base          10
                       mod_base = um
modified_base          21
                       mod_base = um
source                 1..21
                       mol_type = other RNA
                       organism = synthetic construct
SEQUENCE: 8
agatcaccct ccttaaatat t                                              21

SEQ ID NO: 9           moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) sense strand S-9
modified_base          2
                       mod_base = gm
modified_base          4
                       mod_base = um
modified_base          20
                       mod_base = um
source                 1..21
                       mol_type = other RNA
                       organism = synthetic construct
SEQUENCE: 9
agatcaccct ccttaaatat t                                              21

SEQ ID NO: 10          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) sense strand S-10
modified_base          2
                       mod_base = gm
modified_base          4
                       mod_base = um
modified_base          21
                       mod_base = um
source                 1..21
                       mol_type = other RNA
                       organism = synthetic construct
SEQUENCE: 10
agatcaccct ccttaaatat t                                              21

SEQ ID NO: 11          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-A
modified_base          8
                       mod_base = gm
modified_base          17
                       mod_base = um
source                 1..21
                       mol_type = other RNA
                       organism = synthetic construct
SEQUENCE: 11
tatttaagga gggtgatctt t                                              21

SEQ ID NO: 12          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-B
```

```
modified_base           9
                        mod_base = gm
modified_base           12
                        mod_base = gm
modified_base           15
                        mod_base = gm
source                  1..21
                        mol_type = other RNA
                        organism = synthetic construct
SEQUENCE: 12
tatttaagga gggtgatctt t                                                    21

SEQ ID NO: 13           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-C
modified_base           5
                        mod_base = um
modified_base           11
                        mod_base = gm
modified_base           14
                        mod_base = um
modified_base           17
                        mod_base = um
source                  1..21
                        mol_type = other RNA
                        organism = synthetic construct
SEQUENCE: 13
tatttaagga gggtgatctt t                                                    21

SEQ ID NO: 14           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-D
modified_base           8
                        mod_base = gm
modified_base           17
                        mod_base = um
source                  1..21
                        mol_type = other RNA
                        organism = synthetic construct
SEQUENCE: 14
tatttaagga gggtgatctt c                                                    21

SEQ ID NO: 15           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-E
modified_base           8
                        mod_base = gm
modified_base           17
                        mod_base = um
modified_base           20
                        mod_base = um
source                  1..21
                        mol_type = other RNA
                        organism = synthetic construct
SEQUENCE: 15
tatttaagga gggtgatctt c                                                    21

SEQ ID NO: 16           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-F
```

```
modified_base         8
                      mod_base = gm
modified_base         15
                      mod_base = gm
modified_base         17
                      mod_base = um
modified_base         20
                      mod_base = um
source                1..21
                      mol_type = other RNA
                      organism = synthetic construct
SEQUENCE: 16
tatttaagga gggtgatctt c                                              21

SEQ ID NO: 17         moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) antisense strand AS-G
modified_base         9
                      mod_base = gm
modified_base         12
                      mod_base = gm
modified_base         15
                      mod_base = gm
source                1..21
                      mol_type = other RNA
                      organism = synthetic construct
SEQUENCE: 17
tatttaagga gggtgatctt t                                              21

SEQ ID NO: 18         moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) antisense strand AS-H
modified_base         8
                      mod_base = gm
modified_base         9
                      mod_base = gm
modified_base         12
                      mod_base = gm
modified_base         15
                      mod_base = gm
modified_base         17
                      mod_base = um
source                1..21
                      mol_type = other RNA
                      organism = synthetic construct
SEQUENCE: 18
tatttaagga gggtgatctt t                                              21

SEQ ID NO: 19         moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) antisense strand AS-1
modified_base         8
                      mod_base = gm
modified_base         13
                      mod_base = gm
modified_base         15
                      mod_base = gm
modified_base         17
                      mod_base = um
modified_base         20
                      mod_base = um
source                1..21
                      mol_type = other RNA
                      organism = synthetic construct
```

```
SEQUENCE: 19
tatttaagga gggtgatctt c                                              21

SEQ ID NO: 20           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-2
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 20
tatttaagga gggtgatctt c                                              21

SEQ ID NO: 21           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-3
modified_base           4
                        mod_base = um
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 21
tatttaagga gggtgatctt c                                              21

SEQ ID NO: 22           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-4
modified_base           3
                        mod_base = um
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 22
tatttaagga gggtgatctt c                                              21

SEQ ID NO: 23           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-5
modified_base           1
                        mod_base = um
modified_base           8
                        mod_base = gm
modified_base           15
                        mod_base = gm
```

```
modified_base        17
                     mod_base = um
modified_base        20
                     mod_base = um
source               1..21
                     mol_type = other RNA
                     organism = synthetic construct
SEQUENCE: 23
tatttaagga gggtgatctt c                                              21

SEQ ID NO: 24        moltype = RNA  length = 21
FEATURE              Location/Qualifiers
misc_feature         1..21
                     note = synthetic polo-like kinase 1 (PLK-1),
                      serine/threonine protein kinase 13 (STPK13) small
                      interfering RNA (siRNA) antisense strand AS-6
modified_base        8
                     mod_base = gm
modified_base        13
                     mod_base = gm
modified_base        15
                     mod_base = gm
modified_base        20
                     mod_base = um
modified_base        17
                     mod_base = um
source               1..21
                     mol_type = other RNA
                     organism = synthetic construct
SEQUENCE: 24
tatttaagga gggtgatctt c                                              21

SEQ ID NO: 25        moltype = RNA  length = 21
FEATURE              Location/Qualifiers
misc_feature         1..21
                     note = synthetic polo-like kinase 1 (PLK-1),
                      serine/threonine protein kinase 13 (STPK13) small
                      interfering RNA (siRNA) antisense strand AS-7
modified_base        4
                     mod_base = um
modified_base        8
                     mod_base = gm
modified_base        13
                     mod_base = gm
modified_base        15
                     mod_base = gm
modified_base        17
                     mod_base = um
modified_base        20
                     mod_base = um
source               1..21
                     mol_type = other RNA
                     organism = synthetic construct
SEQUENCE: 25
tatttaagga gggtgatctt c                                              21

SEQ ID NO: 26        moltype = RNA  length = 21
FEATURE              Location/Qualifiers
misc_feature         1..21
                     note = synthetic polo-like kinase 1 (PLK-1),
                      serine/threonine protein kinase 13 (STPK13) small
                      interfering RNA (siRNA) antisense strand AS-8
modified_base        3
                     mod_base = um
modified_base        8
                     mod_base = gm
modified_base        13
                     mod_base = gm
modified_base        15
                     mod_base = gm
modified_base        17
                     mod_base = um
modified_base        20
                     mod_base = um
source               1..21
                     mol_type = other RNA
                     organism = synthetic construct
```

```
SEQUENCE: 26
tatttaagga gggtgatctt c                                              21

SEQ ID NO: 27          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-9
modified_base          1
                       mod_base = um
modified_base          8
                       mod_base = gm
modified_base          15
                       mod_base = gm
modified_base          13
                       mod_base = gm
modified_base          17
                       mod_base = um
modified_base          20
                       mod_base = um
source                 1..21
                       mol_type = other RNA
                       organism = synthetic construct
SEQUENCE: 27
tatttaagga gggtgatctt c                                              21

SEQ ID NO: 28          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-10
modified_base          1
                       mod_base = um
modified_base          3
                       mod_base = um
modified_base          8
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 28
tatttaagga gggtgatctt c                                              21

SEQ ID NO: 29          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-11
modified_base          1
                       mod_base = um
modified_base          4
                       mod_base = um
modified_base          8
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 29
tatttaagga gggtgatctt c                                              21
```

```
SEQ ID NO: 30           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-12
modified_base           1
                        mod_base = um
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 30
tatttaagga gggtgatctt c                                                   21

SEQ ID NO: 31           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-13
modified_base           3
                        mod_base = um
modified_base           4
                        mod_base = um
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 31
tatttaagga gggtgatctt c                                                   21

SEQ ID NO: 32           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-14
modified_base           3
                        mod_base = um
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 32
tatttaagga gggtgatctt c                                                   21
```

```
SEQ ID NO: 33          moltype = RNA   length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-15
modified_base          4
                       mod_base = um
modified_base          8
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 33
tatttaagga gggtgatctt c                                                    21

SEQ ID NO: 34          moltype = RNA   length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-16
modified_base          1
                       mod_base = um
modified_base          3
                       mod_base = um
modified_base          8
                       mod_base = gm
modified_base          13
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 34
tatttaagga gggtgatctt c                                                    21

SEQ ID NO: 35          moltype = RNA   length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-17
modified_base          1
                       mod_base = um
modified_base          4
                       mod_base = um
modified_base          8
                       mod_base = gm
modified_base          13
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 35
tatttaagga gggtgatctt c                                                    21
```

| | |
|---|---|
| SEQ ID NO: 36 | moltype = RNA   length = 21 |
| FEATURE | Location/Qualifiers |
| misc_feature | 1..21 |
| | note = synthetic polo-like kinase 1 (PLK-1), |
| | serine/threonine protein kinase 13 (STPK13) small |
| | interfering RNA (siRNA) antisense strand AS-18 |
| modified_base | 1 |
| | mod_base = um |
| modified_base | 8 |
| | mod_base = gm |
| modified_base | 13 |
| | mod_base = gm |
| modified_base | 15 |
| | mod_base = gm |
| modified_base | 17 |
| | mod_base = um |
| modified_base | 20 |
| | mod_base = um |
| source | 1..21 |
| | mol_type = other RNA |
| | organism = synthetic construct |
| SEQUENCE: 36 | |
| tatttaagga gggtgatctt c | 21 |
| | |
| SEQ ID NO: 37 | moltype = RNA   length = 21 |
| FEATURE | Location/Qualifiers |
| misc_feature | 1..21 |
| | note = synthetic polo-like kinase 1 (PLK-1), |
| | serine/threonine protein kinase 13 (STPK13) small |
| | interfering RNA (siRNA) antisense strand AS-A |
| source | 1..21 |
| | mol_type = other RNA |
| | organism = synthetic construct |
| SEQUENCE: 37 | |
| tatttaagga gggtgatctt c | 21 |
| | |
| SEQ ID NO: 38 | moltype = RNA   length = 21 |
| FEATURE | Location/Qualifiers |
| misc_feature | 1..21 |
| | note = synthetic polo-like kinase 1 (PLK-1), |
| | serine/threonine protein kinase 13 (STPK13) small |
| | interfering RNA (siRNA) antisense strand AS-20 |
| modified_base | 3 |
| | mod_base = um |
| modified_base | 8 |
| | mod_base = gm |
| modified_base | 13 |
| | mod_base = gm |
| modified_base | 15 |
| | mod_base = gm |
| modified_base | 17 |
| | mod_base = um |
| modified_base | 20 |
| | mod_base = um |
| source | 1..21 |
| | mol_type = other RNA |
| | organism = synthetic construct |
| SEQUENCE: 38 | |
| tatttaagga gggtgatctt c | 21 |
| | |
| SEQ ID NO: 39 | moltype = RNA   length = 21 |
| FEATURE | Location/Qualifiers |
| misc_feature | 1..21 |
| | note = synthetic polo-like kinase 1 (PLK-1), |
| | serine/threonine protein kinase 13 (STPK13) small |
| | interfering RNA (siRNA) antisense strand AS-21 |
| modified_base | 4 |
| | mod_base = um |
| modified_base | 8 |
| | mod_base = gm |
| modified_base | 13 |
| | mod_base = gm |
| modified_base | 15 |
| | mod_base = gm |
| modified_base | 17 |
| | mod_base = um |
| modified_base | 20 |
| | mod_base = um |

```
source                  1..21
                        mol_type = other RNA
                        organism = synthetic construct
SEQUENCE: 39
tatttaagga gggtgatctt c                                                    21

SEQ ID NO: 40           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-22
modified_base           1
                        mod_base = um
modified_base           4
                        mod_base = um
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 40
tatttaagga gggtgatctt c                                                    21

SEQ ID NO: 41           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-23
modified_base           1
                        mod_base = um
modified_base           3
                        mod_base = um
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 41
tatttaagga gggtgatctt c                                                    21

SEQ ID NO: 42           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-24
modified_base           1
                        mod_base = um
modified_base           4
                        mod_base = um
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 42
tatttaagga gggtgatctt c                                                    21
```

```
SEQ ID NO: 43          moltype = RNA   length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-25
modified_base          3
                       mod_base = um
modified_base          4
                       mod_base = um
modified_base          8
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 43
tatttaagga gggtgatctt c                                                  21

SEQ ID NO: 44          moltype = RNA   length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-26
modified_base          1
                       mod_base = um
modified_base          4
                       mod_base = um
modified_base          8
                       mod_base = gm
modified_base          13
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 44
tatttaagga gggtgatctt c                                                  21

SEQ ID NO: 45          moltype = RNA   length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-27
modified_base          1
                       mod_base = um
modified_base          3
                       mod_base = um
modified_base          8
                       mod_base = gm
modified_base          13
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 45
tatttaagga gggtgatctt c                                                  21
```

| | |
|---|---|
| SEQ ID NO: 46 | moltype = RNA length = 21 |
| FEATURE | Location/Qualifiers |
| misc_feature | 1..21<br>note = synthetic polo-like kinase 1 (PLK-1),<br>serine/threonine protein kinase 13 (STPK13) small<br>interfering RNA (siRNA) antisense strand AS-28 |
| modified_base | 1<br>mod_base = um |
| modified_base | 4<br>mod_base = um |
| modified_base | 8<br>mod_base = gm |
| modified_base | 13<br>mod_base = gm |
| modified_base | 15<br>mod_base = gm |
| modified_base | 17<br>mod_base = um |
| modified_base | 20<br>mod_base = um |
| source | 1..21<br>mol_type = other RNA<br>organism = synthetic construct |
| SEQUENCE: 46 | |
| tatttaagga gggtgatctt c | 21 |

| | |
|---|---|
| SEQ ID NO: 47 | moltype = RNA length = 21 |
| FEATURE | Location/Qualifiers |
| misc_feature | 1..21<br>note = synthetic polo-like kinase 1 (PLK-1),<br>serine/threonine protein kinase 13 (STPK13) small<br>interfering RNA (siRNA) antisense strand AS-29 |
| modified_base | 3<br>mod_base = um |
| modified_base | 4<br>mod_base = um |
| modified_base | 8<br>mod_base = gm |
| modified_base | 13<br>mod_base = gm |
| modified_base | 17<br>mod_base = um |
| modified_base | 15<br>mod_base = gm |
| modified_base | 20<br>mod_base = um |
| source | 1..21<br>mol_type = other RNA<br>organism = synthetic construct |
| SEQUENCE: 47 | |
| tatttaagga gggtgatctt c | 21 |

| | |
|---|---|
| SEQ ID NO: 48 | moltype = RNA length = 21 |
| FEATURE | Location/Qualifiers |
| misc_feature | 1..21<br>note = synthetic polo-like kinase 1 (PLK-1),<br>serine/threonine protein kinase 13 (STPK13) small<br>interfering RNA (siRNA) antisense strand AS-30 |
| modified_base | 1<br>mod_base = um |
| modified_base | 4<br>mod_base = um |
| modified_base | 8<br>mod_base = gm |
| modified_base | 15<br>mod_base = gm |
| modified_base | 17<br>mod_base = um |
| modified_base | 20<br>mod_base = um |
| source | 1..21<br>mol_type = other RNA<br>organism = synthetic construct |
| SEQUENCE: 48 | |
| tatttaagga gggtgatctt c | 21 |

| | |
|---|---|
| SEQ ID NO: 49 | moltype = RNA length = 21 |
| FEATURE | Location/Qualifiers |

```
misc_feature          1..21
                      note = synthetic polo-like kinase 1 (PLK-1),
                       serine/threonine protein kinase 13 (STPK13) small
                       interfering RNA (siRNA) antisense strand AS-31
modified_base         1
                      mod_base = um
modified_base         4
                      mod_base = um
modified_base         8
                      mod_base = gm
modified_base         13
                      mod_base = gm
modified_base         17
                      mod_base = um
modified_base         15
                      mod_base = gm
modified_base         20
                      mod_base = um
source                1..21
                      mol_type = other RNA
                      organism = synthetic construct
SEQUENCE: 49
tatttaagga gggtgatctt c                                               21

SEQ ID NO: 50         moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) antisense strand AS-32
modified_base         8
                      mod_base = gm
modified_base         9
                      mod_base = gm
modified_base         15
                      mod_base = gm
modified_base         17
                      mod_base = um
modified_base         20
                      mod_base = um
source                1..21
                      mol_type = other RNA
                      organism = synthetic construct
SEQUENCE: 50
tatttaagga gggtgatctt c                                               21

SEQ ID NO: 51         moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) antisense strand AS-33
modified_base         8
                      mod_base = gm
modified_base         12
                      mod_base = gm
modified_base         15
                      mod_base = gm
modified_base         17
                      mod_base = um
modified_base         20
                      mod_base = um
source                1..21
                      mol_type = other RNA
                      organism = synthetic construct
SEQUENCE: 51
tatttaagga gggtgatctt c                                               21

SEQ ID NO: 52         moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) antisense strand AS-34
```

```
modified_base           8
                        mod_base = gm
modified_base           9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 52
tatttaagga gggtgatctt c                                              21

SEQ ID NO: 53           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-35
modified_base           1
                        mod_base = um
modified_base           8..9
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 53
tatttaagga gggtgatctt c                                              21

SEQ ID NO: 54           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-36
modified_base           3
                        mod_base = um
modified_base           8..9
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 54
tatttaagga gggtgatctt c                                              21

SEQ ID NO: 55           moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-37
modified_base           4
                        mod_base = um
modified_base           8..9
                        mod_base = gm
modified_base           15
                        mod_base = gm
modified_base           17
                        mod_base = um
```

```
modified_base            20
                         mod_base = um
source                   1..21
                         mol_type = other RNA
                         organism = synthetic construct
SEQUENCE: 55
tatttaagga gggtgatctt c                                              21

SEQ ID NO: 56            moltype = RNA  length = 21
FEATURE                  Location/Qualifiers
misc_feature             1..21
                         note = synthetic polo-like kinase 1 (PLK-1),
                           serine/threonine protein kinase 13 (STPK13) small
                           interfering RNA (siRNA) antisense strand AS-38
modified_base            8..9
                         mod_base = gm
modified_base            15
                         mod_base = gm
modified_base            17
                         mod_base = um
modified_base            20
                         mod_base = um
source                   1..21
                         mol_type = other RNA
                         organism = synthetic construct
SEQUENCE: 56
tatttaagga gggtgatctt c                                              21

SEQ ID NO: 57            moltype = RNA  length = 21
FEATURE                  Location/Qualifiers
misc_feature             1..21
                         note = synthetic polo-like kinase 1 (PLK-1),
                           serine/threonine protein kinase 13 (STPK13) small
                           interfering RNA (siRNA) antisense strand AS-39
modified_base            1
                         mod_base = um
modified_base            8
                         mod_base = gm
modified_base            12
                         mod_base = gm
modified_base            15
                         mod_base = gm
modified_base            17
                         mod_base = um
modified_base            20
                         mod_base = um
source                   1..21
                         mol_type = other RNA
                         organism = synthetic construct
SEQUENCE: 57
tatttaagga gggtgatctt c                                              21

SEQ ID NO: 58            moltype = RNA  length = 21
FEATURE                  Location/Qualifiers
misc_feature             1..21
                         note = synthetic polo-like kinase 1 (PLK-1),
                           serine/threonine protein kinase 13 (STPK13) small
                           interfering RNA (siRNA) antisense strand AS-40
modified_base            3
                         mod_base = um
modified_base            8
                         mod_base = gm
modified_base            12
                         mod_base = gm
modified_base            15
                         mod_base = gm
modified_base            17
                         mod_base = um
modified_base            20
                         mod_base = um
source                   1..21
                         mol_type = other RNA
                         organism = synthetic construct
SEQUENCE: 58
tatttaagga gggtgatctt c                                              21

SEQ ID NO: 59            moltype = RNA  length = 21
FEATURE                  Location/Qualifiers
misc_feature             1..21
```

```
                        note = synthetic polo-like kinase 1 (PLK-1),
                         serine/threonine protein kinase 13 (STPK13) small
                         interfering RNA (siRNA) antisense strand AS-41
modified_base           4
                        mod_base = um
modified_base           8
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 59
tatttaagga gggtgatctt c                                                  21

SEQ ID NO: 60           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-42
modified_base           8
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 60
tatttaagga gggtgatctt c                                                  21

SEQ ID NO: 61           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-43
modified_base           1
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 61
tatttaagga gggtgatctt c                                                  21

SEQ ID NO: 62           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-44
modified_base           3
                        mod_base = um
modified_base           8..9
                        mod_base = gm
modified_base           12
                        mod_base = gm
```

```
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 62
tatttaagga gggtgatctt c                                              21

SEQ ID NO: 63          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-45
modified_base          4
                       mod_base = um
modified_base          8..9
                       mod_base = gm
modified_base          12
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 63
tatttaagga gggtgatctt c                                              21

SEQ ID NO: 64          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-46
modified_base          8..9
                       mod_base = gm
modified_base          12
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 64
tatttaagga gggtgatctt c                                              21

SEQ ID NO: 65          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-47
modified_base          1
                       mod_base = um
modified_base          3
                       mod_base = um
modified_base          8..9
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
```

-continued

```
SEQUENCE: 65
tatttaagga gggtgatctt c                                                        21

SEQ ID NO: 66           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-48
modified_base           1
                        mod_base = um
modified_base           4
                        mod_base = um
modified_base           8..9
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 66
tatttaagga gggtgatctt c                                                        21

SEQ ID NO: 67           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-49
modified_base           1
                        mod_base = um
modified_base           8..9
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 67
tatttaagga gggtgatctt c                                                        21

SEQ ID NO: 68           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-50
modified_base           3
                        mod_base = um
modified_base           4
                        mod_base = um
modified_base           8..9
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 68
tatttaagga gggtgatctt c                                                        21

SEQ ID NO: 69           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-51
```

-continued

```
modified_base      3
                   mod_base = um
modified_base      8..9
                   mod_base = gm
modified_base      15
                   mod_base = gm
modified_base      17
                   mod_base = um
modified_base      20
                   mod_base = um
source             1..21
                   mol_type = other RNA
                   organism = synthetic construct
SEQUENCE: 69
tatttaagga gggtgatctt c                                              21

SEQ ID NO: 70      moltype = RNA  length = 21
FEATURE            Location/Qualifiers
misc_feature       1..21
                   note = synthetic polo-like kinase 1 (PLK-1),
                   serine/threonine protein kinase 13 (STPK13) small
                   interfering RNA (siRNA) antisense strand AS-52
modified_base      4
                   mod_base = um
modified_base      8..9
                   mod_base = gm
modified_base      15
                   mod_base = gm
modified_base      17
                   mod_base = um
modified_base      20
                   mod_base = um
source             1..21
                   mol_type = other RNA
                   organism = synthetic construct
SEQUENCE: 70
tatttaagga gggtgatctt c                                              21

SEQ ID NO: 71      moltype = RNA  length = 21
FEATURE            Location/Qualifiers
misc_feature       1..21
                   note = synthetic polo-like kinase 1 (PLK-1),
                   serine/threonine protein kinase 13 (STPK13) small
                   interfering RNA (siRNA) antisense strand AS-53
modified_base      1
                   mod_base = um
modified_base      3
                   mod_base = um
modified_base      8
                   mod_base = gm
modified_base      12
                   mod_base = gm
modified_base      15
                   mod_base = gm
modified_base      17
                   mod_base = um
modified_base      20
                   mod_base = um
source             1..21
                   mol_type = other RNA
                   organism = synthetic construct
SEQUENCE: 71
tatttaagga gggtgatctt c                                              21

SEQ ID NO: 72      moltype = RNA  length = 21
FEATURE            Location/Qualifiers
misc_feature       1..21
                   note = synthetic polo-like kinase 1 (PLK-1),
                   serine/threonine protein kinase 13 (STPK13) small
                   interfering RNA (siRNA) antisense strand AS-54
modified_base      1
                   mod_base = um
modified_base      4
                   mod_base = um
modified_base      8
                   mod_base = gm
modified_base      12
                   mod_base = gm
modified_base      15
```

```
                          mod_base = gm
modified_base             17
                          mod_base = um
modified_base             20
                          mod_base = um
source                    1..21
                          mol_type = other RNA
                          organism = synthetic construct
SEQUENCE: 72
tatttaagga gggtgatctt c                                              21

SEQ ID NO: 73             moltype = RNA   length = 21
FEATURE                   Location/Qualifiers
misc_feature              1..21
                          note = synthetic polo-like kinase 1 (PLK-1),
                           serine/threonine protein kinase 13 (STPK13) small
                           interfering RNA (siRNA) antisense strand AS-55
modified_base             1
                          mod_base = um
modified_base             8
                          mod_base = gm
modified_base             12
                          mod_base = gm
modified_base             15
                          mod_base = gm
modified_base             17
                          mod_base = um
modified_base             20
                          mod_base = um
source                    1..21
                          mol_type = other RNA
                          organism = synthetic construct
SEQUENCE: 73
tatttaagga gggtgatctt c                                              21

SEQ ID NO: 74             moltype = RNA   length = 21
FEATURE                   Location/Qualifiers
misc_feature              1..21
                          note = synthetic polo-like kinase 1 (PLK-1),
                           serine/threonine protein kinase 13 (STPK13) small
                           interfering RNA (siRNA) antisense strand AS-56
modified_base             3
                          mod_base = um
modified_base             4
                          mod_base = um
modified_base             8
                          mod_base = gm
modified_base             12
                          mod_base = gm
modified_base             15
                          mod_base = gm
modified_base             17
                          mod_base = um
modified_base             20
                          mod_base = um
source                    1..21
                          mol_type = other RNA
                          organism = synthetic construct
SEQUENCE: 74
tatttaagga gggtgatctt c                                              21

SEQ ID NO: 75             moltype = RNA   length = 21
FEATURE                   Location/Qualifiers
misc_feature              1..21
                          note = synthetic polo-like kinase 1 (PLK-1),
                           serine/threonine protein kinase 13 (STPK13) small
                           interfering RNA (siRNA) antisense strand AS-57
modified_base             3
                          mod_base = um
modified_base             8
                          mod_base = gm
modified_base             15
                          mod_base = gm
modified_base             17
                          mod_base = um
modified_base             20
                          mod_base = um
source                    1..21
                          mol_type = other RNA
```

```
                        organism = synthetic construct
SEQUENCE: 75
tatttaagga gggtgatctt c                                                    21

SEQ ID NO: 76           moltype = RNA   length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-58
modified_base           4
                        mod_base = um
modified_base           8
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 76
tatttaagga gggtgatctt c                                                    21

SEQ ID NO: 77           moltype = RNA   length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-59
modified_base           1
                        mod_base = um
modified_base           3
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 77
tatttaagga gggtgatctt c                                                    21

SEQ ID NO: 78           moltype = RNA   length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-60
modified_base           1
                        mod_base = um
modified_base           4
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 78
tatttaagga gggtgatctt c                                                    21

SEQ ID NO: 79           moltype = RNA   length = 21
```

```
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-61
modified_base           1
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 79
tatttaagga gggtgatctt c                                              21

SEQ ID NO: 80           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-62
modified_base           3
                        mod_base = um
modified_base           4
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 80
tatttaagga gggtgatctt c                                              21

SEQ ID NO: 81           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-63
modified_base           3
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 81
tatttaagga gggtgatctt c                                              21

SEQ ID NO: 82           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-64
```

```
modified_base          4
                       mod_base = um
modified_base          8..9
                       mod_base = gm
modified_base          12
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 82
tatttaagga gggtgatctt c                                              21

SEQ ID NO: 83          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-65
modified_base          1
                       mod_base = um
modified_base          4
                       mod_base = um
modified_base          8..9
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 83
tatttaagga gggtgatctt c                                              21

SEQ ID NO: 84          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-66
modified_base          1
                       mod_base = um
modified_base          3
                       mod_base = um
modified_base          8..9
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 84
tatttaagga gggtgatctt c                                              21

SEQ ID NO: 85          moltype = RNA  length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-67
modified_base          1
                       mod_base = um
modified_base          4
                       mod_base = um
modified_base          8..9
                       mod_base = gm
modified_base          15
```

```
                       mod_base = gm
modified_base          17
                       mod_base = um
modified_base          20
                       mod_base = um
source                 1..21
                       mol_type = other RNA
                       organism = synthetic construct
SEQUENCE: 85
tatttaagga gggtgatctt c                                              21

SEQ ID NO: 86          moltype = RNA   length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-68
modified_base          3
                       mod_base = um
modified_base          4
                       mod_base = um
modified_base          8..9
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 86
tatttaagga gggtgatctt c                                              21

SEQ ID NO: 87          moltype = RNA   length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-69
modified_base          1
                       mod_base = um
modified_base          3
                       mod_base = um
modified_base          8
                       mod_base = gm
modified_base          12
                       mod_base = gm
modified_base          15
                       mod_base = gm
modified_base          17
                       mod_base = um
modified_base          20
                       mod_base = um
source                 1..21
                       mol_type = other RNA
                       organism = synthetic construct
SEQUENCE: 87
tatttaagga gggtgatctt c                                              21

SEQ ID NO: 88          moltype = RNA   length = 21
FEATURE                Location/Qualifiers
misc_feature           1..21
                       note = synthetic polo-like kinase 1 (PLK-1),
                        serine/threonine protein kinase 13 (STPK13) small
                        interfering RNA (siRNA) antisense strand AS-70
modified_base          1
                       mod_base = um
modified_base          4
                       mod_base = um
modified_base          8
                       mod_base = gm
modified_base          12
                       mod_base = gm
modified_base          15
                       mod_base = um
modified_base          17
                       mod_base = um
```

```
modified_base         20
                      mod_base = um
source                1..21
                      mol_type = other RNA
                      organism = synthetic construct
SEQUENCE: 88
tatttaagga gggtgatctt c                                                  21

SEQ ID NO: 89         moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) antisense strand AS-71
modified_base         1
                      mod_base = um
modified_base         3
                      mod_base = um
modified_base         8
                      mod_base = gm
modified_base         12
                      mod_base = gm
modified_base         15
                      mod_base = gm
modified_base         17
                      mod_base = um
modified_base         20
                      mod_base = um
source                1..21
                      mol_type = other RNA
                      organism = synthetic construct
SEQUENCE: 89
tatttaagga gggtgatctt c                                                  21

SEQ ID NO: 90         moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) antisense strand AS-72
modified_base         3
                      mod_base = um
modified_base         4
                      mod_base = um
modified_base         8
                      mod_base = gm
modified_base         12
                      mod_base = gm
modified_base         15
                      mod_base = gm
modified_base         17
                      mod_base = um
modified_base         20
                      mod_base = um
source                1..21
                      mol_type = other RNA
                      organism = synthetic construct
SEQUENCE: 90
tatttaagga gggtgatctt c                                                  21

SEQ ID NO: 91         moltype = RNA  length = 21
FEATURE               Location/Qualifiers
misc_feature          1..21
                      note = synthetic polo-like kinase 1 (PLK-1),
                       serine/threonine protein kinase 13 (STPK13) small
                       interfering RNA (siRNA) antisense strand AS-73
modified_base         1
                      mod_base = um
modified_base         4
                      mod_base = um
modified_base         8..9
                      mod_base = gm
modified_base         12
                      mod_base = gm
modified_base         15
                      mod_base = gm
modified_base         17
                      mod_base = um
modified_base         20
```

```
                        mod_base = um
source                  1..21
                        mol_type = other RNA
                        organism = synthetic construct
SEQUENCE: 91
tatttaagga gggtgatctt c                                              21

SEQ ID NO: 92           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-74
modified_base           1
                        mod_base = um
modified_base           3
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 92
tatttaagga gggtgatctt c                                              21

SEQ ID NO: 93           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-75
modified_base           1
                        mod_base = um
modified_base           4
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 93
tatttaagga gggtgatctt c                                              21

SEQ ID NO: 94           moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-76
modified_base           3..4
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
```

```
                        organism = synthetic construct
SEQUENCE: 94
tatttaagga gggtgatctt c                                              21

SEQ ID NO: 95           moltype = RNA   length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-77
modified_base           1
                        mod_base = um
modified_base           4
                        mod_base = um
modified_base           8..9
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 95
tatttaagga gggtgatctt c                                              21

SEQ ID NO: 96           moltype = RNA   length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-78
modified_base           1
                        mod_base = um
modified_base           4
                        mod_base = um
modified_base           8
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 96
tatttaagga gggtgatctt c                                              21

SEQ ID NO: 97           moltype = RNA   length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-79
modified_base           1
                        mod_base = um
modified_base           4
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 97
tatttaagga gggtgatctt c                                              21
```

| | |
|---|---|
| SEQ ID NO: 98 | moltype = RNA  length = 21 |
| FEATURE | Location/Qualifiers |
| misc_feature | 1..21 |
| | note = synthetic polo-like kinase 1 (PLK-1), serine/threonine protein kinase 13 (STPK13) small interfering RNA (siRNA) antisense strand AS-80 |
| modified_base | 8..9 |
| | mod_base = gm |
| modified_base | 12 |
| | mod_base = gm |
| modified_base | 15 |
| | mod_base = gm |
| modified_base | 17 |
| | mod_base = um |
| modified_base | 20 |
| | mod_base = um |
| source | 1..21 |
| | mol_type = other RNA |
| | organism = synthetic construct |
| SEQUENCE: 98 | |
| tatttaagga gggtgatctt c | 21 |

| | |
|---|---|
| SEQ ID NO: 99 | moltype = RNA  length = 21 |
| FEATURE | Location/Qualifiers |
| misc_feature | 1..21 |
| | note = synthetic polo-like kinase 1 (PLK-1), serine/threonine protein kinase 13 (STPK13) small interfering RNA (siRNA) antisense strand AS-81 |
| modified_base | 8 |
| | mod_base = gm |
| modified_base | 12 |
| | mod_base = gm |
| modified_base | 15 |
| | mod_base = gm |
| modified_base | 17 |
| | mod_base = um |
| modified_base | 20 |
| | mod_base = um |
| source | 1..21 |
| | mol_type = other RNA |
| | organism = synthetic construct |
| SEQUENCE: 99 | |
| tatttaagga gggtgatctt c | 21 |

| | |
|---|---|
| SEQ ID NO: 100 | moltype = RNA  length = 21 |
| FEATURE | Location/Qualifiers |
| misc_feature | 1..21 |
| | note = synthetic polo-like kinase 1 (PLK-1), serine/threonine protein kinase 13 (STPK13) small interfering RNA (siRNA) antisense strand AS-82 |
| modified_base | 8..9 |
| | mod_base = gm |
| modified_base | 12 |
| | mod_base = gm |
| modified_base | 15 |
| | mod_base = gm |
| modified_base | 17 |
| | mod_base = um |
| modified_base | 20 |
| | mod_base = um |
| source | 1..21 |
| | mol_type = other RNA |
| | organism = synthetic construct |
| SEQUENCE: 100 | |
| tatttaagga gggtgatctt c | 21 |

| | |
|---|---|
| SEQ ID NO: 101 | moltype = RNA  length = 21 |
| FEATURE | Location/Qualifiers |
| misc_feature | 1..21 |
| | note = synthetic polo-like kinase 1 (PLK-1), serine/threonine protein kinase 13 (STPK13) small interfering RNA (siRNA) antisense strand AS-83 |
| modified_base | 1 |
| | mod_base = um |
| modified_base | 8..9 |
| | mod_base = gm |
| modified_base | 13 |
| | mod_base = gm |

```
modified_base        15
                     mod_base = gm
modified_base        17
                     mod_base = um
modified_base        20
                     mod_base = um
source               1..21
                     mol_type = other RNA
                     organism = synthetic construct
SEQUENCE: 101
tatttaagga gggtgatctt c                                              21

SEQ ID NO: 102       moltype = RNA  length = 21
FEATURE              Location/Qualifiers
misc_feature         1..21
                     note = synthetic polo-like kinase 1 (PLK-1),
                      serine/threonine protein kinase 13 (STPK13) small
                      interfering RNA (siRNA) antisense strand AS-84
modified_base        3
                     mod_base = um
modified_base        8..9
                     mod_base = gm
modified_base        13
                     mod_base = gm
modified_base        15
                     mod_base = gm
modified_base        17
                     mod_base = um
modified_base        20
                     mod_base = um
source               1..21
                     mol_type = other RNA
                     organism = synthetic construct
SEQUENCE: 102
tatttaagga gggtgatctt c                                              21

SEQ ID NO: 103       moltype = RNA  length = 21
FEATURE              Location/Qualifiers
misc_feature         1..21
                     note = synthetic polo-like kinase 1 (PLK-1),
                      serine/threonine protein kinase 13 (STPK13) small
                      interfering RNA (siRNA) antisense strand AS-85
modified_base        4
                     mod_base = um
modified_base        8..9
                     mod_base = gm
modified_base        13
                     mod_base = gm
modified_base        15
                     mod_base = gm
modified_base        17
                     mod_base = um
modified_base        20
                     mod_base = um
source               1..21
                     mol_type = other RNA
                     organism = synthetic construct
SEQUENCE: 103
tatttaagga gggtgatctt c                                              21

SEQ ID NO: 104       moltype = RNA  length = 21
FEATURE              Location/Qualifiers
misc_feature         1..21
                     note = synthetic polo-like kinase 1 (PLK-1),
                      serine/threonine protein kinase 13 (STPK13) small
                      interfering RNA (siRNA) antisense strand AS-86
modified_base        8..9
                     mod_base = gm
modified_base        13
                     mod_base = gm
modified_base        15
                     mod_base = gm
modified_base        17
                     mod_base = um
modified_base        20
                     mod_base = um
source               1..21
                     mol_type = other RNA
                     organism = synthetic construct
```

```
SEQUENCE: 104
tatttaagga gggtgatctt c                                              21

SEQ ID NO: 105          moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-87
modified_base           1
                        mod_base = um
modified_base           8
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 105
tatttaagga gggtgatctt c                                              21

SEQ ID NO: 106          moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-88
modified_base           3
                        mod_base = um
modified_base           8
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 106
tatttaagga gggtgatctt c                                              21

SEQ ID NO: 107          moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-89
modified_base           4
                        mod_base = um
modified_base           8
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 107
tatttaagga gggtgatctt c                                              21

SEQ ID NO: 108          moltype = RNA   length = 21
FEATURE                 Location/Qualifiers
misc_feature            1..21
                        note = synthetic polo-like kinase 1 (PLK-1),
```

```
                            serine/threonine protein kinase 13 (STPK13) small
                            interfering RNA (siRNA) antisense strand AS-90
modified_base               8
                            mod_base = gm
modified_base               12
                            mod_base = gm
modified_base               17
                            mod_base = um
modified_base               15
                            mod_base = gm
modified_base               20
                            mod_base = um
source                      1..21
                            mol_type = other RNA
                            organism = synthetic construct
SEQUENCE: 108
tatttaagga gggtgatctt c                                                   21

SEQ ID NO: 109              moltype = RNA   length = 21
FEATURE                     Location/Qualifiers
misc_feature                1..21
                            note = synthetic polo-like kinase 1 (PLK-1),
                            serine/threonine protein kinase 13 (STPK13) small
                            interfering RNA (siRNA) antisense strand AS-91
modified_base               1
                            mod_base = um
modified_base               8..9
                            mod_base = gm
modified_base               12
                            mod_base = gm
modified_base               15
                            mod_base = gm
modified_base               17
                            mod_base = um
modified_base               20
                            mod_base = um
source                      1..21
                            mol_type = other RNA
                            organism = synthetic construct
SEQUENCE: 109
tatttaagga gggtgatctt c                                                   21

SEQ ID NO: 110              moltype = RNA   length = 21
FEATURE                     Location/Qualifiers
misc_feature                1..21
                            note = synthetic polo-like kinase 1 (PLK-1),
                            serine/threonine protein kinase 13 (STPK13) small
                            interfering RNA (siRNA) antisense strand AS-92
modified_base               3
                            mod_base = um
modified_base               8..9
                            mod_base = gm
modified_base               12
                            mod_base = gm
modified_base               15
                            mod_base = gm
modified_base               17
                            mod_base = um
modified_base               20
                            mod_base = um
source                      1..21
                            mol_type = other RNA
                            organism = synthetic construct
SEQUENCE: 110
tatttaagga gggtgatctt c                                                   21

SEQ ID NO: 111              moltype = RNA   length = 21
FEATURE                     Location/Qualifiers
misc_feature                1..21
                            note = synthetic polo-like kinase 1 (PLK-1),
                            serine/threonine protein kinase 13 (STPK13) small
                            interfering RNA (siRNA) antisense strand AS-93
modified_base               4
                            mod_base = um
modified_base               8..9
                            mod_base = gm
modified_base               12
                            mod_base = gm
modified_base               15
```

|                | mod_base = gm |
| --- | --- |
| modified_base | 17 |
|                | mod_base = um |
| modified_base | 20 |
|                | mod_base = um |
| source         | 1..21 |
|                | mol_type = other RNA |
|                | organism = synthetic construct |

SEQUENCE: 111
tatttaagga gggtgatctt c                                    21

|                | |
| --- | --- |
| SEQ ID NO: 112 | moltype = RNA length = 21 |
| FEATURE        | Location/Qualifiers |
| misc_feature   | 1..21 |
|                | note = synthetic polo-like kinase 1 (PLK-1), serine/threonine protein kinase 13 (STPK13) small interfering RNA (siRNA) antisense strand AS-94 |
| modified_base  | 8..9 |
|                | mod_base = gm |
| modified_base  | 12 |
|                | mod_base = gm |
| modified_base  | 17 |
|                | mod_base = um |
| modified_base  | 15 |
|                | mod_base = gm |
| modified_base  | 20 |
|                | mod_base = um |
| source         | 1..21 |
|                | mol_type = other RNA |
|                | organism = synthetic construct |

SEQUENCE: 112
tatttaagga gggtgatctt c                                    21

|                | |
| --- | --- |
| SEQ ID NO: 113 | moltype = RNA length = 21 |
| FEATURE        | Location/Qualifiers |
| misc_feature   | 1..21 |
|                | note = synthetic polo-like kinase 1 (PLK-1), serine/threonine protein kinase 13 (STPK13) small interfering RNA (siRNA) antisense strand AS-95 |
| modified_base  | 1 |
|                | mod_base = um |
| modified_base  | 3 |
|                | mod_base = um |
| modified_base  | 8..9 |
|                | mod_base = gm |
| modified_base  | 13 |
|                | mod_base = gm |
| modified_base  | 15 |
|                | mod_base = gm |
| modified_base  | 17 |
|                | mod_base = um |
| modified_base  | 20 |
|                | mod_base = um |
| source         | 1..21 |
|                | mol_type = other RNA |
|                | organism = synthetic construct |

SEQUENCE: 113
tatttaagga gggtgatctt c                                    21

|                | |
| --- | --- |
| SEQ ID NO: 114 | moltype = RNA length = 21 |
| FEATURE        | Location/Qualifiers |
| misc_feature   | 1..21 |
|                | note = synthetic polo-like kinase 1 (PLK-1), serine/threonine protein kinase 13 (STPK13) small interfering RNA (siRNA) antisense strand AS-96 |
| modified_base  | 1 |
|                | mod_base = um |
| modified_base  | 4 |
|                | mod_base = um |
| modified_base  | 8..9 |
|                | mod_base = gm |
| modified_base  | 13 |
|                | mod_base = gm |
| modified_base  | 15 |
|                | mod_base = gm |
| modified_base  | 17 |
|                | mod_base = um |
| modified_base  | 20 |
|                | mod_base = um |

```
source                  1..21
                        mol_type = other RNA
                        organism = synthetic construct
SEQUENCE: 114
tatttaagga gggtgatctt c                                                    21

SEQ ID NO: 115          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-97
modified_base           1
                        mod_base = um
modified_base           8..9
                        mod_base = gm
modified_base           13
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 115
tatttaagga gggtgatctt c                                                    21

SEQ ID NO: 116          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-98
modified_base           3
                        mod_base = um
modified_base           4
                        mod_base = um
modified_base           8..9
                        mod_base = gm
modified_base           13
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 116
tatttaagga gggtgatctt c                                                    21

SEQ ID NO: 117          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-99
modified_base           3
                        mod_base = um
modified_base           8..9
                        mod_base = gm
modified_base           13
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 117
tatttaagga gggtgatctt c                                                    21
```

```
SEQ ID NO: 118           moltype = RNA  length = 21
FEATURE                  Location/Qualifiers
misc_feature             1..21
                         note = synthetic polo-like kinase 1 (PLK-1),
                          serine/threonine protein kinase 13 (STPK13) small
                          interfering RNA (siRNA) antisense strand AS-100
modified_base            4
                         mod_base = um
modified_base            8..9
                         mod_base = gm
modified_base            13
                         mod_base = gm
modified_base            17
                         mod_base = um
modified_base            15
                         mod_base = gm
modified_base            20
                         mod_base = um
source                   1..21
                         mol_type = other RNA
                         organism = synthetic construct
SEQUENCE: 118
tatttaagga gggtgatctt c                                                   21

SEQ ID NO: 119           moltype = RNA  length = 21
FEATURE                  Location/Qualifiers
misc_feature             1..21
                         note = synthetic polo-like kinase 1 (PLK-1),
                          serine/threonine protein kinase 13 (STPK13) small
                          interfering RNA (siRNA) antisense strand AS-101
modified_base            1
                         mod_base = um
modified_base            3
                         mod_base = um
modified_base            8
                         mod_base = gm
modified_base            12
                         mod_base = gm
modified_base            15
                         mod_base = gm
modified_base            17
                         mod_base = um
modified_base            20
                         mod_base = um
source                   1..21
                         mol_type = other RNA
                         organism = synthetic construct
SEQUENCE: 119
tatttaagga gggtgatctt c                                                   21

SEQ ID NO: 120           moltype = RNA  length = 21
FEATURE                  Location/Qualifiers
misc_feature             1..21
                         note = synthetic polo-like kinase 1 (PLK-1),
                          serine/threonine protein kinase 13 (STPK13) small
                          interfering RNA (siRNA) antisense strand AS-102
modified_base            1
                         mod_base = um
modified_base            4
                         mod_base = um
modified_base            8
                         mod_base = gm
modified_base            12
                         mod_base = gm
modified_base            15
                         mod_base = gm
modified_base            17
                         mod_base = um
modified_base            20
                         mod_base = um
source                   1..21
                         mol_type = other RNA
                         organism = synthetic construct
SEQUENCE: 120
tatttaagga gggtgatctt c                                                   21

SEQ ID NO: 121           moltype = RNA  length = 21
FEATURE                  Location/Qualifiers
```

```
misc_feature            1..21
                        note = synthetic polo-like kinase 1 (PLK-1),
                         serine/threonine protein kinase 13 (STPK13) small
                         interfering RNA (siRNA) antisense strand AS-103
modified_base           1
                        mod_base = um
modified_base           8
                        mod_base = gm
modified_base           12
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 121
tatttaagga gggtgatctt c                                              21

SEQ ID NO: 122          moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-104
modified_base           3..4
                        mod_base = um
modified_base           8
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 122
tatttaagga gggtgatctt c                                              21

SEQ ID NO: 123          moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-105
modified_base           3
                        mod_base = um
modified_base           8
                        mod_base = gm
modified_base           12
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 123
tatttaagga gggtgatctt c                                              21

SEQ ID NO: 124          moltype = RNA   length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-106
modified_base           4
                        mod_base = um
modified_base           8
```

```
                        mod_base = gm
modified_base           12
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 124
tatttaagga gggtgatctt c                                              21

SEQ ID NO: 125          moltype = RNA  length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-107
modified_base           1
                        mod_base = um
modified_base           3
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 125
tatttaagga gggtgatctt c                                              21

SEQ ID NO: 126          moltype = RNA  length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-108
modified_base           1
                        mod_base = um
modified_base           4
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 126
tatttaagga gggtgatctt c                                              21

SEQ ID NO: 127          moltype = RNA  length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-109
modified_base           1
                        mod_base = um
modified_base           8..9
                        mod_base = gm
modified_base           12
                        mod_base = gm
```

| | | |
|---|---|---|
| modified_base | 17 | |
| | mod_base = um | |
| modified_base | 15 | |
| | mod_base = gm | |
| modified_base | 20 | |
| | mod_base = um | |
| source | 1..21 | |
| | mol_type = other RNA | |
| | organism = synthetic construct | |
| SEQUENCE: 127 | | |
| tatttaagga gggtgatctt c | | 21 |
| | | |
| SEQ ID NO: 128 | moltype = RNA  length = 21 | |
| FEATURE | Location/Qualifiers | |
| misc_feature | 1..21 | |
| | note = synthetic polo-like kinase 1 (PLK-1), serine/threonine protein kinase 13 (STPK13) small interfering RNA (siRNA) antisense strand AS-110 | |
| modified_base | 3 | |
| | mod_base = um | |
| modified_base | 4 | |
| | mod_base = um | |
| modified_base | 8..9 | |
| | mod_base = gm | |
| modified_base | 12 | |
| | mod_base = gm | |
| modified_base | 15 | |
| | mod_base = gm | |
| modified_base | 17 | |
| | mod_base = um | |
| modified_base | 20 | |
| | mod_base = um | |
| source | 1..21 | |
| | mol_type = other RNA | |
| | organism = synthetic construct | |
| SEQUENCE: 128 | | |
| tatttaagga gggtgatctt c | | 21 |
| | | |
| SEQ ID NO: 129 | moltype = RNA  length = 21 | |
| FEATURE | Location/Qualifiers | |
| misc_feature | 1..21 | |
| | note = synthetic polo-like kinase 1 (PLK-1), serine/threonine protein kinase 13 (STPK13) small interfering RNA (siRNA) antisense strand AS-111 | |
| modified_base | 3 | |
| | mod_base = um | |
| modified_base | 8..9 | |
| | mod_base = gm | |
| modified_base | 12 | |
| | mod_base = gm | |
| modified_base | 17 | |
| | mod_base = um | |
| modified_base | 15 | |
| | mod_base = gm | |
| modified_base | 20 | |
| | mod_base = um | |
| source | 1..21 | |
| | mol_type = other RNA | |
| | organism = synthetic construct | |
| SEQUENCE: 129 | | |
| tatttaagga gggtgatctt c | | 21 |
| | | |
| SEQ ID NO: 130 | moltype = RNA  length = 21 | |
| FEATURE | Location/Qualifiers | |
| misc_feature | 1..21 | |
| | note = synthetic polo-like kinase 1 (PLK-1), serine/threonine protein kinase 13 (STPK13) small interfering RNA (siRNA) antisense strand AS-112 | |
| modified_base | 4 | |
| | mod_base = um | |
| modified_base | 8..9 | |
| | mod_base = gm | |
| modified_base | 12 | |
| | mod_base = gm | |
| modified_base | 17 | |
| | mod_base = um | |
| modified_base | 15 | |
| | mod_base = gm | |
| modified_base | 20 | |

-continued

```
                        mod_base = um
source                  1..21
                        mol_type = other RNA
                        organism = synthetic construct
SEQUENCE: 130
tatttaagga gggtgatctt c                                              21

SEQ ID NO: 131          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-113
modified_base           1
                        mod_base = um
modified_base           4
                        mod_base = um
modified_base           8..9
                        mod_base = gm
modified_base           13
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 131
tatttaagga gggtgatctt c                                              21

SEQ ID NO: 132          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-114
modified_base           1
                        mod_base = um
modified_base           3
                        mod_base = um
modified_base           8..9
                        mod_base = gm
modified_base           13
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 132
tatttaagga gggtgatctt c                                              21

SEQ ID NO: 133          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-115
modified_base           1
                        mod_base = um
modified_base           4
                        mod_base = um
modified_base           8..9
                        mod_base = gm
modified_base           13
                        mod_base = gm
modified_base           17
                        mod_base = um
modified_base           15
                        mod_base = gm
modified_base           20
                        mod_base = um
```

```
source               1..21
                     mol_type = other RNA
                     organism = synthetic construct
SEQUENCE: 133
tatttaagga gggtgatctt c                                              21

SEQ ID NO: 134       moltype = RNA  length = 21
FEATURE              Location/Qualifiers
misc_feature         1..21
                     note = synthetic polo-like kinase 1 (PLK-1),
                       serine/threonine protein kinase 13 (STPK13) small
                       interfering RNA (siRNA) antisense strand AS-116
modified_base        3..4
                     mod_base = um
modified_base        8..9
                     mod_base = gm
modified_base        13
                     mod_base = gm
modified_base        17
                     mod_base = um
modified_base        15
                     mod_base = gm
modified_base        20
                     mod_base = um
source               1..21
                     mol_type = other RNA
                     organism = synthetic construct
SEQUENCE: 134
tatttaagga gggtgatctt c                                              21

SEQ ID NO: 135       moltype = RNA  length = 21
FEATURE              Location/Qualifiers
misc_feature         1..21
                     note = synthetic polo-like kinase 1 (PLK-1),
                       serine/threonine protein kinase 13 (STPK13) small
                       interfering RNA (siRNA) antisense strand AS-117
modified_base        1
                     mod_base = um
modified_base        3
                     mod_base = um
modified_base        8
                     mod_base = gm
modified_base        12
                     mod_base = gm
modified_base        15
                     mod_base = gm
modified_base        17
                     mod_base = um
modified_base        20
                     mod_base = um
source               1..21
                     mol_type = other RNA
                     organism = synthetic construct
SEQUENCE: 135
tatttaagga gggtgatctt c                                              21

SEQ ID NO: 136       moltype = RNA  length = 21
FEATURE              Location/Qualifiers
misc_feature         1..21
                     note = synthetic polo-like kinase 1 (PLK-1),
                       serine/threonine protein kinase 13 (STPK13) small
                       interfering RNA (siRNA) antisense strand AS-118
modified_base        1
                     mod_base = um
modified_base        4
                     mod_base = um
modified_base        8
                     mod_base = gm
modified_base        12
                     mod_base = gm
modified_base        17
                     mod_base = um
modified_base        15
                     mod_base = gm
modified_base        20
                     mod_base = um
source               1..21
                     mol_type = other RNA
                     organism = synthetic construct
```

```
SEQUENCE: 136
tatttaagga gggtgatctt c                                                21

SEQ ID NO: 137          moltype = RNA  length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-119
modified_base           1
                        mod_base = um
modified_base           3
                        mod_base = um
modified_base           8
                        mod_base = gm
modified_base           12
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 137
tatttaagga gggtgatctt c                                                21

SEQ ID NO: 138          moltype = RNA  length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-120
modified_base           3..4
                        mod_base = um
modified_base           8
                        mod_base = gm
modified_base           12
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 138
tatttaagga gggtgatctt c                                                21

SEQ ID NO: 139          moltype = RNA  length = 21
FEATURE                 Location/Qualifiers
misc_feature            1..21
                        note = synthetic polo-like kinase 1 (PLK-1),
                          serine/threonine protein kinase 13 (STPK13) small
                          interfering RNA (siRNA) antisense strand AS-121
modified_base           1
                        mod_base = um
modified_base           4
                        mod_base = um
modified_base           8..9
                        mod_base = gm
modified_base           12
                        mod_base = gm
modified_base           15
                        mod_base = gm
modified_base           17
                        mod_base = um
modified_base           20
                        mod_base = um
source                  1..21
                        mol_type = other RNA
                        organism = synthetic construct
SEQUENCE: 139
tatttaagga gggtgatctt c                                                21
```

```
SEQ ID NO: 140          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-122
modified_base           1
                        mod_base = um
modified_base           3
                        mod_base = um
modified_base           8..9
                        mod_base = gm
modified_base           12
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 140
tatttaagga gggtgatctt c                                              21

SEQ ID NO: 141          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-123
modified_base           1
                        mod_base = um
modified_base           4
                        mod_base = um
modified_base           8..9
                        mod_base = gm
modified_base           12
                        mod_base = gm
modified_base           20
                        mod_base = um
modified_base           15
                        mod_base = gm
modified_base           20
                        mod_base = um
source                  1..21
                        mol_type = other RNA
                        organism = synthetic construct
SEQUENCE: 141
tatttaagga gggtgatctt c                                              21

SEQ ID NO: 142          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-124
modified_base           3..4
                        mod_base = um
modified_base           8..9
                        mod_base = gm
modified_base           12
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 142
tatttaagga gggtgatctt c                                              21

SEQ ID NO: 143          moltype = RNA  length = 21
FEATURE                 Location/Qualifiers
misc_feature            1..21
```

```
                        note = synthetic polo-like kinase 1 (PLK-1),
                         serine/threonine protein kinase 13 (STPK13) small
                         interfering RNA (siRNA) antisense strand AS-125
modified_base           1
                        mod_base = um
modified_base           4
                        mod_base = um
modified_base           8..9
                        mod_base = gm
modified_base           13
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 143
tatttaagga gggtgatctt c                                              21

SEQ ID NO: 144          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-126
modified_base           1
                        mod_base = um
modified_base           4
                        mod_base = um
modified_base           8
                        mod_base = gm
modified_base           12
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 144
tatttaagga gggtgatctt c                                              21

SEQ ID NO: 145          moltype = RNA  length = 21
FEATURE                 Location/Qualifiers
misc_feature            1..21
                        note = synthetic polo-like kinase 1 (PLK-1),
                         serine/threonine protein kinase 13 (STPK13) small
                         interfering RNA (siRNA) antisense strand AS-127
modified_base           1
                        mod_base = um
modified_base           4
                        mod_base = um
modified_base           8..9
                        mod_base = gm
modified_base           12
                        mod_base = gm
modified_base           17
                        mod_base = um
modified_base           15
                        mod_base = gm
modified_base           20
                        mod_base = um
source                  1..21
                        mol_type = other RNA
                        organism = synthetic construct
SEQUENCE: 145
tatttaagga gggtgatctt c                                              21

SEQ ID NO: 146          moltype = RNA  length = 19
FEATURE                 Location/Qualifiers
misc_feature            1..19
                        note = synthetic polo-like kinase 1 (PLK-1),
```

```
                        serine/threonine protein kinase 13 (STPK13) small
                        interfering RNA (siRNA) antisense strand
source                  1..19
                        mol_type = other RNA
                        organism = synthetic construct
SEQUENCE: 146
tatttaagga gggtgatct                                                    19

SEQ ID NO: 147          moltype = RNA   length = 19
FEATURE                 Location/Qualifiers
misc_feature            1..19
                        note = synthetic polo-like kinase 1 (PLK-1),
                        serine/threonine protein kinase 13 (STPK13) small
                        interfering RNA (siRNA) sense strand
source                  1..19
                        mol_type = other RNA
                        organism = synthetic construct
SEQUENCE: 147
agatcaccct ccttaaata                                                    19

SEQ ID NO: 148          moltype = RNA   length = 21
FEATURE                 Location/Qualifiers
misc_feature            1..21
                        note = synthetic polo-like kinase 1 (PLK-1),
                        serine/threonine protein kinase 13 (STPK13) small
                        interfering RNA (siRNA) sense strand
source                  1..21
                        mol_type = other RNA
                        organism = synthetic construct
SEQUENCE: 148
agacctacct ccggatcaat t                                                 21

SEQ ID NO: 149          moltype = RNA   length = 21
FEATURE                 Location/Qualifiers
misc_feature            1..21
                        note = synthetic polo-like kinase 1 (PLK-1),
                        serine/threonine protein kinase 13 (STPK13) small
                        interfering RNA (siRNA) antisense strand
source                  1..21
                        mol_type = other RNA
                        organism = synthetic construct
SEQUENCE: 149
ttgatccgga ggtaggtctt t                                                 21
```

LIPID FORMULATIONS FOR DELIVERY OF THERAPEUTIC AGENTS

CROSS-REFERENCE TO RELATED APPLICATIONS

This application is a continuation of U.S. application Ser. No. 16/109,130, filed Aug. 22, 2018, which is a continuation of U.S. application Ser. No. 15/818,064, filed Nov. 20, 2017, which is a continuation of U.S. application Ser. No. 14/606,905, filed Jan. 27, 2015, now U.S. Pat. No. 9,878,042, issued on Jan. 30, 2018, which is a continuation of U.S. application Ser. No. 13/566,952, filed Aug. 3, 2012, which is a continuation of U.S. application Ser. No. 12/828,189, filed Jun. 30, 2010, now U.S. Pat. No. 8,283,333, issued on Oct. 9, 2012, which claims priority to U.S. Provisional Application No. 61/295,134, filed Jan. 14, 2010, and U.S. Provisional Application No. 61/222,469, filed Jul. 1, 2009, the disclosures of which are hereby incorporated by reference in their entirety for all purposes.

REFERENCE TO A SEQUENCE LISTING

A Sequence Listing conforming to the rules of WIPO Standard ST.26 is hereby incorporated by reference in its entirety. Said Sequence Listing has been filed as an electronic document via Patent Center in XML, format. The electronic document, created on Apr. 2, 2023, is entitled "104290-009660US-1340935_ST26.xml", and is 505,137 bytes in size.

BACKGROUND OF THE INVENTION

Cell proliferation and programmed cell death play important roles in the growth and development of an organism. In proliferative diseases such as cancer, the processes of cell proliferation and/or programmed cell death are often perturbed. For example, a cancer cell may have unregulated cell division through either the overexpression of a positive regulator of the cell cycle or the loss of a negative regulator of the cell cycle, perhaps by mutation. Alternatively, a cancer cell may have lost the ability to undergo programmed cell death through the overexpression of a negative regulator of apoptosis. Therefore, there is a need to develop new therapeutic agents that will restore the processes of checkpoint control and programmed cell death to cancerous cells.

RNA interference (RNAi) is an evolutionarily conserved process in which recognition of double-stranded RNA (dsRNA) ultimately leads to posttranscriptional suppression of gene expression. In particular, RNAi induces specific degradation of mRNA through complementary base pairing between the dsRNA and the target mRNA. In several model systems, this natural response has been developed into a powerful tool for the investigation of gene function (see, e.g., Elbashir et al., *Genes Dev.*, 15:188-200 (2001); Hammond et al., Nat. Rev. Genet., 2:110-119 (2001)).

RNAi is generally mediated by short dsRNAs such as small interfering RNA (siRNA) duplexes of 21-23 nucleotides in length or by longer Dicer-substrate dsRNAs of 25-30 nucleotides in length. Unlike siRNAs, Dicer-substrate dsRNAs are cleaved by Dicer endonuclease, a member of the RNase III family, to produce smaller functional 21-mer siRNA duplexes. The 21-mer siRNA (whether synthesized or processed by Dicer) recruits the RNA-induced silencing complex (RISC) and enables effective gene silencing via sequence-specific cleavage of the target sequence.

Although the precise mechanism is still unclear, RNAi provides a powerful approach to downregulate or silence the transcription and translation of a gene of interest. In particular, for the treatment of neoplastic disorders such as cancer, RNAi may be used to modulate (e.g., reduce) the expression of certain genes, e.g., an anti-apoptotic molecule, a growth factor, a growth factor receptor, a mitotic spindle protein, a cell cycle protein, an angiogenic factor, an oncogene, an intracellular signal transducer, a molecular chaperone, and combinations thereof.

However, a safe and effective nucleic acid delivery system is required for RNAi to be therapeutically useful. Viral vectors are relatively efficient gene delivery systems, but suffer from a variety of limitations, such as the potential for reversion to the wild-type as well as immune response concerns. Furthermore, viral systems are rapidly cleared from the circulation, limiting transfection to "first-pass" organs such as the lungs, liver, and spleen. In addition, these systems induce immune responses that compromise delivery with subsequent injections. As a result, nonviral gene delivery systems are receiving increasing attention (Worgall et al., *Human Gene Therapy*, 8:37 (1997); Peeters et al., *Human Gene Therapy*, 7:1693 (1996); Yei et al., *Gene Therapy*, 1:192 (1994); Hope et al., *Molecular Membrane Biology*, 15:1 (1998)).

Complexes of nucleic acid and cationic liposomes (i.e., lipoplexes) are a commonly employed nonviral gene delivery vehicle. For instance, lipoplexes made of an amphipathic compound, a neutral lipid, and a detergent for transfecting insect cells are disclosed in U.S. Pat. No. 6,458,382. Lipoplexes are also disclosed in U.S. Patent Publication No. 20030073640. However, lipoplexes are large, poorly defined systems that are not suited for systemic applications and can elicit considerable toxic side-effects (Harrison et al., *Biotechniques*, 19:816 (1995); Li et al., *The Gene*, 4:891 (1997); Tam et al, *Gene Ther.*, 7:1867 (2000)). As large, positively charged aggregates, lipoplexes are rapidly cleared when administered in vivo, with highest expression levels observed in first-pass organs, particularly the lungs (Huang et al., *Nature Biotechnology*, 15:620 (1997); Templeton et al., *Nature Biotechnology*, 15:647 (1997); Hofland et al., *Pharmaceutical Research*, 14:742 (1997)).

Other liposomal delivery systems include, for example, the use of reverse micelles, anionic liposomes, and polymer liposomes. Reverse micelles are disclosed in U.S. Pat. No. 6,429,200. Anionic liposomes are disclosed in U.S. Patent Publication No. 20030026831. Polymer liposomes that incorporate dextrin or glycerol-phosphocholine polymers are disclosed in U.S. Patent Publication Nos. 20020081736 and 20030082103, respectively. However, such liposomal delivery systems are unsuitable for delivering nucleic acids such as interfering RNA to tumors because they are not of the desired size (i.e., less than about 150 nm diameter), are not preferentially delivered to tumor sites, and do not remain intact in the circulation for an extended period of time in order to achieve delivery to tumor sites. Rather, effective intracellular delivery of nucleic acids such as interfering RNA to tumors requires a highly stable, serum-resistant nucleic acid-containing particle that preferentially targets tumors such as solid tumors and does not interact with cells and other components of the vascular compartment.

Thus, there remains a strong need in the art for novel compositions and methods for preferentially introducing nucleic acids such as interfering RNA into tumor cells. In addition, there is a need in the art for methods of downregulating the expression of genes associated with tumorigenesis or cell transformation to treat or prevent cancer. The present invention addresses these and other needs.

BRIEF SUMMARY OF THE INVENTION

The present invention provides novel, serum-stable lipid particles comprising one or more active agents or therapeutic agents, methods of making the lipid particles, and methods of delivering and/or administering the lipid particles (e.g., for the treatment of a disease or disorder). More particularly, the present invention provides serum-stable nucleic acid-lipid particles (SNALP) comprising a nucleic acid (e.g., one or more interfering RNA), methods of making the SNALP, and methods of delivering and/or administering the SNALP (e.g., for the treatment of cancer).

In certain preferred embodiments, the present invention provides tumor-directed lipid particles (e.g., tumor-directed SNALP) that preferentially target solid tumors. Advantageously, the tumor-directed SNALP formulations of the present invention are capable of preferentially delivering the nucleic acid payload to cells of solid tumors compared to non-cancerous cells. In addition, it has been unexpectedly found that the tumor-directed SNALP formulations of the present invention comprising at least one interfering RNA as described herein demonstrate increased potency (i.e., increased silencing activity) and/or increased tolerability (e.g., a more favorable toxicity profile) when targeting a gene of interest such as PLK-1 in a tumor cell when compared to other nucleic acid-lipid particle compositions previously described. In preferred embodiments, the present invention provides nucleic acid-lipid particles (e.g., SNALP) comprising one or more (e.g., a cocktail) of the PLK-1 siRNA molecules described herein and the cationic lipid DLinDMA and methods of use thereof, which nucleic acid-lipid particles (e.g., SNALP) unexpectedly possess increased potency and increased tolerability when silencing PLK-1 expression in cells of solid tumors in vivo compared to other nucleic acid-lipid particle compositions previously described.

In some aspects, the nucleic acid-lipid particle (e.g., SNALP) comprises: (a) one or more nucleic acids (e.g., interfering RNA); (b) one or more of cationic lipids comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In some embodiments, the nucleic acid-lipid particle comprises: (a) a nucleic acid (e.g., an interfering RNA); (b) a cationic lipid comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:54" formulation. In certain instances, the non-cationic lipid mixture in the 7:54 formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the 7:54 formulation is a four-component system which comprises about 7 mol % PEG-lipid conjugate (e.g., a PEG-lipid conjugate having an average molecular weight of from about 550 daltons to about 1000 daltons such as PEG750-C-DMA), about 54 mol % cationic lipid or a salt thereof (e.g., DLinDMA and/or any other cationic lipid as described herein), about 7 mol % DPPC (or DSPC), and about 32 mol % cholesterol (or derivative thereof). In preferred embodiments, the nucleic acid present in the 7:54 formulation is an interfering RNA such as an siRNA.

In other embodiments, the nucleic acid-lipid particle comprises: (a) a nucleic acid (e.g., an interfering RNA); (b) a cationic lipid comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:58" formulation. In one particular embodiment, the 7:58 formulation is a three-component system which is phospholipid-free and comprises about 7 mol % PEG-lipid conjugate (e.g., a PEG-lipid conjugate having an average molecular weight of from about 550 daltons to about 1000 daltons such as PEG750-C-DMA), about 58 mol % cationic lipid or a salt thereof (e.g., DLinDMA and/or any other cationic lipid as described herein), and about 35 mol % cholesterol (or derivative thereof). Preferably, the nucleic acid present in the 7:58 formulation is an interfering RNA such as an siRNA.

In certain preferred embodiments, the nucleic acid (e.g., interfering RNA) is fully encapsulated within the lipid portion of the nucleic acid-lipid particle such that the nucleic acid is resistant in aqueous solution to nuclease degradation. Non-limiting examples of interfering RNA include siRNA, aiRNA, miRNA, Dicer-substrate dsRNA, shRNA, and mixtures thereof. In certain other preferred embodiments, the nucleic acid-lipid particles are substantially non-toxic to mammals such as humans.

The present invention also provides pharmaceutical compositions comprising a nucleic acid-lipid particle described herein (e.g., SNALP) and a pharmaceutically acceptable carrier.

In another aspect, the present invention provides methods for introducing one or more nucleic acids (e.g., interfering RNA) into a cell, the method comprising contacting the cell with a nucleic acid-lipid particle described herein (e.g., SNALP). In one embodiment, the cell (e.g., a cancer cell such as a solid tumor cell) is in a mammal and the mammal is a human.

In yet another aspect, the present invention provides methods for the in vivo delivery of one or more nucleic acids (e.g., interfering RNA) to solid tumors, the method comprising administering to a mammal a nucleic acid-lipid particle described herein (e.g., SNALP). Advantageously, the nucleic acid-lipid particles of the invention preferentially deliver the nucleic acid to solid tumors as compared to other tissues. In some embodiments, the nucleic acid-lipid particles (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles (e.g., SNALP) are administered systemically, e.g., via enteral or parenteral routes of administration. In preferred embodiments, the mammal is a human.

In a further aspect, the present invention provides methods for treating a cell proliferative disorder such as cancer in a mammal in need thereof, the method comprising administering to the mammal a therapeutically effective amount of a nucleic acid-lipid particle (e.g., SNALP) comprising one or more nucleic acids (e.g., interfering RNA). In certain embodiments, the nucleic acid-lipid particle (e.g., SNALP) can be administered in combination with a chemotherapy drug. The nucleic acid-lipid particle can additionally or alternatively be co-administered with conventional hormonal, immunotherapeutic, and/or radiotherapeutic agents. In certain other embodiments, the nucleic acid-lipid particle (e.g., SNALP) can be administered in combination with a dose of a glucocorticoid such as, e.g., dexamethasone, wherein the glucocorticoid is administered prior to (i.e., pretreatment with the glucocorticoid), during, and/or after administering the nucleic acid-lipid particle. Non-limiting examples of suitable glucocorticoid dosing regimens are described in U.S. Patent Publication No. 20070054873, the disclosure of which is herein incorporated by reference in its entirety for all purposes.

In one particular aspect, the present invention provides methods for introducing an interfering RNA (e.g., an siRNA molecule) that silences the expression of a gene associated with tumorigenesis or cell transformation into a tumor cell of a mammal (e.g., a human), the method comprising administering to the mammal a nucleic acid-lipid particle described herein (e.g., SNALP), wherein the interfering RNA (e.g., siRNA molecule) is preferentially introduced into the tumor cell as compared to other cells (e.g., normal or non-tumor cells).

The nucleic acid-lipid particles of the invention (e.g., SNALP) are advantageous and suitable for use in the administration of nucleic acid such as interfering RNA to a subject (e.g., a mammal such as a human) because they are stable in circulation, of a size required for pharmacodynamic behavior resulting in access to extravascular sites, and are capable of reaching target cell populations (e.g., solid tumor cells).

Other objects, features, and advantages of the present invention will be apparent to one of skill in the art from the following detailed description and figures.

DETAILED DESCRIPTION OF THE INVENTION

I. Introduction

Figure 1:
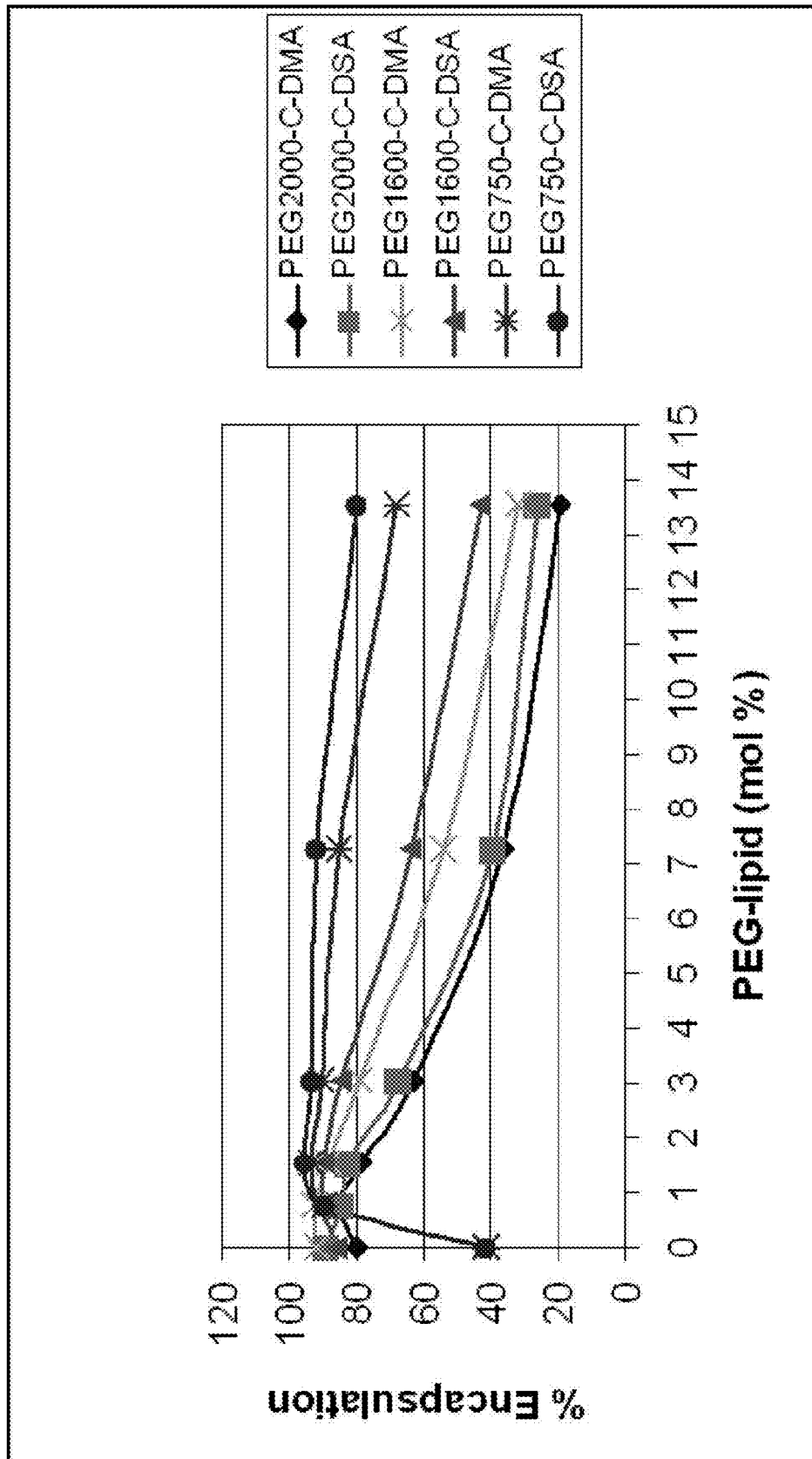
FIG. 1 shows that better encapsulation efficiencies were achieved when a higher mol % of a PEG750-lipid conjugate was used in SNALP formulations.

The present invention is based in part on the surprising discovery that lipid particles (e.g., SNALP) containing a higher mol % of PEG-lipid conjugates with shorter PEG chain lengths impart beneficial tumor-targeting properties to the particles while retaining high payload encapsulation efficiencies. Advantageously, it has been discovered that the tumor-directed lipid particles of the invention are more effectively shielded by the PEG-lipid conjugate following in vivo administration because the PEG-lipid conjugate is more evenly distributed over the particle surface when present at a higher concentration. As a result, the lipid particles of the invention are capable of targeting distal tumor sites and provide desirable tumor-targeting properties such as longer blood circulation times, enhanced tumor delivery, and decreased delivery to non-tumor tissues. In certain embodiments, the tumor-targeting properties of the lipid particles described herein are further enhanced by using PEG-lipid conjugates with longer alkyl chain lengths, which are more effectively incorporated into the particle and provide longer blood circulation times.

Using the 7:54 DLinDMA SNALP formulation as an exemplary tumor-directed lipid particle formulation, the Examples set forth herein demonstrate that lipid particles containing about 7 mol % of a PEG750-lipid conjugate advantageously provide better nucleic acid encapsulation efficiencies, longer blood circulation times, enhanced tumor delivery, and decreased delivery to non-tumor tissues when compared to lipid particles containing a lower mol % of a PEG-lipid conjugate with a longer PEG chain length. For instance, Example 2 illustrates that better encapsulation efficiencies were achieved when a higher mol % of a PEG750-lipid conjugate such as PEG750-C-DMA was used. Example 3 illustrates that extended blood circulation times were observed for the tumor-directed 7:54 DLinDMA SNALP formulation, thereby enabling the increased accumulation and activity of such particles at distal tumor sites. Example 4 illustrates that the tumor-directed 7:54 DLinDMA SNALP formulation displayed enhanced silencing activity in liver tumors compared to normal liver tissue. Example 5 illustrates that the tumor-directed 7:54 DLinDMA SNALP formulation displayed increased potency at distal tumor sites and thus can also be used to preferentially target solid tumors outside of the liver. Example 8 illustrates that the tumor-directed 7:54 DLinDMA SNALP formulation is a safe and non-immunogenic nucleic acid delivery system. Example 9 illustrates that tumor-directed 7:54 SNALP formulations which comprise an exemplary cationic lipid of Formula II-XVI as described herein displayed similar potencies as DLinDMA in silencing PLK-1 expression.

As such, the tumor-directed SNALP formulations of the invention are capable of safely, effectively, and preferentially delivering a nucleic acid payload to solid tumor cells compared to non-cancerous cells.

II. Definitions

As used herein, the following terms have the meanings ascribed to them unless specified otherwise.

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized. The disclosures of each of the above patent documents are herein incorporated by reference in their entirety for all purposes.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. As used herein, the term "siRNA" includes RNA-RNA duplexes as well as DNA-RNA hybrids (see, e.g., PCT Publication No. WO 2004/078941).

Preferably, siRNA are chemically synthesized. siRNA can also be generated by cleavage of longer dsRNA (e.g., dsRNA greater than about 25 nucleotides in length) with the E. coli RNase III or Dicer. These enzymes process the dsRNA into biologically active siRNA (see, e.g., Yang et al., Proc. Natl. Acad. Sci. USA, 99:9942-9947 (2002); Calegari et al., Proc. Natl. Acad. Sci. USA, 99:14236 (2002); Byrom et al., Ambion TechNotes, 10(1):4-6 (2003); Kawasaki et al., Nucleic Acids Res., 31:981-987 (2003); Knight et al., Science, 293:2269-2271 (2001); and Robertson et al., J. Biol. Chem., 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "inhibiting expression of a target gene" refers to the ability of an interfering RNA (e.g., siRNA) to silence, reduce, or inhibit the expression of a target gene (e.g., PLK-1). To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with an interfering RNA (e.g., siRNA) that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the interfering RNA (e.g., siRNA). The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the interfering RNAs (e.g., siRNAs) of the present invention are capable of silencing, reducing, or inhibiting the expression of a target gene (e.g., PLK-1) by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the interfering RNA. Suitable assays for determining the level of target gene expression include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

An "effective amount" or "therapeutically effective amount" of an active agent or therapeutic agent such as an interfering RNA is an amount sufficient to produce the desired effect, e.g., an inhibition of expression of a target sequence in comparison to the normal expression level detected in the absence of an interfering RNA. Inhibition of expression of a target gene or target sequence is achieved when the value obtained with an interfering RNA relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, IL-8, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-8, IL-10, IL-12, IL-13, TGF, and combinations thereof. Detectable immune responses also include, e.g., induction of interferon-induced protein with tetratricopeptide repeats 1 (IFIT1) mRNA.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology-Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology*, Ausubel et al., eds. (1995 supplement)).

Non-limiting examples of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/). Another example is a global alignment algorithm for determining percent sequence identity such as the Needleman-Wunsch algorithm for aligning protein or nucleotide (e.g., RNA) sequences.

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide (e.g., PLK-1).

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver an active agent or therapeutic agent, such as a nucleic acid (e.g., an interfering RNA), to a target site of interest (e.g., cell, tissue, organ, and the like). In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the active agent or therapeutic agent, such as a nucleic acid, may be encapsulated in the lipid portion of the particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., an interfering RNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides an active agent or therapeutic agent, such as a nucleic acid (e.g., an interfering RNA that targets PLK-1), with full encapsulation, partial encapsulation, or both. In a preferred embodiment, the nucleic acid is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. Provisional Application No. 61/294,828, filed Jan. 13, 2010, and U.S. Provisional Application No. 61/295,140, filed Jan. 14, 2010), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lyso-phosphatidylcholine, lysophosphatidylethanolamine, dipalmitoylphosphatidylcholine, dioleoylphosphatidylcholine, di stearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an interfering RNA (e.g., siRNA) within an organism. Some techniques of administration can lead to the systemic delivery of certain agents, but not others.

Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an interfering RNA (e.g., siRNA) directly to a target site within an organism. For example, an agent can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma. As used herein, a "tumor" comprises one or more cancerous cells.

The term "polo-like kinase 1," "PLK-1," "polo-like kinase," or "PLK" refers to a serine/threonine kinase containing two functional domains: (1) a kinase domain; and (2) a polo-box domain (see, e.g., Barr et al., *Nat. Rev. Mol. Cell Biol.,* 5:429-440 (2004)). The activity and cellular concentration of PLK-1 are crucial for the precise regulation of cell division. PLK-1 expression and activity are low throughout the G0, G1, and S phases of the cell cycle, but begin to rise in G2 and peak during M phase. PLK-1 is essential for mitosis and cell division and contributes to the following processes: centrosome maturation and the activation of maturation-promoting factors by Cdc25C and cyclinB1 phosphorylation; bipolar spindle formation; and DNA damage checkpoint adaptation (DNA damage inhibits PLK-1 in G2 and mitosis). PLK-1 is also involved in the activation of components of the anaphase promoting complex for mitotic exit and cytokinesis. PLK-1 is overexpressed in many cancer types including hepatoma and colon cancer, and PLK-1 expression often correlates with poor patient prognosis. Overexpression of PLK-1 (wild-type or kinase inactive) results in multinucleation (genetic instability). Hyperactive PLK-1 overrides the DNA damage checkpoint. Constitutive PLK-1 expression causes transformation of NIH 3T3 cells. PLK-1 phosphorylates the p53 tumor suppressor, thereby inhibiting the pro-apoptotic effects of p53. Human PLK-1 mRNA sequences are set forth in Genbank Accession Nos. NM_005030, X73458, BC014846, BC003002, HSU01038, and L19559. A mouse PLK-1 mRNA sequence is set forth in Genbank Accession No. NM_011121. PLK-1 is also known as serine/threonine protein kinase 13 (STPK13).

III. Description of the Embodiments

The present invention provides novel, serum-stable lipid particles comprising one or more active agents or therapeutic agents, methods of making the lipid particles, and methods of delivering and/or administering the lipid particles (e.g., for the treatment of a disease or disorder).

In certain embodiments, the active agent or therapeutic agent comprises a nucleic acid. In some instances, the nucleic acid comprises an interfering RNA molecule such as, e.g., an siRNA, Dicer-substrate dsRNA, shRNA, aiRNA, miRNA, or mixtures thereof. In other instances, the nucleic acid comprises single-stranded or double-stranded DNA, RNA, or a DNA/RNA hybrid such as, e.g., an antisense oligonucleotide, a ribozyme, a plasmid, an immunostimulatory oligonucleotide, or mixtures thereof.

In one aspect, the present invention provides lipid particles comprising: (a) one or more active agents or therapeutic agents; (b) one or more cationic lipids comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

More particularly, the present invention provides serum-stable nucleic acid-lipid particles (SNALP) comprising a nucleic acid (e.g., one or more interfering RNA), methods of making the SNALP, and methods of delivering and/or administering the SNALP (e.g., for the treatment of cancer). In certain preferred embodiments, the present invention provides tumor-directed lipid particles (e.g., tumor-directed SNALP) that preferentially target solid tumors. Advantageously, the tumor-directed SNALP formulations described herein are capable of preferentially delivering a nucleic acid payload such as an interfering RNA that silences the expression of a gene associated with tumorigenesis or cell transformation to cells of solid tumors compared to non-cancerous cells.

In some aspects, the nucleic acid-lipid particle (e.g., SNALP) comprises: (a) a nucleic acid (e.g., an interfering RNA); (b) a cationic lipid comprising from about 50 mol % to about 65 mol % of the total lipid present in the particle; (c) a non-cationic lipid comprising from about 25 mol % to about 45 mol % of the total lipid present in the particle; and (d) a conjugated lipid that inhibits aggregation of particles comprising from about 5 mol % to about 10 mol % of the total lipid present in the particle.

In certain embodiments, the nucleic acid-lipid particle comprises: (a) a nucleic acid (e.g., an interfering RNA); (b) a cationic lipid comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:54" formulation.

In certain other embodiments, the nucleic acid-lipid particle comprises: (a) a nucleic acid (e.g., an interfering RNA);

(b) a cationic lipid comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:58" formulation.

In particular embodiments, the interfering RNA (e.g., siRNA) targets a gene of interest in a tumor cell such as PLK-1. In some instances, the interfering RNA comprises a sense strand and a complementary antisense strand, and the interfering RNA comprises a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other instances, the interfering RNA is chemically synthesized. The interfering RNA molecules of the present invention are capable of silencing the expression of a target sequence such as PLK-1 in vitro and/or in vivo.

In certain embodiments, the interfering RNA (e.g., siRNA) of the present invention may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the interfering RNA molecule strikes a balance between reduction or abrogation of the immunostimulatory properties of the interfering RNA and retention of RNAi activity.

In particular embodiments, the interfering RNA (e.g., siRNA) molecules of the present invention comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target sequence or the complementary strand thereof.

In another embodiment, the present invention provides a composition comprising a cocktail (e.g., at least 2, 3, 4, 5, 6, 7, 8, 9, 10, 11, 12, 13, 14, 15, 16, 17, 18, 19, 20, or more) of unmodified and/or modified interfering RNA (e.g., siRNA) sequences that target one or more genes of interest in a tumor cell such as PLK-1. The cocktail of interfering RNA (e.g., siRNA) may comprise sequences which are directed to the same region or domain (e.g., a "hot spot") and/or to different regions or domains of one or more target genes. In particular embodiments, at least 1, 2, 3, 4, 5, 6, 7, 8, 9, 10, 11, 12, 13, 14, 15, 16, 17, 18, 19, 20, or more (e.g., all) of these sequences are chemically modified (e.g., 2'OMe-modified) as described herein.

In certain embodiments, the sense strand comprises or consists of a sequence that is at least about 80%, 85%, 86%, 87%, 88%, 89%, 90%, 91%, 92%, 93%, 94%, 95%, 96%, 97%, 98%, 99%, or 100% identical to the target sequence or a portion thereof. In certain other embodiments, the sense strand comprises or consists of at least about 15 contiguous nucleotides (e.g., at least about 15, 16, 17, 18, or 19 contiguous nucleotides) of a sequence that is identical to the target sequence or a portion thereof. In preferred embodiments, the interfering RNA (e.g., siRNA) comprising such a sense strand sequence is capable of mediating target-specific RNAi.

In some embodiments, the antisense strand comprises or consists of a sequence that is at least about 80%, 85%, 86%, 87%, 88%, 89%, 90%, 91%, 92%, 93%, 94%, 95%, 96%, 97%, 98%, 99%, or 100% complementary to the target sequence or a portion thereof. In other embodiments, the antisense strand comprises or consists of at least about 15 contiguous nucleotides (e.g., at least about 15, 16, 17, 18, or 19 contiguous nucleotides) of a sequence that is complementary to the target sequence or a portion thereof. In further embodiments, the antisense strand comprises or consists of a sequence that specifically hybridizes to the target sequence or a portion thereof. In preferred embodiments, the interfering RNA (e.g., siRNA) comprising such an antisense strand sequence is capable of mediating target-specific RNAi.

In one preferred embodiment, the PLK-1 siRNA comprises an antisense strand comprising the following sequence: 5'-UAUUUAAGGAGGGUGAUCU-3'. In another preferred embodiment, the PLK-1 siRNA further comprises a sense strand comprising the following sequence: 5'-AGAUCACCCUCCUUAAAUA-3'. In some embodiments, the PLK-1 siRNA comprises at least one 2'OMe nucleotide, e.g., at least one 2'OMe-guanosine and/or 2'OMe-uridine nucleotide. In certain instances, the PLK-1 siRNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the PLK-1 siRNA comprises a sense strand comprising at least one, at least two, at least three, at least four, at least five, at least six, at least seven, or more 2'OMe nucleotides, e.g., 2'OMe-guanosine and/or 2'OMe-uridine nucleotides.

In particular embodiments, from about 20%-40%, 25%-40%, 30%-40%, 20%-35%, 25%-35%, 20%-30%, 25%-30%, 26%-34%, 27%-33%, 28%-32%, or about 25%, 26%, 27%, 28%, 29%, 30%, 31%, 32%, 33%, 34%, 35%, 36%, 37%, 38%, 39%, or 40% of the nucleotides in the double-stranded region of the siRNA comprise modified nucleotides such as, e.g., 2'OMe nucleotides (e.g., 2'OMe-guanosine and/or 2'OMe-uridine nucleotides).

In some embodiments, the PLK-1 siRNA of the invention comprises a 3' overhang in one or both strands of the siRNA. In one particular embodiment, the antisense strand comprises a 5'-UC-3' overhang and the sense strand comprises a 5'-UU-3' overhang. In certain instances, the 3' overhangs on one or both strands of the siRNA comprise at least one 2'OMe nucleotide, e.g., at least one 2'OMe-guanosine and/or 2'OMe-uridine nucleotide. In other embodiments, the 3' overhangs on one or both strands of the siRNA molecule comprise 1-4 deoxythymidine (dT) nucleotides, 1-4 modified and/or unmodified uridine (U) ribonucleotides, or 1-2 additional ribonucleotides having complementarity to the target sequence or the complementary strand thereof.

In some embodiments, the PLK-1 siRNA comprises one of the following sense strand sequences set forth in Table 1, wherein the bolded and underlined nucleotides are 2'OMe nucleotides.

TABLE 1

| Name | Sense Strand Sequence |
| --- | --- |
| S-1 | 5'-AGAUCACCCUCCUUAAAUAUU-3' |
| S-2 | 5'-AGAUCACCCUCCUUAAAUAUU-3' |
| S-3 | 5'-AGAUCACCCUCCUUAAAUAUU-3' |
| S-4 | 5'-AGAUCACCCUCCUUAAAUAUU-3' |
| S-5 | 5'-AGAUCACCCUCCUUAAAUAUU-3' |
| S-6 | 5'-AGAUCACCCUCCUUAAAUAUU-3' |
| S-7 | 5'-AGAUCACCCUCCUUAAAUAUU-3' |
| S-8 | 5'-AGAUCACCCUCCUUAAAUAUU-3' |
| S-9 | 5'-AGAUCACCCUCCUUAAAUAUU-3' |
| S-10 | 5'-AGAUCACCCUCCUUAAAUAUU-3' |

In other embodiments, the PLK-1 siRNA comprises one of the following antisense strand sequences set forth in Table 2, wherein the bolded and underlined nucleotides are 2'OMe nucleotides.

TABLE 2

| Name | Antisense Strand Sequence |
| --- | --- |
| AS-A | 5'-UAUUUAAGGAGGGUGAUCUUU-3' |
| AS-B | 5'-UAUUUAAGGAGGGUGAUCUUU-3' |
| AS-C | 5'-UAUUUAAGGAGGGUGAUCUUU-3' |
| AS-D | 5'-UAUUUAAGGAGGGUGAUCUUC-3' |
| AS-E | 5'-UAUUUAAGGAGGGUGAUCUUC-3' |
| AS-F | 5'-UAUUUAAGGAGGGUGAUCUUC-3' |
| AS-G | 5'-UAUUUAAGGAGGGUGAUCUUU-3' |
| AS-H | 5'-UAUTUAAGGAGGGUGAUCUUU-3' |
| AS-1 | 5'-UAUUUAAGGAGGGUGAUCUUC-3' |
| AS-2 | 5'-UAUUUAAGGAGGGUGAUCUUC-3' |
| AS-3 | 5'-UAUUUAAGGAGGGUGAUCUUC-3' |
| AS-4 | 5'-UAUUUAAGGAGGGUGAUCUUC-3' |
| AS-5 | 5'-UAUUUAAGGAGGGUGAUCUUC-3' |
| AS-6 | 5'-UAUUUAAGGAGGGUGAUCUUC-3' |
| AS-7 | 5'-UAUUUAAGGAGGGUGAUCUUC-3' |
| AS-8 | 5'-UAUUUAAGGAGGGUGAUCUUC-3' |
| AS-9 | 5'-UAUUUAAGGAGGGUGAUCUUC-3' |
| AS-10 | 5'-UAUUUAAGGAGGGUGAUCUUC-3' |
| AS-11 | 5'-UAUUUAAGGAGGGUGAUCUUC-3' |
| AS-12 | 5'-UAUUUAAGGAGGGUGAUCUUC-3' |
| AS-13 | 5'-UAUUUAAGGAGGGUGAUCUUC-3' |
| AS-14 | 5'-UAUUUAAGGAGGGUGAUCUUC-3' |
| AS-15 | 5'-UAUUUAAGGAGGGUGAUCUUC-3' |
| AS-16 | 5'-UAUUUAAGGAGGGUGAUCUUC-3' |
| AS-17 | 5'-UAUUUAAGGAGGGUGAUCUUC-3' |
| AS-18 | 5'-UAUUUAAGGAGGGUGAUCUUC-3' |
| AS-19 | 5'-UAUUUAAGGAGGGUGAUCUUC-3' |
| AS-20 | 5'-UAUUUAAGGAGGGUGAUCUUC-3' |
| AS-21 | 5'-UAUUUAAGGAGGGUGAUCUUC-3' |
| AS-22 | 5'-UAUUUAAGGAGGGUGAUCUUC-3' |
| AS-23 | 5'-UAUUUAAGGAGGGUGAUCUUC-3' |
| AS-24 | 5'-UAUUUAAGGAGGGUGAUCUUC-3' |
| AS-25 | 5'-UAUUUAAGGAGGGUGAUCUUC-3' |
| AS-26 | 5'-UAUUUAAGGAGGGUGAUCUUC-3' |
| AS-27 | 5'-UAUUUAAGGAGGGUGAUCUUC-3' |
| AS-28 | 5'-UAUUUAAGGAGGGUGAUCUUC-3' |
| AS-29 | 5'-UAUUUAAGGAGGGUGAUCUUC-3' |
| AS-30 | 5'-UAUUUAAGGAGGGUGAUCUUC-3' |
| AS-31 | 5'-UAUUUAAGGAGGGUGAUCUUC-3' |
| AS-32 | 5'-UAUUUAAGGAGGGUGAUCUUC-3' |
| AS-33 | 5'-UAUUUAAGGAGGGUGAUCUUC-3' |
| AS-34 | 5'-UAUUUAAGGAGGGUGAUCUUC-3' |
| AS-35 | 5'-UAUUUAAGGAGGGUGAUCUUC-3' |
| AS-36 | 5'-UAUUUAAGGAGGGUGAUCUUC-3' |
| AS-37 | 5'-UAUUUAAGGAGGGUGAUCUUC-3' |
| AS-38 | 5'-UAUUUAAGGAGGGUGAUCUUC-3' |
| AS-39 | 5'-UAUUUAAGGAGGGUGAUCUUC-3' |
| AS-40 | 5'-UAUUUAAGGAGGGUGAUCUUC-3' |

TABLE 2-continued

| Name | Antisense Strand Sequence |
|---|---|
| AS-41 | 5'-UAUUUAA<u>GG</u>AG<u>GG</u>U<u>GA</u>UCU<u>U</u>C-3' |
| AS-42 | 5'-UAUUUAA<u>GG</u>AG<u>GG</u>U<u>GA</u>UCUUC-3' |
| AS-43 | 5'-<u>U</u>AUUUAA<u>GG</u>AG<u>GG</u>U<u>GA</u>UCUUC-3' |
| AS-44 | 5'-<u>U</u>A<u>U</u>UUAA<u>GG</u>AG<u>GG</u>U<u>GA</u>UC<u>UU</u>C-3' |
| AS-45 | 5'-UA<u>UU</u>UAA<u>GG</u>AG<u>GG</u>U<u>GA</u>U<u>C</u>UUC-3' |
| AS-46 | 5'-<u>U</u>A<u>U</u>UUAA<u>GG</u>AG<u>GG</u>U<u>GA</u>UCUUC-3' |
| AS-47 | 5'-<u>U</u>AUUUAA<u>GG</u>AG<u>GG</u>U<u>GA</u>UC<u>UU</u>C-3' |
| AS-48 | 5'-<u>U</u>A<u>U</u>UUA<u>GG</u>AG<u>GG</u>U<u>GA</u>UC<u>UU</u>C-3' |
| AS-49 | 5'-<u>U</u>AUUUAA<u>GG</u>AG<u>GG</u>U<u>GA</u>UCUUC-3' |
| AS-50 | 5'-UA<u>UU</u>UAA<u>GG</u>AG<u>GG</u>U<u>GA</u>UC<u>UU</u>C-3' |
| AS-51 | 5'-<u>U</u>A<u>U</u>UUAA<u>GG</u>AG<u>GG</u>U<u>GA</u>UCUUC-3' |
| AS-52 | 5'-UA<u>U</u>UUAA<u>GG</u>AG<u>GG</u>U<u>GA</u>UC<u>UU</u>C-3' |
| AS-53 | 5'-<u>U</u>AUUUAA<u>GG</u>AG<u>GG</u>U<u>GA</u>UCUUC-3' |
| AS-54 | 5'-UA<u>U</u>UUAA<u>GG</u>AG<u>GG</u>U<u>GA</u>UC<u>UU</u>C-3' |
| AS-55 | 5'-<u>U</u>AUUUAA<u>GG</u>AG<u>GG</u>U<u>GA</u>UCUUC-3' |
| AS-56 | 5'-UA<u>UU</u>UAA<u>GG</u>AG<u>GG</u>U<u>GA</u>UCUUC-3' |
| AS-57 | 5'-UA<u>U</u>UUAA<u>GG</u>AG<u>GG</u>U<u>GA</u>UC<u>UU</u>C-3' |
| AS-58 | 5'-UA<u>U</u>UUAA<u>GG</u>AG<u>GG</u>U<u>GA</u>UCUUC-3' |
| AS-59 | 5'-<u>U</u>A<u>U</u>UUAA<u>GG</u>AG<u>GG</u>U<u>GA</u>UCUUC-3' |
| AS-60 | 5'-<u>U</u>A<u>U</u>UUAA<u>GG</u>AG<u>GG</u>U<u>GA</u>UCUUC-3' |
| AS-61 | 5'-<u>U</u>AUUUAA<u>GG</u>AG<u>GG</u>U<u>GA</u>UCUUC-3' |
| AS-62 | 5'-UA<u>U</u>UUAA<u>GG</u>AG<u>GG</u>U<u>GA</u>UC<u>UU</u>C-3' |
| AS-63 | 5'-<u>U</u>AUUUAA<u>GG</u>AG<u>GG</u>U<u>GA</u>UCUUC-3' |
| AS-64 | 5'-UA<u>U</u>UUAA<u>GG</u>AG<u>GG</u>U<u>GA</u>UC<u>UU</u>C-3' |
| AS-65 | 5'-<u>U</u>A<u>U</u>UUAA<u>GG</u>AG<u>GG</u>U<u>GA</u>UCUUC-3' |
| AS-66 | 5'-<u>U</u>A<u>U</u>UUAA<u>GG</u>AG<u>GG</u>U<u>GA</u>UC<u>UU</u>C-3' |
| AS-67 | 5'-<u>U</u>AUUUAA<u>GG</u>AG<u>GG</u>U<u>GA</u>UCUUC-3' |
| AS-68 | 5'-UA<u>UU</u>AA<u>GG</u>AG<u>GG</u>U<u>GA</u>UC<u>UU</u>C-3' |
| AS-69 | 5'-<u>U</u>A<u>U</u>UUAA<u>GG</u>AG<u>GG</u>U<u>GA</u>UCUUC-3' |
| AS-70 | 5'-<u>U</u>A<u>U</u>UUAA<u>GG</u>AG<u>GG</u>U<u>GA</u>UC<u>UU</u>C-3' |
| AS-71 | 5'-<u>U</u>A<u>U</u>UUAA<u>GG</u>AG<u>GG</u>U<u>GA</u>UCUUC-3' |
| AS-72 | 5'-UA<u>U</u>UUAA<u>GG</u>AG<u>GG</u>U<u>GA</u>UC<u>UU</u>C-3' |
| AS-73 | 5'-<u>U</u>AUUUAA<u>GG</u>AG<u>GG</u>U<u>GA</u>UCUUC-3' |
| AS-74 | 5'-<u>U</u>A<u>U</u>UUAA<u>GG</u>AG<u>GG</u>U<u>GA</u>UCUUC-3' |
| AS-75 | 5'-UA<u>U</u>UUAA<u>GG</u>AG<u>GG</u>U<u>GA</u>UC<u>UU</u>C-3' |
| AS-76 | 5'-<u>U</u>A<u>U</u>UUAA<u>GG</u>AG<u>GG</u>U<u>GA</u>UCUUC-3' |
| AS-77 | 5'-<u>U</u>A<u>U</u>UUAA<u>GG</u>AG<u>GG</u>U<u>GA</u>UCUUC-3' |
| AS-78 | 5'-<u>U</u>A<u>U</u>UUAA<u>GG</u>AG<u>GG</u>U<u>GA</u>UCUUC-3' |
| AS-79 | 5'-<u>U</u>A<u>U</u>UUAA<u>GG</u>AG<u>GG</u>U<u>GA</u>UC<u>UU</u>C-3' |
| AS-80 | 5'-UAUUUAA<u>GG</u>AG<u>GG</u>U<u>GA</u>UCUUC-3' |
| AS-81 | 5'-UAUUUAA<u>GG</u>AG<u>GG</u>U<u>GA</u>UCUUC-3' |
| AS-82 | 5'-UAUUUAA<u>GG</u>AG<u>GG</u>U<u>GA</u>UCUUC-3' |
| AS-83 | 5'-<u>U</u>AUUUAA<u>GG</u>AG<u>GG</u>U<u>GA</u>UCUUC-3' |
| AS-84 | 5'-UA<u>U</u>UUAA<u>GG</u>AG<u>GG</u>U<u>GA</u>UC<u>UU</u>C-3' |
| AS-85 | 5'-UA<u>UU</u>UAA<u>GG</u>AG<u>GG</u>U<u>GA</u>UCUUC-3' |
| AS-86 | 5'-UAUUUAA<u>GG</u>AG<u>GG</u>U<u>GA</u>UCUUC-3' |
| AS-87 | 5'-<u>U</u>AUUUAA<u>GG</u>AG<u>GG</u>U<u>GA</u>UCUUC-3' |
| AS-88 | 5'-UA<u>U</u>UUAA<u>GG</u>AG<u>GG</u>U<u>GA</u>UCUUC-3' |
| AS-89 | 5'-UA<u>UU</u>UAA<u>GG</u>AG<u>GG</u>U<u>GA</u>UC<u>UU</u>C-3' |
| AS-90 | 5'-UAUUUAA<u>GG</u>AG<u>GG</u>U<u>GA</u>UCUUC-3' |
| AS-91 | 5'-<u>U</u>AUUUAA<u>GG</u>AG<u>GG</u>U<u>GA</u>UCUUC-3' |
| AS-92 | 5'-UA<u>U</u>UUAA<u>GG</u>AG<u>GG</u>U<u>GA</u>UCUUC-3' |
| AS-93 | 5'-UA<u>UU</u>UAA<u>GG</u>AG<u>GG</u>U<u>GA</u>UCUUC-3' |
| AS-94 | 5'-UAUUUAA<u>GG</u>AG<u>GG</u>U<u>GA</u>UCUUC-3' |
| AS-95 | 5'-<u>U</u>AUUUAA<u>GG</u>AG<u>GG</u>U<u>GA</u>UCUUC-3' |
| AS-96 | 5'-<u>U</u>A<u>U</u>UUAA<u>GG</u>AG<u>GG</u>U<u>GA</u>UCUUC-3' |
| AS-97 | 5'-<u>U</u>A<u>U</u>UUAA<u>GG</u>AG<u>GG</u>U<u>GA</u>UC<u>UU</u>C-3' |
| AS-98 | 5'-UA<u>UU</u>UAA<u>GG</u>AG<u>GG</u>U<u>GA</u>UCUUC-3' |
| AS-99 | 5'-<u>U</u>A<u>U</u>UUAA<u>GG</u>AG<u>GG</u>U<u>GA</u>UC<u>UU</u>C-3' |
| AS-100 | 5'-UA<u>UU</u>UAA<u>GG</u>AG<u>GG</u>U<u>GA</u>UCUUC-3' |
| AS-101 | 5'-<u>U</u>AUUUAA<u>GG</u>AG<u>GG</u>U<u>GA</u>UCUUC-3' |
| AS-102 | 5'-<u>U</u>AUUUAA<u>GG</u>AG<u>GG</u>U<u>GA</u>UCUUC-3' |
| AS-103 | 5'-UAUUUAA<u>GG</u>AG<u>GG</u>U<u>GA</u>UCUUC-3' |
| AS-104 | 5'-UA<u>U</u>UUAA<u>GG</u>AG<u>GG</u>U<u>GA</u>UCUUC-3' |
| AS-105 | 5'-UA<u>UU</u>UAA<u>GG</u>AG<u>GG</u>U<u>GA</u>UC<u>UU</u>C-3' |
| AS-106 | 5'-UAUUUAA<u>GG</u>AG<u>GG</u>U<u>GA</u>UCUUC-3' |
| AS-107 | 5'-<u>U</u>AUUUAA<u>GG</u>AG<u>GG</u>U<u>GA</u>UCUUC-3' |
| AS-108 | 5'-<u>U</u>A<u>U</u>UUAA<u>GG</u>AG<u>GG</u>U<u>GA</u>UCUUC-3' |
| AS-109 | 5'-<u>U</u>A<u>U</u>UUAA<u>GG</u>AG<u>GG</u>U<u>GA</u>UCUUC-3' |
| AS-110 | 5'-UA<u>UU</u>UAA<u>GG</u>AG<u>GG</u>U<u>GA</u>UCUUC-3' |
| AS-111 | 5'-UA<u>U</u>UUAA<u>GG</u>AG<u>GG</u>U<u>GA</u>UCUUC-3' |
| AS-112 | 5'-UA<u>UU</u>UAA<u>GG</u>AG<u>GG</u>U<u>GA</u>UC<u>UU</u>C-3' |
| AS-113 | 5'-<u>U</u>AUUUAA<u>GG</u>AG<u>GG</u>U<u>GA</u>UCUUC-3' |
| AS-114 | 5'-<u>U</u>AUUUAA<u>GG</u>AG<u>GG</u>U<u>GA</u>UC<u>UU</u>C-3' |
| AS-115 | 5'-UA<u>UU</u>UAA<u>GG</u>AG<u>GG</u>U<u>GA</u>UCUUC-3' |
| AS-116 | 5'-UA<u>UU</u>UAA<u>GG</u>AG<u>GG</u>U<u>GA</u>UC<u>UU</u>C-3' |
| AS-117 | 5'-<u>U</u>A<u>U</u>UUAA<u>GG</u>AG<u>GG</u>U<u>GA</u>UCUUC-3' |
| AS-118 | 5'-<u>U</u>A<u>U</u>UUAA<u>GG</u>AG<u>GG</u>U<u>GA</u>UC<u>UU</u>C-3' |

TABLE 2-continued

| Name | Antisense Strand Sequence |
|---|---|
| AS-119 | 5'-<u>UA</u>U<u>U</u>UAA<u>GG</u>AG<u>GG</u>U<u>G</u>A<u>U</u>C<u>UU</u>C-3' |
| AS-120 | 5'-UA<u>UU</u>UAA<u>GG</u>AG<u>GG</u>U<u>G</u>A<u>U</u>C<u>UU</u>C-3' |
| AS-121 | 5'-<u>UA</u>U<u>U</u>UAA<u>GG</u>AG<u>GG</u>U<u>G</u>A<u>U</u>C<u>UU</u>C-3' |
| AS-122 | 5'-<u>UA</u>U<u>U</u>UAA<u>GG</u>AG<u>GG</u>U<u>G</u>A<u>U</u>C<u>UU</u>C-3' |
| AS-123 | 5'-<u>UA</u>U<u>U</u>UAA<u>GG</u>AG<u>GG</u>U<u>G</u>A<u>U</u>C<u>UU</u>C-3' |
| AS-124 | 5'-UA<u>UU</u>UAA<u>GG</u>AG<u>GG</u>U<u>G</u>A<u>U</u>C<u>UU</u>C-3' |
| AS-125 | 5'-<u>UA</u>U<u>U</u>UAA<u>GG</u>AG<u>GG</u>U<u>G</u>A<u>U</u>C<u>UU</u>C-3' |
| AS-126 | 5'-<u>UA</u>U<u>U</u>UAA<u>GG</u>AG<u>GG</u>U<u>G</u>A<u>U</u>C<u>UU</u>C-3' |
| AS-127 | 5'-<u>UA</u>U<u>U</u>UAA<u>GG</u>AG<u>GG</u>U<u>G</u>A<u>U</u>C<u>UU</u>C-3' |

In one preferred embodiment, the PLK-1 siRNA comprises: an antisense strand comprising the sequence 5'-UAUUUAAGGAGGGUGAUCU-3' and at least one, two, three, four, five, six, or more 2'OMe nucleotides, e.g., at least one, two, three, four, five, six, or more 2'OMe-guanosine and/or 2'OMe-uridine nucleotides; and a sense strand comprising the sequence 5'-AGAUCACCCUCC-UUAAAUA-3' and at least one, two, three, four, five, six, or more 2'OMe nucleotides, e.g., at least one, two, three, four, five, six, or more 2'OMe-guanosine and/or 2'OMe-uridine nucleotides. In another preferred embodiment, the PLK-1 siRNA of the invention comprises: a sense strand comprising nucleotides 1-19 of any one of S-1 to S-10; and an antisense strand comprising nucleotides 1-19 of any one of AS-A to AS-H or AS-1 to AS-127. In a particularly preferred embodiment, the PLK-1 siRNA consists of: a sense strand selected from any one of S-1 to 5-10; and an antisense strand selected from any one of AS-A to AS-H or AS-1 to AS-127.

In one particular embodiment, the PLK-1 siRNA consists of the following sense and antisense strand sequences:

5'-AGA<u>U</u>CACCC<u>U</u>CC<u>UU</u>AAA<u>U</u>A<u>UU</u>-3'

3'-C<u>UU</u>C<u>U</u>A<u>G</u>U<u>GGG</u>A<u>GG</u>AA<u>UUU</u>AU-5', ("S-3+AS-F", "PLK1424 S3/ASF", or "PLK1424 2/6"), wherein the bolded and underlined nucleotides are 2'OMe nucleotides.

In another particular embodiment, the PLK-1 siRNA consists of the following sense and antisense strand sequences:

5'-AGA<u>U</u>CACCC<u>U</u>CC<u>UU</u>AAA<u>U</u>A<u>UU</u>-3'

3'-C<u>UU</u>C<u>U</u>A<u>G</u>U<u>GGG</u>A<u>GG</u>AA<u>UUU</u>AU-5', ("S-3+AS-1" or "PLK1424 S3/AS1"), wherein the bolded and underlined nucleotides are 2' OMe nucleotides.

In yet another particular embodiment, the PLK-1 siRNA consists of the following sense and antisense strand sequences:

5'-AGA<u>U</u>CACCC<u>U</u>CC<u>UU</u>AAA<u>U</u>A<u>UU</u>-3'

3'-C<u>UU</u>C<u>U</u>A<u>G</u>U<u>GGG</u>A<u>GG</u>AA<u>UUU</u>AU-5', ("S-3+AS-2" or "PLK1424 S3/AS2"), wherein the bolded and underlined nucleotides are 2' OMe nucleotides.

In still yet another particular embodiment, the PLK-1 siRNA consists of the following sense and antisense strand sequences:

5'-AGA<u>U</u>CACCC<u>U</u>CC<u>UU</u>AAA<u>U</u>A<u>UU</u>-3'

3'-C<u>UU</u>C<u>U</u>A<u>G</u>U<u>GGG</u>A<u>GG</u>AA<u>UUU</u>AU-5', ("S-3+AS-3" or "PLK1424 S3/AS3"), wherein the bolded and underlined nucleotides are 2' OMe nucleotides.

In another particular embodiment, the PLK-1 siRNA consists of the following sense and antisense strand sequences:

5'-AGA<u>U</u>CACCC<u>U</u>CC<u>UU</u>AAA<u>U</u>A<u>UU</u>-3'

3'-C<u>UU</u>C<u>U</u>A<u>G</u>U<u>GGG</u>A<u>GG</u>AA<u>UUU</u>AU-5', ("S-3+AS-4" or "PLK1424 S3/AS4"), wherein the bolded and underlined nucleotides are 2' OMe nucleotides.

In yet another particular embodiment, the PLK-1 siRNA consists of the following sense and antisense strand sequences:

5'-AGA<u>U</u>CACCC<u>U</u>CC<u>UU</u>AAA<u>U</u>A<u>UU</u>-3'

3'-C<u>UU</u>C<u>U</u>A<u>G</u>U<u>GGG</u>A<u>GG</u>AA<u>UUU</u>A<u>U</u>-5', ("S-3+AS-5" or "PLK1424 S3/AS5"), wherein the bolded and underlined nucleotides are 2' OMe nucleotides.

In still yet another particular embodiment, the PLK-1 siRNA consists of the following sense and antisense strand sequences:

5'-AGA<u>U</u>CACCC<u>U</u>CC<u>UU</u>AAA<u>U</u>A<u>UU</u>-3'

3'-C<u>UU</u>C<u>U</u>A<u>G</u>U<u>GGG</u>A<u>GG</u>AA<u>UUU</u>AU-5', ("S-3+AS-6" or "PLK1424 S3/AS6"), wherein the bolded and underlined nucleotides are 2' OMe nucleotides.

In another particular embodiment, the PLK-1 siRNA consists of the following sense and antisense strand sequences:

5'-AGA<u>U</u>CACCC<u>U</u>CC<u>UU</u>AAA<u>U</u>A<u>UU</u>-3'

3'-C<u>UU</u>C<u>U</u>A<u>G</u>U<u>GGG</u>A<u>GG</u>AA<u>UUU</u>AU-5', ("S-3+AS-7" or "PLK1424 S3/AS7"), wherein the bolded and underlined nucleotides are 2' OMe nucleotides.

In yet another particular embodiment, the PLK-1 siRNA consists of the following sense and antisense strand sequences:

5'-AGA<u>U</u>CACCC<u>U</u>CC<u>UU</u>AAA<u>U</u>A<u>UU</u>-3'

3'-C<u>UU</u>C<u>U</u>A<u>G</u>U<u>GGG</u>A<u>GG</u>AA<u>UUU</u>A<u>U</u>-5', ("S-3+AS-8" or "PLK1424 S3/AS8"), wherein the bolded and underlined nucleotides are 2' OMe nucleotides.

In still yet another particular embodiment, the PLK-1 siRNA consists of the following sense and antisense strand sequences:

5'-AGA<u>U</u>CACCC<u>U</u>CC<u>U</u>UAAA<u>U</u>A<u>UU</u>-3'

3'-C<u>UU</u>C<u>U</u>A<u>G</u>UGGGAG<u>G</u>AAUUUA<u>U</u>-5', ("S-3+AS-9" or "PLK1424 S3/AS9"), wherein the bolded and underlined nucleotides are 2' OMe nucleotides.

In another particular embodiment, the PLK-1 siRNA consists of the following sense and antisense strand sequences:

5'-AGA<u>U</u>CACCC<u>U</u>CC<u>U</u>UAAA<u>U</u>A<u>UU</u>-3'

3'-C<u>UU</u>C<u>U</u>A<u>G</u>UGGGAG<u>G</u>AAUU<u>UU</u>A<u>U</u>-5', ("S-3+AS-10" or "PLK1424 S3/AS10"), wherein the bolded and underlined nucleotides are 2' OMe nucleotides.

In yet another particular embodiment, the PLK-1 siRNA consists of the following sense and antisense strand sequences:

5'-AGA<u>U</u>CACCC<u>U</u>CC<u>U</u>UAAA<u>U</u>A<u>UU</u>-3'

3'-C<u>UU</u>C<u>U</u>A<u>G</u>UGGGAG<u>G</u>AA<u>U</u>U<u>U</u>A<u>U</u>-5', ("S-3+AS-11" or "PLK1424 S3/AS11"), wherein the bolded and underlined nucleotides are 2' OMe nucleotides.

In still yet another particular embodiment, the PLK-1 siRNA consists of the following sense and antisense strand sequences:

5'-AGA<u>U</u>CACCC<u>U</u>CC<u>U</u>UAAA<u>U</u>A<u>U</u>U-3'

3'-C<u>UU</u>C<u>U</u>A<u>G</u>UGGGAG<u>G</u>AAUUUA<u>U</u>-5', ("S-3+AS-12" or "PLK1424 S3/AS12"), wherein the bolded and underlined nucleotides are 2' OMe nucleotides.

In another particular embodiment, the PLK-1 siRNA consists of the following sense and antisense strand sequences:

5'-AGA<u>U</u>CACCC<u>U</u>CC<u>U</u>UAAA<u>U</u>A<u>U</u>U-3'

3'-C<u>UU</u>C<u>U</u>A<u>G</u>UGGGAG<u>G</u>AAU<u>UU</u>AU-5', ("S-3+AS-13" or "PLK1424 S3/AS13"), wherein the bolded and underlined nucleotides are 2' OMe nucleotides.

In yet another particular embodiment, the PLK-1 siRNA consists of the following sense and antisense strand sequences:

5'-AGA<u>U</u>CACCC<u>U</u>CC<u>U</u>UAAA<u>U</u>A<u>U</u>U-3'

3'-C<u>UU</u>C<u>U</u>A<u>G</u>UGGGAG<u>G</u>AAU<u>UU</u>A<u>U</u>-5', ("S-3+AS-14" or "PLK1424 S3/AS14"), wherein the bolded and underlined nucleotides are 2' OMe nucleotides.

In still yet another particular embodiment, the PLK-1 siRNA consists of the following sense and antisense strand sequences:

5'-AGA<u>U</u>CACCC<u>U</u>CC<u>U</u>UAAA<u>U</u>A<u>UU</u>-3'

3'-C<u>UU</u>C<u>U</u>A<u>G</u>UGGGAG<u>G</u>AAU<u>UU</u>AU-5', ("S-3+AS-15" or "PLK1424 S3/AS15"), wherein the bolded and underlined nucleotides are 2' OMe nucleotides.

In another particular embodiment, the PLK-1 siRNA consists of the following sense and antisense strand sequences:

5'-AGA<u>U</u>CACCC<u>U</u>CC<u>U</u>UAAA<u>U</u>A<u>UU</u>-3'

3'-C<u>UU</u>C<u>U</u>A<u>G</u>UGGGAG<u>G</u>AAUUUAU-5', ("S-4+AS-F" or "PLK1424 S4/ASF"), wherein the bolded and underlined nucleotides are 2' OMe nucleotides.

In yet another particular embodiment, the PLK-1 siRNA consists of the following sense and antisense strand sequences:

5'-AGA<u>U</u>CACCC<u>U</u>CC<u>U</u>UAAA<u>U</u>A<u>UU</u>-3'

3'-C<u>UU</u>C<u>U</u>A<u>G</u>U<u>G</u>GGAG<u>G</u>AAUUUAU-5', ("S-4+AS-1" or "PLK1424 S4/AS1"), wherein the bolded and underlined nucleotides are 2' OMe nucleotides.

In still yet another particular embodiment, the PLK-1 siRNA consists of the following sense and antisense strand sequences:

5'-AGA<u>U</u>CACCC<u>U</u>CC<u>U</u>UAAA<u>U</u>A<u>UU</u>-3'

3'-C<u>UU</u>C<u>U</u>A<u>G</u>UGGGAG<u>G</u>AAUUUAU-5', ("S-4+AS-2" or "PLK1424 S4/AS2"), wherein the bolded and underlined nucleotides are 2'OMe nucleotides.

In another particular embodiment, the PLK-1 siRNA consists of the following sense and antisense strand sequences:

5'-AGA<u>U</u>CACCC<u>U</u>CC<u>U</u>UAAA<u>U</u>A<u>UU</u>-3'

3'-C<u>UU</u>C<u>U</u>A<u>G</u>UGGGAG<u>G</u>AAU<u>UU</u>AU-5', ("S-4+AS-3" or "PLK1424 S4/AS3"), wherein the bolded and underlined nucleotides are 2' OMe nucleotides.

In yet another particular embodiment, the PLK-1 siRNA consists of the following sense and antisense strand sequences:

5'-AGA<u>U</u>CACCC<u>U</u>CC<u>U</u>UAAA<u>U</u>A<u>UU</u>-3'

3'-C<u>UU</u>C<u>U</u>A<u>G</u>UGGGAG<u>G</u>AAU<u>UU</u>AU-5', ("S-4+AS-4" or "PLK1424 S4/AS4"), wherein the bolded and underlined nucleotides are 2' OMe nucleotides.

In still yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-4+AS-5" or "PLK1424 S4/AS5"), wherein the bolded and underlined nucleotides are 2' OMe nucleotides.

In another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-4+AS-6" or "PLK1424 S4/AS6"), wherein the bolded and underlined nucleotides are 2' OMe nucleotides.

In yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-4+AS-7" or "PLK1424 S4/AS7"), wherein the bolded and underlined nucleotides are 2' OMe nucleotides.

In still yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-4+AS-8" or "PLK1424 S4/AS8"), wherein the bolded and underlined nucleotides are 2' OMe nucleotides.

In another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-4+AS-9" or "PLK1424 S4/AS9"), wherein the bolded and underlined nucleotides are 2' OMe nucleotides.

In yet another particular embodiment, the PLK-1 siRNA consists of the following sense and antisense strand sequences:

5'-AGAUCACCCUCCUUAAAUAUU-3'

3'-CUUCUAGUGGGAGGAAUUUUAU-5', ("S-4+AS-10" or "PLK1424 S4/AS10"), wherein the bolded and underlined nucleotides are 2' OMe nucleotides.

In still yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-4+AS-11" or "PLK1424 S4/AS11"), wherein the bolded and underlined nucleotides are 2' OMe nucleotides.

In another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-4+AS-12" or "PLK1424 S4/AS12"), wherein the bolded and underlined nucleotides are 2' OMe nucleotides.

In yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-4+AS-13" or "PLK1424 S4/AS13"), wherein the bolded and underlined nucleotides are 2' OMe nucleotides.

In still yet another particular embodiment, the PLK-1 siRNA consists of the following sense and antisense strand sequences:

5'-AGAUCACCCUCCUUAAAUAUU-3'

3'-CUUCUAGUGGGAGGAAUUUUAU-5', ("S-4+AS-14" or "PLK1424 S4/AS14"), wherein the bolded and underlined nucleotides are 2' OMe nucleotides.

In another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-4+AS-15" or "PLK1424 S4/AS15"), wherein the bolded and underlined nucleotides are 2' OMe nucleotides.

In yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-9+AS-F" or "PLK1424 S9/ASF"), wherein the bolded and underlined nucleotides are 2' OMe nucleotides.

In still yet another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-1" or "PLK1424 S9/AS1"), wherein the bolded and underlined nucleotides are 2' OMe nucleotides.

In another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-2" or "PLK1424 S9/AS2"), wherein the bolded and underlined nucleotides are 2' OMe nucleotides.

In yet another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-3" or "PLK1424 S9/AS3"), wherein the bolded and underlined nucleotides are 2' OMe nucleotides.

In still yet another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-4" or "PLK1424 S9/AS4"), wherein the bolded and underlined nucleotides are 2' OMe nucleotides.

In another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-5" or "PLK1424 S9/AS5"), wherein the bolded and underlined nucleotides are 2' OMe nucleotides.

In yet another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-6" or "PLK1424 S9/AS6"), wherein the bolded and underlined nucleotides are 2' OMe nucleotides.

In still yet another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-7" or "PLK1424 S9/AS7"), wherein the bolded and underlined nucleotides are 2' OMe nucleotides.

In another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-8" or "PLK1424 S9/AS8"), wherein the bolded and underlined nucleotides are 2' OMe nucleotides.

In yet another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-9" or "PLK1424 S9/AS9"), wherein the bolded and underlined nucleotides are 2' OMe nucleotides.

In still yet another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-10" or "PLK1424 S9/AS10"), wherein the bolded and underlined nucleotides are 2' OMe nucleotides.

In another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-11" or "PLK1424 S9/AS11"), wherein the bolded and underlined nucleotides are 2' OMe nucleotides.

In yet another particular embodiment, the PLK-1 siRNA consists of the following sense and antisense strand sequences:

```
5'-AGAUCACCCUCCUUAAAUAUU-3'
3'-CUUCUAGUGGGAGGAAUUUAU-5',
```

("S-9+AS-12" or "PLK1424 S9/AS12"), wherein the bolded and underlined nucleotides are 2'OMe nucleotides.

In still yet another particular embodiment, the PLK-1 siRNA consists of the following sense and antisense strand sequences:

5'-AG<u>A</u>U<u>C</u>ACCC<u>U</u>CC<u>UU</u>AAA<u>U</u>A<u>U</u>U-3'

3'-C<u>UU</u>C<u>U</u>A<u>G</u>UGGGAG<u>G</u>AAU<u>UU</u>AU-5', ("S-9+AS-13" or "PLK1424 S9/AS13"), wherein the bolded and underlined nucleotides are 2' OMe nucleotides.

In another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>UU</u>-3'

3'-C<u>UU</u>C<u>U</u>A<u>G</u>UGGGAG<u>G</u>AAU<u>UU</u>AU-5', ("S-9+AS-14" or "PLK1424 S9/AS14"), wherein the bolded and underlined nucleotides are 2' OMe nucleotides.

In yet another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>U</u>U-3'

3'-C<u>UU</u>C<u>U</u>A<u>G</u>UGGGA<u>G</u>AAU<u>UU</u>AU-5', ("S-9+AS-15" or "PLK1424 S9/AS15"), wherein the bolded and underlined nucleotides are 2' OMe nucleotides.

In still yet another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>UU</u>-3'

3'-C<u>UU</u>C<u>U</u>A<u>G</u>UGGGAGG<u>AA</u>U<u>UU</u>AU-5', ("S-10+AS-F" or "PLK1424 S10/ASF"), wherein the bolded and underlined nucleotides are 2' OMe nucleotides.

In another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>UU</u>-3'

3'-C<u>UU</u>C<u>U</u>A<u>G</u>U<u>G</u>GGAG<u>G</u>AAU<u>UU</u>AU-5', ("S-10+AS-1" or "PLK1424 S10/AS1"), wherein the bolded and underlined nucleotides are 2' OMe nucleotides.

In yet another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>UU</u>-3'

3'-C<u>UU</u>C<u>U</u>A<u>G</u>UGGGAG<u>G</u>AAU<u>UU</u>AU-5', ("S-10+AS-2" or "PLK1424 S10/AS2"), wherein the bolded and underlined nucleotides are 2' OMe nucleotides.

In still yet another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>U</u>U-3'

3'-C<u>U</u>UC<u>U</u>A<u>G</u>UGGGAG<u>G</u>AAU<u>UU</u>AU-5', ("S-10+AS-3" or "PLK1424 S10/AS3"), wherein the bolded and underlined nucleotides are 2' OMe nucleotides.

In another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>UU</u>-3'

3'-C<u>UU</u>C<u>U</u>A<u>G</u>UGGGAG<u>G</u>AAU<u>UU</u>AU-5', ("S-10+AS-4" or "PLK1424 S10/AS4"), wherein the bolded and underlined nucleotides are 2' OMe nucleotides.

In yet another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>UU</u>-3'

3'-C<u>UU</u>C<u>U</u>A<u>G</u>UGGGAG<u>G</u>AAU<u>UU</u>A<u>U</u>-5', ("S-10+AS-5" or "PLK1424 S10/AS5"), wherein the bolded and underlined nucleotides are 2' OMe nucleotides.

In still yet another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>UU</u>-3'

3'-C<u>UU</u>C<u>U</u>A<u>G</u>UGGGAGG<u>AA</u>U<u>UU</u>AU-5', ("S-10+AS-6" or "PLK1424 S10/AS6"), wherein the bolded and underlined nucleotides are 2'OMe nucleotides.

In another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>UU</u>-3'

3'-C<u>UU</u>C<u>U</u>A<u>G</u>U<u>G</u>GGAG<u>G</u>AAU<u>UU</u>AU-5', ("S-10+AS-7" or "PLK1424 S10/AS7"), wherein the bolded and underlined nucleotides are 2' OMe nucleotides.

In yet another particular embodiment, the PLK-1 siRNA consists of the following sense and antisense strand sequences:

5'-A<u>G</u>A<u>U</u>CACCC<u>U</u>CC<u>UU</u>AAA<u>U</u>A<u>UU</u>-3'

3'-C<u>UU</u>C<u>U</u>A<u>G</u>UGGGAG<u>G</u>AAU<u>UU</u>AU-5', ("S-10+AS-8" or "PLK1424 S10/AS8"), wherein the bolded and underlined nucleotides are 2'OMe nucleotides.

In still yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-10+AS-9" or "PLK1424 S10/AS9"), wherein the bolded and underlined nucleotides are 2' OMe nucleotides.

In another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-10+AS-10" or "PLK1424 S10/AS10"), wherein the bolded and underlined nucleotides are 2' OMe nucleotides.

In yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-10+AS-11" or "PLK1424 S10/AS11"), wherein the bolded and underlined nucleotides are 2' OMe nucleotides.

In still yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-10+AS-12" or "PLK1424 S10/AS12"), wherein the bolded and underlined nucleotides are 2' OMe nucleotides.

In another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-10+AS-13" or "PLK1424 S10/AS13"), wherein the bolded and underlined nucleotides are 2' OMe nucleotides.

In yet another particular embodiment, the PLK-1 siRNA consists of the following sense and antisense strand sequences:

5-AGAUCACCCUCCUUAAAUAUU-3'

3'-CUUCUAGUGGGAGGAAUUUAU-5', ("S-10+AS-14" or "PLK1424 S10/AS14"), wherein the bolded and underlined nucleotides are 2' OMe nucleotides.

In still yet another particular embodiment, the PLK-1 siRNA consists of the following sense and antisense strand sequences:

5'-AGAUCACCCUCCUUAAAUAUU-3'

3'-CUUCUAGUGGGAGGAAUUUAU-5', ("S-10+AS-15" or "PLK1424 S10/AS15"), wherein the bolded and underlined nucleotides are 2'OMe nucleotides.

In a further embodiment, the PLK-1 siRNA consists of the following sense and antisense strand sequences:

5'-AGACCUACCUCCGGAUCAAUU-3'

3'-UUUCUGGAUGGAGGCCUAGUU-5'.

It will be readily apparent to those of skill in the art that the foregoing PLK-1 siRNA can also be chemically modified, if desired, to reduce its immunostimulatory properties, while maintaining its silencing activities.

The nucleic acid-lipid particles (e.g., SNALP) typically comprise one or more (e.g., a cocktail) of the interfering RNAs described herein, a cationic lipid, and a non-cationic lipid. In certain instances, the nucleic acid-lipid particles (e.g., SNALP) further comprise a conjugated lipid that inhibits aggregation of particles. Preferably, the nucleic acid-lipid particles (e.g., SNALP) comprise one or more (e.g., a cocktail) of the interfering RNAs described herein, a cationic lipid, a non-cationic lipid, and a conjugated lipid that inhibits aggregation of particles. In particular embodiments, the nucleic acid-lipid particles (e.g., SNALP) of the present invention comprise 1, 2, 3, 4, 5, 6, 7, 8, or more unmodified and/or modified interfering RNAs that silence 1, 2, 3, 4, 5, 6, 7, 8, or more different genes associated with a cell proliferative disorder such as cancer, a cationic lipid, a non-cationic lipid, and a conjugated lipid that inhibits aggregation of particles.

In some embodiments, the interfering RNAs (e.g., siRNAs) are fully encapsulated in the nucleic acid-lipid particle (e.g., SNALP). With respect to formulations comprising an interfering RNA cocktail, the different types of interfering RNA species present in the cocktail (e.g., interfering RNA compounds with different sequences) may be co-encapsulated in the same particle, or each type of interfering RNA species present in the cocktail may be encapsulated in a separate particle. The interfering RNA cocktail may be formulated in the particles described herein using a mixture of two or more individual interfering RNAs (each having a unique sequence) at identical, similar, or different concentrations or molar ratios. In one embodiment, a cocktail of interfering RNAs (corresponding to a plurality of interfering RNAs with different sequences) is formulated using identical, similar, or different concentrations or molar ratios of each interfering RNA species, and the different types of interfering RNAs are co-encapsulated in the same particle. In another embodiment, each type of interfering RNA species present in the cocktail is encapsulated in different particles at identical, similar, or different interfering RNA concentrations or molar ratios, and the particles thus formed (each containing a different interfering RNA payload) are administered separately (e.g., at different times in accordance with a therapeutic regimen), or are combined and administered together as a single unit dose (e.g., with a pharmaceutically acceptable carrier). The lipid particles described herein are serum-stable, are resistant to nuclease degradation, and are substantially non-toxic to mammals such as humans.

The cationic lipid in the lipid particles of the invention (e.g., SNALP) may comprise, e.g., one or more cationic lipids of Formula I-XVI described herein or any other cationic lipid species. In one particular embodiment, the cationic lipid comprises 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)[1,3]-dioxolane (DLin-K-C2-DMA), 2,2-dilinoleyl-4-dimethylaminomethyl[1,3]-dioxolane (DLin-K-DMA), or a mixture thereof.

The non-cationic lipid in the lipid particles of the invention (e.g., SNALP) may comprise, e.g., one or more anionic lipids and/or neutral lipids. In some embodiments, the non-cationic lipid comprises one of the following neutral lipid components: (1) a mixture of a phospholipid and cholesterol or a derivative thereof; (2) cholesterol or a derivative thereof; or (3) a phospholipid. In certain preferred embodiments, the phospholipid comprises dipalmitoylphosphatidylcholine (DPPC), di stearoylphosphatidylcholine (DSPC), or a mixture thereof. In a particularly preferred embodiment, the non-cationic lipid is a mixture of DPPC and cholesterol.

In one particular embodiment, the non-cationic lipid component of the lipid particle formulation comprises a mixture of a phospholipid and cholesterol (or a derivative thereof). In certain instances, the mixture comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In another particular embodiment, the non-cationic lipid component is cholesterol, a derivative thereof, or a mixture thereof.

The lipid conjugate in the lipid particles of the invention (e.g., SNALP) inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof. In another embodiment, the lipid conjugate comprises a POZ-lipid conjugate such as a POZ-DAA conjugate. In particular embodiments, the lipid conjugate (e.g., PEG-lipid conjugate) comprises from about 6 mol % to about 8 mol % of the total lipid present in the particle.

The PEG moiety of the PEG-lipid conjugates described herein may comprise an average molecular weight ranging from about 550 daltons to about 10,000 daltons. In certain instances, the PEG moiety has an average molecular weight of from about 550 daltons to about 1000 daltons. In other instances, the PEG moiety has an average molecular weight of from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In one particular embodiment, the PEG moiety has an average molecular weight of about 750 daltons. In some embodiments, the terminal hydroxyl group of the PEG moiety is substituted with a methyl group. In a preferred embodiment, the PEG-lipid conjugate comprises PEG750-C-DMA, wherein the "750" denotes the average molecular weight of the PEG, wherein the "C" denotes a carbamate linker moiety, and wherein the "DMA" denotes dimyristyloxypropyl.

In one particular embodiment, the lipid particles of the invention (e.g., SNALP) comprise a four-component system, wherein:
the cationic lipid comprises from about 50 mol % to about 60 mol % (e.g., about 54 mol %) of the total lipid present in the particle,
the non-cationic lipid comprises a mixture of a phospholipid and cholesterol or a derivative thereof, wherein the phospholipid comprises from about 5 mol % to about 10 mol % (e.g., about 7 mol %) of the total lipid present in the particle and the cholesterol or derivative thereof comprises from about 25 mol % to about 35 mol % (e.g., about 32 mol %) of the total lipid present in the particle, and
the conjugated lipid that inhibits aggregation of particles (i.e., lipid conjugate) comprises from about 6 mol % to about 8 mol % (e.g., about 7 mol %) of the total lipid present in the particle.

In exemplary aspects of this embodiment, the cationic lipid is DLinDMA or DLin-K-C2-DMA ("C2K"), the non-cationic lipid comprises a mixture of a DPPC and cholesterol, and the lipid conjugate is a PEG-lipid conjugate such as a PEG750-DMA conjugate (e.g., PEG750-C-DMA).

In another particular embodiment, the lipid particles of the invention (e.g., SNALP) comprise a three-component system which is phospholipid-free, wherein:
the cationic lipid comprises from about 55 mol % to about 65 mol % (e.g., about 58 mol %) of the total lipid present in the particle,
the non-cationic lipid comprises cholesterol or a derivative thereof, wherein the cholesterol or derivative thereof comprises from about 30 mol % to about 40 mol % (e.g., about 35 mol %) of the total lipid present in the particle, and
the conjugated lipid that inhibits aggregation of particles (i.e., lipid conjugate) comprises from about 6 mol % to about 8 mol (e.g., about 7 mol %) of the total lipid present in the particle.

In exemplary aspects of this embodiment, the cationic lipid is DLinDMA or DLin-K-C2-DMA ("C2K"), the non-cationic lipid is cholesterol, and the lipid conjugate is a PEG-lipid conjugate such as a PEG750-DMA conjugate (e.g., PEG750-C-DMA).

In one preferred aspect, the present invention provides a nucleic acid-lipid particle (e.g., SNALP) comprising:
(a) an interfering RNA (e.g., dsRNA such as siRNA);
(b) a cationic lipid comprising about 54 mol % of the total lipid present in the particle;
(c) a phospholipid comprising about 7 mol % of the total lipid present in the particle;
(d) cholesterol or a derivative thereof comprising about 32 mol % of the total lipid present in the particle; and
(e) a PEG-lipid conjugate comprising about 7 mol % of the total lipid present in the particle.

In another preferred aspect, the present invention provides a nucleic acid-lipid particle (e.g., SNALP) comprising:
(a) an interfering RNA (e.g., dsRNA such as siRNA);
(b) a cationic lipid comprising about 58 mol % of the total lipid present in the particle;

(c) cholesterol or a derivative thereof comprising about 35 mol % of the total lipid present in the particle; and (d) a PEG-lipid conjugate comprising about 7 mol % of the total lipid present in the particle.

The present invention also provides pharmaceutical compositions comprising a lipid particle described herein (e.g., a nucleic acid-lipid particle) and a pharmaceutically acceptable carrier.

In another aspect, the present invention provides methods for introducing one or more active agents such as nucleic acids (e.g., interfering RNA) into a cell, the method comprising contacting the cell with a lipid particle described herein (e.g., a nucleic acid-lipid particle). In one particular embodiment, the cell is a tumor cell such as, e.g., a cell present in a solid tumor of a mammal (e.g., a human). In some instances, the solid tumor is a liver tumor. In other instances, the solid tumor is located outside of the liver. In certain embodiments, the cell is a non-tumor cell present in a mammal that produces one or more angiogenic and/or growth factors associated with cell proliferation, tumorigenesis, or cell transformation.

In yet another aspect, the present invention provides methods for the in vivo delivery of one or more active agents such as nucleic acids (e.g., interfering RNA) to solid tumors, the method comprising administering to a mammal (e.g., human) a lipid particle described herein (e.g., SNALP).

In a related aspect, the present invention provides methods for treating cancer in a mammal (e.g., human) in need thereof, the method comprising administering to the mammal a therapeutically effective amount of a lipid particle (e.g., SNALP) comprising one or more active agents such as nucleic acids (e.g., interfering RNA).

As described in the Examples below, lipid particles such as nucleic acid-lipid particles (e.g., SNALP) can preferentially deliver a payload such as an interfering RNA to solid tumors as compared to other tissues, e.g., for the treatment of cancer. In one particular embodiment, the solid tumor is a liver tumor. In another particular embodiment, the solid tumor is located outside of the liver.

In some embodiments, the lipid particles described herein (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles are administered systemically, e.g., via enteral or parenteral routes of administration.

In one particular aspect, the present invention provides methods for introducing an interfering RNA such as an siRNA that silences the expression of a gene associated with cell proliferation, tumorigenesis, or cell transformation into a tumor cell of a mammal, the method comprising administering to the mammal a nucleic acid-lipid particle described herein (e.g., SNALP), wherein the siRNA is preferentially introduced into the tumor cell as compared to other cells. In certain embodiments, the tumor cell is present in a solid tumor of a mammal such as a human. In some instances, the solid tumor is a liver tumor. In other instances, the solid tumor is located outside of the liver. In certain other embodiments, the siRNA can also be introduced (e.g., preferentially) into non-tumor cells present in a mammal that produce one or more angiogenic and/or growth factors associated with cell proliferation, tumorigenesis, or cell transformation.

In some embodiments, the present invention provides methods for treating a cell proliferative disorder such as cancer by administering a nucleic acid such as an interfering RNA (e.g., siRNA) in nucleic acid-lipid particles (e.g., SNALP), alone or in combination with a chemotherapy drug. The methods can be carried out in vitro using standard tissue culture techniques or in vivo by administering the interfering RNA (e.g., siRNA) using any means known in the art. In preferred embodiments, the interfering RNA (e.g., siRNA) is delivered to a cancer cell in a mammal such as a human, alone or in combination with a chemotherapy drug. The nucleic acid-lipid particles and/or chemotherapy drugs may also be co-administered with conventional hormonal, immunotherapeutic, and/or radiotherapeutic agents.

In particular embodiments, the interfering RNA molecule (e.g., siRNA) silences the expression of a gene associated with cell proliferation, tumorigenesis, or cell transformation. Non-limiting examples of suitable oncology target genes are provided herein. In an exemplary preferred embodiment, the siRNA silences polo-like kinase 1 (PLK-1) gene expression. Non-limiting examples of siRNA molecules targeting the PLK-1 gene include those described herein and in U.S. Patent Publication Nos. 20050107316 and 20070265438, and PCT Publication No. WO 09/082817, the disclosures of which are herein incorporated by reference in their entirety for all purposes. Additional embodiments related to treating a cell proliferative disorder using a lipid particle are described in, e.g., U.S. Patent Publication No. 20090149403, PCT Publication No. WO 09/129319, and U.S. Provisional Application No. 61/245,143, filed Sep. 23, 2009, the disclosures of which are herein incorporated by reference in their entirety for all purposes.

The nucleic acid-lipid particles of the invention (e.g., SNALP) are useful for the therapeutic delivery of interfering RNA (e.g., siRNA) molecules that silence the expression of one or more genes associated with cell proliferation, tumorigenesis, or cell transformation (e.g., PLK-1). In some embodiments, a cocktail of siRNAs that target one or more genes expressed in tumor cells is formulated into the same or different nucleic acid-lipid particles (e.g., SNALP), and the particles are administered to a mammal (e.g., a human) requiring such treatment. In certain instances, a therapeutically effective amount of the nucleic acid-lipid particles (e.g., SNALP) can be administered to the mammal, e.g., for treating, preventing, reducing the risk of developing, or delaying the onset of cancer, e.g., by preferentially targeting a solid tumor.

As described in the Examples below, it has surprisingly been found that the SNALP formulations of the present invention containing at least one cationic lipid of Formulas I-XVI (either alone or in combination with other cationic lipids) and at least one interfering RNA as described herein show increased potency (i.e., increased silencing activity) and/or increased tolerability (e.g., a more favorable toxicity profile) when targeting a gene of interest in a tumor cell, such as PLK-1, when compared to other SNALP formulations. Thus, in certain embodiments, the present invention provides methods for treating a disease or disorder associated with overexpression of PLK-1 in a mammal (e.g., human) in need thereof, the method comprising administering to the mammal a therapeutically effective amount of a lipid particle (e.g., SNALP) comprising one or more interfering RNA molecules that silence PLK-1 expression. Diseases and disorders associated with overexpression of PLK-1 are described herein and include, but are not limited to, cell proliferative disorders such as cancer.

In some embodiments, the interfering RNA (e.g., siRNA) molecules described herein are used in methods for silencing PLK-1 gene expression, e.g., in a cell such as a tumor cell. In particular, it is an object of the invention to provide methods for treating, preventing, reducing the risk of developing, or delaying the onset of a cell proliferative disorder in a mammal by downregulating or silencing the transcription and/or translation of the PLK-1 gene. In certain embodiments, the present invention provides a method for introducing one or more interfering RNA (e.g., siRNA) molecules described herein into a cell by contacting the cell with a nucleic acid-lipid particle described herein (e.g., a SNALP formulation). In one particular embodiment, the cell is a tumor cell such as, e.g., a cell present in solid tumor tissue of a mammal (e.g., a human). In another embodiment, the present invention provides a method for the in vivo delivery of one or more interfering RNA (e.g., siRNA) molecules described herein to a tumor cell by administering to a mammal (e.g., human) a nucleic acid-lipid particle described herein (e.g., a SNALP formulation).

In some embodiments, the nucleic acid-lipid particles described herein (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles are administered systemically, e.g., via enteral or parenteral routes of administration.

In certain aspects, the present invention provides methods for silencing PLK-1 gene expression in a mammal (e.g., human) in need thereof, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the PLK-1 gene). In some embodiments, administration of nucleic acid-lipid particles comprising one or more siRNAs described herein reduces mRNA levels of the target gene (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to mRNA levels of the target gene detected in the absence of the siRNA (e.g., buffer control or irrelevant siRNA control). In other embodiments, administration of nucleic acid-lipid particles comprising one or more siRNAs described herein reduces mRNA levels of the target gene (e.g., in a human or in an animal model such as a mouse model or monkey model) for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant siRNA control.

In certain other aspects, the present invention provides methods for treating, preventing, reducing the risk or likelihood of developing (e.g., reducing the susceptibility to), delaying the onset of, and/or ameliorating one or more symptoms associated with a cell proliferative disorder in a mammal (e.g., human) in need thereof, the method comprising administering to the mammal a therapeutically effective amount of a nucleic acid-lipid particle (e.g., a SNALP formulation) comprising one or more interfering RNA molecules (e.g., siRNAs) described herein (e.g., one or more siRNAs targeting the PLK-1 gene).

In a related aspect, the present invention provides a method for treating and/or ameliorating one or more symptoms associated with a cell proliferative disorder such as cancer in a mammal (e.g., human) in need thereof, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the PLK-1 gene). In some embodiments, administration of nucleic acid-lipid particles comprising one or more siRNA molecules described herein reduces tumor size and/or volume (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to the tumor size and/or volume detected in the absence of the siRNA (e.g., buffer control or irrelevant siRNA control).

In another related aspect, the present invention provides a method for reducing the risk or likelihood of developing (e.g., reducing the susceptibility to) a cell proliferative disorder such as cancer in a mammal (e.g., human) at risk of developing the cell proliferative disorder, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the PLK-1 gene). In some embodiments, administration of nucleic acid-lipid particles comprising one or more siRNA molecules described herein reduces the risk or likelihood of developing a cell proliferative disorder (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to the risk or likelihood of developing the cell proliferative disorder in the absence of the siRNA (e.g., buffer control or irrelevant siRNA control).

In yet another related aspect, the present invention provides a method for preventing or delaying the onset of a cell proliferative disorder such as cancer in a mammal (e.g., human) at risk of developing the cell proliferative disorder, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the PLK-1 gene).

IV. Lipid Particles

The lipid particles of the invention typically comprise an active agent or therapeutic agent, a cationic lipid, a non-cationic lipid, and a conjugated lipid that inhibits aggregation of particles. In some embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. The lipid particles of the invention also typically have a lipid:therapeutic agent (e.g., lipid:nucleic acid) ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1.

Lipid particles include, but are not limited to, lipid vesicles such as liposomes. As used herein, a lipid vesicle includes a structure having lipid-containing membranes enclosing an aqueous interior. In particular embodiments, lipid vesicles comprising one or more of the cationic lipids described herein are used to encapsulate nucleic acids within the lipid vesicles. In other embodiments, lipid vesicles comprising one or more of the cationic lipids described herein are complexed with nucleic acids to form lipoplexes.

In preferred embodiments, the lipid particles of the invention are serum-stable nucleic acid-lipid particles (SNALP) which comprise an interfering RNA (e.g., dsRNA such as siRNA, Dicer-substrate dsRNA, shRNA, aiRNA, and/or miRNA), a cationic lipid (e.g., one or more cationic lipids of Formula I-XVI or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The SNALP may comprise at least 1, 2, 3, 4, 5, 6, 7, 8, 9, 10, or more unmodified and/or modified interfering RNA (e.g., siRNA) that target one or more of the genes described herein. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the nucleic acid may be fully encapsulated within the lipid portion of the particle, thereby protecting the nucleic acid from nuclease degradation. In preferred embodiments, a SNALP comprising a nucleic acid such as an interfering RNA is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, CA) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., *Gene Ther.*, 6:271-281 (1999)).

In other embodiments, the present invention provides a nucleic acid-lipid particle (e.g., SNALP) composition comprising a plurality of nucleic acid-lipid particles.

In some instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles of the invention, the proportions of the components can be varied and the delivery efficiency of a particular formulation can be measured using, e.g., an endosomal release parameter (ERP) assay.

In particular embodiments, the present invention provides a lipid particle (e.g., SNALP) composition comprising a plurality of lipid particles described herein and an antioxidant. In certain instances, the antioxidant in the lipid particle composition reduces, prevents, and/or inhibits the degradation of a cationic lipid present in the lipid particle. In instances wherein the active agent is a therapeutic nucleic acid such as an interfering RNA (e.g., siRNA), the antioxidant in the lipid particle composition reduces, prevents, and/or inhibits the degradation of the nucleic acid payload, e.g., by reducing, preventing, and/or inhibiting the formation of adducts between the nucleic acid and the cationic lipid. Non-limiting examples of antioxidants include hydrophilic antioxidants such as chelating agents (e.g., metal chelators such as ethylenediaminetetraacetic acid (EDTA), citrate, and the like), lipophilic antioxidants (e.g., vitamin E isomers, polyphenols, and the like), salts thereof; and mixtures thereof. If needed, the antioxidant is typically present in an amount sufficient to prevent, inhibit, and/or reduce the degradation of the cationic lipid and/or active agent present in the particle, e.g., at least about 20 mM EDTA or a salt thereof, or at least about 100 mM citrate or a salt thereof. An antioxidant such as EDTA and/or citrate may be included at any step or at multiple steps in the lipid particle formation process described in Section V (e.g., prior to, during, and/or after lipid particle formation).

Additional embodiments related to methods of preventing the degradation of cationic lipids and/or active agents (e.g., therapeutic nucleic acids) present in lipid particles, compositions comprising lipid particles stabilized by these methods, methods of making these lipid particles, and methods of delivering and/or administering these lipid particles are described in U.S. Provisional Application No. 61/265,671, entitled "SNALP Formulations Containing Antioxidants," filed Dec. 1, 2009, the disclosure of which is herein incorporated by reference in its entirety for all purposes.

A. Active Agents

Active agents (e.g., therapeutic agents) include any molecule or compound capable of exerting a desired effect on a cell, tissue, organ, or subject. Such effects may be, e.g., biological, physiological, and/or cosmetic. Active agents may be any type of molecule or compound including, but not limited to, nucleic acids, peptides, polypeptides, small molecules, and mixtures thereof. Non-limiting examples of nucleic acids include interfering RNA molecules (e.g., dsRNA such as siRNA, Dicer-substrate dsRNA, shRNA, aiRNA, and/or miRNA), antisense oligonucleotides, plasmids, ribozymes, immunostimulatory oligonucleotides, and mixtures thereof. Examples of peptides or polypeptides include, without limitation, antibodies (e.g., polyclonal antibodies, monoclonal antibodies, antibody fragments; humanized antibodies, recombinant antibodies, recombinant human antibodies, and/or Primatized™ antibodies), cytokines, growth factors, apoptotic factors, differentiation-inducing factors, cell-surface receptors and their ligands, hormones, and mixtures thereof. Examples of small molecules include, but are not limited to, small organic molecules or compounds such as any conventional agent or drug known to those of skill in the art.

In some embodiments, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative is a prodrug that lacks therapeutic activity, but becomes active upon further modification.

1. Nucleic Acids

In certain embodiments, lipid particles of the present invention are associated with a nucleic acid, resulting in a nucleic acid-lipid particle (e.g., SNALP). In some embodiments, the nucleic acid is fully encapsulated in the lipid particle. As used herein, the term "nucleic acid" includes any oligonucleotide or polynucleotide, with fragments containing up to 60 nucleotides generally termed oligonucleotides, and longer fragments termed polynucleotides. In particular embodiments, oligonucletoides of the invention are from about 15 to about 60 nucleotides in length. Nucleic acid may be administered alone in the lipid particles of the invention, or in combination (e.g., co-administered) with lipid particles of the invention comprising peptides, polypeptides, or small molecules such as conventional drugs. Similarly, when used to treat a cell proliferative disorder such as cancer, the nucleic acid, such as the interfering RNA molecule (e.g., siRNA), can be administered alone or co-administered (i.e., concurrently or consecutively) with conventional agents used to treat, e.g., a cell proliferative disorder such as cancer. Such agents include chemotherapy drugs as well as conventional hormonal, immunotherapeutic, and/or radiotherapeutic agents.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a nucleic acid-lipid particle according to this invention includes any form of nucleic acid that is known. The nucleic acids used herein can be single-stranded DNA or RNA, or double-stranded DNA or RNA, or DNA-RNA hybrids. In preferred embodiments, the nucleic acids are double-stranded RNA. Examples of double-stranded RNA are described herein and include, e.g., siRNA and other RNAi agents such as Dicer-substrate dsRNA, shRNA, aiRNA, and pre-miRNA. In other preferred embodiments, the nucleic acids are single-stranded nucleic acids. Single-stranded nucleic acids include, e.g., antisense oligonucleotides, ribozymes, mature miRNA, and triplex-forming oligonucleotides. In further embodiments, the nucleic acids are double-stranded DNA. Examples of double-stranded DNA include, e.g., DNA-DNA hybrids comprising a DNA sense strand and a DNA antisense strand as described in PCT Publication No. WO 2004/104199, the disclosure of which is herein incorporated by reference in its entirety for all purposes.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

a) siRNA

The siRNA component of the nucleic acid-lipid particles of the present invention is capable of silencing the expression of a target gene of interest, such as PLK-1. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the siRNA. In some preferred embodiments, one or more of the uridine and/or guanosine nucleotides are modified (e.g., 2'OMe-modified) in one strand (i.e., sense or antisense) or both strands of the siRNA. In these embodiments, the modified siRNA can further comprise one or more modified (e.g., 2'OMe-modified) adenosine and/or modified (e.g., 2'OMe-modified) cytosine nucleotides. In other preferred embodiments, only uridine and/or guanosine nucleotides are modified (e.g., 2'OMe-modified) in one strand (i.e., sense or antisense) or both strands of the siRNA. The siRNA sequences may have overhangs (e.g., 3' or 5' overhangs as described in Elbashir et al., *Genes Dev.,* 15:188 (2001) or Nykanen et al., *Cell,* 107:309 (2001)), or may lack overhangs (i.e., have blunt ends).

In particular embodiments, the selective incorporation of modified nucleotides such as 2'OMe uridine and/or guanosine nucleotides into the double-stranded region of either or both strands of the siRNA reduces or completely abrogates the immune response to that siRNA molecule. In certain instances, the immunostimulatory properties of specific siRNA sequences and their ability to silence gene expression can be balanced or optimized by the introduction of minimal and selective 2'OMe modifications within the double-stranded region of the siRNA duplex. This can be achieved at therapeutically viable siRNA doses without cytokine induction, toxicity, and off-target effects associated with the use of unmodified siRNA.

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides. In certain other embodiments, some or all of the modified nucleotides in the double-stranded region of the siRNA are 1, 2, 3, 4, 5, 6, 7, 8, 9, 10, or more nucleotides apart from each other. In one preferred embodiment, none of the modified nucleotides in the double-stranded region of the siRNA are adjacent to each other (e.g., there is a gap of at least 1, 2, 3, 4, 5, 6, 7, 8, 9, or 10 unmodified nucleotides between each modified nucleotide). In another preferred embodiment, at least two of the modified nucleotides in the double-stranded region of the siRNA are adjacent to each other (e.g., there are no unmodified nucleotides between two or more modified nucleotides). In other preferred embodiments, at least three, at least four, or at least five of the modified nucleotides in the double-stranded region of the siRNA are adjacent to each other.

In some embodiments, less than about 50% (e.g., less than about 49%, 48%, 47%, 46%, 45%, 44%, 43%, 42%, 41%, 40%, 39%, 38%, 37%, or 36%, preferably less than about 35%, 34%, 33%, 32%, 31%, or 30%) of the nucleotides in the double-stranded region of the siRNA comprise modified (e.g., 2'OMe) nucleotides. In one aspect of these embodiments, less than about 50% of the uridine and/or guanosine nucleotides in the double-stranded region of one or both strands of the siRNA are selectively (e.g., only) modified. In another aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In other embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 25%-39%, 25%-38%, 25%-37%, 25%-36%, 26%-39%, 26%-38%, 26%-37%, 26%-36%, 27%-39%, 27%-38%, 27%-37%, 27%-36%, 28%-39%, 28%-38%, 28%-37%, 28%-36%, 29%-39%, 29%-38%, 29%-37%, 29%-36%, 30%-40%, 30%-39%, 30%-38%, 30%-37%, 30%-36%, 31%-39%, 31%-38%, 31%-37%, 31%-36%, 32%-39%, 32%-38%, 32%-37%, 32%-36%, 33%-39%, 33%-38%, 33%-37%, 33%-36%, 34%-39%, 34%-38%, 34%-37%, 34%-36%, 35%-40%, 5%-35%, 10%-35%, 15%-35%, 20%-35%, 21%-35%, 22%-35%, 23%-35%, 24%-35%, 25%-35%, 26%-35%, 27%-35%, 28%-35%, 29%-35%, 30%-35%, 31%-35%, 32%-35%, 33%-35%, 34%-35%, 30%-34%, 31%-34%, 32%-34%, 33%-34%, 30%-33%, 31%-33%, 32%-33%, 30%-32%, 31%-32%, 25%-34%, 25%-33%, 25%-32%, 25%-31%, 26%-34%, 26%-33%, 26%-32%, 26%-31%, 27%-34%, 27%-33%, 27%-32%, 27%-31%, 28%-34%, 28%-33%, 28%-32%, 28%-31%, 29%-34%, 29%-33%, 29%-32%, 29%-31%, 5%-30%, 10%-30%, 15%-30%, 20%-34%, 20%-33%, 20%-32%, 20%-31%, 20%-30%, 21%-30%, 22%-30%, 23%-30%, 24%-30%, 25%-30%, 25%-29%, 25%-28%, 25%-27%, 25%-26%, 26%-30%, 26%-29%, 26%-28%, 26%-27%, 27%-30%, 27%-29%, 27%-28%, 28%-30%, 28%-29%, 29%-30%, 5%-25%, 10%-25%, 15%-25%, 20%-29%, 20%-28%, 20%-27%, 20%-26%, 20%-25%, 5%-20%, 10%-20%, 15%-20%, 5%-15%, 10%-15%, or 5%-10%) of the nucleotides in the double-stranded region of the siRNA comprise modified nucleotides. In one aspect of these embodiments, from about 1% to about 50% of the uridine and/or guanosine nucleotides in the double-stranded region of one or both strands of the siRNA are selectively (e.g., only) modified. In another aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In certain embodiments, the siRNA component of the nucleic acid-lipid particles of the present invention (e.g., SNALP) comprises an asymmetric siRNA duplex as described in PCT Publication No. WO 2004/078941, which comprises a double-stranded region consisting of a DNA sense strand and an RNA antisense strand (e.g., a DNA-RNA hybrid), wherein a blocking agent is located on the siRNA duplex. In some instances, the asymmetric siRNA duplex can be chemically modified as described herein. Other non-limiting examples of asymmetric siRNA duplexes are described in PCT Publication No. WO 2006/074108, which discloses self-protected oligonucleotides comprising a region having a sequence complementary to one, two, three, or more same or different target mRNA sequences (e.g., multivalent siRNAs) and one or more self-complementary regions. Yet other non-limiting examples of asymmetric siRNA duplexes are described in PCT Publication No. WO 2009/076321, which discloses self-forming asymmetric precursor polynucleotides comprising a targeting region comprising a polynucleotide sequence complementary to a region of one, two, three, or more same or different target mRNA sequences (e.g., multivalent siRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions. The disclosures of each of the above patent documents are herein incorporated by reference in their entirety for all purposes.

Additional ranges, percentages, and patterns of modifications that may be introduced into siRNA are described in U.S. Patent Publication No. 20070135372, the disclosure of which is herein incorporated by reference in its entirety for all purposes.

(1) Selection of siRNA Sequences

Suitable siRNA sequences can be identified using any means known in the art. Typically, the methods described in Elbashir et al., *Nature,* 411:494-498 (2001) and Elbashir et al., *EMBO J.* 20:6877-6888 (2001) are combined with rational design rules set forth in Reynolds et al., *Nature Biotech.,* 22(3):326-330 (2004).

As a non-limiting example, the nucleotide sequence 3' of the AUG start codon of a transcript from the target gene of interest may be scanned for dinucleotide sequences (e.g., AA, NA, CC, GG, or UU, wherein N=C, G, or U) (see, e.g., Elbashir et al., *EMBO* 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://ihome.ust.hk/~bokcmho/siRNA/siRNA.html. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., Cell, 115:209-216 (2003); and Schwarz et al., Cell, 115:199-208 (2003). In other embodiments, potential siRNA sequences may be further analyzed based on secondary structure at the target site as described in, e.g., Luo et al., Biophys. Res. Commun., 318:303-310 (2004). For example, secondary structure at the target site can be modeled using the Mfold algorithm (available at http://mfold.burnet.edu.au/rna_form) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3', 5'-UGU-3', 5'-GUGU-3', 5'-UGUGU- 3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-8, IL-12, or a combination thereof. An siRNA identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., Radioimmunoassay Methods, E. and S. Livingstone, Edinburgh (1970)); the "Western blot" method of Gordon et al. (U.S. Pat. No. 4,452,901); immunoprecipitation of labeled ligand (Brown et al., J. Biol. Chem., 255:4980-4983 (1980)); enzyme-linked immunosorbent assays (ELISA) as described, for example, by Raines et al., J. Biol. Chem., 257:5154-5160 (1982); immunocytochemical techniques, including the use of fluorochromes (Brooks et al., Clin. Exp. Immunol., 39:477 (1980)); and neutralization of activity (Bowen-Pope et al., Proc. Natl. Acad. Sci. USA, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., Mol. Ther., 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, NJ); human IL-6 and TNF-α (eBioscience; San Diego, CA); and mouse IL-6, TNF-α, and IFN-γ (BD Biosciences; San Diego, CA)).

Monoclonal antibodies that specifically bind cytokines and growth factors are commercially available from multiple sources and can be generated using methods known in the art (see, e.g., Kohler et al., *Nature,* 256: 495-497 (1975) and Harlow and Lane, ANTIBODIES, A LABORATORy MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

(2) Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); *and Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol. Alternatively, syntheses at the 0.2 μmol scale can be performed on a 96-well plate synthesizer from Protogene (Palo Alto, CA). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

(3) Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.*, 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-((3-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties, in Modern Synthetic Methods*, VCH, 331-417 (1995); Mesmaeker et al., *Novel Backbone Replacements for Oligonucleotides, in Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides, modified (e.g., 2'OMe) and/or unmodified uridine ribonucleotides, and/or any other combination of modified (e.g., 2'OMe) and unmodified nucleotides.

Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

(4) Target Genes

The siRNA component of the nucleic acid-lipid particles of the present invention (e.g., SNALP) can be used to downregulate or silence the translation (i.e., expression) of a gene of interest. As previously mentioned, it has been unexpectedly found that the nucleic acid-lipid particles of the present invention (i.e., SNALP formulations) containing at least one siRNA as disclosed herein show increased potency (i.e., increased silencing) and/or increased tolerability (e.g., decreased toxicity) when targeting a gene of interest in a tumor cell, when compared to other nucleic acid-lipid particle compositions previously described. In preferred embodiments, the siRNA silences the expression of a gene associated with cell proliferation, tumorigenesis, and/or cell transformation (e.g., a cell proliferative disorder such as cancer). Other genes of interest include, but are not limited to, angiogenic genes, receptor ligand genes, immunomodulator genes (e.g., those associated with inflammatory and autoimmune responses), genes associated with metabolic diseases and disorders (e.g., liver diseases and disorders), genes associated with viral infection and survival, and genes associated with neurodegenerative disorders.

Genes associated with tumorigenesis or cell transformation (e.g., cancer or other neoplasia) include, for example, genes involved in p53 ubiquitination, c-Jun ubiquitination, histone deacetylation, cell cycle regulation, transcriptional regulation, and combinations thereof. Non-limiting examples of gene sequences associated with tumorigenesis or cell transformation include serine/threonine kinases such as polo-like kinase 1 (PLK-1) (Genbank Accession No. NM_005030; Barr et al., *Nat. Rev. Mol. Cell Biol.,* 5:429-440 (2004)) and cyclin-dependent kinase 4 (CDK4) (Genbank Accession No. NM_000075); ubiquitin ligases such as COP1 (RFWD2; Genbank Accession Nos. NM_022457 and NM_001001740) and ring-box 1 (RBX1) (ROC1; Genbank Accession No. NM_014248); tyrosine kinases such as WEE1 (Genbank Accession Nos. NM_003390 and NM_001143976); mitotic kinesins such as Eg5 (KSP, KIF11; Genbank Accession No. NM_004523); transcription factors such as forkhead box M1 (FOXM1) (Genbank Accession Nos. NM_202002, NM_021953, and NM_202003) and RAM2 (R1 or CDCA7L; Genbank Accession Nos. NM_018719, NM_001127370, and NM_001127371); inhibitors of apoptosis such as XIAP (Genbank Accession No. NM_001167); COPS signalosome subunits such as CSN1, CSN2, CSN3, CSN4, CSN5 (JAB1; Genbank Accession No. NM_006837); CSN6, CSN7A, CSN7B, and CSN8; and histone deacetylases such as HDAC1, HDAC2 (Genbank Accession No. NM_001527), HDAC3, HDAC4, HDAC5, HDAC6, HDAC7, HDAC8, HDAC9, etc.

Non-limiting examples of siRNA molecules targeting the PLK-1 gene include those described herein and in U.S. Patent Publication Nos. 20050107316 and 20070265438; and PCT Publication No. WO 09/082817, the disclosures of which are herein incorporated by reference in their entirety for all purposes. Non-limiting examples of siRNA molecules targeting the Eg5 and XIAP genes include those described in U.S. Patent Publication No. 20090149403, the disclosure of which is herein incorporated by reference in its entirety for all purposes. Non-limiting examples of siRNA molecules targeting the CSN5 gene include those described in PCT Publication No. WO 09/129319, the disclosure of which is herein incorporated by reference in its entirety for all purposes. Non-limiting examples of siRNA molecules targeting the COP1, CSN5, RBX1, HDAC2, CDK4, WEE1, FOXM1, and RAM2 genes include those described in U.S. Provisional Application No. 61/245,143, filed Sep. 23, 2009, the disclosure of which is herein incorporated by reference in its entirety for all purposes.

Additional examples of gene sequences associated with tumorigenesis or cell transformation include translocation sequences such as MLL fusion genes, BCR-ABL (Wilda et al., *Oncogene,* 21:5716 (2002); Scherr et al., *Blood,* 101: 1566 (2003)), TEL-AML1, EWS-FLI1, TLS-FUS, PAX3-FKHR, BCL-2, AML1-ETO, and AML1-MTG8 (Heidenreich et al., *Blood,* 101:3157 (2003)); overexpressed sequences such as multidrug resistance genes (Nieth et al., *FEBS Lett.,* 545:144 (2003); Wu et al, *Cancer Res.* 63:1515 (2003)), cyclins (Li et al., *Cancer Res.,* 63:3593 (2003); Zou et al., *Genes Dev.,* 16:2923 (2002)), beta-catenin (Verma et al., *Clin Cancer Res.,* 9:1291 (2003)), telomerase genes (Kosciolek et al., *Mol Cancer Ther.,* 2:209 (2003)), c-MYC, N-MYC, BCL-2, growth factor receptors (e.g., EGFR/ErbB1 (Genbank Accession Nos. NM_005228, NM_201282, NM_201283, and NM_201284; see also, Nagy et al. *Exp. Cell Res.,* 285:39-49 (2003)), ErbB2/HER-2 (Genbank Accession Nos. NM_004448 and NM_001005862), ErbB3 (Genbank Accession Nos. NM_001982 and NM_001005915), and ErbB4 (Genbank Accession Nos. NM_005235 and NM_001042599)), and mutated sequences such as RAS (Tuschl and Borkhardt, *Mol. Interventions,* 2:158 (2002)). Non-limiting examples of siRNA molecules targeting the EGFR gene include those described in U.S. Patent Publication No. 20090149403, the disclosure of which is herein incorporated by reference in its entirety for all purposes. siRNA molecules that target VEGFR genes are set forth in, e.g., GB 2396864; U.S. Patent Publication No. 20040142895; and CA 2456444, the disclosures of which are herein incorporated by reference in their entirety for all purposes.

Silencing of sequences that encode DNA repair enzymes find use in combination with the administration of chemotherapeutic agents (Collis et al., *Cancer Res.,* 63:1550 (2003)). Genes encoding proteins associated with tumor migration are also target sequences of interest, for example, integrins, selectins, and metalloproteinases. The foregoing examples are not exclusive. Those of skill in the art will understand that any whole or partial gene sequence that facilitates or promotes tumorigenesis or cell transformation, tumor growth, or tumor migration can be included as a template sequence.

Angiogenic genes are able to promote the formation of new vessels. Angiogenic genes of particular interest include, but are not limited to, vascular endothelial growth factor (VEGF) (Reich et al., *Mol. Vis.,* 9:210 (2003)), placental growth factor (PGF), VEGFR-1 (Flt-1), VEGFR-2 (KDR/Flk-1), and the like. siRNA molecules that target VEGFR genes are set forth in, e.g., GB 2396864; U.S. Patent Publication No. 20040142895; and CA 2456444, the disclosures of which are herein incorporated by reference in their entirety for all purposes.

Immunomodulator genes are genes that modulate one or more immune responses. Examples of immunomodulator genes include, without limitation, growth factors (e.g., TGF-α, TGF-β, EGF, FGF, IGF, NGF, PDGF, CGF, GM-CSF, SCF, etc.), interleukins (e.g., IL-2, IL-4, IL-12 (Hill et al., *J. Immunol.,* 171:691 (2003)), IL-15, IL-18, IL-20, etc.), interferons (e.g., IFN-α, IFN-β, IFN-γ, etc.), and TNF. Fas and Fas ligand genes are also immunomodulator target sequences of interest (Song et al., *Nat. Med.,* 9:347 (2003)). Genes encoding secondary signaling molecules in hematopoietic and lymphoid cells are also included in the present invention, for example, Tec family kinases such as Bruton's tyrosine kinase (Btk) (Heinonen et al., *FEBS Lett.,* 527:274 (2002)).

Cell receptor ligand genes include ligands that are able to bind to cell surface receptors (e.g., cytokine receptors, growth factor receptors, receptors with tyrosine kinase activity, G-protein coupled receptors, insulin receptor, EPO receptor, etc.) to modulate (e.g., inhibit) the physiological pathway that the receptor is involved in (e.g., cell proliferation, tumorigenesis, cell transformation, mitogenesis, etc.). Non-limiting examples of cell receptor ligand genes include cytokines (e.g., TNF-α, interferons such as IFN-α, IFN-β, and IFN-γ, interleukins such as IL-1α, IL-1β, IL-2, IL-4, IL-5, IL-6, IL-7, IL-8, IL-9, IL-10, IL-12, IL-13, IL-15, IL-17, IL-23, IL-27, chemokines, etc.), growth factors (e.g., EGF, HB-EGF, VEGF, PEDF, SDGF, bFGF, HGF, TGF-α, TGF-β, BMP1-BMP15, PDGF, IGF, NGF, 13-NGF, BDNF, NT3, NT4, GDF-9, CGF, G-CSF, GM-CSF, GDF-8, EPO, TPO, etc.), insulin, glucagon, G-protein coupled receptor ligands, etc.

Genes associated with viral infection and survival include those expressed by a host (e.g., a host factor such as tissue factor (TF)) or a virus in order to bind, enter, and replicate in a cell. Of particular interest are viral sequences associated with chronic viral diseases. Viral sequences of particular interest include sequences of Filoviruses such as Ebola virus and Marburg virus (see, e.g., Geisbert et al., *J Infect. Dis.*, 193:1650-1657 (2006)); Arenaviruses such as Lassa virus, Junin virus, Machupo virus, Guanarito virus, and Sabia virus (Buchmeier et al., *Arenaviridae*: the viruses and their replication, In: Fields Virology, Knipe et al. (eds.), 4th ed., Lippincott-Raven, Philadelphia, (2001)); Influenza viruses such as Influenza A, B, and C viruses, (see, e.g., Steinhauer et al., *Annu Rev Genet.*, 36:305-332 (2002); and Neumann et al., *J Gen Virol.*, 83:2635-2662 (2002)); Hepatitis viruses (see, e.g., Hamasaki et al., *FEBS Lett.*, 543:51 (2003); Yokota et al., *EMBO Rep.*, 4:602 (2003); Schlomai et al., *Hepatology*, 37:764 (2003); Wilson et al., *Proc. Natl. Acad. Sci. USA*, 100:2783 (2003); Kapadia et al., *Proc. Natl. Acad. Sci. USA*, 100:2014 (2003); and Fields V*irology*, Knipe et al. (eds.), 4th ed., Lippincott-Raven, Philadelphia (2001)); Human Immunodeficiency Virus (HIV) (Banerj ea et al., *Mol. Ther.*, 8:62 (2003); Song et al., *J. Virol.*, 77:7174 (2003); Stephenson, *JAMA*, 289:1494 (2003); Qin et al., *Proc. Natl. Acad. Sci. USA*, 100:183 (2003)); Herpes viruses (Jia et al., *J. Virol.*, 77:3301 (2003)); and Human Papilloma Viruses (HPV) (Hall et al., *J. Virol.*, 77:6066 (2003); Jiang et al., *Oncogene*, 21:6041 (2002)).

Exemplary Filovirus nucleic acid sequences that can be silenced include, but are not limited to, nucleic acid sequences encoding structural proteins (e.g., VP30, VP35, nucleoprotein (NP), polymerase protein (L-pol)) and membrane-associated proteins (e.g., VP40, glycoprotein (GP), VP24). Complete genome sequences for Ebola virus are set forth in, e.g., Genbank Accession Nos. NC_002549; AY769362; NC_006432; NC_004161; AY729654; AY354458; AY142960; AB050936; AF522874; AF499101; AF272001; and AF086833. Ebola virus VP24 sequences are set forth in, e.g., Genbank Accession Nos. U77385 and AY058897. Ebola virus L-pol sequences are set forth in, e.g., Genbank Accession No. X67110. Ebola virus VP40 sequences are set forth in, e.g., Genbank Accession No. AY058896. Ebola virus NP sequences are set forth in, e.g., Genbank Accession No. AY058895. Ebola virus GP sequences are set forth in, e.g., Genbank Accession No. AY058898; Sanchez et al., *Virus Res.*, 29:215-240 (1993); Will et al., *J. Virol.*, 67:1203-1210 (1993); Volchkov et al., *FEBS Lett.*, 305:181-184 (1992); and U.S. Pat. No. 6,713,069. Additional Ebola virus sequences are set forth in, e.g., Genbank Accession Nos. L11365 and X61274. Complete genome sequences for Marburg virus are set forth in, e.g., Genbank Accession Nos. NC_001608; AY430365; AY430366; and AY358025. Marburg virus GP sequences are set forth in, e.g., Genbank Accession Nos. AF005734; AF005733; and AF005732. Marburg virus VP35 sequences are set forth in, e.g., Genbank Accession Nos. AF005731 and AF005730. Additional Marburg virus sequences are set forth in, e.g., Genbank Accession Nos. X64406; Z29337; AF005735; and Z12132. Non-limiting examples of siRNA molecules targeting Ebola virus and Marburg virus nucleic acid sequences include those described in U.S. Patent Publication No. 20070135370 and U.S. Provisional Application No. 61/286,741, filed Dec. 15, 2009, the disclosures of which are herein incorporated by reference in their entirety for all purposes.

Exemplary Arenavirus nucleic acid sequences that can be silenced include, but are not limited to, nucleic acid sequences encoding nucleoprotein (NP), glycoprotein (GP), L-polymerase (L), and Z protein (Z). Complete genome sequences for Lassa virus are set forth in, e.g., Genbank Accession Nos. NC_004296 (LASV segment S) and NC_004297 (LASV segment L). Non-limiting examples of siRNA molecules targeting Lassa virus nucleic acid sequences include those described in U.S. Provisional Application No. 61/319,855, filed Mar. 31, 2010, the disclosure of which is herein incorporated by reference in its entirety for all purposes.

Exemplary host nucleic acid sequences that can be silenced include, but are not limited to, nucleic acid sequences encoding host factors such as tissue factor (TF) that are known to play a role in the pathogenisis of hemorrhagic fever viruses. The mRNA sequence of TF is set forth in Genbank Accession No. NM_001993. Those of skill in the art will appreciate that TF is also known as F3, coagulation factor III, thromboplastin, and CD142. Non-limiting examples of siRNA molecules targeting TF nucleic acid sequences include those described in U.S. Provisional Application No. 61/319,855, filed Mar. 31, 2010, the disclosure of which is herein incorporated by reference in its entirety for all purposes.

Exemplary Influenza virus nucleic acid sequences that can be silenced include, but are not limited to, nucleic acid sequences encoding nucleoprotein (NP), matrix proteins (M1 and M2), nonstructural proteins (NS1 and NS2), RNA polymerase (PA, PB1, PB2), neuraminidase (NA), and haemagglutinin (HA). Influenza A NP sequences are set forth in, e.g., Genbank Accession Nos. NC_004522; AY818138; AB166863; AB188817; AB189046; AB189054; AB189062; AY646169; AY646177; AY651486; AY651493; AY651494; AY651495; AY651496; AY651497; AY651498; AY651499; AY651500; AY651501; AY651502; AY651503; AY651504; AY651505; AY651506; AY651507; AY651509; AY651528; AY770996; AY790308; AY818138; and AY818140. Influenza A PA sequences are set forth in, e.g., Genbank Accession Nos. AY818132; AY790280; AY646171; AY818132; AY818133; AY646179; AY818134; AY551934; AY651613; AY651610; AY651620; AY651617; AY651600; AY651611; AY651606; AY651618; AY651608; AY651607; AY651605; AY651609; AY651615; AY651616; AY651640; AY651614; AY651612; AY651621; AY651619; AY770995; and AY724786. Non-limiting examples of siRNA molecules targeting Influenza virus nucleic acid sequences include those described in U.S. Patent Publication No. 20070218122, the disclosure of which is herein incorporated by reference in its entirety for all purposes.

Exemplary hepatitis virus nucleic acid sequences that can be silenced include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., Fields VIROLOGY, supra). Exemplary Hepatitis C virus (HCV) nucleic acid sequences that can be silenced include, but are not limited to, the 5'-untranslated region (5'-UTR), the 3'-untranslated region (3'-UTR), the polyprotein translation initiation codon region, the internal ribosome entry site (IRES) sequence, and/or nucleic acid sequences encoding the core protein, the E1 protein, the E2 protein, the p7 protein, the NS2 protein, the NS3 protease/helicase, the NS4A protein, the NS4B protein, the NS5A protein, and/or the NS5B RNA-dependent RNA polymerase. HCV genome sequences are set forth in, e.g., Genbank Accession Nos. NC_004102 (HCV genotype 1a), AJ238799 (HCV genotype 1b), NC_009823 (HCV genotype 2), NC_009824 (HCV genotype 3), NC_009825 (HCV genotype 4), NC_009826 (HCV genotype 5), and NC_009827 (HCV genotype 6). Hepatitis A virus nucleic acid sequences are set forth in, e.g., Genbank Accession No. NC_001489; Hepatitis B virus nucleic acid sequences are set forth in, e.g., Genbank Accession No. NC_003977; Hepatitis D virus nucleic acid sequence are set forth in, e.g., Genbank Accession No. NC_001653; Hepatitis E virus nucleic acid sequences are set forth in, e.g., Genbank Accession No. NC_001434; and Hepatitis G virus nucleic acid sequences are set forth in, e.g., Genbank Accession No. NC_001710. Silencing of sequences that encode genes associated with viral infection and survival can conveniently be used in combination with the administration of conventional agents used to treat the viral condition. Non-limiting examples of siRNA molecules targeting hepatitis virus nucleic acid sequences include those described in U.S. Patent Publication Nos. 20060281175, 20050058982, and 20070149470; U.S. Pat. No. 7,348,314; and PCT Application No. PCT/CA2010/000444, entitled "Compositions and Methods for Silencing Hepatitis C Virus Expression," filed Mar. 19, 2010, the disclosures of which are herein incorporated by reference in their entirety for all purposes.

Genes associated with metabolic diseases and disorders (e.g., disorders in which the liver is the target and liver diseases and disorders) include, but are not limited to, genes expressed in dyslipidemia, such as, e.g., apolipoprotein B (APOB) (Genbank Accession No. NM_000384), apolipoprotein CIII (APOC3) (Genbank Accession Nos. NM_000040 and NG 008949 REGION: 5001 . . . 8164), apolipoprotein E (APOE) (Genbank Accession Nos. NM_000041 and NG 007084 REGION: 5001 . . . 8612), proprotein convertase subtilisin/kexin type 9 (PCSK9) (Genbank Accession No. NM_174936), diacylglycerol O-acyltransferase type 1 (DGAT1) (Genbank Accession No. NM_012079), diacylglyerol O-acyltransferase type 2 (DGAT2) (Genbank Accession No. NM_032564), liver X receptors such as LXRα and LXRβ (Genback Accession No. NM_007121), farnesoid X receptors (FXR) (Genbank Accession No. NM_005123), sterol-regulatory element binding protein (SREBP), site-1 protease (S1P), 3-hydroxy-3-methylglutaryl coenzyme-A reductase (HMG coenzyme-A reductase); and genes expressed in diabetes, such as, e.g., glucose 6-phosphatase (see, e.g., Forman et al., *Cell*, 81:687 (1995); Seol et al., *Mot Endocrinol.*, 9:72 (1995), Zavacki et al., *Proc. Natl. Acad. Sci. USA*, 94:7909 (1997); Sakai et al., *Cell*, 85:1037-1046 (1996); Duncan et al., *J. Biol. Chem.*, 272:12778-12785 (1997); Willy et al., *Genes Dev.*, 9:1033-1045 (1995); Lehmann et al., *J. Biol. Chem.*, 272:3137-3140 (1997); Janowski et al., *Nature*, 383:728-731 (1996); and Peet et al., *Cell*, 93:693-704 (1998)).

One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder. Non-limiting examples of siRNA molecules targeting the APOB gene include those described in U.S. Patent Publication Nos. 20060134189, 20060105976, and 20070135372, and PCT Publication No. WO 04/091515, the disclosures of which are herein incorporated by reference in their entirety for all purposes. Non-limiting examples of siRNA molecules targeting the APOC3 gene include those described in PCT Application No. PCT/CA2010/000120, filed Jan. 26, 2010, the disclosure of which is herein incorporated by reference in its entirety for all purposes. Non-limiting examples of siRNA molecules targeting the PCSK9 gene include those described in U.S. Patent Publication Nos. 20070173473, 20080113930, and 20080306015, the disclosures of which are herein incorporated by reference in their entirety for all purposes. Exemplary siRNA molecules targeting the DGAT1 gene may be designed using the antisense compounds described in U.S. Patent Publication No. 20040185559, the disclosure of which is herein incorporated by reference in its entirety for all purposes. Exemplary siRNA molecules targeting the DGAT2 gene may be designed using the antisense compounds described in U.S. Patent Publication No. 20050043524, the disclosure of which is herein incorporated by reference in its entirety for all purposes.

Templates coding for an expansion of trinucleotide repeats (e.g., CAG repeats) find use in silencing pathogenic sequences in neurodegenerative disorders caused by the expansion of trinucleotide repeats, such as spinobulbular muscular atrophy and Huntington's Disease (Caplen et al., *Hum. Mol. Genet.*, 11:175 (2002)).

In addition to its utility in silencing the expression of any of the above-described genes for therapeutic purposes, the siRNA described herein are also useful in research and development applications as well as diagnostic, prophylactic, prognostic, clinical, and other healthcare applications. As a non-limiting example, the siRNA can be used in target validation studies directed at testing whether a gene of interest has the potential to be a therapeutic target. The siRNA can also be used in target identification studies aimed at discovering genes as potential therapeutic targets.

(5) Exemplary siRNA Embodiments

In some embodiments, each strand of the siRNA molecule comprises from about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). In one particular embodiment, the siRNA is chemically synthesized. The siRNA molecules of the invention are capable of silencing the expression of a target sequence in vitro and/or in vivo.

In other embodiments, the siRNA comprises at least one modified nucleotide. In certain embodiments, the siRNA comprises one, two, three, four, five, six, seven, eight, nine, ten, or more modified nucleotides in the double-stranded region. In particular embodiments, less than about 50% (e.g., less than about 50%, 45%, 40%, 35%, 30%, 25%, 20%, 15%, 10%, or 5%) of the nucleotides in the double-stranded region of the siRNA comprise modified nucleotides. In preferred embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 30%-40%, 35%-40%, 5%-35%, 10%-35%, 15%-35%, 20%-35%, 25%-35%, 30%-35%, 5%-30%, 10%-30%, 15%-30%, 20%-30%, 25%-30%, 5%-25%, 10%-25%, 15%-25%, 20%-25%, 5%-20%, 10%-20%, 15%-20%, 5%-15%, 10%-15%, or 5%-10%) of the nucleotides in the double-stranded region of the siRNA comprise modified nucleotides.

In further embodiments, the siRNA comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, e.g., 2'OMe-guanosine nucleotides, 2'OMe-uridine nucleotides, 2'OMe-adenosine nucleotides, 2'OMe-cytosine nucleotides, or mixtures thereof. In one particular embodiment, the siRNA comprises at least one 2'OMe-guanosine nucleotide, 2'OMe-uridine nucleotide, or mixtures thereof. In certain instances, the siRNA does not comprise 2'OMe-cytosine nucleotides. In other embodiments, the siRNA comprises a hairpin loop structure.

In certain embodiments, the siRNA comprises modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In other embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In another embodiment, an unmodified or modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to a negative control (e.g., buffer only, an siRNA sequence that targets a different gene, a scrambled siRNA sequence, etc.).

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. In certain embodiments, the 3' overhang on the sense and/or antisense strand independently comprises one, two, three, four, or more modified nucleotides such as 2'OMe nucleotides and/or any other modified nucleotide described herein or known in the art.

In particular embodiments, siRNAs are administered using a carrier system such as a nucleic acid-lipid particle. In a preferred embodiment, the nucleic acid-lipid particle comprises: (a) one or more siRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

b) Dicer-Substrate dsRNA

As used herein, the term "Dicer-substrate dsRNA" or "precursor RNAi molecule" is intended to include any precursor molecule that is processed in vivo by Dicer to produce an active siRNA which is incorporated into the RISC complex for RNA interference of a target gene, such as PLK-1.

In one embodiment, the Dicer-substrate dsRNA has a length sufficient such that it is processed by Dicer to produce an siRNA. According to this embodiment, the Dicer-substrate dsRNA comprises (i) a first oligonucleotide sequence (also termed the sense strand) that is between about 25 and about 60 nucleotides in length (e.g., about 25-60, 25-55, 25-50, 25-45, 25-40, 25-35, or 25-30 nucleotides in length), preferably between about 25 and about 30 nucleotides in length (e.g., 25, 26, 27, 28, 29, or 30 nucleotides in length), and (ii) a second oligonucleotide sequence (also termed the antisense strand) that anneals to the first sequence under biological conditions, such as the conditions found in the cytoplasm of a cell. The second oligonucleotide sequence may be between about 25 and about 60 nucleotides in length (e.g., about 25-60, 25-55, 25-50, 25-45, 25-40, 25-35, or 25-30 nucleotides in length), and is preferably between about 25 and about 30 nucleotides in length (e.g., 25, 26, 27, 28, 29, or 30 nucleotides in length). In addition, a region of one of the sequences, particularly of the antisense strand, of the Dicer-substrate dsRNA has a sequence length of at least about 19 nucleotides, for example, from about 19 to about 60 nucleotides (e.g., about 19-60, 19-55, 19-50, 19-45, 19-40, 19-35, 19-30, or 19-25 nucleotides), preferably from about 19 to about 23 nucleotides (e.g., 19, 20, 21, 22, or 23 nucleotides) that are sufficiently complementary to a nucleotide sequence of the RNA produced from the target gene to trigger an RNAi response.

In a second embodiment, the Dicer-substrate dsRNA has several properties which enhance its processing by Dicer. According to this embodiment, the dsRNA has a length sufficient such that it is processed by Dicer to produce an siRNA and has at least one of the following properties: (i) the dsRNA is asymmetric, e.g., has a 3'-overhang on the antisense strand; and/or (ii) the dsRNA has a modified 3'-end on the sense strand to direct orientation of Dicer binding and processing of the dsRNA to an active siRNA. According to this latter embodiment, the sense strand comprises from about 22 to about 28 nucleotides and the antisense strand comprises from about 24 to about 30 nucleotides.

In one embodiment, the Dicer-substrate dsRNA has an overhang on the 3'-end of the antisense strand. In another embodiment, the sense strand is modified for Dicer binding and processing by suitable modifiers located at the 3'-end of the sense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the Dicer-substrate dsRNA has an overhang on the 3'-end of the antisense strand and the sense strand is modified for Dicer processing. In another embodiment, the 5'-end of the sense strand has a phosphate. In another embodiment, the 5'-end of the antisense strand has a phosphate. In another embodiment, the antisense strand or the sense strand or both strands have one or more 2'-O-methyl (2'OMe) modified nucleotides. In another embodiment, the antisense strand contains 2'OMe modified nucleotides. In another embodiment, the antisense stand contains a 3'-overhang that is comprised of 2'OMe modified nucleotides. The antisense strand could also include additional 2'OMe modified nucleotides. The sense and antisense strands anneal under biological conditions, such as the conditions found in the cytoplasm of a cell. In addition, a region of one of the sequences, particularly of the antisense strand, of the Dicer-substrate dsRNA has a sequence length of at least about 19 nucleotides, wherein these nucleotides are in the 21-nucleotide region adjacent to the 3'-end of the antisense strand and are sufficiently complementary to a nucleotide sequence of the RNA produced from the target gene, such as PLK-1. Further, in accordance with this embodiment, the Dicer-substrate dsRNA may also have one or more of the following additional properties: (a) the antisense strand has a right shift from the typical 21-mer (i.e., the antisense strand includes nucleotides on the right side of the molecule when compared to the typical 21-mer); (b) the strands may not be completely complementary, i.e., the strands may contain simple mismatch pairings; and (c) base modifications such as locked nucleic acid(s) may be included in the 5'-end of the sense strand.

In a third embodiment, the sense strand comprises from about 25 to about 28 nucleotides (e.g., 25, 26, 27, or 28 nucleotides), wherein the 2 nucleotides on the 3'-end of the sense strand are deoxyribonucleotides. The sense strand contains a phosphate at the 5'-end. The antisense strand comprises from about 26 to about 30 nucleotides (e.g., 26, 27, 28, 29, or 30 nucleotides) and contains a 3'-overhang of 1-4 nucleotides. The nucleotides comprising the 3'-overhang are modified with 2'OMe modified ribonucleotides. The antisense strand contains alternating 2'OMe modified nucleotides beginning at the first monomer of the antisense strand adjacent to the 3'-overhang, and extending 15-19 nucleotides from the first monomer adjacent to the 3'-overhang. For example, for a 27-nucleotide antisense strand and counting the first base at the 5'-end of the antisense strand as position number 1, 2'OMe modifications would be placed at bases 9, 11, 13, 15, 17, 19, 21, 23, 25, 26, and 27. In one embodiment, the Dicer-substrate dsRNA has the following structure:

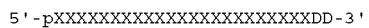

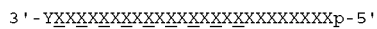

wherein "X"=RNA, "p"=a phosphate group, "X"=2'OMe RNA, "Y" is an overhang domain comprised of 1, 2, 3, or 4 RNA monomers that are optionally 2'OMe RNA monomers, and "D"=DNA. The top strand is the sense strand, and the bottom strand is the antisense strand.

In a fourth embodiment, the Dicer-substrate dsRNA has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3'-overhang on the sense strand; and (ii) the dsRNA has a modified 3'-end on the antisense strand to direct orientation of Dicer binding and processing of the dsRNA to an active siRNA. According to this embodiment, the sense strand comprises from about 24 to about 30 nucleotides (e.g., 24, 25, 26, 27, 28, 29, or 30 nucleotides) and the antisense strand comprises from about 22 to about 28 nucleotides (e.g., 22, 23, 24, 25, 26, 27, or 28 nucleotides). In one embodiment, the Dicer-substrate dsRNA has an overhang on the 3'-end of the sense strand. In another embodiment, the antisense strand is modified for Dicer binding and processing by suitable modifiers located at the 3'-end of the antisense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the dsRNA has an overhang on the 3'-end of the sense strand and the antisense strand is modified for Dicer processing. In one embodiment, the antisense strand has a 5'-phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3'-end of antisense strand and are sufficiently complementary to a nucleotide sequence of the RNA produced from the target gene, such as PLK-1. Further, in accordance with this embodiment, the Dicer-substrate dsRNA may also have one or more of the following additional properties: (a) the antisense strand has a left shift from the typical 21-mer (i.e., the antisense strand includes nucleotides on the left side of the molecule when compared to the typical 21-mer); and (b) the strands may not be completely complementary, i.e., the strands may contain simple mismatch pairings.

In a preferred embodiment, the Dicer-substrate dsRNA has an asymmetric structure, with the sense strand having a 25-base pair length, and the antisense strand having a 27-base pair length with a 2 base 3'-overhang. In certain instances, this dsRNA having an asymmetric structure further contains 2 deoxynucleotides at the 3'-end of the sense strand in place of two of the ribonucleotides. In certain other instances, this dsRNA having an asymmetric structure further contains 2'OMe modifications at positions 9, 11, 13, 15, 17, 19, 21, 23, and 25 of the antisense strand (wherein the first base at the 5'-end of the antisense strand is position 1). In certain additional instances, this dsRNA having an asymmetric structure further contains a 3'-overhang on the antisense strand comprising 1, 2, 3, or 4 2'OMe nucleotides (e.g., a 3'-overhang of 2'OMe nucleotides at positions 26 and 27 on the antisense strand).

In another embodiment, Dicer-substrate dsRNAs may be designed by first selecting an antisense strand siRNA sequence having a length of at least 19 nucleotides. In some instances, the antisense siRNA is modified to include about 5 to about 11 ribonucleotides on the 5'-end to provide a length of about 24 to about 30 nucleotides. When the antisense strand has a length of 21 nucleotides, 3-9, preferably 4-7, or more preferably 6 nucleotides may be added on the 5'-end. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 22 to about 28 nucleotides. The sense strand is substantially complementary with the antisense strand to anneal to the antisense strand under biological conditions. In one embodiment, the sense strand is synthesized to contain a modified 3'-end to direct Dicer processing of the antisense strand. In another embodiment, the antisense strand of the dsRNA has a 3'-overhang. In a further embodiment, the sense strand is synthesized to contain a modified 3'-end for Dicer binding and processing and the antisense strand of the dsRNA has a 3'-overhang.

In a related embodiment, the antisense siRNA may be modified to include about 1 to about 9 ribonucleotides on the 5'-end to provide a length of about 22 to about 28 nucleotides. When the antisense strand has a length of 21 nucleotides, 1-7, preferably 2-5, or more preferably 4 ribonucleotides may be added on the 3'-end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 24 to about 30 nucleotides. The sense strand is substantially complementary with the antisense strand to anneal to the antisense strand under biological conditions. In one embodiment, the antisense strand is synthesized to contain a modified 3'-end to direct Dicer processing. In another embodiment, the sense strand of the dsRNA has a 3'-overhang. In a further embodiment, the antisense strand is synthesized to contain a modified 3'-end for Dicer binding and processing and the sense strand of the dsRNA has a 3'-overhang.

Suitable Dicer-substrate dsRNA sequences can be identified, synthesized, and modified using any means known in the art for designing, synthesizing, and modifying siRNA sequences. In particular embodiments, Dicer-substrate dsRNAs are administered using a carrier system such as a nucleic acid-lipid particle. In a preferred embodiment, the nucleic acid-lipid particle comprises: (a) one or more Dicer-substrate dsRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

Additional embodiments related to the Dicer-substrate dsRNAs of the invention, as well as methods of designing and synthesizing such dsRNAs, are described in U.S. Patent Publication Nos. 20050244858, 20050277610, and 20070265220, and U.S. application Ser. No. 12/794,701, filed Jun. 4, 2010, the disclosures of which are herein incorporated by reference in their entirety for all purposes.

c) Small Hairpin RNA (shRNA)

A "small hairpin RNA" or "short hairpin RNA" or "shRNA" includes a short RNA sequence that makes a tight hairpin turn that can be used to silence gene expression via RNA interference. The shRNAs of the invention may be chemically synthesized or transcribed from a transcriptional cassette in a DNA plasmid. The shRNA hairpin structure is cleaved by the cellular machinery into siRNA, which is then bound to the RNA-induced silencing complex (RISC).

The shRNAs of the invention are typically about 15-60, 15-50, or 15-40 (duplex) nucleotides in length, more typically about 15-30, 15-25, or 19-25 (duplex) nucleotides in length, and are preferably about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, preferably about 20-24, 21-22, or 21-23 nucleotides in length, and the double-stranded shRNA is about 15-60, 15-50, 15-40, 15-30, 15-25, or 19-25 base pairs in length, preferably about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), preferably from about 19 to about 40 nucleotides in length (e.g., about 19-40, 19-35, 19-30, or 19-25 nucleotides in length), more preferably from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In preferred embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional shRNA sequences include, but are not limited to, asymmetric shRNA precursor polynucleotides such as those described in PCT Publication Nos. WO 2006/074108 and WO 2009/076321, the disclosures of which are herein incorporated by reference in their entirety for all purposes. For example, PCT Publication No. WO 2006/074108 discloses self-protected oligonucleotides comprising a region having a sequence complementary to one, two, three, or more same or different target mRNA sequences (e.g., multivalent shRNAs) and one or more self-complementary regions. Similarly, PCT Publication No. WO 2009/076321 discloses self-forming asymmetric precursor polynucleotides comprising a targeting region comprising a polynucleotide sequence complementary to a region of one, two, three, or more same or different target mRNA sequences (e.g., multivalent shRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions.

Suitable shRNA sequences can be identified, synthesized, and modified using any means known in the art for designing, synthesizing, and modifying siRNA sequences. In particular embodiments, shRNAs are administered using a carrier system such as a nucleic acid-lipid particle. In a preferred embodiment, the nucleic acid-lipid particle comprises: (a) one or more shRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

Additional embodiments related to the shRNAs of the invention, as well as methods of designing and synthesizing such shRNAs, are described in U.S. patent application Ser. No. 12/794,701, filed Jun. 4, 2010, the disclosure of which is herein incorporated by reference in its entirety for all purposes.

d) aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., Nat. Biotech., 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or 20 base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In particular embodiments, aiRNAs are administered using a carrier system such as a nucleic acid-lipid particle. In a preferred embodiment, the nucleic acid-lipid particle comprises: (a) one or more aiRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

Suitable aiRNA sequences can be identified, synthesized, and modified using any means known in the art for designing, synthesizing, and modifying siRNA sequences. Additional embodiments related to the aiRNA molecules of the invention are described in U.S. Patent Publication No. 20090291131 and PCT Publication No. WO 09/127060, the disclosures of which are herein incorporated by reference in their entirety for all purposes.

e) miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNA molecules is described, e.g., in Lagos-Quintana et al., *Science,* 294:853-858; Lau et al., *Science,* 294:858-862; and Lee et al., *Science,* 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature,* 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature,* 409: 363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.,* 16:530-535 (2006)). The remaining strand, known as the anti-guide or passenger strand, is degraded as a RISC complex substrate (Gregory et al., *Cell,* 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In some embodiments, miRNA molecules may be used to silence the expression of any of the target genes described above for siRNA sequences, and preferably silence genes associated with cell proliferation, tumorigenesis, and/or cell transformation. In particular embodiments, miRNAs are administered using a carrier system such as a nucleic acid-lipid particle. In a preferred embodiment, the nucleic acid-lipid particle comprises: (a) one or more miRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

In other embodiments, one or more agents that block the activity of an miRNA targeting an mRNA of interest (e.g., PLK-1 mRNA) are administered using a lipid particle of the invention (e.g., a nucleic acid-lipid particle such as SNALP). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target mRNA.

Additional embodiments related to the miRNA molecules of the invention are described in U.S. Patent Publication No. 20090291131 and PCT Publication No. WO 09/127060, the disclosures of which are herein incorporated by reference in their entirety for all purposes.

f) Antisense Oligonucleotides

In one embodiment, the nucleic acid is an antisense oligonucleotide directed to a target gene or sequence of interest. The terms "antisense oligonucleotide" or "antisense" include oligonucleotides that are complementary to a targeted polynucleotide sequence. Antisense oligonucleotides are single strands of DNA or RNA that are complementary to a chosen sequence. Antisense RNA oligonucleotides prevent the translation of complementary RNA strands by binding to the RNA. Antisense DNA oligonucleotides can be used to target a specific, complementary (coding or non-coding) RNA. If binding occurs, this DNA/RNA hybrid can be degraded by the enzyme RNase H. In a particular embodiment, antisense oligonucleotides comprise from about 10 to about 60 nucleotides, more preferably from about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (see, U.S. Pat. Nos. 5,739,119 and 5,759,829). Furthermore, examples of antisense inhibition have been demonstrated with the nuclear protein cyclin, the multiple drug resistance gene (MDR1), ICAM-1, E-selectin, STK-1, striatal GABAA receptor, and human EGF (see, Jaskulski et al., *Science,* 240:1544-6 (1988); Vasanthakumar et al., *Cancer Commun.,* 1:225-32 (1989); Penis et al., *Brain Res Mol Brain Res.,* 15; 57:310-20 (1998); and U.S. Pat. Nos. 5,801,154; 5,789,573; 5,718,709 and 5,610,288). Moreover, antisense constructs have also been described that inhibit and can be used to treat a variety of abnormal cellular proliferations, e.g., cancer (see, U.S. Pat. Nos. 5,747,470; 5,591,317; and 5,783,683). The disclosures of these references are herein incorporated by reference in their entirety for all purposes.

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res.,* 25:3389-402 (1997)).

g) Ribozymes

According to another embodiment of the invention, nucleic acid-lipid particles are associated with ribozymes. Ribozymes are RNA-protein complexes having specific catalytic domains that possess endonuclease activity (see, Kim et al., *Proc. Natl. Acad. Sci. USA,* 84:8788-92 (1987); and Forster et al., *Cell,* 49:211-20 (1987)). For example, a large number of ribozymes accelerate phosphoester transfer reactions with a high degree of specificity, often cleaving only one of several phosphoesters in an oligonucleotide substrate (see, Cech et al., *Cell,* 27:487-96 (1981); Michel et al., *J. Mol. Biol.,* 216:585-610 (1990); Reinhold-Hurek et al., *Nature,* 357:173-6 (1992)). This specificity has been attributed to the requirement that the substrate bind via specific base-pairing interactions to the internal guide sequence ("IGS") of the ribozyme prior to chemical reaction.

At least six basic varieties of naturally-occurring enzymatic RNA molecules are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, hepatitis δ virus, group I intron or RNaseP RNA (in association with an RNA guide sequence), or Neurospora VS RNA motif, for example. Specific examples of hammerhead motifs are described in, e.g., Rossi et al., *Nucleic Acids Res.,* 20:4559-65 (1992). Examples of hairpin motifs are described in, e.g., EP 0360257, Hampel et al., *Biochemistry,* 28:4929-33 (1989); Hampel et al., *Nucleic Acids Res.,* 18:299-304 (1990); and U.S. Pat. No. 5,631,359. An example of the hepatitis δ virus motif is described in, e.g., Perrotta et al., *Biochemistry,* 31:11843-52 (1992). An example of the RNaseP motif is described in, e.g., Guerrier-Takada et al., *Cell,* 35:849-57 (1983). Examples of the Neurospora VS RNA ribozyme motif is described in, e.g., Saville et al., *Cell,* 61:685-96 (1990); Saville et al., *Proc. Natl. Acad. Sci. USA,* 88:8826-30 (1991); Collins et al., *Biochemistry,* 32:2795-9 (1993). An example of the Group I intron is described in, e.g., U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus, the ribozyme constructs need not be limited to specific motifs mentioned herein. The disclosures of these references are herein incorporated by reference in their entirety for all purposes.

Methods of producing a ribozyme targeted to any polynucleotide sequence are known in the art. Ribozymes may be designed as described in, e.g., PCT Publication Nos. WO 93/23569 and WO 94/02595, and synthesized to be tested in vitro and/or in vivo as described therein. The disclosures of these PCT publications are herein incorporated by reference in their entirety for all purposes.

Ribozyme activity can be optimized by altering the length of the ribozyme binding arms or chemically synthesizing ribozymes with modifications that prevent their degradation by serum ribonucleases (see, e.g., PCT Publication Nos. WO 92/07065, WO 93/15187, WO 91/03162, and WO 94/13688; EP 92110298.4; and U.S. Pat. No. 5,334,711, which describe various chemical modifications that can be made to the sugar moieties of enzymatic RNA molecules, the disclosures of which are each herein incorporated by reference in their entirety for all purposes), modifications which enhance their efficacy in cells, and removal of stem II bases to shorten RNA synthesis times and reduce chemical requirements.

h) Immunostimulatory Oligonucleotides

Nucleic acids associated with lipid particles of the present invention may be immunostimulatory, including immunostimulatory oligonucleotides (ISS; single- or double-stranded) capable of inducing an immune response when administered to a subject, which may be a mammal such as a human. ISS include, e.g., certain palindromes leading to hairpin secondary structures (see, Yamamoto et al., *J. Immunol.*, 148:4072-6 (1992)), or CpG motifs, as well as other known ISS features (such as multi-G domains; see; PCT Publication No. WO 96/11266, the disclosure of which is herein incorporated by reference in its entirety for all purposes).

Immunostimulatory nucleic acids are considered to be non-sequence specific when it is not required that they specifically bind to and reduce the expression of a target sequence in order to provoke an immune response. Thus, certain immunostimulatory nucleic acids may comprise a sequence corresponding to a region of a naturally-occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in the CpG dinucleotide is methylated. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of the CpG dinucleotides comprises a methylated cytosine. Examples of immunostimulatory oligonucleotides suitable for use in the compositions and methods of the present invention are described in PCT Publication Nos. WO 02/069369, WO 01/15726, and WO 09/086558; U.S. Pat. No. 6,406,705; and Raney et al., *J. Pharm. Exper. Ther.*, 298:1185-92 (2001), the disclosures of which are herein incorporated by reference in their entirety for all purposes. In certain embodiments, the oligonucleotides used in the compositions and methods of the invention have a phosphodiester ("PO") backbone or a phosphorothioate ("PS") backbone, and/or at least one methylated cytosine residue in a CpG motif.

2. Other Active Agents

In certain embodiments, the active agent associated with the lipid particles of the invention may comprise one or more therapeutic proteins, polypeptides, or small organic molecules or compounds. Non-limiting examples of such therapeutically effective agents or drugs include oncology drugs (e.g., chemotherapy drugs, hormonal therapeutic agents, immunotherapeutic agents, radiotherapeutic agents, etc.), lipid-lowering agents, anti-viral drugs, anti-inflammatory compounds, antidepressants, stimulants, analgesics, antibiotics, birth control medication, antipyretics, vasodilators, anti-angiogenics, cytovascular agents, signal transduction inhibitors, cardiovascular drugs such as anti-arrhythmic agents, hormones, vasoconstrictors, and steroids. These active agents may be administered alone in the lipid particles of the invention, or in combination (e.g., co-administered) with lipid particles of the invention comprising nucleic acid such as interfering RNA.

Non-limiting examples of chemotherapy drugs include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil (5-FU), azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel (taxol), docetaxel, etc.), topoisomerase inhibitors (e.g., irinotecan (CPT-11; Camptosar), topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), tyrosine kinase inhibitors (e.g., gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), etc.), pharmaceutically acceptable salts thereof, stereoisomers thereof, derivatives thereof, analogs thereof, and combinations thereof.

Examples of conventional hormonal therapeutic agents include, without limitation, steroids (e.g., dexamethasone), finasteride, aromatase inhibitors, tamoxifen, and goserelin as well as other gonadotropin-releasing hormone agonists (GnRH).

Examples of conventional immunotherapeutic agents include, but are not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y or $^{131}$I, etc.).

Examples of conventional radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Additional oncology drugs that may be used according to the invention include, but are not limited to, alkeran, allopurinol, altretamine, amifostine, anastrozole, araC, arsenic trioxide, bexarotene, biCNU, carmustine, CCNU, celecoxib, cladribine, cyclosporin A, cytosine arabinoside, cytoxan, dexrazoxane, DTIC, estramustine, exemestane, FK506, gemtuzumab-ozogamicin, hydrea, hydroxyurea, idarubicin, interferon, letrozole, leustatin, leuprolide, litretinoin, megastrol, L-PAM, mesna, methoxsalen, mithramycin, nitrogen mustard, pamidronate, Pegademase, pentostatin, porfimer sodium, prednisone, rituxan, streptozocin, STI-571, taxotere, temozolamide, VM-26, toremifene, tretinoin, ATRA, valrubicin, and velban. Other examples of oncology drugs that may be used according to the invention are ellipticin and ellipticin analogs or derivatives, epothilones, intracellular kinase inhibitors, and camptothecins.

Non-limiting examples of lipid-lowering agents for treating a lipid disease or disorder associated with elevated triglycerides, cholesterol, and/or glucose include statins, fibrates, ezetimibe, thiazolidinediones, niacin, beta-blockers, nitroglycerin, calcium antagonists, fish oil, and mixtures thereof.

Examples of anti-viral drugs include, but are not limited to, abacavir, aciclovir, acyclovir, adefovir, amantadine, amprenavir, arbidol, atazanavir, atripla, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, ibacitabine, imunovir, idoxuridine, imiquimod, indinavir, inosine, integrase inhibitors, interferon type III (e.g., IFN-λmolecules such as IFN-λ1, IFN-λ2, and IFN-λ3), interferon type II (e.g., IFN-γ), interferon type I (e.g., IFN-α such as PEGylated IFN-α, IFN-β, IFN-κ, IFN-δ, IFN-ε, IFN-τ, IFN-ω, and IFN-ζ), interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine, pharmaceutically acceptable salts thereof, stereoisomers thereof, derivatives thereof, analogs thereof, and mixtures thereof.

B. Cationic Lipids

Any of the cationic lipids of Formula I-XVI or salts thereof as set forth herein may be used in the lipid particles of the present invention (e.g., SNALP), either alone or in combination with one or more other cationic lipid species or non-cationic lipid species. The cationic lipids include the (R) and/or (S) enantiomers thereof.

In some embodiments, the cationic lipid comprises a racemic mixture. In other embodiments, the cationic lipid comprises a mixture of one or more diastereomers. In certain embodiments, the cationic lipid is enriched in one enantiomer, such that the cationic lipid comprises at least about 55%, 60%, 65%, 70%, 75%, 80%, 85%, 90%, or 95% enantiomeric excess. In certain other embodiments, the cationic lipid is enriched in one diastereomer, such that the cationic lipid comprises at least about 55%, 60%, 65%, 70%, 75%, 80%, 85%, 90%, or 95% diastereomeric excess. In certain additional embodiments, the cationic lipid is chirally pure (e.g., comprises a single optical isomer). In further embodiments, the cationic lipid is enriched in one optical isomer (e.g., an optically active isomer), such that the cationic lipid comprises at least about 55%, 60%, 65%, 70%, 75%, 80%, 85%, 90%, or 95% isomeric excess. The present invention provides the synthesis of the cationic lipids of Formulas I-XVI as a racemic mixture or in optically pure form.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids.

The term "salts" includes any anionic and cationic complex, such as the complex formed between a cationic lipid disclosed herein and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" mean that, when substituted, at least one hydrogen atom is replaced with a substituent. In the case of an oxo substituent (=O), two hydrogen atoms are replaced. In this regard, substituents include, but are not limited to, oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, R$^x$ and R$^y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$. The term "optionally substituted," when used before a list of substituents, means that each of the substituents in the list may be optionally substituted as described herein.

The term "halogen" includes fluoro, chloro, bromo, and iodo.

In one aspect, cationic lipids of Formula I having the following structure (or salts thereof) are useful in the present invention:

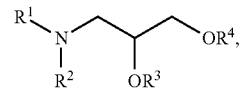

(I)

wherein R$^1$ and R2 are either the same or different and are independently H or an optionally substituted C$_1$-C$_6$ alkyl, C$_2$-C$_6$ alkenyl, or C$_2$-C$_6$ alkynyl, or R$^1$ and R2 may join to form an optionally substituted heterocyclic ring of 4 to 6 carbon atoms and 1 or 2 heteroatoms chosen from nitrogen and oxygen; R3 and R4 are either the same or different and are independently an optionally substituted C$_{12}$-C$_{24}$ alkyl, C$_{12}$-C$_{24}$ alkenyl, C$_{12}$-C$_{24}$ alkynyl, or C$_{12}$-C$_{24}$ acyl; and at least one of R3 and R4 comprises at least two sites of unsaturation.

In some embodiments, R$^1$ and R$^2$ are independently an optionally substituted C$_1$-C$_4$ alkyl, C$_2$-C$_4$ alkenyl, or C$_2$-C$_4$ alkynyl. In a preferred embodiment, R$^1$ and R$^2$ are both methyl groups.

In other embodiments, R$^3$ and R$^4$ are independently an optionally substituted C$_{12}$-C$_{24}$, C$_{12}$-C$_{22}$, C$_{12}$-C$_{20}$, C$_{14}$-C$_{24}$, C$_{14}$-C$_{22}$, C$_{14}$-C$_{20}$, C$_{16}$-C$_{24}$, C$_{16}$-C$_{22}$, or C$_{16}$-C$_{20}$ alkyl, alkenyl, alkynyl, or acyl group (i.e., C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, or C$_{24}$ alkyl, alkenyl, alkynyl, or acyl group). In certain embodiments, at least one or both R$^3$ and R$^4$ independently comprises at least 2, 3, 4, 5, or 6 sites of unsaturation (e.g., 2, 3, 4, 5, 6, 2-3, 2-4, 2-5, or 2-6 sites of unsaturation). In certain instances, R$^3$ and R$^4$ may independently comprise a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, R$^3$ and R$^4$ are both linoleyl moieties. In other instances, the octadecatrienyl moiety is a linolenyl moiety or a γ-linolenyl moiety. In particular embodiments, R$^3$ and R$^4$ are both linolenyl moieties or γ-linolenyl moieties. In certain instances, R$^3$ and R$^4$ are different, e.g., R$^3$ is a tetradectrienyl (C$_{14}$) and R$^4$ is linoleyl (C$_{18}$). In a preferred embodiment, the cationic lipid of Formula I is symmetrical, i.e., R$^3$ and R$^4$ are both the same. In further embodiments, the double bonds present in one or both R$^3$ and R$^4$ may be in the cis and/or trans configuration.

In some groups of embodiments to the cationic lipids of Formula I, R$^3$ and R$^4$ are either the same or different and are independently selected from the group consisting of:

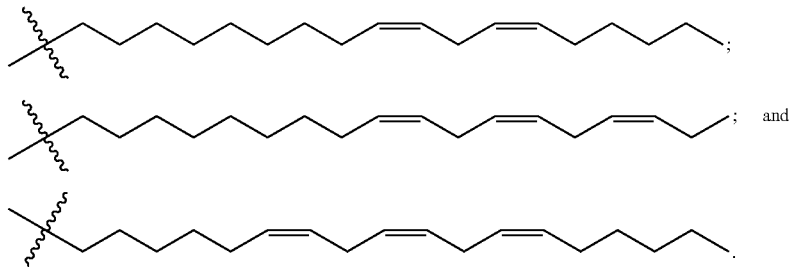

In particular embodiments, the cationic lipid of Formula I comprises 1,2-dilinoleyloxy-N,N-dimethylaminopropane (DLinDMA), 1,2-dilinolenyloxy-N,N-dimethylaminopropane (DLenDMA), or mixtures thereof.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

In another aspect, cationic lipids of Formula II having the following structure (or salts thereof) are useful in the present invention:

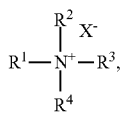

(II)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradectrienyl ($C_{14}$) and $R^4$ is linoleyl ($C_{18}$). In a preferred embodiment, the cationic lipid of Formula II is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

The synthesis of cationic lipids such as DLinDMA and DLenDMA, as well as additional cationic lipids falling within the scope of Formulas I and II, is described in U.S. Patent Publication No. 20060083780, the disclosure of which is herein incorporated by reference in its entirety for all purposes.

In yet another aspect, cationic lipids of Formula III having the following structure (or salts thereof) are useful in the present invention:

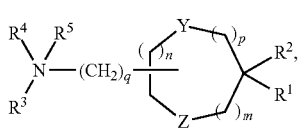

(III)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alky- nyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^3$ and $R^4$ are independently an optionally substituted $C_1$-$C_4$ alkyl, $C_2$-$C_4$ alkenyl, or $C_2$-$C_4$ alkynyl. In a preferred embodiment, $R^3$ and $R^4$ are both methyl groups. In one embodiment, q is 1 or 2. In another embodiment, q is 1-2, 1-3, 1-4, 2-3, or 2-4. In further embodiments, $R^5$ is absent when the pH is above the $pK_a$ of the cationic lipid and $R^5$ is hydrogen when the pH is below the $pK_a$ of the cationic lipid such that the amino head group is protonated. In an alternative embodiment, $R^5$ is an optionally substituted $C_1$-$C_4$ alkyl to provide a quaternary amine. In additional embodiments, Y and Z are both O.

In other embodiments, $R^1$ and $R^2$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^1$ and $R^2$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^1$ and $R^2$ are both linoleyl moieties. In other instances, the octadecatrienyl moiety is a linolenyl moiety or a γ-linolenyl moiety. In particular embodiments, $R^1$ and $R^2$ are both linolenyl moieties or γ-linolenyl moieties.

In embodiments where one or both $R^1$ and $R^2$ independently comprises at least 1, 2, 3, 4, 5, or 6 sites of unsaturation, the double bonds present in one or both $R^1$ and $R^2$ may be in the cis and/or trans configuration. In certain instances, $R^1$ and $R^2$ are both the same, e.g., 1e and $R^2$ are both linoleyl ($C_{18}$) moieties, etc. In certain other instances, $R^1$ and $R^2$ are different, e.g., $R^1$ is a tetradectrienyl ($C_{14}$) moiety and $R^2$ is a linoleyl ($C_{18}$) moiety. In a preferred embodiment, the cationic lipid of Formula III is symmetrical, i.e., $R^1$ and $R^2$ are both the same. In another preferred embodiment, at least one or both $R^1$ and $R^2$ comprises at least two sites of unsaturation (e.g., 2, 3, 4, 5, 6, 2-3, 2-4, 2-5, or 2-6 sites of unsaturation).

In embodiments where one or both $R^1$ and $R^2$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, $R^1$ and $R^2$ are both phytanyl moieties.

In some groups of embodiments to the cationic lipids of Formula III, $R^1$ and $R^2$ are either the same or different and are independently selected from the group consisting of:

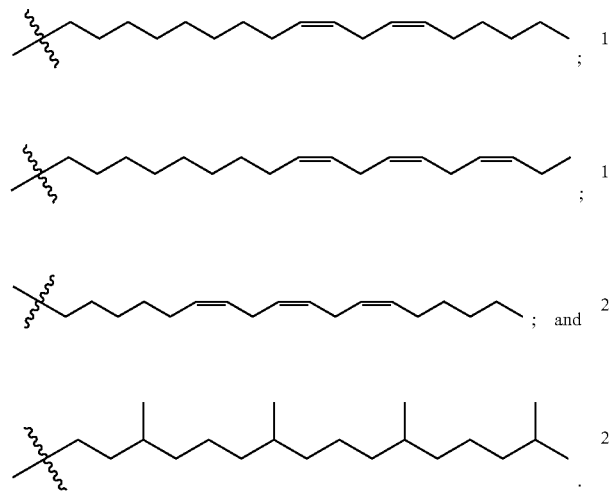

In certain embodiments, cationic lipids falling within the scope of Formula III include, but are not limited to, the following: 2,2-dilinoleyl-4-(2-dimethylaminoethyl)-[1,3]-dioxolane (DLin-K-C2-DMA; "XTC2" or "C2K"), 2,2-dilinoleyl-4-dimethylaminomethyl-[1,3]-dioxolane (DLin-K-DMA), 2,2-dilinoleyl-4-(3-dimethylaminopropyl)[1,3]-dioxolane (DLin-K-C3-DMA; "C3K"), 2,2-dilinoleyl-4-(4-dimethylaminobutyl)[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis(dimethylaminomethyl)[1,3]-dioxolane (DLin-K2-DMA), 2,2-dilinoleyl-4-methylpiperzine-[1,3]-dioxolane (D-Lin-K—N-methylpiperzine), DLen-C2K-DMA, γ-DLen-C2K-DMA, DPan-C2K-DMA, DPan-C3K-DMA, or mixtures thereof. In preferred embodiments, the cationic lipid of Formula III comprises DLin-K-C2-DMA and/or DLin-K-DMA.

In some embodiments, the cationic lipids of Formula III form a salt (preferably a crystalline salt) with one or more anions. In one particular embodiment, the cationic lipid of Formula III is the oxalate (e.g., hemioxalate) salt thereof, which is preferably a crystalline salt.

The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.Cl, DLin-K2-DMA, D-Lin-K—N-methylpiperzine, as well as additional cationic lipids, is described in PCT Publication No. WO 2010/042877, the disclosure of which is incorporated herein by reference in its entirety for all purposes.

The synthesis of cationic lipids such as DLin-K-DMA, as well as additional cationic lipids, is described in PCT Publication No. WO 09/086558, the disclosure of which is herein incorporated by reference in its entirety for all purposes.

In a preferred embodiment, cationic lipids of Formula IV having the following structure (or salts thereof) are useful in the present invention:

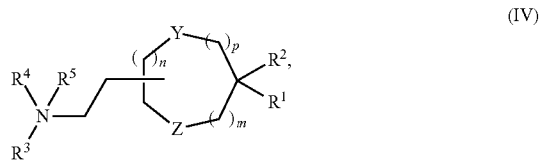

(IV)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; and Y and Z are either the same or different and are independently O, S, or NH.

In some embodiments, $R^3$ and $R^4$ are independently an optionally substituted $C_1$-$C_4$ alkyl, $C_2$-$C_4$ alkenyl, or $C_2$-$C_4$ alkynyl. In a preferred embodiment, $R^3$ and $R^4$ are both methyl groups. In further embodiments, $R^5$ is absent when the pH is above the $pK_a$ of the cationic lipid and $R^5$ is hydrogen when the pH is below the $pK_a$ of the cationic lipid such that the amino head group is protonated. In an alternative embodiment, $R^5$ is an optionally substituted $C_1$-$C_4$ alkyl to provide a quaternary amine. In additional embodiments, Y and Z are both O.

In other embodiments, $R^1$ and $R^2$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^1$ and $R^2$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^1$ and $R^2$ are both linoleyl moieties. In other instances, the octadecatrienyl moiety is a linolenyl moiety or a γ-linolenyl moiety. In particular embodiments, $R^1$ and $R^2$ are both linolenyl moieties or γ-linolenyl moieties.

In embodiments where one or both $R^1$ and $R^2$ independently comprises at least 1, 2, 3, 4, 5, or 6 sites of unsaturation, the double bonds present in one or both $R^1$ and $R^2$ may be in the cis and/or trans configuration. In certain instances, $R^1$ and $R^2$ are both the same, e.g., $R^1$ and $R^2$ are both linoleyl ($C_{18}$) moieties, etc. In certain other instances, $R^1$ and $R^2$ are different, e.g., $R^1$ is a tetradectrienyl ($C_{14}$) moiety and $R^2$ is a linoleyl ($C_{18}$) moiety. In a preferred embodiment, the cationic lipid of Formula IV is symmetrical, i.e., $R^1$ and $R^2$ are both the same. In another preferred embodiment, at least one or both $R^1$ and $R^2$ comprises at least two sites of unsaturation (e.g., 2, 3, 4, 5, 6, 2-3, 2-4, 2-5, or 2-6 sites of unsaturation).

anions. In one particular embodiment, the cationic lipid of Formula IV is the oxalate (e.g., hemioxalate) salt thereof, which is preferably a crystalline salt.

The synthesis of DLin-K-C2-DMA (C2K) is described in PCT Publication No. WO 2010/042877, the disclosure of which is incorporated herein by reference in its entirety for all purposes.

In a further aspect, cationic lipids of Formula V having the following structure are useful in the present invention:

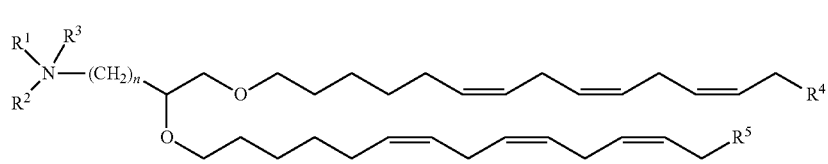

(V)

In embodiments where one or both $R^1$ and $R^2$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, $R^1$ and $R^2$ are both phytanyl moieties.

In some groups of embodiments to the cationic lipids of Formula IV, $R^1$ and $R^2$ are either the same or different and are independently selected from the group consisting of:

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either absent or present and when present are either the same or different and are independently an optionally substituted $C_1$-$C_{10}$ alkyl or $C_2$-$C_{10}$ alkenyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, $R^4$ and $R^5$ are both butyl groups. In yet another preferred embodiment,

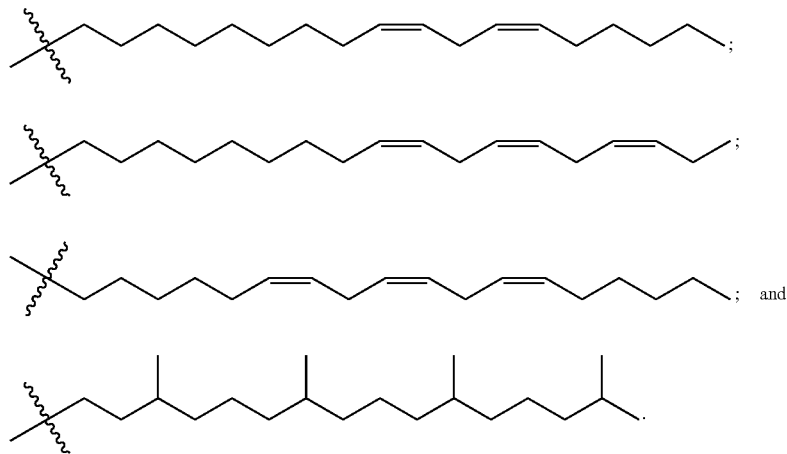

In certain embodiments, cationic lipids falling within the scope of Formula IV include, but are not limited to, the following: 2,2-dilinoleyl-4-(2-dimethylaminoethyl)-[1,3]-dioxolane (DLin-K-C2-DMA; "XTC2" or "C2K"), DLen-C2K-DMA, γ-DLen-C2K-DMA, DPan-C2K-DMA, or mixtures thereof. In preferred embodiments, the cationic lipid of Formula IV comprises DLin-K-C2-DMA.

In some embodiments, the cationic lipids of Formula IV form a salt (preferably a crystalline salt) with one or more n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_2$-$C_6$ or $C_2$-$C_4$ alkyl or $C_2$-$C_6$ or $C_2$-$C_4$ alkenyl.

In an alternative embodiment, the cationic lipid of Formula V comprises ester linkages between the amino head group and one or both of the alkyl chains. In some embodiments, the cationic lipid of Formula V forms a salt (preferably a crystalline salt) with one or more anions. In one particular embodiment, the cationic lipid of Formula V is the oxalate (e.g., hemioxalate) salt thereof, which is preferably a crystalline salt.

Although each of the alkyl chains in Formula V contains cis double bonds at positions 6, 9, and 12 (i.e., cis,cis,cis-$\Delta^6$, $\Delta^9$, $\Delta^{12}$) in an alternative embodiment, one, two, or three of these double bonds in one or both alkyl chains may be in the trans configuration.

In a particularly preferred embodiment, the cationic lipid of Formula V has the structure:

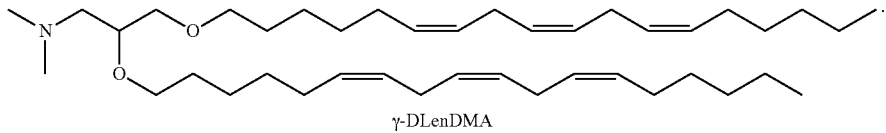 [SMILES: CCCCC/C=C\C/C=C\C/C=C\CCCCCOCC(CN(C)C)OCCCCC/C=C\C/C=C\C/C=C\CCCCC]

γ-DLenDMA below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl (3,7,11,15-tetramethyl-hexadecanyl) moiety. In other preferred embodiments, $R^4$ and $R^5$ are both phytanyl moieties.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $c_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl (3,7, 11,15-tetramethyl-hexadecanoyl) moiety.

In embodiments where at least one of $R^4$ and $R^5$ comprises at least three sites of unsaturation, the double bonds present in one or both alkyl chains may be in the cis and/or trans configuration. In some embodiments, $R^4$ and $R^5$ are independently selected from the group consisting of a dodecatrienyl moiety, a tetradectrienyl moiety, a hexadecatrienyl moiety, an octadecatrienyl moiety, an icosatrienyl moiety, and a phytanyl moiety, as well as acyl derivatives thereof (e.g., linolenoyl, γ-linolenoyl, phytanoyl, etc.). In certain instances, the octadecatrienyl moiety is a linolenyl moiety or a γ-linolenyl moiety. In preferred embodiments, $R^4$ and $R^5$ are both linolenyl moieties or γ-linolenyl moieties. In particular embodiments, $R^4$ and $R^5$ independently comprise a backbone of from about 16 to about 22 carbon atoms, and one or both of $R^4$ and $R^5$ independently comprise at least three, four, five, or six sites of unsaturation.

In some embodiments, the cationic lipid of Formula VI forms a salt (preferably a crystalline salt) with one or more anions. In one particular embodiment, the cationic lipid of Formula VI is the oxalate (e.g., hemioxalate) salt thereof, which is preferably a crystalline salt.

In another aspect, cationic lipids of Formula VI having the following structure are useful in the present invention:

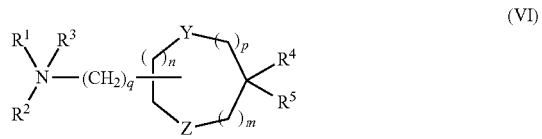

(VI)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least three sites of unsaturation or a substituted $C_{12}$-$C_{24}$ alkyl; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In other embodiments, $R^3$ is absent when the pH is above the $pK_a$ of the cationic lipid and $R^3$ is hydrogen when the pH is In a particularly preferred embodiment, the cationic lipid of Formula VI has a structure selected from the group consisting of:

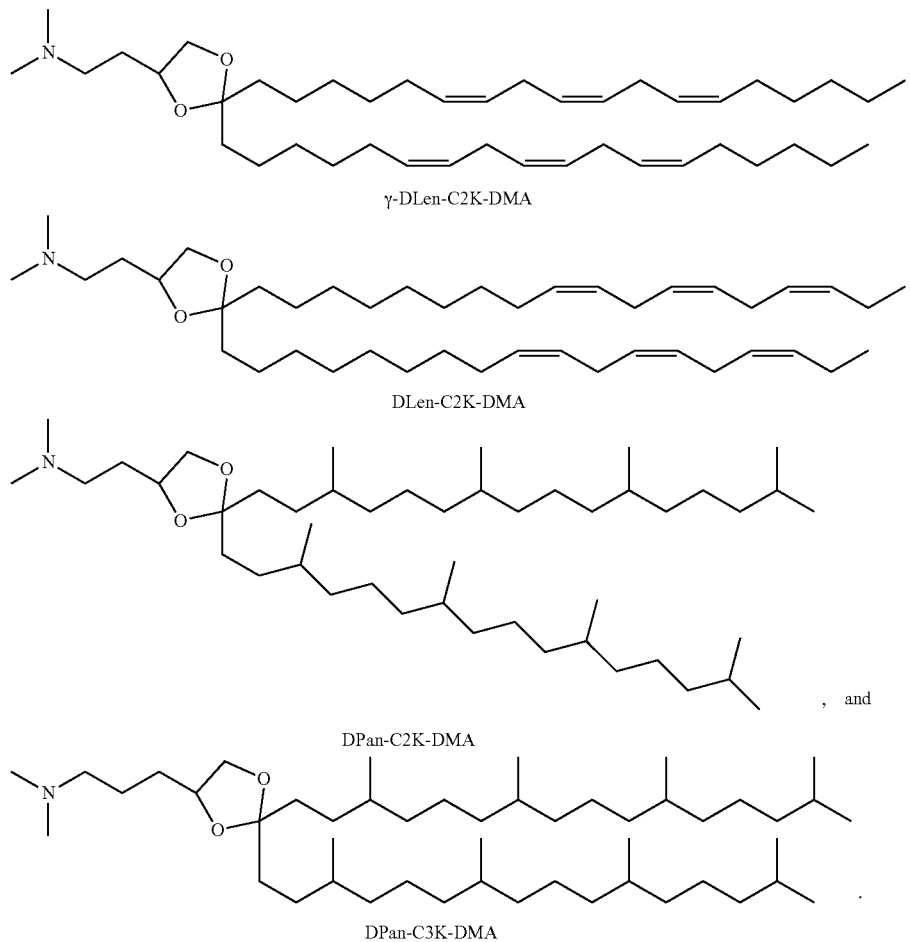

γ-DLen-C2K-DMA,

DLen-C2K-DMA,

DPan-C2K-DMA, and

DPan-C3K-DMA.

In yet another aspect, cationic lipids of Formula VII having the following structure are useful in the present invention:

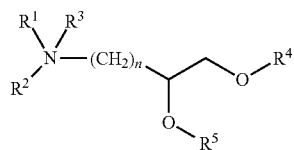

(VII)

or salts thereof, wherein: $R^1$ and $R^2$ are joined to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^1$ and $R^2$ are joined to form a heterocyclic ring of 5 carbon atoms and 1 nitrogen atom. In certain instances, the heterocyclic ring is substituted with a substituent such as a hydroxyl group at the ortho, meta, and/or para positions. In a preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula VII forms a salt (preferably a crystalline salt) with one or more anions. In one particular embodiment, the cationic lipid of Formula VII is the oxalate (e.g., hemioxalate) salt thereof, which is preferably a crystalline salt.

In a particularly preferred embodiment, the cationic lipid of Formula VII has a structure selected from the group consisting of:

methyl groups. In another preferred embodiment, n is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary

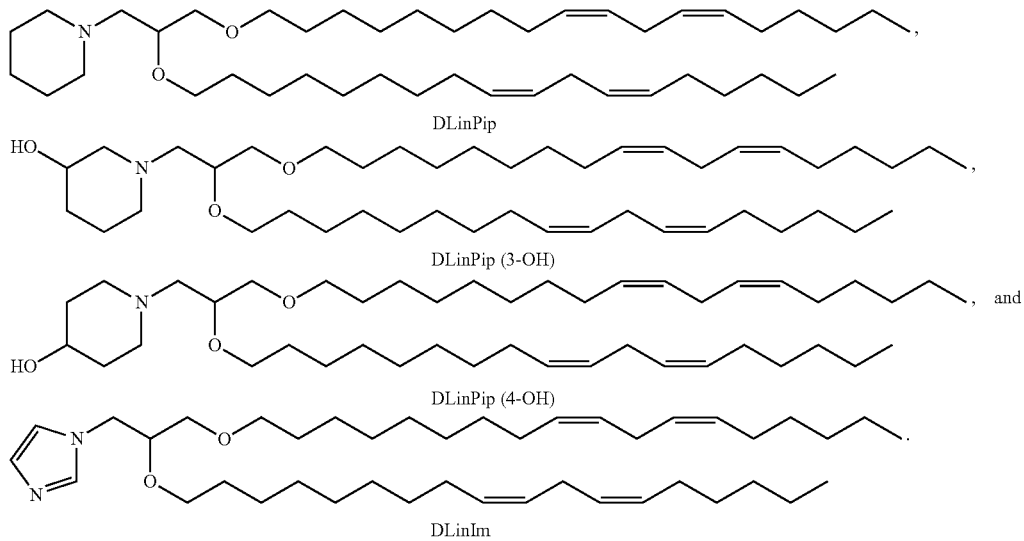

In still yet another aspect, cationic lipids of Formula VIII having the following structure are useful in the present invention:

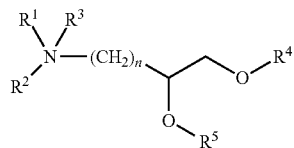

(VIII)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula VIII forms a salt (preferably a crystalline salt) with one or more anions. In one particular embodiment, the cationic lipid of Formula VIII is the oxalate (e.g., hemioxalate) salt thereof, which is preferably a crystalline salt.

In a particularly preferred embodiment, the cationic lipid of Formula VIII has a structure selected from the group consisting of:

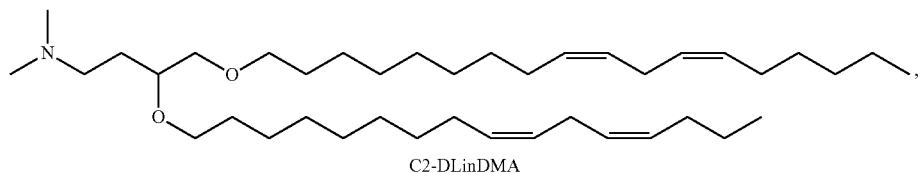

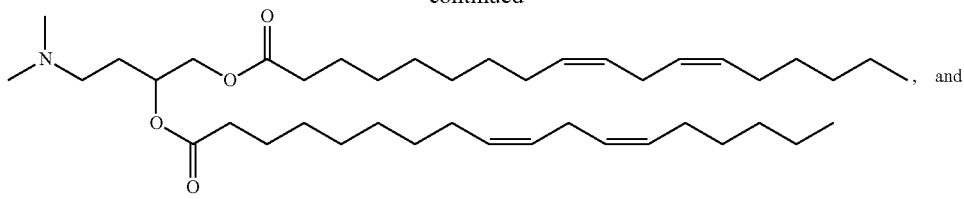

, and

C2-DLinDAP

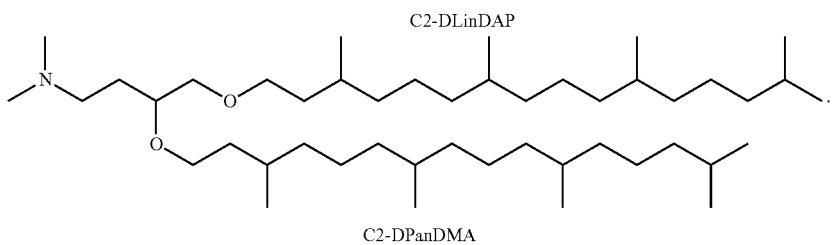

C2-DPanDMA

In another aspect, cationic lipids of Formula IX having the following structure are useful in the present invention:

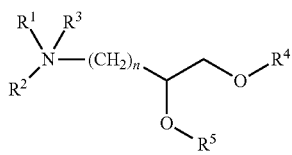

(IX)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl.

In some embodiments, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In certain instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl.

In other embodiments, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In particular embodiments, $R^4$ is a linoleyl moiety, and $R^5$ is a $C_6$ alkyl moiety, a $C_6$ alkenyl moiety, an octadecyl moiety, an oleyl moiety, a linolenyl moiety, a γ-linolenyl moiety, or a phytanyl moiety. In other embodiments, one of $R^4$ or $R^5$ is a phytanyl moiety.

In some embodiments, the cationic lipid of Formula IX forms a salt (preferably a crystalline salt) with one or more anions. In one particular embodiment, the cationic lipid of Formula IX is the oxalate (e.g., hemioxalate) salt thereof, which is preferably a crystalline salt.

In a particularly preferred embodiment, the cationic lipid of Formula IX is an asymmetric lipid having a structure selected from the group consisting of:

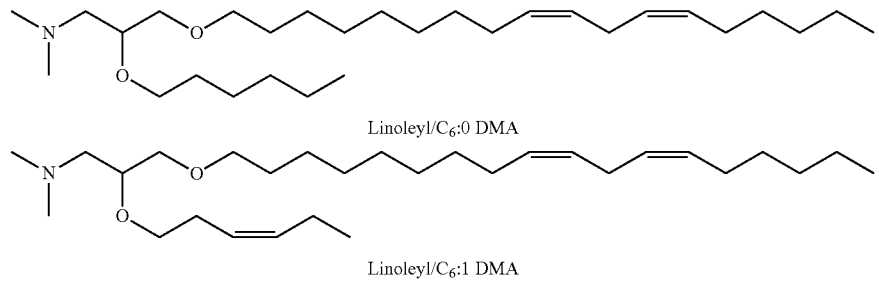

Linoleyl/$C_6$:0 DMA

Linoleyl/$C_6$:1 DMA

-continued

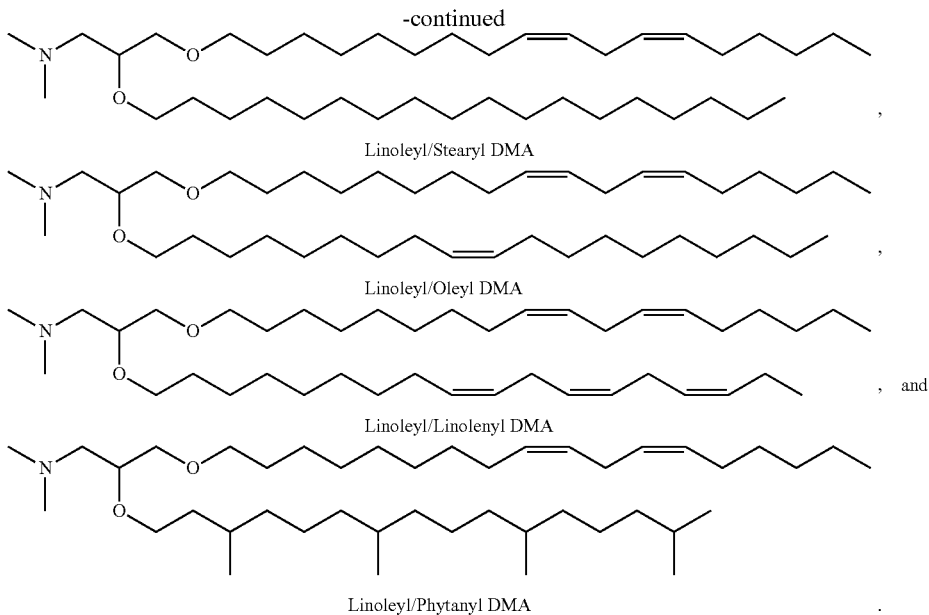

Linoleyl/Stearyl DMA

Linoleyl/Oleyl DMA

Linoleyl/Linolenyl DMA , and

Linoleyl/Phytanyl DMA

In yet another aspect, cationic lipids of Formula X having the following structure are useful in the present invention:

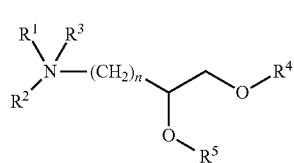

(X)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least four sites of unsaturation or a substituted $C_{12}$-$C_{24}$ alkyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl (3,7,11,15-tetramethyl-hexadecanyl) moiety.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl (3,7,11,15-tetramethyl-hexadecanoyl) moiety.

In embodiments where at least one of $R^4$ and $R^5$ comprises at least four sites of unsaturation, the double bonds present in one or both alkyl chains may be in the cis and/or trans configuration. In a particular embodiment, $R^4$ and $R^5$ independently comprise four, five, or six sites of unsaturation. In some instances, $R^4$ comprises four, five, or six sites of unsaturation and $R^5$ comprises zero, one, two, three, four, five, or six sites of unsaturation. In other instances, $R^4$ comprises zero, one, two, three, four, five, or six sites of unsaturation and $R^5$ comprises four, five, or six sites of unsaturation. In a preferred embodiment, both $R^4$ and $R^5$ comprise four, five, or six sites of unsaturation. In particular embodiments, $R^4$ and $R^5$ independently comprise a backbone of from about 18 to about 24 carbon atoms, and one or both of $R^4$ and $R^5$ independently comprise at least four, five, or six sites of unsaturation.

In some embodiments, the cationic lipid of Formula X forms a salt (preferably a crystalline salt) with one or more anions. In one particular embodiment, the cationic lipid of Formula X is the oxalate (e.g., hemioxalate) salt thereof, which is preferably a crystalline salt.

In a particularly preferred embodiment, the cationic lipid of Formula X has a structure selected from the group consisting of:

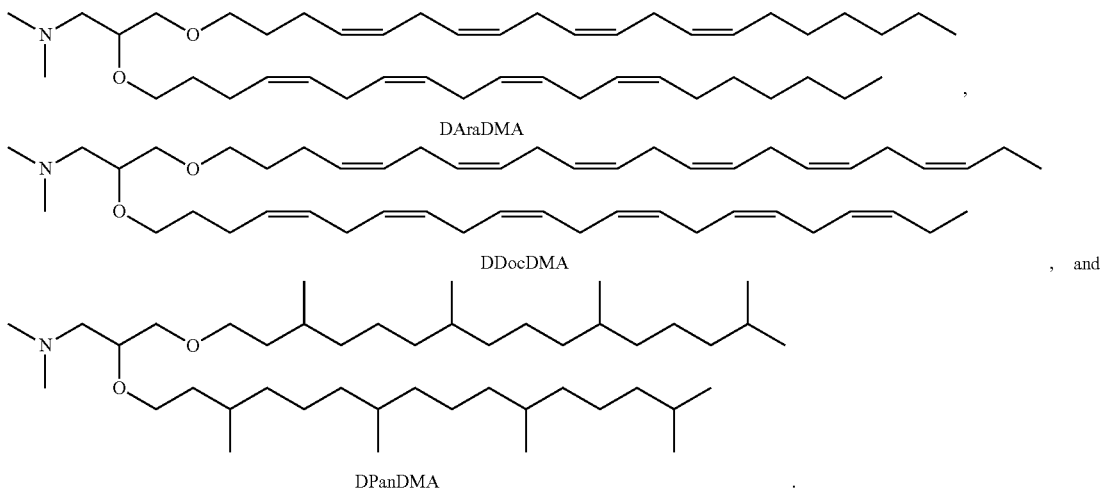

In still yet another aspect, cationic lipids of Formula XI having the following structure are useful in the present invention:

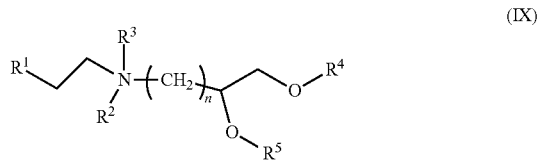

(IX)

or salts thereof, wherein: $R^1$ is hydrogen (H) or —$(CH_2)_q$—$NR^6R^7R^8$, wherein: $R^6$ and $R^7$ are either the same or different and are independently an optionally substituted $C_1$-$C_6$ alkyl, $C_2$-$C_6$ alkenyl, or $C_2$-$C_6$ alkynyl, or $R^6$ and $R^7$ may join to form an optionally substituted heterocyclic ring of 4 to 6 carbon atoms and 1 or 2 heteroatoms selected from the group consisting of nitrogen (N), oxygen (O), and mixtures thereof; $R^8$ is either absent or is hydrogen (H) or a $C_1$-$C_6$ alkyl to provide a quaternary amine; and q is 0, 1, 2, 3, or 4; $R^2$ is an optionally substituted $C_1$-$C_6$ alkyl, $C_2$-$C_6$ alkenyl, or $C_2$-$C_6$ alkynyl; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^2$ is an optionally substituted $C_1$-$C_4$ alkyl, $C_2$-$C_4$ alkenyl, or $C_2$-$C_4$ alkynyl. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In certain embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In further embodiments, $R^6$ and $R^7$ are independently an optionally substituted $C_1$-$C_4$ alkyl, $C_2$-$C_4$ alkenyl, or $C_2$-$C_4$ alkynyl. In other embodiments, $R^8$ is absent when the pH is above the $pK_a$ of the cationic lipid and $R^8$ is hydrogen when the pH is below the $pK_a$ of the cationic lipid such that the amino head group is protonated. In an alternative embodiment, $R^8$ is an optionally substituted $C_1$-$C_4$ alkyl to provide a quaternary amine.

In a preferred embodiment, $R^1$ is hydrogen and $R^2$ is an ethyl group. In another preferred embodiment, $R^6$ and $R^7$ are both methyl groups. In certain instances, n is 1. In certain other instances, q is 1.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula XI forms a salt (preferably a crystalline salt) with one or more anions. In one particular embodiment, the cationic lipid of Formula XI is the oxalate (e.g., hemioxalate) salt thereof, which is preferably a crystalline salt.

In a particularly preferred embodiment, the cationic lipid of Formula XI has a structure selected from the group consisting of:

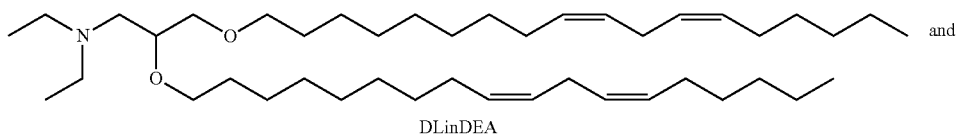

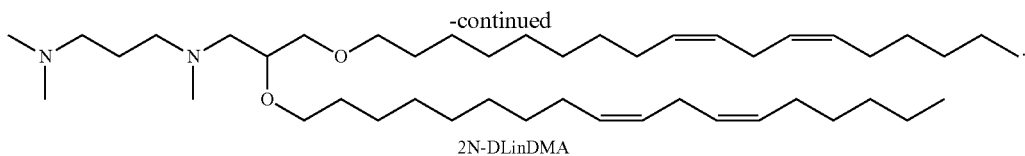

2N-DLinDMA

In another aspect, cationic lipids of Formula XII having the following structure are useful in the present invention:

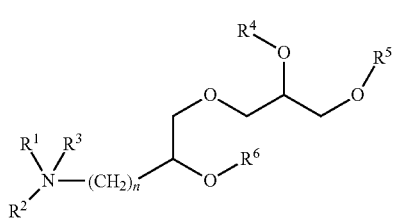

(XII)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$, $R^5$, and $R^6$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the pK$_a$ of the cationic lipid and $R^3$ is hydrogen when the pH is below the pK$_a$ of the cationic lipid such that the amino head group is protonated. In an alternative embodiment, $R^3$ is an optionally substituted $C_1$-$C_4$ alkyl to provide a quaternary amine. In further embodiments, $R^4$, $R^5$, and $R^6$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$, $R^5$, and $R^6$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$, $R^5$, and $R^6$ are all linoleyl moieties, linolenyl moieties, γ-linolenyl moieties, or phytanyl moieties.

In some embodiments, the cationic lipid of Formula XII forms a salt (preferably a crystalline salt) with one or more anions. In one particular embodiment, the cationic lipid of Formula XII is the oxalate (e.g., hemioxalate) salt thereof, which is preferably a crystalline salt.

In a particularly preferred embodiment, the cationic lipid of Formula XII has a structure selected from the group consisting of:

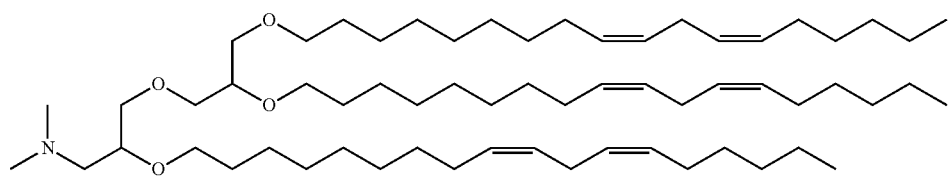

TLinDMA

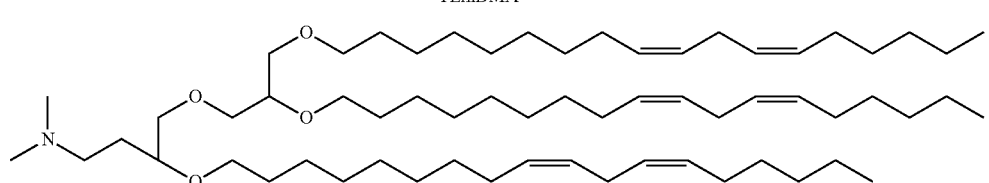

C2-TLinDMA , and

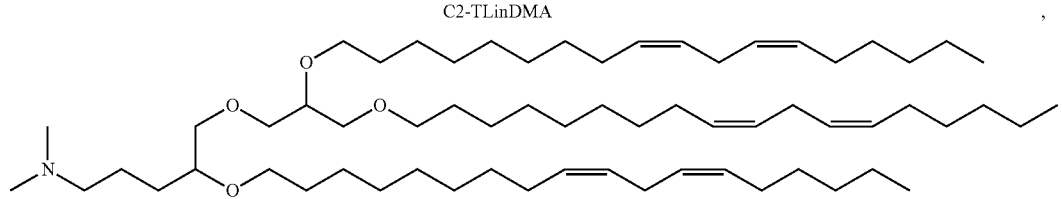

C3-TLinDMA

In yet another aspect, cationic lipids of Formula XIII having the following structure are useful in the present invention:

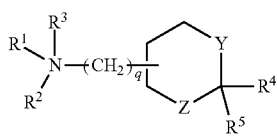

(XIII)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; q is 0, 1, 2, 3, or 4; and Y and Z are either the same or different and are independently O, S, or NH, wherein if q is 1, $R^1$ and $R^2$ are both methyl groups, $R^4$ and $R^5$ are both linoleyl moieties, and Y and Z are both 0, then the alkylamino group is attached to one of the two carbons adjacent to Y or Z (i.e., at the '4' or '6' position of the 6-membered ring).

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In a particular embodiments, Y and Z are both oxygen (O). In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In other embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

The alkylamino head group of Formula XIII may be attached to the '4' or '5' position of the 6-membered ring as shown below in an exemplary embodiment wherein $R^1$ and $R^2$ are both methyl groups:

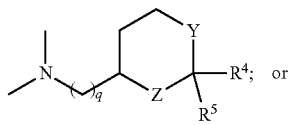

Head Group at '4' Position

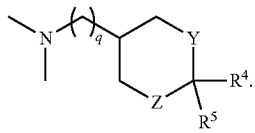

Head Group at '5' Position

In further embodiments, the 6-membered ring of Formula XIII may be substituted with 1, 2, 3, 4, or 5 independently selected $C_1$-$C_6$ alkyl, $C_2$-$C_6$ alkenyl, $C_2$-$C_6$ alkynyl, $C_1$-$C_6$ alkoxyl, or hydroxyl substituents. In one particular embodiment, the 6-membered ring is substituted with 1, 2, 3, 4, or 5 independently selected $C_1$-$C_4$ alkyl (e.g., methyl, ethyl, propyl, or butyl) substituents. An exemplary embodiment of a cationic lipid of Formula XIII having a substituted 6-membered ring (methyl group attached to the '4' position) and wherein $R^1$ and $R^2$ are both methyl groups is shown below:

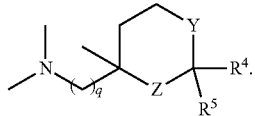

In particular embodiments, the cationic lipids of Formula XIII may be synthesized using 2-hydroxymethyl-1,4-butanediol and 1,3,5-pentanetriol (or 3-methyl-1,3,5-pentanetriol) as starting materials.

In some embodiments, the cationic lipid of Formula XIII forms a salt (preferably a crystalline salt) with one or more anions. In one particular embodiment, the cationic lipid of Formula XIII is the oxalate (e.g., hemioxalate) salt thereof, which is preferably a crystalline salt.

In a particularly preferred embodiment, the cationic lipid of Formula XIII has the structure:

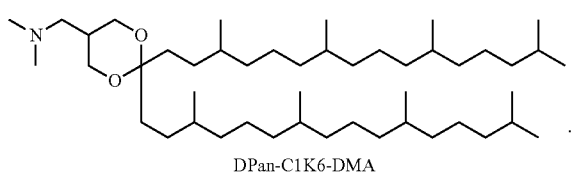 [SMILES: CC(C)CCCC(C)CCCC(C)CCCC(C)CCC1(CCC(C)CCCC(C)CCCC(C)CCCC(C)C)OCC(CN(C)C)CO1]

DPan-C1K6-DMA

In still yet another aspect, the present invention provides a cationic lipid of Formula XIV having the following structure:

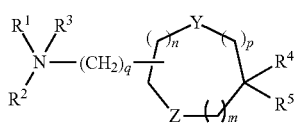

(XIV)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least one site of unsaturation in the trans (F) configuration; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, at least one of $R^4$ and $R^5$ further comprises one, two, three, four, five, six, or more sites of unsaturation in the cis and/or trans configuration. In some instances, $R^4$ and $R^5$ are independently selected from any of the substituted or unsubstituted alkyl or acyl groups described herein, wherein at least one or both of $R^4$ and $R^5$ comprises at least one, two, three, four, five, or six sites of unsaturation in the trans configuration. In one particular embodiment, $R^4$ and $R^5$ independently comprise a backbone of from about 12 to about 22 carbon atoms (e.g., 12, 13, 14, 15, 16, 17, 18, 19, 20, 21, or 22 carbon atoms), and one or both of $R^4$ and $R^5$ independently comprise at least one, two, three, four, five, or six sites of unsaturation in the trans configuration. In some preferred embodiments, at least one of $R^4$ and $R^5$ comprises an (E)-heptadeceyl moiety. In other preferred embodiments, $R^4$ and $R^5$ are both (E)-8-heptadeceyl moieties.

In some embodiments, the cationic lipid of Formula XIV forms a salt (preferably a crystalline salt) with one or more anions. In one particular embodiment, the cationic lipid of Formula XIV is the oxalate (e.g., hemioxalate) salt thereof, which is preferably a crystalline salt.

In a particularly preferred embodiment, the cationic lipid of Formula XIV has the structure:

In another aspect, the present invention provides a cationic lipid of Formula XV having the following structure:

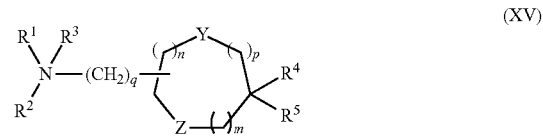

or salts thereof, wherein: $R^1$ and $R^2$ are joined to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are joined to form a heterocyclic ring of 5 carbon atoms and 1 nitrogen atom. In certain instances, the heterocyclic ring is substituted with a substituent such as a hydroxyl group at the ortho, meta, and/or para positions. In a preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

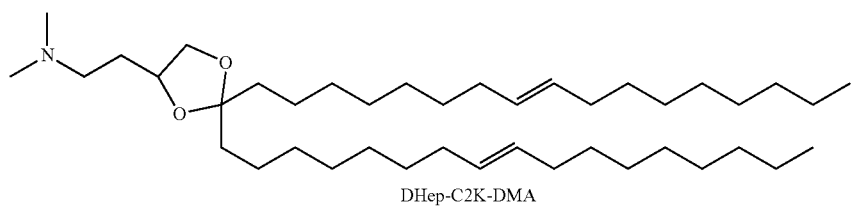 [SMILES: CCCCCCCC/C=C/CCCCCCCC1(CCCCCCC/C=C/CCCCCCCC)OCC(CCN(C)C)O1]

DHep-C2K-DMA

In some embodiments, the cationic lipid of Formula XV forms a salt (preferably a crystalline salt) with one or more anions. In one particular embodiment, the cationic lipid of Formula XV is the oxalate (e.g., hemioxalate) salt thereof, which is preferably a crystalline salt.

In a particularly preferred embodiment, the cationic lipid of Formula XV has the structure:

another particular embodiment, n is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine.

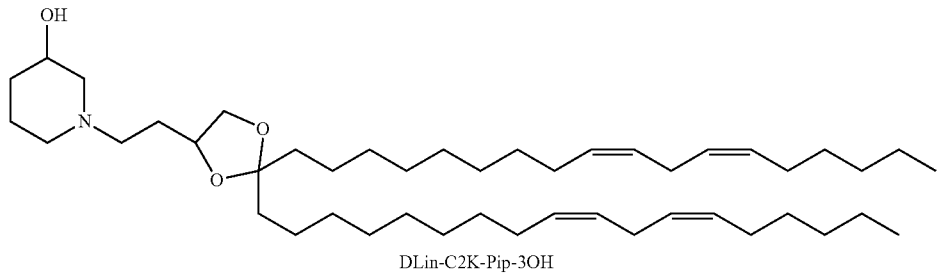 [SMILES: CCCCC/C=C\C/C=C\CCCCCCCCC1(CCCCCCCC/C=C\C/C=C\CCCCC)OCC(CCN2CCCC(O)C2)O1]

DLin-C2K-Pip-3OH

In yet another aspect, the present invention provides a cationic lipid of Formula XVI having the following structure:

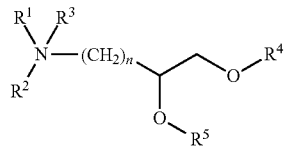

(XVI)

or salts thereof, wherein:
  $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;
  $R^3$ is either absent or is hydrogen (H) or a $C_1$-$C_6$ alkyl to provide a quaternary amine;
  $R^4$ and $R^5$ are either the same or different and are independently a substituted $C_{12}$-$C_{24}$ alkyl; and
  n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In one particular embodiment, n is 1. In In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl (3,7,11,15-tetramethyl-hexadecanyl) moiety. In particular embodiments, $R^4$ and $R^5$ are both phytanyl moieties.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl (3,7,11,15-tetramethyl-hexadecanoyl) moiety. In particular embodiments, $R^4$ and $R^5$ are both phytanoyl moieties.

In some embodiments, the cationic lipid of Formula XVI forms a salt (preferably a crystalline salt) with one or more anions. In one particular embodiment, the cationic lipid of Formula XVI is the oxalate (e.g., hemioxalate) salt thereof, which is preferably a crystalline salt.

In a particularly preferred embodiment, the cationic lipid of Formula XVI has a structure selected from the group consisting of:

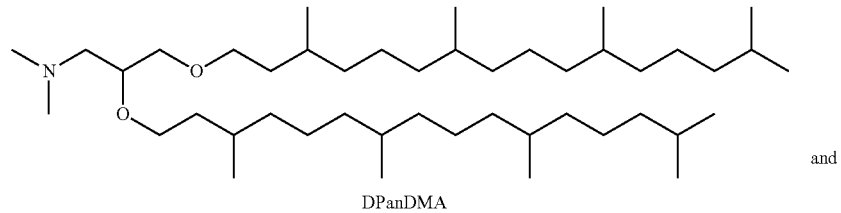

and

DPanDMA

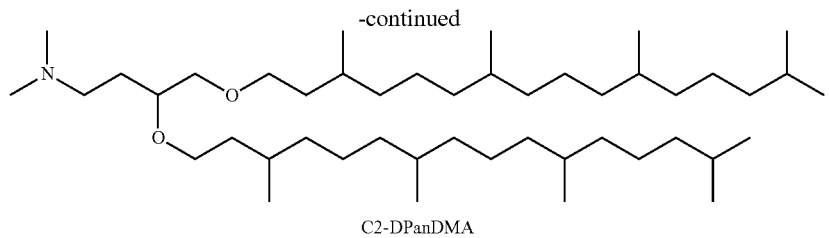

C2-DPanDMA

The synthesis of cationic lipids of Formulas V-XVI is described herein and in PCT Application No. PCT/CA2010/_____, entitled "Improved Cationic Lipids and Methods for the Delivery of Therapeutic Agents," filed Jun. 30, 2010, the disclosure of which is herein incorporated by reference in its entirety for all purposes.

Other cationic lipids or salts thereof which may be included in the lipid particles of the present invention include, but are not limited to, 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), dilinoleylmethyl-3-dimethylaminopropionate (DLin-M-K-DMA; also known as DLin-M-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl) cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), and mixtures thereof.

Additional cationic lipids suitable for use in combination with one or more cationic lipids described herein include, without limitation, cationic lipids such as (6Z,9Z,28Z,31Z)-heptatriaconta-6,9,28,31-tetraen-19-yl 4-(dimethylamino) butanoate (DLin-M-C3-DMA or "MC3") and certain analogs thereof as described in U.S. Provisional Patent Application No. 61/334,104, entitled "Novel Cationic Lipids and Methods of Use Thereof," filed May 12, 2010, and PCT Publication Nos. WO 2010/054401, WO 2010/054405, WO 2010/054406, and WO 2010/054384, the disclosures of which are herein incorporated by reference in their entirety for all purposes.

The synthesis of cationic lipids such as DO-C-DAP, DMDAP, DOTAP.Cl, DLin-M-K-DMA, as well as additional cationic lipids, is described in PCT Publication No. WO 2010/042877, the disclosure of which is incorporated herein by reference in its entirety for all purposes.

The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086558, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes.

The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from GIBCO/BRL); LIPOFECTAMINE® (including DOSPA and DOPE, available from GIBCO/BRL); and TRANSFECTAM® (including DOGS, available from Promega Corp.).

In some embodiments, the cationic lipid comprises from about 45 mol % to about 90 mol %, from about 45 mol % to about 85 mol %, from about 45 mol % to about 80 mol %, from about 45 mol % to about 75 mol %, from about 45 mol % to about 70 mol %, from about 45 mol % to about 65 mol %, from about 45 mol % to about 60 mol %, from about 45 mol % to about 55 mol %, from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol % or from about 55 mol % to about 70 mol % (or any fraction thereof or range therein) of the total lipid present in the particle.

In certain preferred embodiments, the cationic lipid comprises from about 50 mol % to about 58 mol %, from about 51 mol % to about 59 mol %, from about 51 mol % to about 58 mol %, from about 51 mol % to about 57 mol %, from about 52 mol % to about 58 mol %, from about 52 mol % to about 57 mol %, from about 52 mol % to about 56 mol %, or from about 53 mol % to about 55 mol % (or any fraction thereof or range therein) of the total lipid present in the particle.

In certain other preferred embodiments, the cationic lipid comprises from about 54 mol % to about 62 mol %, from about 55 mol % to about 61 mol %, from about 55 mol % to about 60 mol %, from about 55 mol % to about 59 mol %, from about 56 mol % to about 62 mol %, from about 56 mol % to about 61 mol %, from about 56 mol % to about 60 mol %, or from about 57 mol % to about 59 mol % (or any fraction thereof or range therein) of the total lipid present in the particle.

In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof or range therein) of the total lipid present in the particle. In certain other embodiments, the cationic lipid comprises (at least) about 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

It should be understood that the percentage of cationic lipid present in the lipid particles of the invention is a target amount, and that the actual amount of cationic lipid present in the formulation may vary, for example, by ±5 mol %. Typically, in the 7:54 lipid particle (e.g., SNALP) formulation, the target amount of cationic lipid is 54.06 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

C. Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 7:54 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. In other embodiments, the cholesterol component in the mixture comprises about 36, 37, 38, 39, 40, 41, 42, 43, 44, or 45 mol % (or any fraction thereof or range therein) of the total lipid present in the particle. Typically, a 7:54 lipid particle formulation comprising a mixture of phospholipid and cholesterol may comprise cholesterol or a cholesterol derivative at about 32 mol % (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle. As a non-limiting example, a 7:58 lipid particle formulation may comprise cholesterol at about 35 mol % (or any fraction thereof) of the total lipid present in the particle.

It should be understood that the percentage of non-cationic lipid present in the lipid particles of the invention is a target amount, and that the actual amount of non-cationic lipid present in the formulation may vary, for example, by ±5 mol %. For example, in the 7:54 lipid particle (e.g., SNALP) formulation, the target amount of phospholipid is 6.75 mol % and the target amount of cholesterol is 32.43 mol %, but the actual amount of phospholipid may be ±2 mol %, 1.5 mol %, 1 mol %, 0.75 mol %, 0.5 mol %, 0.25 mol %, or ±0.1 mol % of that target amount, and the actual amount of cholesterol may be ±3 mol %, ±2 mol %, 1 mol %, 0.75 mol %, 0.5 mol %, 0.25 mol %, or ±0.1 mol % of that target amount, with the balance of the formulation being made up of other lipid components (adding up to 100 mol % of total lipids present in the particle).

D. Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-di-oxaoctanyl]carbamoyl-w-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-$NH_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-$NH_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-$CH_2COOH$) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

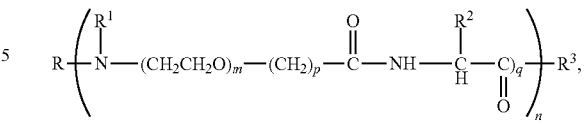

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

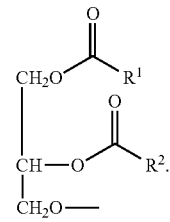

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

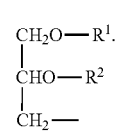

In a preferred embodiment, the PEG-lipid is a PEG-DAA conjugate having the following formula:

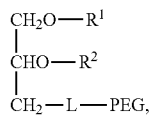
(XX)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula XX above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

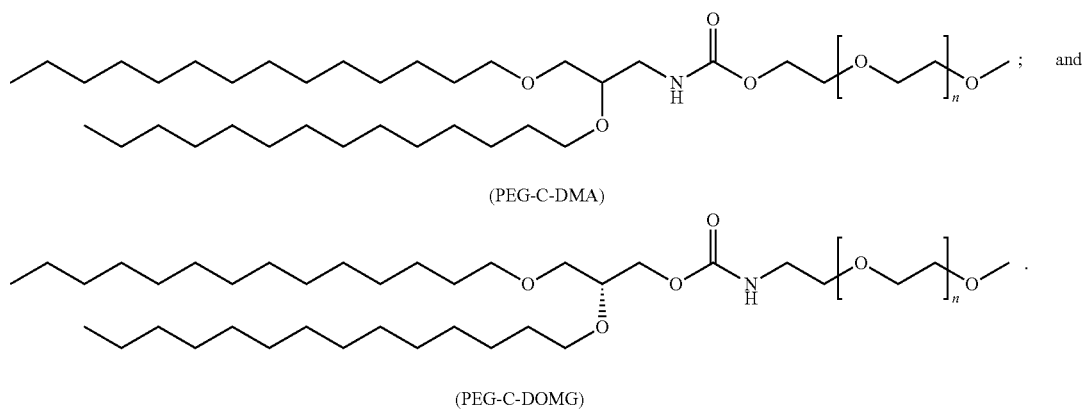

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 daltons. In particularly preferred embodiments, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles (e.g., SNALP) of the present invention can further comprise cationic poly(ethylene glycol) (PEG) lipids or CPLs (see, e.g., Chen et al., Bioconj. Chem., 11:433-437 (2000); U.S. Pat. No. 6,852,334; PCT Publication No. WO 00/62813, the disclosures of which are herein incorporated by reference in their entirety for all purposes).

Suitable CPLs include compounds of Formula XXI:

$$A\text{-}W\text{-}Y \quad (XXI),$$

wherein A, W, and Y are as described below.

With reference to Formula XXI, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) may comprise from about 2 mol % to about 15 mol %, from about 2 mol % to about 12 mol %, from about 5 mol % to about 12 mol %, from about 4 mol % to about 15 mol %, or from about 4 mol % to about 10 mol % (or any fraction thereof or range therein) of the total lipid present in the particle. In certain preferred embodiments, the lipid conjugate (e.g., PEG-lipid) comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

It should be understood that the percentage of lipid conjugate (e.g., PEG-lipid) present in the lipid particles of the invention is a target amount, and that the actual amount of lipid conjugate present in the formulation may vary, for example, by ±2 mol %. Typically, in the 7:54 lipid particle (e.g., SNALP) formulation, the target amount of lipid conjugate is 6.76 mol %, but the actual amount of lipid conjugate may be ±2 mol %, ±1.5 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

V. Preparation of Lipid Particles

The lipid particles of the present invention, e.g., SNALP, in which an active agent or therapeutic agent such as an interfering RNA (e.g., siRNA) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise one or more of the cationic lipids described herein or salts thereof, alone or in combination with other cationic lipids. In other embodiments, the non-cationic lipids are egg sphingomyelin (ESM), di stearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles (e.g., SNALP) produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles (e.g., SNALP) produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wisconsin, USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 µg nucleic acid per 10 mg total lipid or a nucleic acid to lipid mass ratio of about 0.01 to about 0.08 and, more preferably, about 0.04, which corresponds to 1.25 mg of total lipid per 50 µg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

VI. Kits

The present invention also provides lipid particles (e.g., SNALP) in kit form. In some embodiments, the kit comprises a container which is compartmentalized for holding the various elements of the lipid particles (e.g., the active agents or therapeutic agents such as nucleic acids and the individual lipid components of the particles). Preferably, the kit comprises a container (e.g., a vial or ampoule) which holds the lipid particles of the invention (e.g., SNALP), wherein the particles are produced by one of the processes set forth herein. In certain embodiments, the kit may further comprise an endosomal membrane destabilizer (e.g., calcium ions). The kit typically contains the particle compositions of the invention, either as a suspension in a pharmaceutically acceptable carrier or in dehydrated form, with instructions for their rehydration (if lyophilized) and administration.

As explained herein, the lipid particles of the present invention can be tailored to preferentially target particular tissues, organs, or tumors of interest. For instance, as set forth in the Examples below, it has surprisingly been discovered that the 7:54 lipid particle (e.g., 7:54 DLinDMA SNALP) formulation can be used to preferentially target solid tumors such as liver tumors and tumors outside of the liver. In preferred embodiments, the kits of the invention comprise these tumor-directed lipid particles (e.g., 7:54

DLinDMA SNALP), wherein the particles are present in a container as a suspension or in dehydrated form.

In certain other instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

VII. Administration of Lipid Particles

Once formed, the lipid particles of the invention (e.g., SNALP) are useful for the introduction of active agents or therapeutic agents (e.g., nucleic acids such as interfering RNA) into cells. Accordingly, the present invention also provides methods for introducing an active agent or therapeutic agent such as a nucleic acid (e.g., interfering RNA) into a cell. Preferably, the cell is a tumor cell such as, e.g., a cell present in a solid tumor. In certain embodiments, the cell may be a non-tumor cell that produces one or more angiogenic and/or growth factors associated with tumorigenesis or cell transformation. The methods are carried out in vitro or in vivo by first forming the particles as described above and then contacting the particles with the cells (e.g., cells of a solid tumor) for a period of time sufficient for delivery of the active agent or therapeutic agent to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the active agent or therapeutic agent (e.g., nucleic acid) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, PA, 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more nucleic acids comprising an interfering RNA sequence (e.g., siRNA). In particular, it is an object of this invention to provide in vitro and in vivo methods for treatment of a disease or disorder in a mammal (e.g., a rodent such as a mouse or a primate such as a human, chimpanzee, or monkey) by downregulating or silencing the transcription and/or translation of one or more target nucleic acid sequences or genes of interest. As a non-limiting example, the methods of the invention are useful for in vivo delivery of interfering RNA (e.g., siRNA) to a tumor or other neoplasia of a mammalian subject. In certain embodiments, the disease or disorder is associated with expression and/or overexpression of a gene and expression or overexpression of the gene is reduced by the interfering RNA (e.g., siRNA). In certain other embodiments, a therapeutically effective amount of the lipid particle may be administered to the mammal. In some instances, an interfering RNA (e.g., siRNA) is formulated into a SNALP, and the particles are administered to patients requiring such treatment. In other instances, cells are removed from a patient, the interfering RNA is delivered in vitro (e.g., using a SNALP described herein), and the cells are reinjected into the patient.

A. In vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.,* 101:512 (1983); Mannino et al., *Biotechniques,* 6:682 (1988); Nicolau et al., *Crit. Rev. Ther. Drug Carrier Syst.,* 6:239 (1989); and Behr, *Acc. Chem. Res.,* 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In certain embodiments, the presence of a therapeutic agent such as a nucleic acid is detectable in cells of a tumor such as a solid tumor at about 8, 12, 24, 36, 48, 60, 72 or 96 hours after administration. In other embodiments, downregulation of expression of a target sequence by an interfering RNA (e.g., siRNA) is detectable at about 8, 12, 24, 36, 48, 60, 72 or 96 hours after administration. In yet other embodiments, downregulation of expression of a target sequence by an interfering RNA (e.g., siRNA) occurs preferentially in tumor cells. In further embodiments, the presence or effect of an interfering RNA (e.g., siRNA) in cells at a site proximal or distal to the site of administration or in cells of a tumor is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the present invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., Am. J. Sci., 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, PA, 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic agent such as nucleic acid (e.g., interfering RNA) suspended in diluents such as water, saline, or PEG 400; (b) capsules, sachets, or tablets, each containing a predetermined amount of a therapeutic agent such as nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic agent such as nucleic acid (e.g., interfering RNA) in a flavor, e.g., sucrose, as well as pastilles comprising the therapeutic agent in an inert base, such as gelatin and glycerin or sucrose and acacia emulsions, gels, and the like containing, in addition to the therapeutic agent, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic agent (e.g., nucleic acid) to lipid, the particular therapeutic agent (e.g., nucleic acid) used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of therapeutic agents such as nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells (e.g., tumor cells).

Contact between the cells and the lipid particles, when carried out in vitro, takes place in a biologically compatible medium. The concentration of particles varies widely depending on the particular application, but is generally between about 1 µmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about 103 to about $10^5$ cells/ml, more preferably about $2 \times 10^4$ cells/ml. The concentration of the suspension added to the cells is preferably of from about 0.01 to 0.2 µg/ml, more preferably about 0.1 µg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

C. Cells for Delivery of Lipid Particles

The compositions and methods of the present invention are used to treat a wide variety of cell types, in vivo and in vitro. In preferred embodiments, an active agent or therapeutic agent such as a nucleic acid (e.g., an interfering RNA) is preferentially delivered to cancer cells (e.g., cells of a solid tumor) including, but not limited to, liver cancer cells, lung cancer cells, colon cancer cells, rectal cancer cells, anal cancer cells, bile duct cancer cells, small intestine cancer cells, stomach (gastric) cancer cells, esophageal cancer cells, gallbladder cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In other embodiments, an active agent or therapeutic agent such as a nucleic acid (e.g., an interfering RNA) is delivered to hepatocytes, hematopoietic precursor (stem) cells, fibroblasts, keratinocytes, endothelial cells, skeletal and smooth muscle cells, osteoblasts, neurons, quiescent lymphocytes, terminally differentiated cells, slow or non-cycling primary cells, parenchymal cells, lymphoid cells, epithelial cells, bone cells, and the like.

In vivo delivery of lipid particles such as SNALP encapsulating a nucleic acid (e.g., an interfering RNA) is suited for targeting tumor cells of any cell type. The methods and compositions can be employed with tumor cells of a wide variety of vertebrates, including mammals, such as, e.g. canines, felines, equines, bovines, ovines, caprines, rodents (e.g., mice, rats, and guinea pigs), lagomorphs, swine, and primates (e.g. monkeys, chimpanzees, and humans).

D. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), or a combination thereof 1. Detection of Particles Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, CA (1990); Arnheim & Levinson (Oct. 1, 1990), *C & EN* 36; *The Journal Of NIH Research*, 3:81 (1991); Kwoh et al., *Proc. Natl. Acad. Sci. USA,* 86:1173 (1989); Guatelli et al., *Proc. Natl. Acad. Sci. USA,* 87:1874 (1990); Lomell et al., *J. Clin. Chem.,* 35:1826 (1989); Landegren et al., *Science,* 241:1077 (1988); Van Brunt, *Biotechnology,* 8:291 (1990); Wu and Wallace, *Gene,* 4:560 (1989); Barringer et al., *Gene,* 89:117 (1990); and Sooknanan and Malek, *Biotechnology,* 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.,* 22:1859 1862 (1981), e.g., using an automated synthesizer, as described in Needham VanDevanter et al., *Nucleic Acids Res.,* 12:6159 (1984). Purification of polynucleotides, where necessary, is typically performed by either native acrylamide gel electrophoresis or by anion exchange HPLC as described in Pearson et al., *J. Chrom.,* 255:137 149 (1983). The sequence of the synthetic polynucleotides can be verified using the chemical degradation method of Maxam and Gilbert (1980) in Grossman and Moldave (eds.) Academic Press, New York, *Methods in Enzymology,* 65:499.

An alternative means for determining the level of transcription is in situ hybridization. In situ hybridization assays are well-known and are generally described in Angerer et al., *Methods Enzymol.,* 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

VIII. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Materials and Methods siRNA: All siRNA molecules used in these studies were chemically synthesized and annealed using standard procedures.

Lipid Encapsulation of siRNA: In some embodiments, siRNA were encapsulated into stable nucleic acid-lipid particles (SNALP) composed of the following lipids: (1) the lipid conjugate PEG750-C-DMA (3-N-[(-Methoxypoly(ethylene glycol)750)carbamoyl]-1,2-dimyristyloxypropylamine); (2) the cationic lipid DLinDMA (1,2-Dilinoleyloxy-3-(N,N-dimethyl)aminopropane) or DLin-K-C2-DMA (2,2-dilinoleyl-4-(2-dimethylaminoethyl)-[1,3]-dioxolane; "C2K"); (3) the phospholipid DPPC (1,2-Dipalmitoyl-sn-glycero-3-phosphocholine; Avanti Polar Lipids; Alabaster, AL); and (4) synthetic cholesterol (Sigma-Aldrich Corp.; St. Louis, MO) in the molar ratio 6.76:54.06:6.75:32.43, respectively. In other words, siRNA were encapsulated into SNALP of the following "7:54" formulation: 6.76 mol % PEG750-C-DMA; 54.06 mol % DLinDMA or C2K; 6.75 mol % DPPC; and 32.43 mol % cholesterol.

In other embodiments, siRNA were encapsulated into SNALP composed of the following lipids: (1) the lipid conjugate PEG2000-C-DMA (3-N-[(-Methoxypoly(ethylene glycol)2000)carbamoyl]-1,2-dimyristyloxypropylamine); (2) the cationic lipid DLinDMA or C2K; (3) the phospholipid DPPC; and (4) synthetic cholesterol in the molar ratio 1.4:57.1:7.1:34.3, respectively. In other words, siRNA were encapsulated into SNALP of the following "1:57" formulation: 1.4 mol % PEG2000-C-DMA; 57.1 mol % DLinDMA or C2K; 7.1 mol % DPPC; and 34.3 mol % cholesterol.

It should be understood that the 7:54 formulation and 1:57 formulation are target formulations, and that the amount of lipid (both cationic and non-cationic) present and the amount of lipid conjugate present in the formulation may vary. Typically, in the 7:54 formulation, the amount of cationic lipid will be 54.06 mol %±5 mol %, and the amount of lipid conjugate will be 6.76 mol %±1 mol %, with the balance of the 7:54 formulation being made up of non-cationic lipid (e.g., phospholipid, cholesterol, or a mixture of the two). In the 1:57 formulation, the amount of cationic lipid will typically be 57.1 mol %±5 mol %, and the amount of lipid conjugate will be 1.4 mol %±0.5 mol %, with the balance of the 1:57 formulation being made up of non-cationic lipid (e.g., phospholipid, cholesterol, or a mixture of the two).

For vehicle controls, empty particles with identical lipid composition may be formed in the absence of siRNA.

Example 2. Characterization of the Effect of PEG-Lipid Alkyl Chain Length and PEG Polymer Length on Encapsulation Efficiency PEG-lipid conjugates were titrated into solutions containing fixed concentrations of DLinDMA and cholesterol. A SNALP formulation containing an siRNA molecule targeting luciferase (Luc) was produced by mixing the nucleic acid and lipid solutions using a syringe press method (0.2 mg scale) with a 1 mm T-connector and direct dilution into PBS.

FIG. 1 shows that better encapsulation efficiencies of the siRNA payload were achieved when a higher mol % of a PEG750-lipid conjugate such as PEG750-C-DMA or PEG750-C-DSA was used in the SNALP formulation. In particular, both PEG750-lipid conjugates retained high siRNA encapsulation efficiencies (about 90% or greater) at 7 mol % of PEG-lipid, whereas PEG2000-lipid conjugates displayed only about 40% encapsulation efficiencies at the higher mol % of PEG-lipid.

Example 3. Characterization of the 7:54 DLinDMA SNALP Formulation

A 7:54 DLinDMA SNALP formulation was prepared with an siRNA targeting polo-like kinase 1 (PLK-1) (Genbank Accession No. NM_005030) as the nucleic acid component. The PLK-1 siRNA sequence used in this study is provided in Table 3.

TABLE 3

| SIRNA | PLK-1 siRNA Sequence | % 2'OMe-Modified | % Modified in DS Region |
|---|---|---|---|
| PLK1424 2/6 | 5'-AGA<u>U</u>CACCC<u>U</u>CCUU<u>AAAUAU</u>U-3' (SEQ ID NO: 1) <br> 3'-C<u>UU</u>C<u>UA</u>G<u>U</u>GGGAGG<u>A</u>AUUUAU-5' (SEQ ID NO: 2) | 9/42 = 21.4% | 7/38 = 18.4% |

Column 1: The number after "PLK" refers to the nucleotide position of the 5' base of the sense strand relative to the start codon (ATG) of the human PLK-1 mRNA sequence NM_005030.

Column 2: 2'OMe nucleotides are indicated in bold and underlined. The 3'-overhangs on one or both strands of the siRNA molecule may alternatively comprise 1-4 deoxythymidine (dT) nucleotides, 1-4 modified and/or unmodified uridine (U) ribonucleotides, or 1-2 additional ribonucleotides having complementarity to the target sequence or the complementary strand thereof.

Column 3: The number and percentage of 2'OMe-modified nucleotides in the siRNA molecule are provided.

Column 4: The number and percentage of modified nucleotides in the double-stranded (DS) region of the siRNA molecule are provided.

Table 4 shows the lipid molar ratios and physical characteristics of a representative batch of the 7:54 DLinDMA SNALP formulation. The input lipid:nucleic acid mass ratio for the 7:54 DLinDMA SNALP formulation was about 6.5:1 (mg total lipid:mg siRNA), which produced a typical final SNALP product having a lipid:nucleic acid mass ratio of about 7:1 to about 7.5:1.

TABLE 4

| Description | Composition (mol %) PEG750-C-DMA \| DLinDMA \| Chol \| DPPC | Finished product SNALP Zavg (nm) | Poly | Encaps (%) |
|---|---|---|---|---|
| 7:54 | 6.76 \| 54.06 \| 32.43 \| 6.75 | 79.01 | 0.075 | 93 |

"Zavg" = median diameter of particle;
"Poly" = polydispersity;
"Encaps" = encapsulation efficiency.

Figure 2:
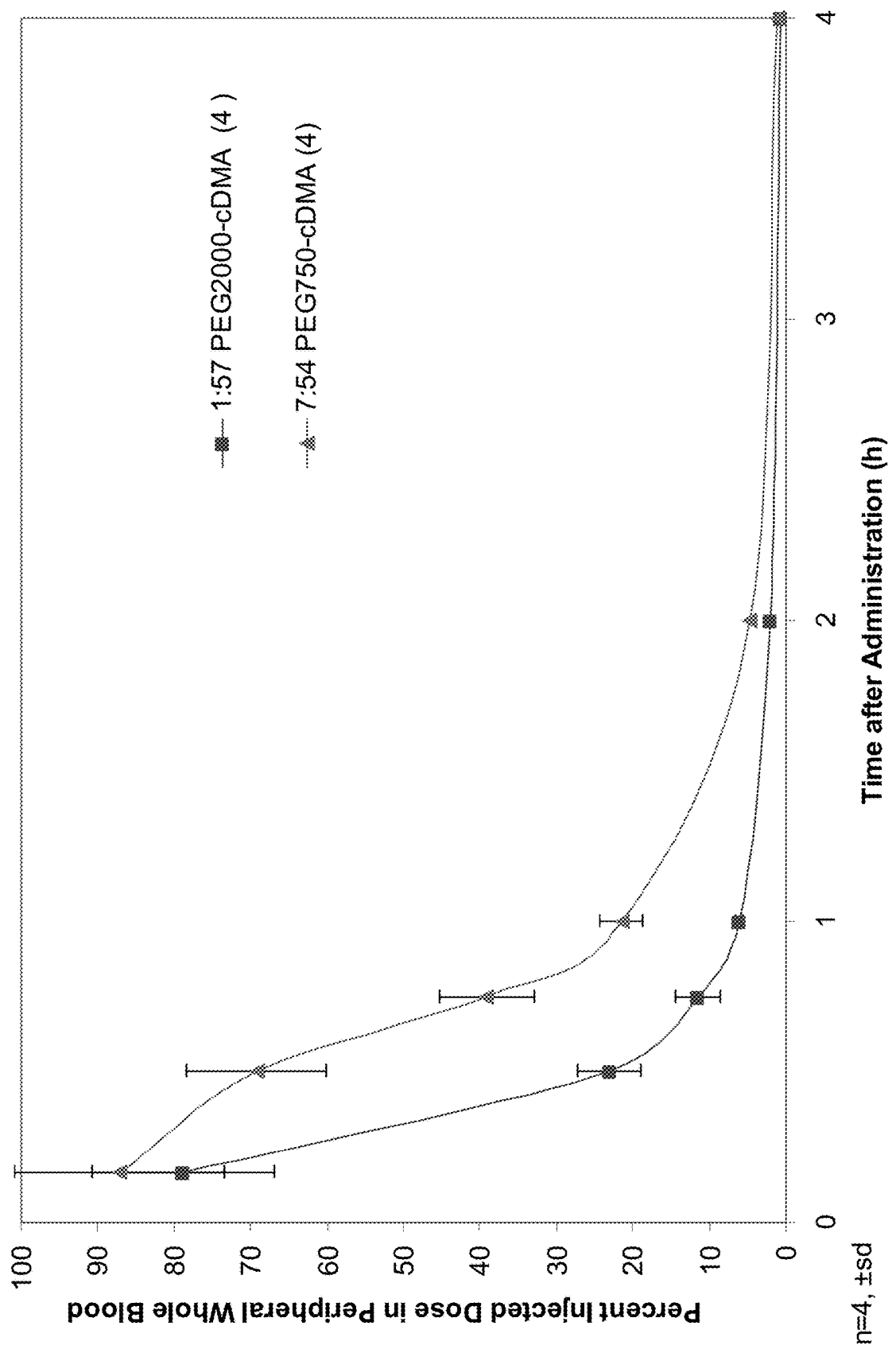
FIG. 2 shows a comparison of the blood clearance profile of exemplary 1:57 and 7:54 DLinDMA SNALP formulations.

FIG. 2 shows a comparison of the blood clearance profile in mice (n=4 each) of PLK-1 7:54 DLinDMA SNALP containing PEG750-C-DMA versus PLK-1 1:57 DLinDMA SNALP containing PEG2000-C-DMA. The extended blood circulation times observed for the 7:54 DLinDMA SNALP formulation enable the increased accumulation and activity of such particles at distal tumor sites. A bolus intravenous (IV) injection (2 mg/kg) of 3H-labeled SNALP was used in this study.

Example 4. Activity of the 7:54 DLinDMA SNALP Formulation in Normal Liver Versus Liver Tumors 7:54 or 1:57 DLinDMA SNALP formulations were prepared with PLK-1 (Table 3) or ApoB siRNA as the nucleic acid component. Mice with normal livers were administered either phosphate buffered saline (PBS), ApoB 1:57 DLinDMA SNALP, or ApoB 7:54 DLinDMA SNALP by intravenous (IV) injection via the lateral tail vein. Mice with established Hep3B intrahepatic tumors were administered either PBS, PLK-1 1:57 DLinDMA SNALP, or PLK-1 7:54 DLinDMA SNALP by IV injection via the lateral tail vein.

Figure 3:
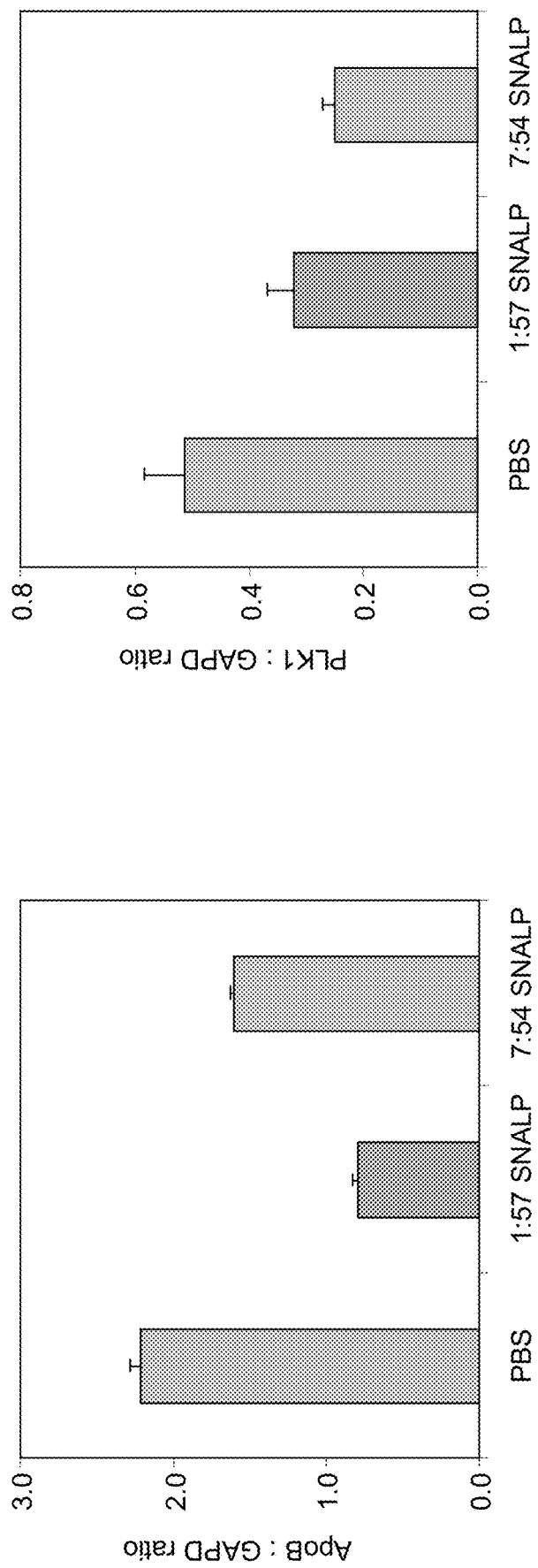
FIG. 3 shows a comparison of the silencing activity of exemplary 1:57 and 7:54 DLinDMA SNALP formulations in normal liver tissue and liver tumors.

FIG. 3 shows that the 1:57 DLinDMA SNALP formulation was capable of silencing ApoB expression in normal liver tissue and PLK-1 expression in Hep3B liver tumors, while the 7:54 DLinDMA SNALP formulation displayed enhanced silencing activity in liver tumors compared to normal liver tissue. As such, this example demonstrates that the 7:54 DLinDMA SNALP formulation preferentially targets tumor cells compared to the normal liver, whereas the 1:57 DLinDMA SNALP formulation preferentially targets normal liver cells compared to solid tumors.

This example further demonstrates that the 7:54 DLinDMA SNALP formulation may help limit PLK-1 silencing in proliferating hepatocytes (e.g., diseased liver state). Hepatocytes in the healthy liver are typically non-dividing and therefore do not express PLK-1. However, in diseased states (e.g., in a cancerous liver), normal hepatocytes are more proliferative (as they attempt to repair the damage) and therefore express PLK-1. Use of the PLK-1 7:54 DLinDMA SNALP formulation avoids the undesired targeting of normal proliferating hepatocytes, thereby limiting PLK-1 silencing in these cells. As a result, there is a reduction or abrogation in the death of these healthy hepatocytes, while PLK-1 expression is effectively silenced in tumor cells.

Figure 4:
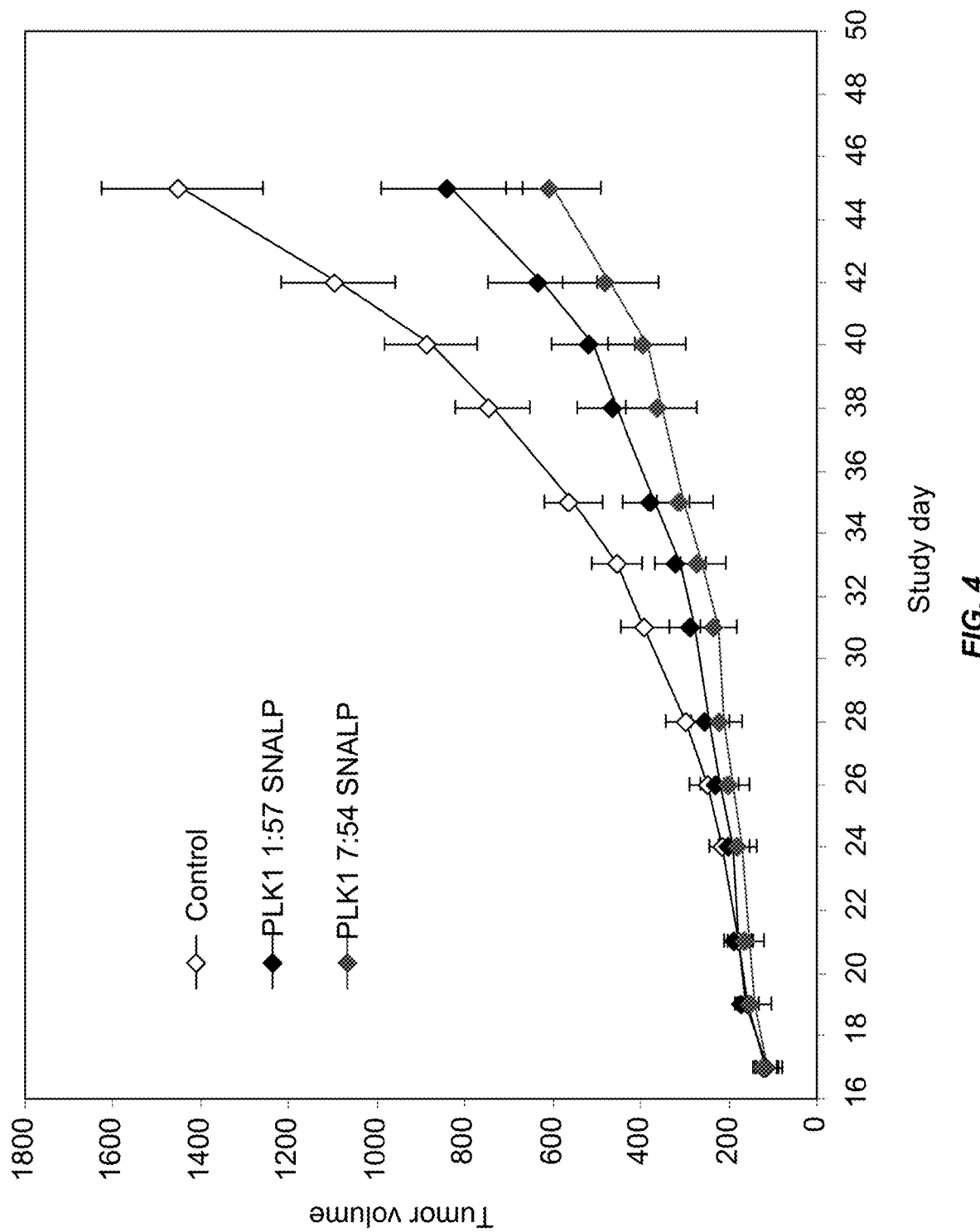
FIG. 4 shows a comparison of the silencing activity of exemplary 1:57 and 7:54 DLinDMA SNALP formulations in subcutaneous tumors.

Example 5. Activity of the 7:54 DLinDMA SNALP Formulation in Tumors Outside of the Liver 7:54 or 1:57 DLinDMA SNALP formulations were prepared with PLK-1 siRNA as the nucleic acid component (Table 3). Mice with established Hep3B subcutaneous (SC) tumors were administered either PBS (Control), PLK-1 1:57 DLinDMA SNALP, or PLK-1 7:54 DLinDMA SNALP by IV injection via the lateral tail vein at a dose of 6×3 mg/kg SNALP twice weekly for 3 weeks (Days 17, 20, 24, 27, 31, 34). FIG. 4 shows that while multiple doses of PLK-1 1:57 DLinDMA SNALP were effective at inducing the regression of established SC Hep3B tumors compared to control mice, multiple doses of PLK-1 7:54 DLinDMA SNALP were more effective at inducing the regression of these SC solid tumors compared to the PLK-1 1:57 DLinDMA SNALP formulation.

Thus, this study shows that the 7:54 DLinDMA SNALP formulation displays increased potency in SC tumors and can be used to preferentially target tumors outside of the liver.

Example 6. Comparison of the Activity of the 7:54 DLinDMA and C2K SNALP Formulations in Liver Tumors 7:54 or 1:57 SNALP formulations comprising either DLinDMA or DLin-K-C2-DMA ("C2K") were prepared with PLK-1 siRNA as the nucleic acid component (Table 3). Mice with established Hep3B intrahepatic tumors were administered either PBS ("Control"), PLK-1 7:54 C2K SNALP, PLK-1 7:54 DLinDMA SNALP, PLK-1 1:57 C2K SNALP, or PLK-1 1:57 DLinDMA SNALP by IV injection via the lateral tail vein. Each SNALP formulation was dosed at 0.25 mg/kg or 1 mg/kg siRNA according to body weight. PLK-1 mRNA levels were measured in liver tumors at 24 hours post-injection.

Figure 5:
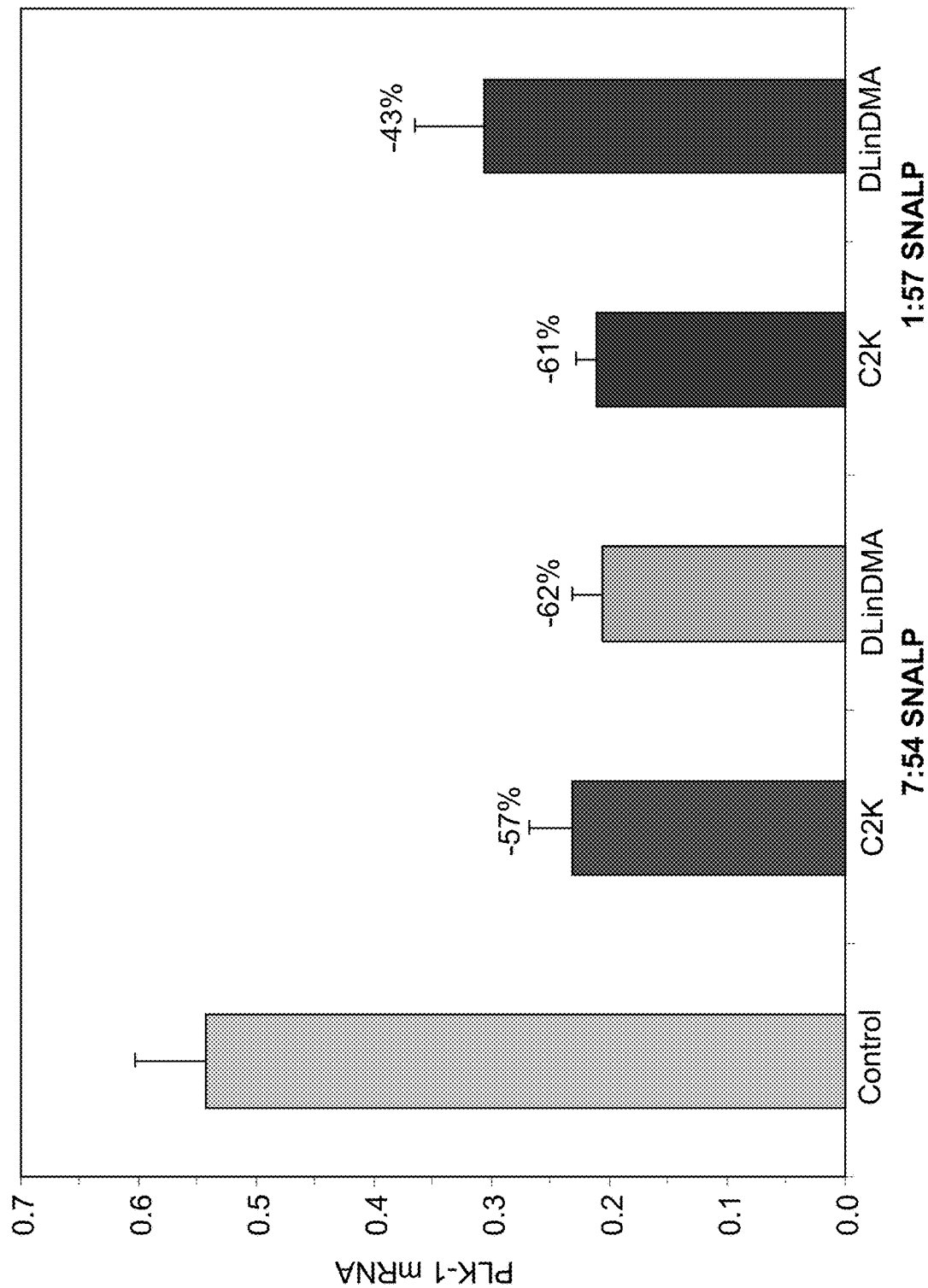
FIG. 5 shows a comparison of the silencing activity of exemplary 7:54 DLinDMA and C2K SNALP formulations in liver tumors.
Figure 6:
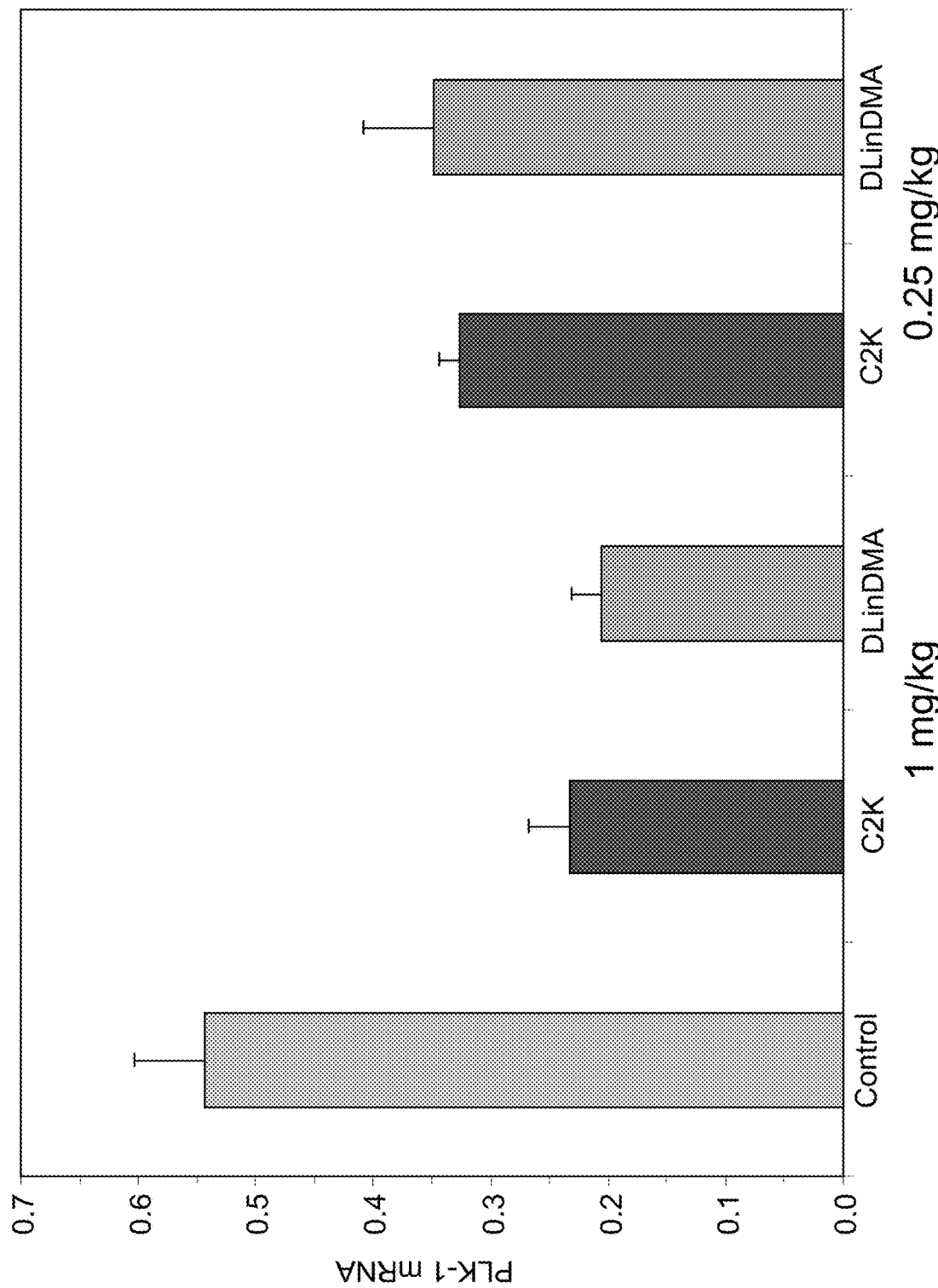
FIG. 6 shows a comparison of the silencing activity of exemplary 7:54 DLinDMA and C2K SNALP formulations in liver tumors at two different doses.

FIG. 5 shows that the 1:57 DLinDMA SNALP formulation was capable of silencing PLK-1 expression in Hep3B liver tumors at a 1 mg/kg siRNA dose, while the 7:54 DLinDMA SNALP formulation displayed enhanced silencing activity in Hep3B liver tumors at the same dose. FIG. 5 also shows that the 1:57 and 7:54 C2K SNALP formulations displayed similar PLK-1 silencing activities in Hep3B liver tumors. FIG. 6 shows that the 7:54 DLinDMA and C2K SNALP formulations had similar potencies in Hep3B liver tumors at two different doses (i.e., 0.25 mg/kg and 1 mg/kg siRNA).

Thus, this example demonstrates that the 7:54 DLinDMA SNALP formulation preferentially targets tumor cells compared to the corresponding 1:57 formulation. This example also demonstrates that the 1:57 and 7:54 C2K SNALP formulations are comparable in potency to the 7:54 DLinDMA SNALP formulation in silencing PLK-1 mRNA in Hep3B liver tumors.

Example 7. Comparison of the Activity of the 7:54 DLinDMA and C2K SNALP Formulations in Tumors Outside of the Liver In one set of experiments, 7:54 or 1:57 SNALP formulations comprising either DLinDMA or DLin-K-C2-DMA ("C2K") were prepared with PLK-1 siRNA as the nucleic acid component (Table 3). Mice with established Hep3B subcutaneous tumors were administered either PBS, PLK-1 7:54 DLinDMA SNALP, PLK-1 1:57 C2K SNALP, or PLK-1 1:57 DLinDMA SNALP by IV injection via the lateral tail vein. Each SNALP formulation was dosed at 1 mg/kg or 3 mg/kg siRNA according to body weight. PLK-1 mRNA levels were measured in tumors at 24 hours post-injection.

Figure 7:
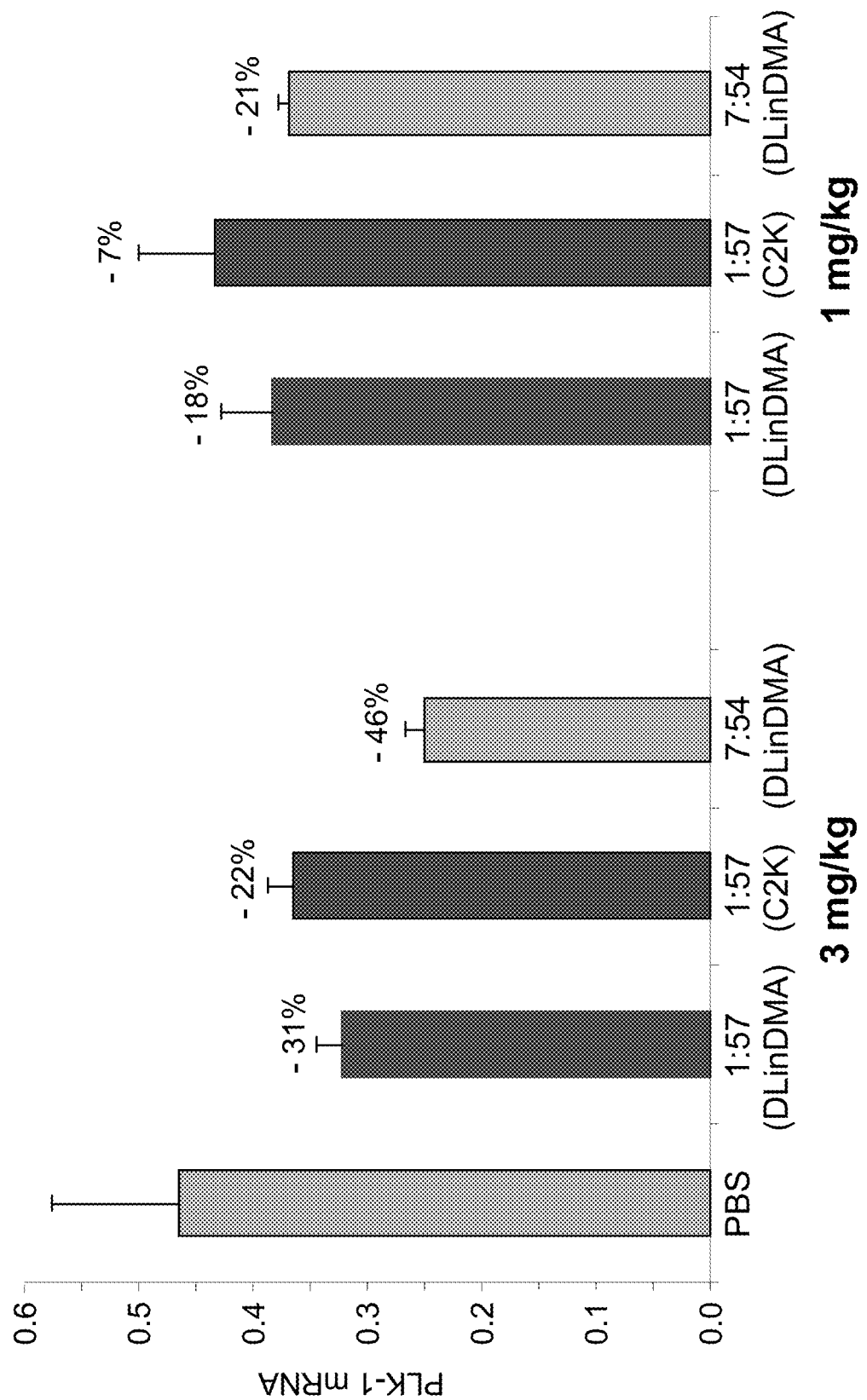
FIG. 7 shows a comparison of the silencing activity of exemplary 1:57 and 7:54 DLinDMA and C2K SNALP formulations in subcutaneous tumors at two different doses.

FIG. 7 shows that the 7:54 DLinDMA SNALP formulation was more potent at silencing PLK-1 expression in Hep3B subcutaneous tumors compared to the 1:57 DLinDMA and C2K SNALP formulations at two different doses (i.e., 1 mg/kg and 3 mg/kg siRNA). The potency of the 7:54 DLinDMA SNALP formulation was supported by tumor histology. In particular, strong histologic effects were observed at both doses of 7:54 DLinDMA SNALP.

In another set of experiments, 7:54 or 1:57 SNALP formulations comprising either DLinDMA or DLin-K-C2-DMA ("C2K") were prepared with PLK-1 siRNA as the nucleic acid component (Table 3). Mice with established Hep3B subcutaneous tumors (SC) were administered either PBS, PLK-1 7:54 C2K SNALP, PLK-1 7:54 DLinDMA SNALP, PLK-1 1:57 C2K SNALP, or PLK-1 1:57 DLinDMA SNALP by IV injection via the lateral tail vein. Each SNALP formulation was dosed at 3 mg/kg siRNA according to body weight as a single dose or as 6 doses (Days 17, 20, 24, 27, 31, and 34). For the single dose studies, PLK-1 mRNA levels were measured in tumors at 24 hours post-injection. For the multi-dose study, tumor volumes were measured at certain time points during the course of the study.

Figure 8:
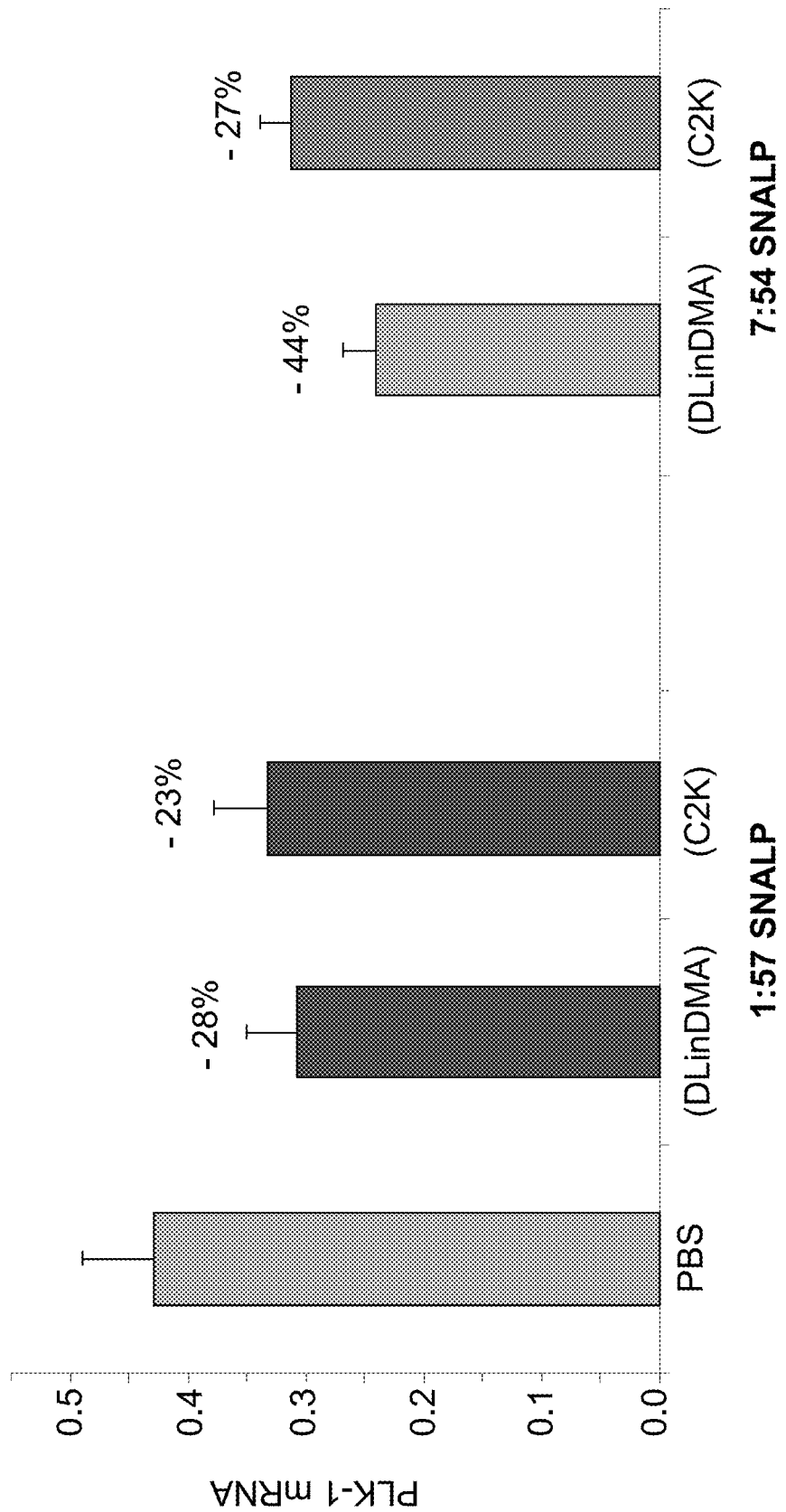
FIG. 8 shows another comparison of the silencing activity of exemplary 1:57 and 7:54 DLinDMA and C2K SNALP formulations in subcutaneous tumors.
Figure 9:
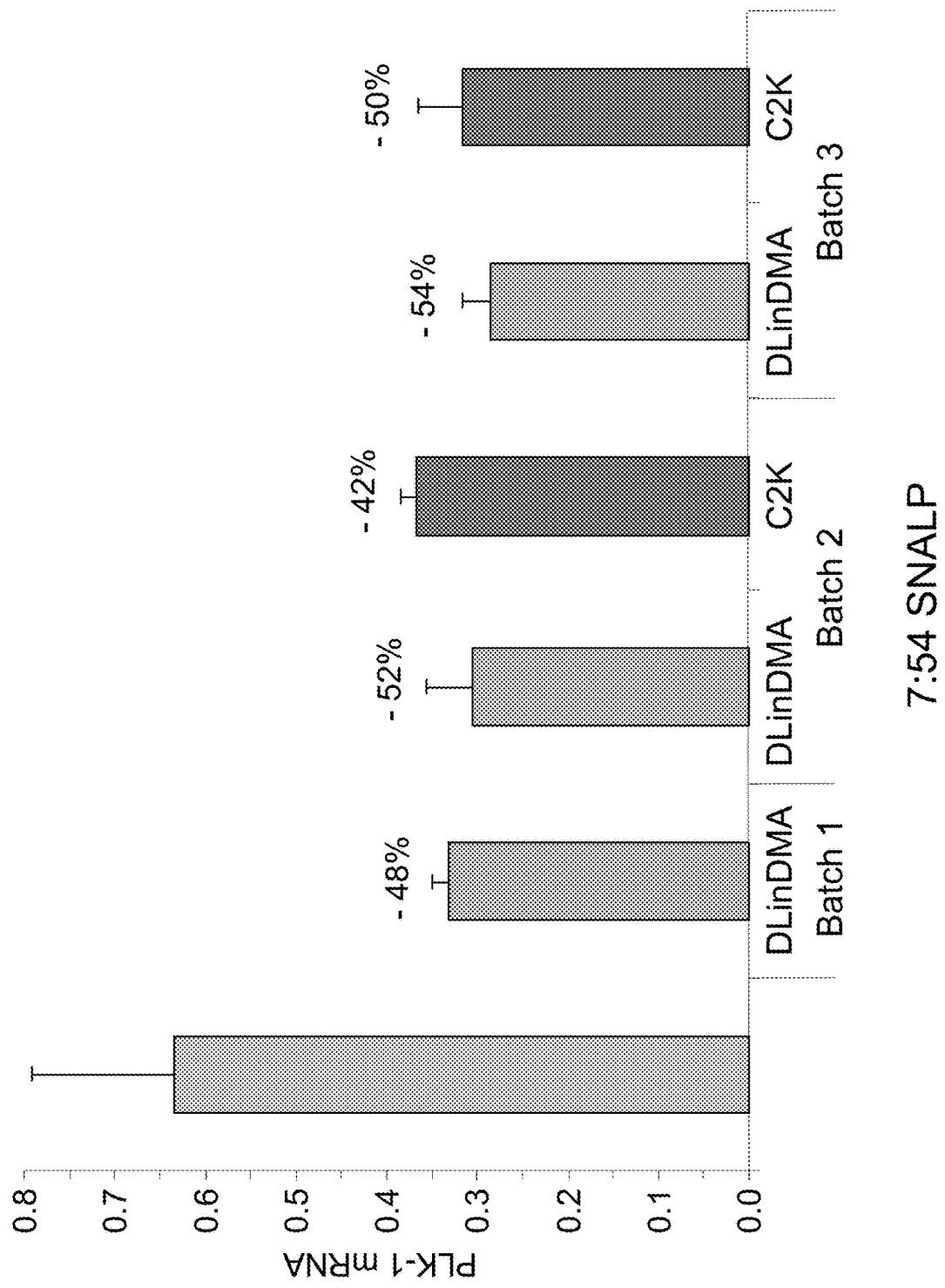
FIG. 9 shows a comparison of the potencies of different batches of 7:54 DLinDMA and C2K SNALP formulations in subcutaneous tumors.
Figure 10:
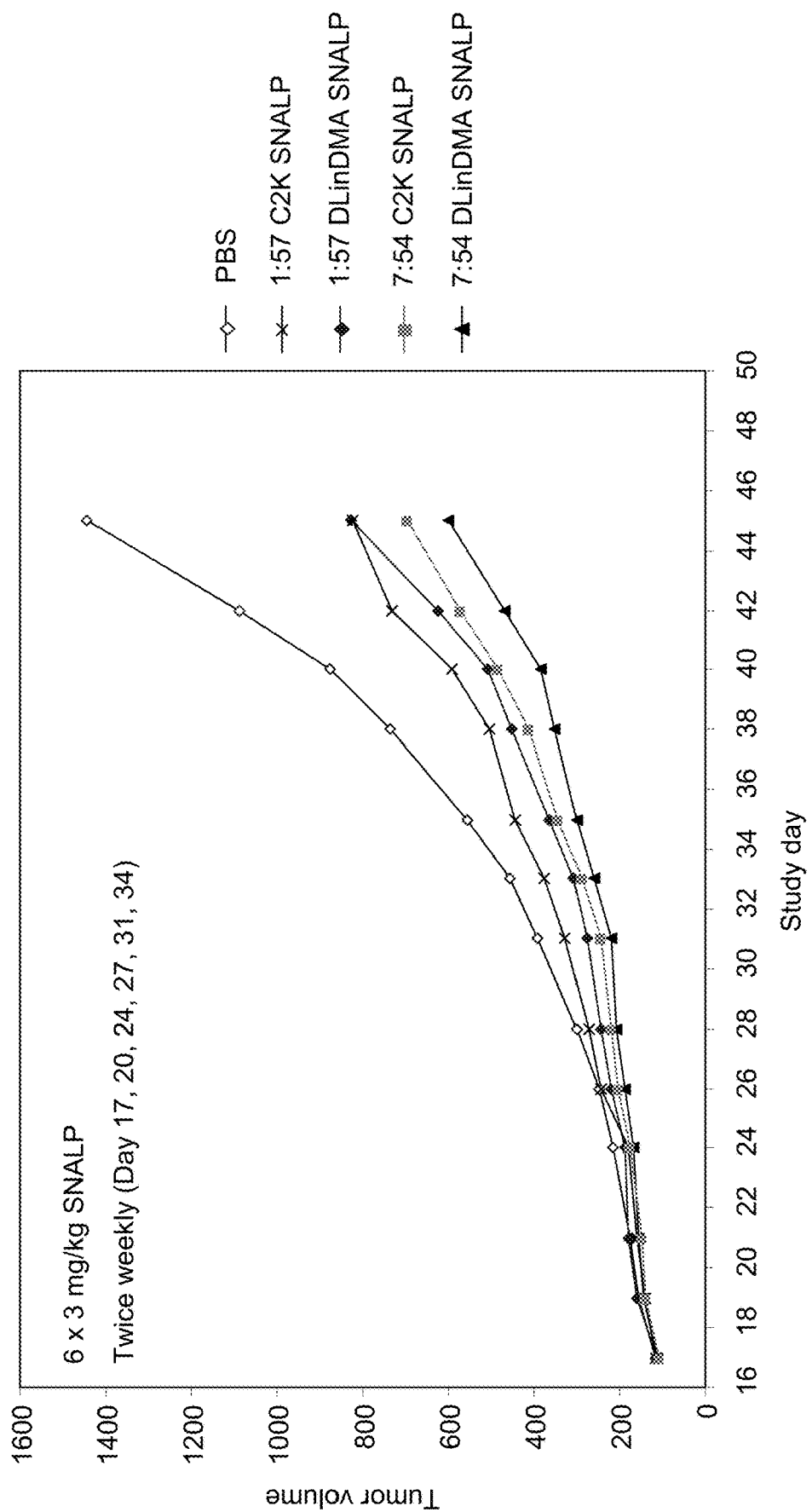
FIG. 10 shows a comparison of the anti-tumor efficacy of exemplary 1:57 and 7:54 DLinDMA and C2K SNALP formulations in reducing subcutaneous tumor volume.

FIG. 8 shows that the 1:57 DLinDMA SNALP, 1:57 C2K SNALP, and 7:54 C2K SNALP formulations were capable of silencing PLK-1 expression in SC tumors, while the 7:54 DLinDMA SNALP formulation displayed enhanced silencing activity in SC tumors at the same dose. FIG. 9 shows as comparison of the potencies of different batches of 7:54 DLinDMA SNALP and 7:54 C2K SNALP formulations in SC tumors. FIG. 10 shows that the 1:57 DLinDMA SNALP, 1:57 C2K SNALP, and 7:54 C2K SNALP formulations were capable of reducing SC mean tumor volumes in the multi-dose study, while the 7:54 DLinDMA SNALP formulation was more efficacious at reducing SC mean tumor volumes. The anti-tumor efficacy observed in the multi-dose study correlated with relative PLK-1 mRNA silencing activity.

Thus, this example demonstrates that the 7:54 DLinDMA SNALP formulation displays increased potency in SC tumors and can be used to preferentially target tumors outside of the liver. This example also demonstrates that the 1:57 and 7:54 C2K SNALP formulations had similar potencies in SC tumors.

Example 8. Tolerability of the 7:54 DLinDMA and C2K SNALP Formulations

Figure 11:
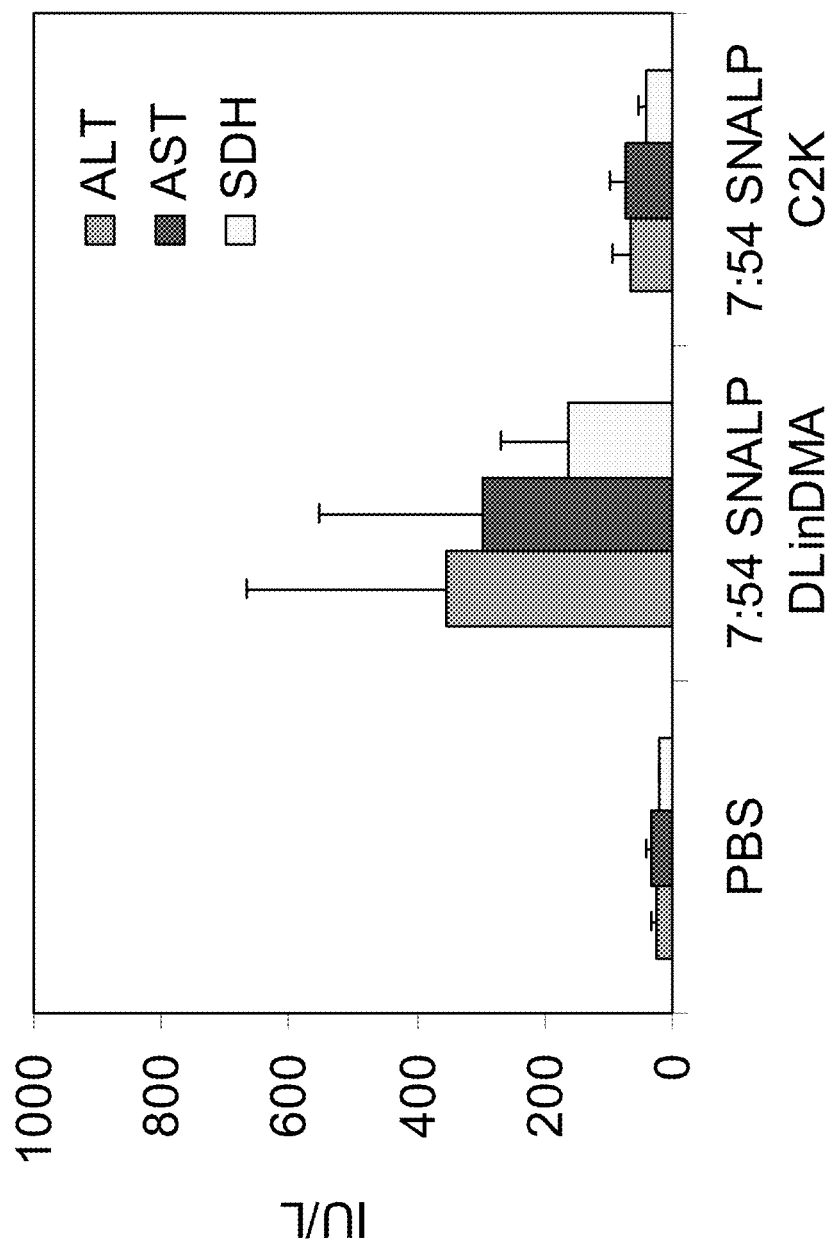
FIG. 11 shows the effect of administering exemplary 7:54 DLinDMA and C2K SNALP formulations on liver enzyme levels.

The tolerability of the 7:54 DLinDMA and C2K SNALP formulations was evaluated with a single IV administration of SNALP at 20 mg/kg in mice. Liver enzyme levels were measured at 48 hours post-injection. FIG. 11 shows that both 7:54 SNALP formulations did not significantly elevate liver enzyme levels compared to the PBS control.

Figure 12:
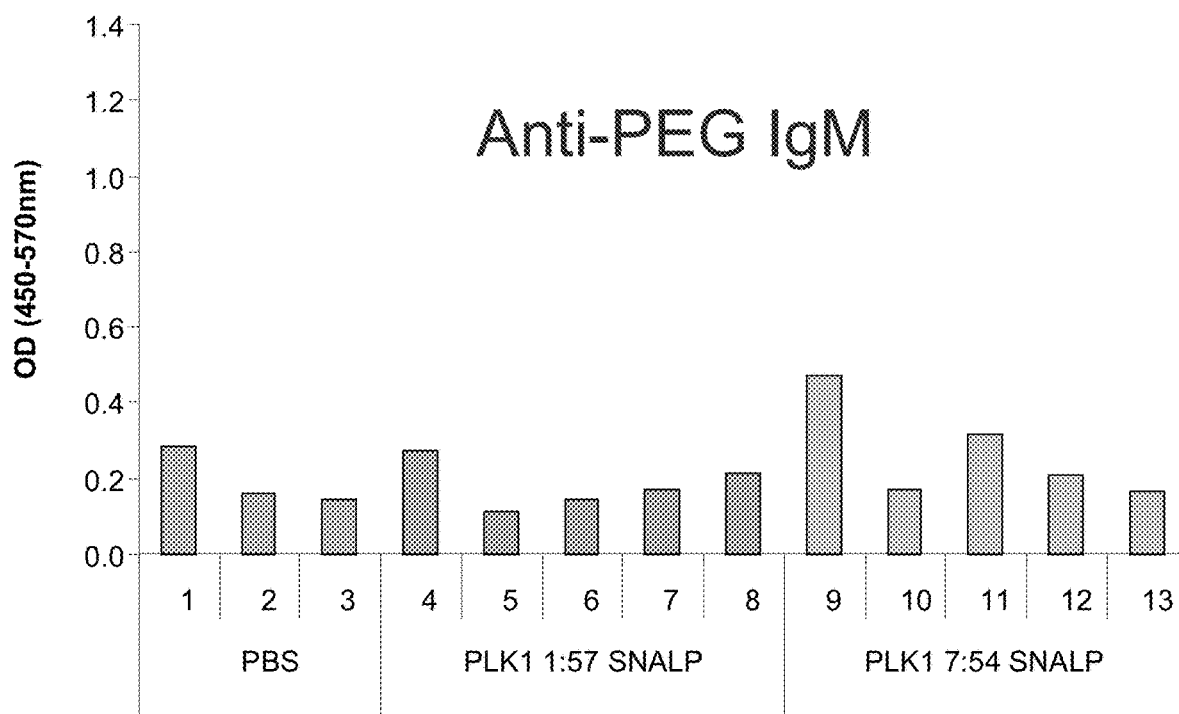
FIG. 12 shows the immunogenic effect of administering exemplary 1:57 or 7:54 DLinDMA SNALP formulations.
Figure 12:
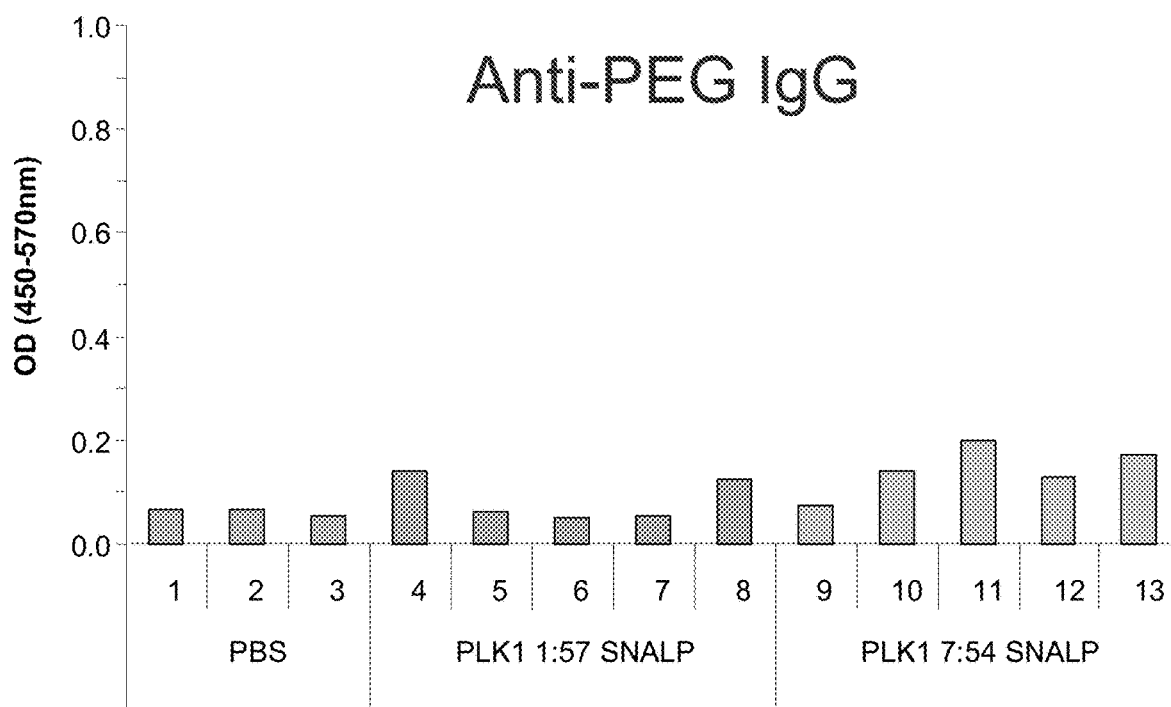

The tolerability of the 7:54 DLinDMA SNALP formulation was further evaluated by testing for the induction of an antibody response against the PEG-lipid component of the SNALP. ICR mice were administered 1:57 or 7:54 DLinDMA PLK-1 SNALP at a 2×3 mg/kg weekly dose. Anti-PEG-lipid IgM and IgG antibody levels in plasma were measured by ELISA. FIG. 12 shows that there was no evidence of significant immunogenicity after PLK-1 1:57 or 7:54 DLinDMA SNALP administration. As such, both 1:57 and 7:54 SNALP formulations do not significantly induce IgM and IgG antibody responses against the PEG-lipid component.

Example 9. Characterization of Tumor-Directed SNALP Formulations Containing Various Cationic Lipids This example demonstrates the efficacy of tumor-directed SNALP formulations containing various novel cationic lipids described herein with an siRNA targeting polo-like kinase 1 (PLK-1) in a mouse distal tumor model. The PLK-1 siRNA sequence used in this study is provided in Table 3 above.

7:54 SNALP formulations containing encapsulated PLK-1 siRNA were prepared with the following cationic lipids: (1) DLinDMA; (2) TLinDMA; (3) DLin-C1K-DMA ("DLin-K-DMA"); (4) DPanDMA; (5) DPan-C2-DMA ("C2-DPanDMA"); (6) DPan-C2K-DMA; (7) DPan-C3K-DMA; and (8) DPan-C1K6-DMA.

Each SNALP formulation was administered by intravenous (IV) injection at 3 mg/kg into Scid mice containing Hep3B tumors (n=4 per group). Tumor tissue was collected at 24 hours after SNALP administration and tumor PLK-1 mRNA levels were evaluated by performing a PLK-1/GAPDH QG assay. Table 5 provides a characterization of the SNALP formulations used in this in vivo study.

TABLE 5

| Mol % | Composition | Initial | Finished Product | | |
|---|---|---|---|---|---|
| PEG-lipid \| Cationic \| Chol \| DPPC | PEG-lipid | Cationic Lipid | Encaps. (%) | Z-Avg (nm) | Poly | Encaps. (%) |
| 6.76 \| 54.06 \| 32.43 \| 6.75 | PEG750-C-DMA | DLinDMA | 75 | 74 | 0.08 | 98 |
| | | TLinDMA | 70 | 126 | 0.07 | 100 |
| | | DLin-C1K-DMA | 56 | 84 | 0.05 | 98 |
| | | DPanDMA | 75 | 76 | 0.08 | 100 |
| | | DPan-C2-DMA | 86 | 81 | 0.06 | 100 |
| | | DPan-C2K-DMA | 84 | 76 | 0.08 | 100 |
| | | DPan-C3K-DMA | 86 | 81 | 0.06 | 100 |
| | | DPan-C1K6-DMA | 71 | 80 | 0.06 | 99 |

Figure 13:
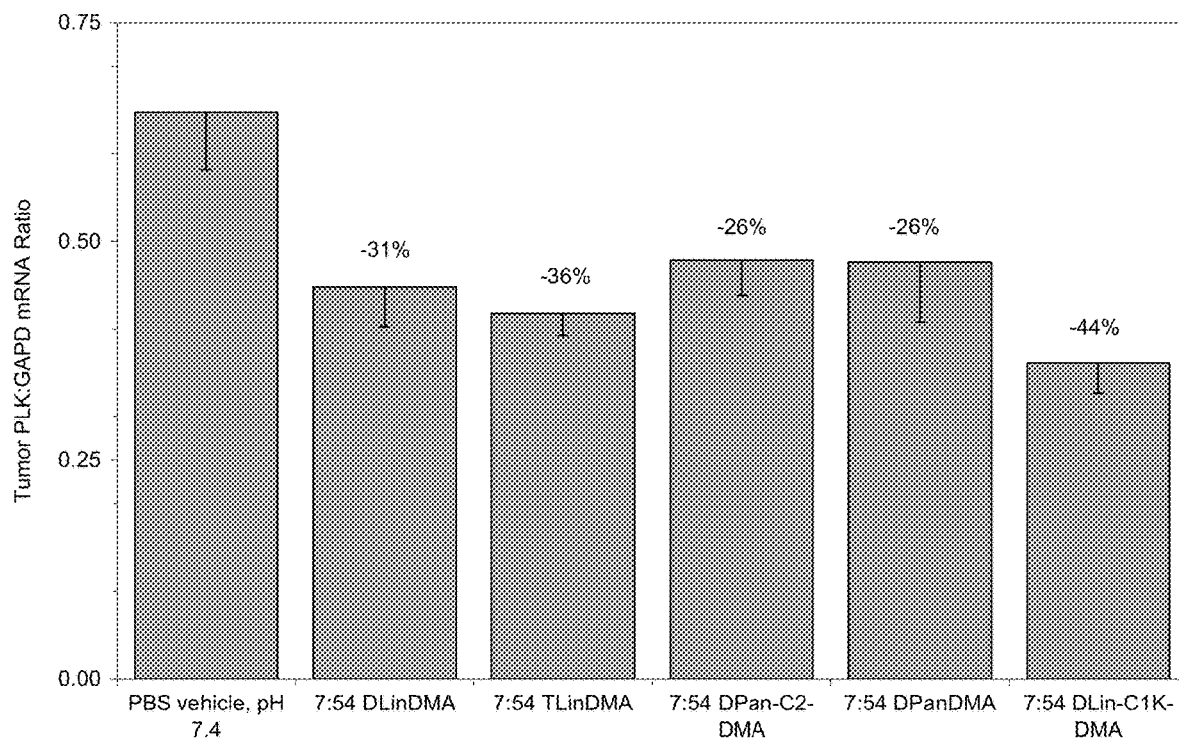
FIG. 13 shows a comparison of the tumor PLK-1 mRNA knockdown activity of exemplary 7:54 SNALP formulations containing various cationic lipids described herein.
Figure 13:
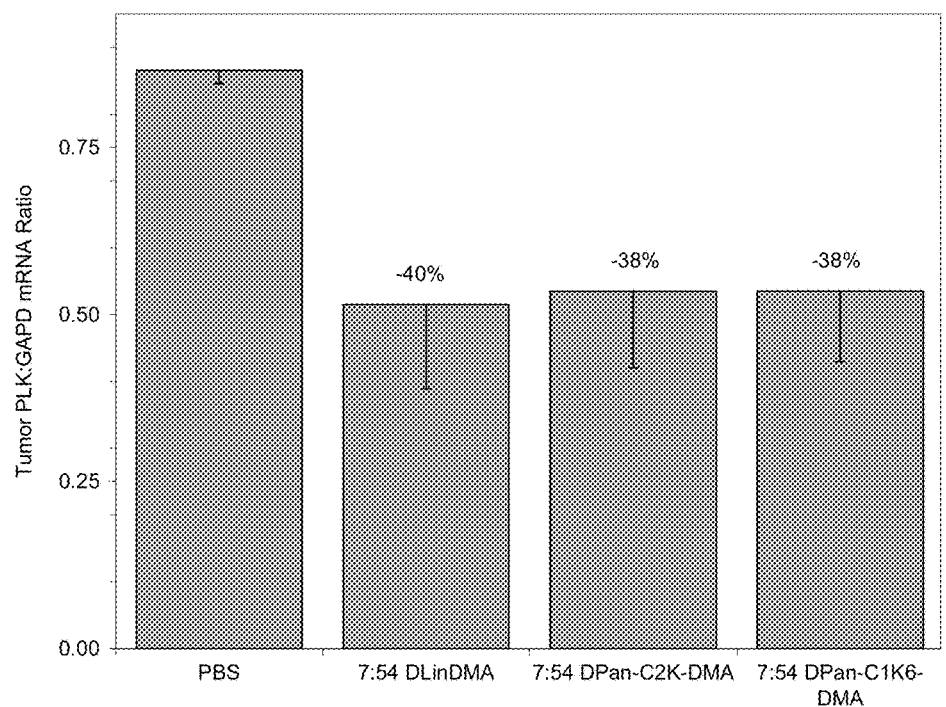

FIG. 13 illustrates that all of the cationic lipids tested in the tumor-directed 7:54 SNALP formulation displayed similar potencies in silencing PLK-1 expression.

Example 10. Characterization of Inflammatory Response to Tumor-Directed SNALP Formulations in Human Whole Blood Inflammatory response to tumor-directed SNALPs containing an siRNA targeting a gene of interest such as PLK-1 can be evaluated by measuring cytokine induction ex vivo in whole blood samples taken from human subjects. In certain instances, the SNALPs can contain either no siRNA payload ("empty") or an siRNA payload. The siRNAs tested can include, e.g., any of the PLK-1 siRNA molecules described herein. Briefly, fresh blood is isolated, immediately diluted 1:1 with 0.9% saline solution, and plated 0.45 mL/well into 48 well tissue culture treated plates. SNALPs are diluted in formulation PBS and added to the plated blood samples at a concentration of either 300 nM or 1200 nM. After 24 hours, the plates are centrifuged at 1200 rpm for 20 minutes and the supernatant (plasma) is collected. Cytokine induction (e.g., TNFα, IL-8, etc.) can be measured by ELISA and/or Cytometric Bead Array.

In particular embodiments, increasing the number of selective 2'OMe modifications to the siRNA sequence (e.g., 2'OMe modifications at G's and/or U's in the double-stranded and/or 3' overhang regions of the siRNA sequence) can decrease the immunostimulatory response to the siRNA.

Example 11. In Vitro and In Vivo Activity Screen of Modified PLK-1 siRNAs in Tumor-Directed SNALP Formulations PLK-1 siRNAs of the same nucleotide sequence were modified to incorporate an increasing number and alternate patterns of 2'OMe nucleotides. Ten different sense strands (S-1 to S-10) and 135 different antisense strands (AS-A to AS-H and AS-1 to AS-127) were designed. PLK-1 double-stranded siRNAs were generated by mix and match annealing of all possible combinations of sense strands and antisense strands. The number of modifications for double-stranded PLK-1 siRNAs ranged from 7 to 11 2'OMe nucleotides in the double-stranded region. Additionally, some of the patterns of modification include 2' OMe-modified nucleotides in the 3' overhang of one or both strands of the siRNA, such that the number of modifications are further increased to about 9 to about 14 in the entire siRNA molecule. Table 6 shows exemplary modified double-stranded PLK-1 siRNAs that resulted from the mix and match annealing of sense strands S-1 to S-10 with antisense strands AS-A to AS-H and AS-1 to AS-127.

TABLE 6

| SIRNA | PLK-1 siRNA Sequence | % 2'OMe-Modified | % Modified in DS Region |
|---|---|---|---|
| PLK1424 S3/ASF | 5'-AGA_U_CACCC_U_CC_UU_AAA_U_A_U_U-3'<br>3'-C_UU_C_U_AG_U_GGGAG_G_AA_U_UUAU-5' | 9/42 = 21.4% | 7/38 = 18.4% |
| PLK1424 S3/AS1 | 5'-AGA_U_CACCC_U_CC_UU_AAA_U_A_U_U-3'<br>3'-C_UU_C_U_AG_U_GGGAG_G_AA_U_UUAU-5' | 10/42 = 23.8% | 8/38 = 21.1% |
| PLK1424 S3/AS3 | 5'-AGA_U_CACCC_U_CC_UU_AAA_U_A_U_U-3'<br>3'-C_UU_C_U_AG_U_GGGAG_G_AA_U_UUAU-5' | 10/42 = 23.8% | 8/38 = 21.1% |
| PLK1424 S3/AS4 | 5'-AGA_U_CACCC_U_CC_UU_AAA_U_A_U_U-3'<br>3'-C_UU_C_U_AG_U_GGGAG_G_AA_U_UUAU-5' | 10/42 = 23.8% | 8/38 = 21.1% |
| PLK1424 S3/AS5 | 5'-AGA_U_CACCC_U_CC_UU_AAA_U_A_U_U-3'<br>3'-C_UU_C_U_AG_U_GGGAG_G_AA_U_UUA_U_-5' | 10/42 = 23.8% | 8/38 = 21.1% |
| PLK1424 S3/AS6 | 5'-AGA_U_CACCC_U_CC_UU_AAA_U_A_U_U-3'<br>3'-C_UU_C_U_AG_U_GGGAG_G_AA_U_UUAU-5' | 11/42 = 26.2% | 9/38 = 23.7% |
| PLK1424 S3/AS7 | 5'-AGA_U_CACCC_U_CC_UU_AAA_U_A_U_U-3'<br>3'-C_UU_C_U_AG_U_GGGAG_G_AA_UU_UAU-5' | 11/42 = 26.2% | 9/38 = 23.7% |
| PLK1424 S3/AS8 | 5'-AGA_U_CACCC_U_CC_UU_AAA_U_A_U_U-3'<br>3'-C_UU_C_U_AG_U_GGGAG_G_AA_U_U_U_AU-5' | 11/42 = 26.2% | 9/38 = 23.7% |
| PLK1424 S3/AS9 | 5'-AGA_U_CACCC_U_CC_UU_AAA_U_A_U_U-3'<br>3'-C_UU_C_U_AG_U_GGGAG_G_AA_U_UUA_U_-5' | 11/42 = 26.2% | 9/38 = 23.7% |
| PLK1424 S3/AS10 | 5'-AGA_U_CACCC_U_CC_UU_AAA_U_A_U_U-3'<br>3'-C_UU_C_U_AG_U_GGGAG_G_AA_U_UU_U_A_U_-5 | 11/42 = 26.2% | 9/38 = 23.7% |
| PLK1424 S3/AS11 | 5'-AGA_U_CACCC_U_CC_UU_AAA_U_A_U_U-3'<br>3'-C_UU_C_U_AG_U_GGGAG_G_AA_U_UUA_U_-5' | 11/42 = 26.2% | 9/38 = 23.7% |
| PLK1424 S3/AS12 | 5'-AGA_U_CACCC_U_CC_UU_AAA_U_A_U_U-3'<br>3'-C_UU_C_U_AG_U_GGGAG_G_AA_U_UUA_U_-5 | 11/42 = 26.2% | 9/38 = 23.7% |
| PLK1424 S3/AS13 | 5'-AGA_U_CACCC_U_CC_UU_AAA_U_A_U_U-3'<br>3'-C_UU_C_U_AG_U_GGGAG_G_AA_U_UUAU-5' | 11/42 = 26.2% | 9/38 = 23.7% |
| PLK1424 S3/AS14 | 5'-AGA_U_CACCC_U_CC_UU_AAA_U_A_U_U-3'<br>3'-C_UU_C_U_AG_U_GGGAG_G_AA_U_U_U_AU-5' | 11/42 = 26.2% | 9/38 = 23.7% |
| PLK1424 S3/AS15 | 5'-AGA_U_CACCC_U_CC_UU_AAA_U_A_U_U-3'<br>3'-C_UU_C_U_AG_U_GGGAG_G_AA_U_U_U_AU-5' | 11/42 = 26.2% | 9/38 = 23.7% |

TABLE 6-continued

| SIRNA | PLK-1 siRNA Sequence | % 2'OMe-Modified | % Modified in DS Region |
|---|---|---|---|
| PLK1424 S4/ASF | 5'-AGA<u>U</u>CACCC<u>U</u>CC<u>U</u>UAAA<u>U</u>A<u>UU</u>-3'<br>3'-C<u>UU</u>C<u>U</u>A<u>G</u>UGGGAG<u>G</u>AAUUUAU-5' | 10/42 = 23.8% | 7/38 = 18.4% |
| PLK1424 S4/AS1 | 5'-AGA<u>U</u>CACCC<u>U</u>CC<u>U</u>UAAA<u>U</u>A<u>UU</u>-3'<br>3'-C<u>U</u>UC<u>U</u>A<u>G</u>UGGGAG<u>G</u>AAUUUA<u>U</u>-5' | 11/42 = 26.2% | 8/38 = 21.1% |
| PLK1424 S4/AS2 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>UGGGAG<u>G</u>AAU<u>U</u>UAU-5' | 11/42 = 26.2% | 8/38 = 21.1% |
| PLK1424 S4/AS3 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>UGGGAG<u>G</u>AAU<u>UU</u>AU-5' | 11/42 = 26.2% | 8/38 = 21.1% |
| PLK1424 S4/AS4 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>UGGGAG<u>G</u>AAU<u>UU</u>A<u>U</u>-5' | 11/42 = 26.2% | 8/38 = 21.1% |
| PLK1424 S4/AS5 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>UGGGAG<u>G</u>AAUUUA<u>U</u>-5' | 11/42 = 26.2% | 8/38 = 21.1% |
| PLK1424 S4/AS6 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>U<u>G</u>GGAG<u>G</u>AAUUUAU-5' | 12/42 = 28.6% | 9/38 = 23.7% |
| PLK1424 S4/AS7 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>U<u>G</u>GGAG<u>G</u>AAUUUA<u>U</u>-5' | 12/42 = 28.6% | 9/38 = 23.7% |
| PLK1424 S4/AS8 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>U<u>G</u>GGAG<u>G</u>AAU<u>U</u>UAU-5' | 12/42 = 28.6% | 9/38 = 23.7% |
| PLK1424 S4/AS9 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>U<u>G</u>GGAG<u>G</u>AAU<u>UU</u>AU-5' | 12/42 = 28.6% | 9/38 = 23.7% |
| PLK1424 S4/AS10 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>U<u>G</u>GGAG<u>G</u>AAU<u>UU</u>A<u>U</u>-5' | 12/42 = 28.6% | 9/38 = 23.7% |
| PLK1424 S4/AS11 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>U<u>G</u>GGAG<u>G</u>AAUUUA<u>U</u>-5' | 12/42 = 28.6% | 9/38 = 23.7% |
| PLK1424 S4/AS12 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>UGGGAG<u>G</u>AAU<u>UU</u>AU-5' | 12/42 = 28.6% | 9/38 = 23.7% |
| PLK1424 S4/AS13 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>UGGGAG<u>G</u>AA<u>UUU</u>AU-5' | 12/42 = 28.6% | 9/38 = 23.7% |
| PLK1424 S4/AS14 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>UGGGAG<u>G</u>AAU<u>UU</u>A<u>U</u>-5' | 12/42 = 28.6% | 9/38 = 23.7% |
| PLK1424 S4/AS15 | 5'-AGA<u>U</u>CACCC<u>U</u>CC<u>U</u>UAAA<u>U</u>A<u>UU</u>-3'<br>3'-C<u>UU</u>C<u>U</u>A<u>G</u>UGGGAG<u>G</u>AAU<u>U</u>UA<u>U</u>-5' | 12/42 = 28.6% | 9/38 = 23.7% |
| PLK1424 S9/ASF | 5'-A<u>G</u>A<u>U</u>CACCC<u>U</u>CC<u>UU</u>AAA<u>U</u>A<u>UU</u>-3'<br>3'-C<u>UU</u>C<u>U</u>A<u>G</u>UGGGAG<u>G</u>AAUUUAU-5' | 11/42 = 26.2% | 9/38 = 23.7% |
| PLK1424 S9/AS1 | 5'-A<u>G</u>A<u>U</u>CACCC<u>U</u>CC<u>UU</u>AAA<u>U</u>A<u>UU</u>-3'<br>3'-C<u>UU</u>C<u>U</u>A<u>G</u>UGGGAG<u>G</u>AAUUUA<u>U</u>-5' | 12/42 = 28.6% | 10/38 = 26.3% |
| PLK1424 S9/AS2 | 5'-A<u>G</u>A<u>U</u>CACCC<u>U</u>CC<u>UU</u>AAA<u>U</u>A<u>UU</u>-3'<br>3'-C<u>UU</u>C<u>U</u>A<u>G</u>UGGGAG<u>G</u>AAU<u>U</u>UAU-5' | 12/42 = 28.6% | 10/38 = 26.3% |
| PLK1424 S9/AS3 | 5'-A<u>G</u>A<u>U</u>CACCC<u>U</u>CC<u>UU</u>AAA<u>U</u>A<u>UU</u>-3'<br>3'-C<u>UU</u>C<u>U</u>A<u>G</u>UGGGAG<u>G</u>AAU<u>UU</u>AU-5' | 12/42 = 28.6% | 10/38 = 26.3% |
| PLK1424 S9/AS4 | 5'-A<u>G</u>A<u>U</u>CACCC<u>U</u>CC<u>UU</u>AAA<u>U</u>A<u>UU</u>-3'<br>3'-C<u>UU</u>C<u>U</u>A<u>G</u>UGGGAG<u>G</u>AAU<u>UU</u>A<u>U</u>-5' | 12/42 = 28.6% | 10/38 = 26.3% |
| PLK1424 S9/AS5 | 5'-A<u>G</u>A<u>U</u>CACCC<u>U</u>CC<u>UU</u>AAA<u>U</u>A<u>UU</u>-3'<br>3'-C<u>UU</u>C<u>U</u>A<u>G</u>UGGGAG<u>G</u>AAUUUA<u>U</u>-5' | 12/42 = 28.6% | 10/38 = 26.3% |
| PLK1424 S9/AS6 | 5'-A<u>G</u>A<u>U</u>CACCC<u>U</u>CC<u>UU</u>AAA<u>U</u>A<u>UU</u>-3'<br>3'-C<u>UU</u>C<u>U</u>A<u>G</u>U<u>G</u>GGAG<u>G</u>AAUUUAU-5' | 13/42 = 31.0% | 11/38 = 28.9% |
| PLK1424 S9/AS7 | 5'-A<u>G</u>A<u>U</u>CACCC<u>U</u>CC<u>UU</u>AAA<u>U</u>A<u>UU</u>-3'<br>3'-C<u>UU</u>C<u>U</u>A<u>G</u>U<u>G</u>GGAG<u>G</u>AAUUUA<u>U</u>-5' | 13/42 = 31.0% | 11/38 = 28.9% |
| PLK1424 S9/AS8 | 5'-A<u>G</u>A<u>U</u>CACCC<u>U</u>CC<u>UU</u>AAA<u>U</u>A<u>UU</u>-3'<br>3'-C<u>UU</u>C<u>U</u>A<u>G</u>U<u>G</u>GGAG<u>G</u>AAU<u>U</u>UAU-5' | 13/42 = 31.0% | 11/38 = 28.9% |

TABLE 6-continued

| SIRNA | PLK-1 siRNA Sequence | % 2'OMe-Modified | % Modified in DS Region |
|---|---|---|---|
| PLK1424 S9/AS9 | 5'-AGAUCACCCUCCUUAAAUAUU-3'<br>3'-CUUCUAGUGGGAGGAAUUUAU-5' | 13/42 = 31.0% | 11/38 = 28.9% |
| PLK1424 S9/AS10 | 5'-AGAUCACCCUCCUUAAAUAUU-3'<br>3'-CUUCUAGUGGGAGGAAUUUAU-5' | 13/42 = 31.0% | 11/38 = 28.9% |
| PLK1424 S9/AS11 | 5'-AGAUCACCCUCCUUAAAUAUU-3'<br>3'-CUUCUAGUGGGAGGAAUUUAU-5' | 13/42 = 31.0% | 11/38 = 28.9% |
| PLK1424 S9/AS12 | 5'-AGAUCACCCUCCUUAAAUAUU-3'<br>3'-CUUCUAGUGGGAGGAAUUUAU-5' | 13/42 = 31.0% | 11/38 = 28.9% |
| PLK1424 S9/AS13 | 5'-AGAUCACCCUCCUUAAAUAUU-3'<br>3'-CUUCUAGUGGGAGGAAUUUAU-5' | 13/42 = 31.0% | 11/38 = 28.9% |
| PLK1424 S9/AS14 | 5'-AGAUCACCCUCCUUAAAUAUU-3'<br>3'-CUUCUAGUGGGAGGAAUUUAU-5' | 13/42 = 31.0% | 11/38 = 28.9% |
| PLK1424 S9/AS15 | 5'-AGAUCACCCUCCUUAAAUAUU-3'<br>3'-CUUCUAGUGGGAGGAAUUUAU-5' | 13/42 = 31.0% | 11/38 = 28.9% |
| PLK1424 S10/ASF | 5'-AGAUCACCCUCCUUAAAUAUU-3'<br>3'-CUUCUAGUGGGAGGAAUUUAU-5' | 12/42 = 28.6% | 9/38 = 23.7% |
| PLK1424 S10/AS1 | 5'-AGAUCACCCUCCUUAAAUAUU-3'<br>3'-CUUCUAGUGGGAGGAAUUUAU-5' | 13/42 = 31.0% | 10/38 = 26.3% |
| PLK1424 S10/AS2 | 5'-AGAUCACCCUCCUUAAAUAUU-3'<br>3'-CUUCUAGUGGGAGGAAUUUAU-5' | 13/42 = 31.0% | 10/38 = 26.3% |
| PLK1424 S10/AS3 | 5'-AGAUCACCCUCCUUAAAUAUU-3'<br>3'-CUUCUAGUGGGAGGAAUUUAU-5' | 13/42 = 31.0% | 10/38 = 26.3% |
| PLK1424 S10/AS4 | 5'-AGAUCACCCUCCUUAAAUAUU-3'<br>3'-CUUCUAGUGGGAGGAAUUUAU-5' | 13/42 = 31.0% | 10/38 = 26.3% |
| PLK1424 S10/AS5 | 5'-AGAUCACCCUCCUUAAAUAUU-3'<br>3'-CUUCUAGUGGGAGGAAUUUAU-5' | 13/42 = 31.0% | 10/38 = 26.3% |
| PLK1424 S10/AS6 | 5'-AGAUCACCCUCCUUAAAUAUU-3'<br>3'-CUUCUAGUGGGAGGAAUUUAU-5' | 14/42 = 33.3% | 11/38 = 28.9% |
| PLK1424 S10/AS7 | 5'-AGAUCACCCUCCUUAAAUAUU-3'<br>3'-CUUCUAGUGGGAGGAAUUUAU-5' | 14/42 = 33.3% | 11/38 = 28.9% |
| PLK1424 S10/AS8 | 5'-AGAUCACCCUCCUUAAAUAUU-3'<br>3'-CUUCUAGUGGGAGGAAUUUAU-5' | 14/42 = 33.3% | 11/38 = 28.9% |
| PLK1424 S10/AS9 | 5'-AGAUCACCCUCCUUAAAUAUU-3'<br>3'-CUUCUAGUGGGAGGAAUUUAU-5' | 14/42 = 33.3% | 11/38 = 28.9% |
| PLK1424 S10/AS10 | 5'-AGAUCACCCUCCUUAAAUAUU-3'<br>3'-CUUCUAGUGGGAGGAAUUUAU-5' | 14/42 = 33.3% | 11/38 = 28.9% |
| PLK1424 S10/AS11 | 5'-AGAUCACCCUCCUUAAAUAUU-3'<br>3'-CUUCUAGUGGGAGGAAUUUAU-5' | 14/42 = 33.3% | 11/38 = 28.9% |
| PLK1424 S10/AS12 | 5'-AGAUCACCCUCCUUAAAUAUU-3'<br>3'-CUUCUAGUGGGAGGAAUUUAU-5' | 14/42 = 33.3% | 11/38 = 28.9% |
| PLK1424 S10/AS13 | 5'-AGAUCACCCUCCUUAAAUAUU-3'<br>3'-CUUCUAGUGGGAGGAAUUUAU-5' | 14/42 = 33.3% | 11/38 = 28.9% |
| PLK1424 S10/AS14 | 5'-AGAUCACCCUCCUUAAAUAUU-3'<br>3'-CUUCUAGUGGGAGGAAUUUAU-5' | 14/42 = 33.3% | 11/38 = 28.9% |
| PLK1424 S10/AS15 | 5'-AGAUCACCCUCCUUAAAUAUU-3'<br>3'-CUUCUAGUGGGAGGAAUUUAU-5' | 14/42 = 33.3% | 11/38 = 28.9% |

Tumor-directed SNALP formulations (e.g., 7:54 and/or 7:58 SNALP) containing encapsulated PLK-1 duplexes as described in Table 6 can be prepared as described herein. For in vitro siRNA activity assays, cell lines such as Hep3B, HepG2, HT29, LS174T, and Neuro2a cells can be cultured in 96 well plates in the presence of SNALP-formulated siRNA. Cell viability can be assessed after 72 h using the resazurin dye CellTiter Blue (Promega Corp). Corresponding PLK-1 mRNA silencing activity can be assessed in replicate plates at 24 h by the bDNA assay (Panomics Inc.).

The level of Caspase 3 and 7 enzyme activity in siRNA-treated cells can be assessed using the fluorescent Caspase 3/7 substrate (Z-DEVD)2-Rhodamine 110 reagent Apo-ONE (Promega Corp.).

For in vivo siRNA activity assays, an intrahepatic tumor model can be utilized. Liver tumors are established in mice by direct intrahepatic injection of Hep3B or Neuro2a tumor cells. Female scid/beige mice (Charles River Laboratories) and/or male A/J mice (Jackson Laboratories) are used as hosts for the Hep3B or Neuro2a tumors. Animals can receive Anafen by SC injection immediately prior to surgery. Individual mice can be anaesthetized by isoflourane gas inhalation and eye lube applied to prevent excessive eye drying. While maintained under gas anaesthesia, a single 1.5 cm incision across the midline can be made below the sternum and the left lateral hepatic lobe exteriorized. $1 \times 10^6$ Hep3B cells or $1 \times 10^5$ Neuro2a cells suspended in 25 μL PBS can be injected slowly into the lobe at a shallow angle using a Hamilton syringe and 30 G needle. A swab is then applied to the puncture wound to stop any bleeding prior to suturing. Mice are allowed to recover from anaesthesia in a sterile cage and monitored closely for 2-4 h before being returned to conventional housing. Eight to 11 days after tumor implantation, mice can be randomized into treatment groups. Tumor-directed SNALP formulations (e.g., 7:54 and/or 7:58 SNALP) containing encapsulated PLK-1 duplexes as described in Table 6 or PBS vehicle control are administered by standard intravenous injection via the lateral tail vein, calculated on a mg siRNA/kg basis according to individual animal weights (10 mL/kg injection volume). Body weights are then monitored throughout the duration of the study as an indicator of developing tumor burden and treatment tolerability. For efficacy studies, defined humane endpoints are determined as a surrogate for survival. Assessments are made by qualified veterinary technicians based on a combination of clinical signs, weight loss, and abdominal distension to define the day of euthanization due to tumor burden.

A subcutaneous tumor model can also be utilized for in vivo siRNA activity assays. Hep3B tumors can be established in female scid/beige mice by subcutaneous injection of $3 \times 10^6$ cells in 50 μL PBS into the left hind flank. Mice are randomized into treatment groups 10-17 days after seeding as tumors became palpable. Tumor-directed SNALP formulations (e.g., 7:54 and/or 7:58 SNALP) containing encapsulated PLK-1 duplexes as described in Table 6 are administered as described above. Tumors can be measured in 2 dimensions (Width×Length) to assess tumor growth using digital calipers. Tumor volume can be calculated using the equation a×b×b/2 where a and b=largest and smallest diameters, respectively, and expressed as group mean +/− SD.

For the in vivo siRNA activity assays, human PLK-1 and GAPDH mRNA can be measured in tumor lystes by the QuantiGene bDNA assay (Panomics) per the manufacturer's instructions (Quantigene 1.0 Manual). Human-specific PLK-1 (NM_005030) and GAPDH (NM_002046) probe sets can be designed to have minimal cross-reactivity to the mouse counterpart mRNA. Data can be expressed as the mean PLK-1:GAPDH ratio +/− SD of individual animals.

In particular embodiments, increasing the number of selective 2'OMe modifications to the siRNA sequence (e.g., 2'OMe modifications at G's and/or U's in the double-stranded and/or 3' overhang regions of the siRNA sequence) does not decrease activity, and in some cases increases silencing activity.

Example 12. Synthesis of
1,2-Di-γ-Linolenyloxy-N,N-Dimethylaminopropane
(γ-DLenDMA)

γ-DLenDMA having the structure shown below was synthesized as described below.

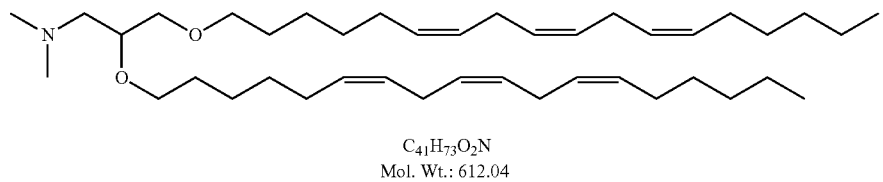 [SMILES: CCCCC/C=C\C/C=C\C/C=C\CCCCCOCC(CN(C)C)OCCCCC/C=C\C/C=C\C/C=C\CCCCC]

$C_{41}H_{73}O_2N$
Mol. Wt.: 612.04

A 250 mL round bottom flask was charged with 3-(dimethylamino)-1,2-propanediol (0.8 g, 6.7 mmol), tetrabutylammonium hydrogen sulphate (1 g), gamma linolenyl mesylate (cis-6,9,12-octadecatriene sulphonic acid) (5 g, 14.6 mmol), and 30 mL toluene. After stirring for 15 minutes, the reaction was cooled to 0-5° C. A solution of 40% sodium hydroxide (15 mL) was added slowly. The reaction was left to stir for approximately 48 hours. An additional 15 mL of toluene was then added to the reaction vessel, along with 40% sodium hydroxide (15 mL). After the reaction was stirred for an additional 12 hours, water (50 mL) and isopropyl acetate (50 mL) were added and stirred for 15 minutes. The mixture was then transferred to a 500 mL separatory funnel and allowed to separate. The lower aqueous phase was run off and the organic phase was washed with saturated sodium chloride (2×50 mL). Since the aqueous and organic phases resulting from the saturated sodium chloride washes could not be completely separated after 20 minutes, the lower aqueous phase (slightly yellow) was run off and back extracted with chloroform (~45 mL). The organic phase was dried with MgSO$_4$, filtered, and the solvent evaporated.

The crude product, an orange liquid, was purified on column chromatography using silica gel (60 g) with 0-3% methanol gradient in dichloromethane to yield 3.19 g. The product was further purified via column chromatography on silica gel (50 g) with 10-30% ethyl acetate gradient in hexanes to yield 1.26 g pure product.

Example 13. Synthesis of 1,2-Diphytanyloxy-3-(N,N-dimethyl)-propylamine (DPanDMA)

DPanDMA having the structure shown below was synthesized as described below.

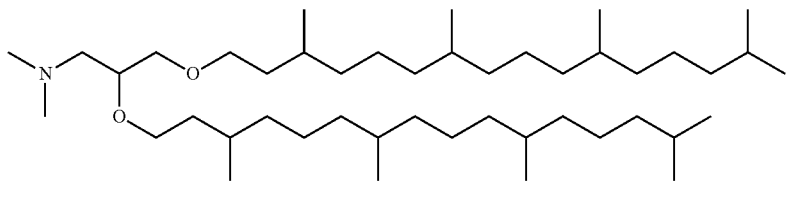

C$_{45}$H$_{93}$NO$_2$
Exact Mass: 679.72
Mol. Wt.: 680.23
C, 79.46; H, 13.78; N, 2.06; O, 4.70

Step 1: Synthesis of Phytanol

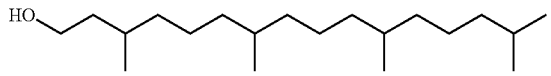

C$_{20}$H$_{42}$O
Exact Mass: 298.32
Mol. Wt.: 298.55
C, 80.46; H, 14.18; O, 5.36

Phytol (21.0 g, 70.8 mmol), ethanol (180 mL) and a stir bar were added to a 500 mL round bottom flask. Raney Nickel 2800 (as purchased, a 50% by weight solution in water if used as purchased, Nickel >89% metal present) (6.8 g, 51.5 mmol) was added, and the flask sealed and flushed with hydrogen. A 12" needle was used to bubble hydrogen through the solution for 10 minutes. The reaction was stirred for 5 days, using a balloon as a hydrogen reservoir. Hydrogen was also bubbled through the reaction mixture at 24 h and 48 h, 5 minutes each time. The metal catalyst was then removed by filtering through Celite. The ethanolic solution was concentrated, and 200 mL of DCM added to the resulting oil. The solution was washed with water (2×100 mL), dried over MgSO$_4$, and concentrated. TLC indicated formation of the phytanol product, yield 20.0 g.

Step 2: Synthesis of Phytanyl Mesylate

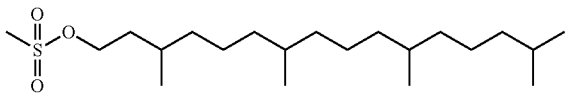

C$_{21}$H$_{44}$O$_3$S
Exact Mass: 376.30
Mol. Wt.: 376.64
C, 66.97; H, 11.78; O, 12.74; S, 8.51

Phytanol (20.0 g, 66.7 mmol), triethylamine (18.6 mL, 133 mmol), and a stir bar were added to a 1000 mL round bottom flask. The flask was sealed and flushed with nitrogen. Anhydrous DCM (250 mL) was added, and the mixture cooled to −15° C. (ice and NaCl). Mesyl Chloride (10.4 mL, 133 mmol) was added slowly via syringe over a 30 minute period, and the reaction stirred at −15° C. for a further 1.5 hours. At this point TLC showed that the starting material had been used up. The solution was diluted with DCM (250 mL) and washed with saturated NaHCO$_3$ (2×200 mL). The organic phase was then dried (MgSO$_4$), filtered, and concentrated (rotovap). The crude product was purified by column chromatography. Yield: 21.5 g, 85.7%.

Step 3: Synthesis of DPanDMA

Sodium hydride (2.5 g, 100 mmol) was added to a 250 mL round bottom flask, along with benzene (40 mL) and a stir bar. In a 50 mL beaker, a solution was made from the N,N-Dimethyl-3-aminopropane-1,2-diol (1.42 g, 12 mmol) and benzene (60 mL). This was added to the reaction vessel and the reaction stirred for 10 minutes (effervescence). Phytanyl Mesylate (10.52 g, 28 mmol) was added and the flask fitted with a condenser, flushed with nitrogen, and heated to reflux. After 18 hours, the flask was removed from the heat and allowed to cool. The volume was made up to 200 mL with benzene. EtOH was added slowly to quench unreacted sodium hydride. Once quenching was complete, the reaction mixture was washed twice with EtOH/H$_2$O, in a ratio to the benzene of 1:1:0.6 benzene:water:ethanol. The aqueous phases were combined and extracted with CHCl$_3$ (2×100 mL). Finally, the organic phase was dried (MgSO$_4$), filtered, and concentrated (rotovap). Purification by column chromatography yielded DPanDMA as a pale yellow oil (6.1 g, 8.97 mmol, 74.7%).

145

Example 14. Synthesis of Cationic Lipids of the TLinDMA Family

The following diagram provides a general scheme for synthesizing members of the C(n)-TLinDMA family of cationic lipids:

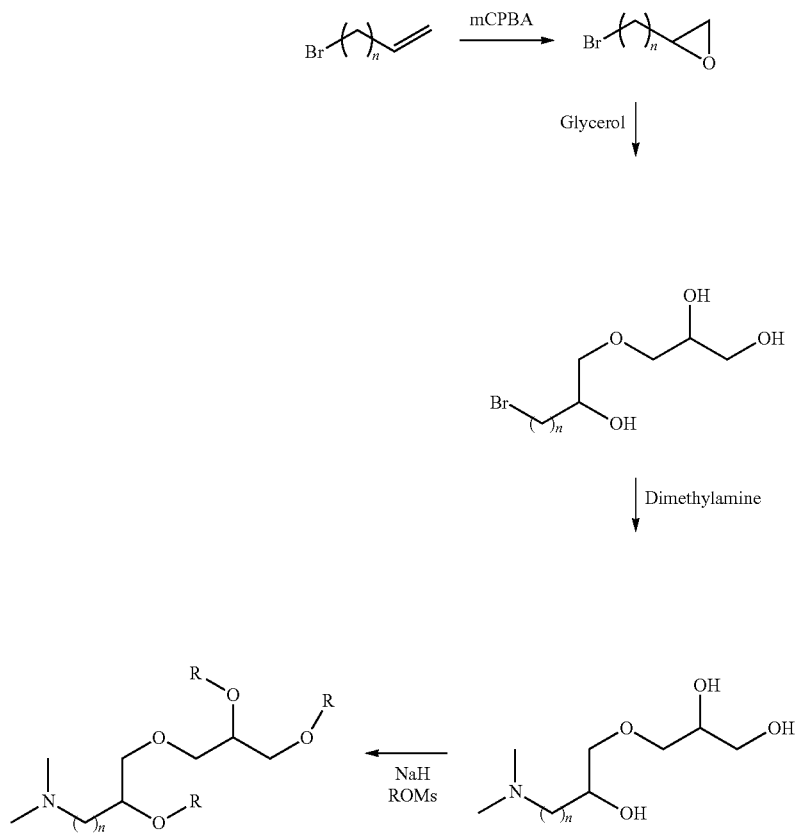

R = Linoleyl; n is 0, 1, 2, 3, or 4

TLinDMA (1-(2,3-linoleyloxypropoxy)-2-(linoleyloxy)-(N,N-dimethyl)-propyl-3-amine) (Compound III) was synthesized as follows:

Synthesis of Compound I

A 1000 ml round bottom flask was charged with epibromohydrin (5 g, 37 mmol), glycerol (10 g, 110 mmol), a stir bar and then flushed with nitrogen. Anhydrous chloroform (350 mL) was added via cannula, followed by $BF_3 \cdot Et_2O$ (0.5 mL, 3.7 mmol) and refluxed for 3 hours under nitrogen. The reaction mixture was cooled and subsequently stirred at room temperature overnight. Upon completion of the reaction, the reaction mixture was concentrated and the crude product (15 g) was purified via column chromatography using silica gel (150 g).

146

Synthesis of Compound II

A 500 mL round bottom flask was charged with Compound I (3.8 g, 17 mmol) and a stir bar. After flushing with nitrogen, dimethylamine in a 2.0 M methyl alcohol solution (170 mL) was added via cannula. The resulting mixture was stirred at room temperature for 48 hours. The progress of the reaction was monitored using TLC. The crude product was used without further purification.

Synthesis of TLinDMA (Compound III)

A 100 mL round bottom flask was charged with a stir bar, NaH (0.6 g, 24 mmol), and 25 mL benzene. Subsequently, Compound II (0.4 g, 2 mmol) was added followed immediately by linoleyl methane sulfonate (2.8 g, 8 mmol). The reaction was flushed with nitrogen and refluxed overnight. Progress of the reaction was monitored via TLC. The reaction mixture was transferred to a 250 mL separatory funnel and diluted with benzene to a final volume of 50 mL. The reaction was quenched with ethanol (30 mL) and then washed with water (50 mL). The lower aqueous phase was run off and the reaction mixture was washed again with ethanol (30 mL) and water (50 mL). The organic phase was dried with MgSO₄, filtered, and solvent removed. The crude product (2.3 g) was purified via column chromatography on silica gel (60 g) with 0-3% methanol gradient in dichloromethane.

C2-TLinDMA (Compound VII) was synthesized as follows:

Synthesis of Compound IV

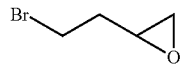

Chemical Formula: C₄H₇BrO
Exact Mass: 150.0
Molecular Weight: 151.0
Elemental Analysis: C, 31.82; H, 4.67; Br, 52.92; O, 10.60

A solution of 4-bromo-1-butene (11.5 g, 85 mmol) in CH₂Cl₂ (anh., 120 ml) was prepared under nitrogen in a 1000 ml RBF with a magnetic stirrer. In a separate flask, a solution of 3-chloroperbenzoic acid (77%, MW 173, 44.05 g, 196 mmol) in CH₂Cl₂ (anh., 250 ml) prepared and added to the reaction mixture by cannula. The reaction was stirred for 3 days, and then concentrated. The product (oil/white solid mixture) was re-dissolved in THF (300 mL) and a solution of 4% sodium dithionite (180 mL) added to remove excess peracid. The mixture (now cloudy) was stirred for 20 minutes and then EtOAc (750 mL) added. The mixture was transferred to a separating funnel and the organic was washed with water (100 mL), sat. NaHCO₃ (2×300 mL, EFFERVESCENCE), water again (300 mL) and brine (300 mL). The solution was concentrated and the product purified by chromatography.

Synthesis of Compound V

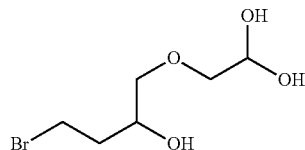

Chemical Formula: C₇H₁₅BrO₄
Exact Mass: 242.0
Molecular Weight: 243.1

A 250 ml round bottom flask was charged with Compound IV (1.3 g, 9 mmol), glycerol (2.5 g, 27 mmol), a stir bar and then flushed with nitrogen. Anhydrous chloroform (100 mL) was added via cannula, followed by BF₃Et₂O (0.15 mL, 1.1 mmol) and refluxed for 3 hours under nitrogen. The reaction mixture was subsequently stirred at room temperature overnight.

Synthesis of Compound VI

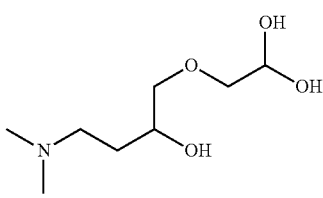

Chemical Formula: C₉H₂₁NO₄
Exact Mass: 207.1
Molecular Weight: 207.3

A 50 mL round bottom flask was charged with Compound V (0.3 g, 1.2 mmol) and a stir bar. After flushing with nitrogen, dimethylamine in a 2.0 M methyl alcohol solution (25 mL) was added via syringe. The resulting mixture was stirred at room temperature for 48 hours. The progress of the reaction was monitored using t.l.c. The reaction mixture was concentrated and the crude product used without further purification.

Synthesis of C2-TLinDMA (Compound VII)

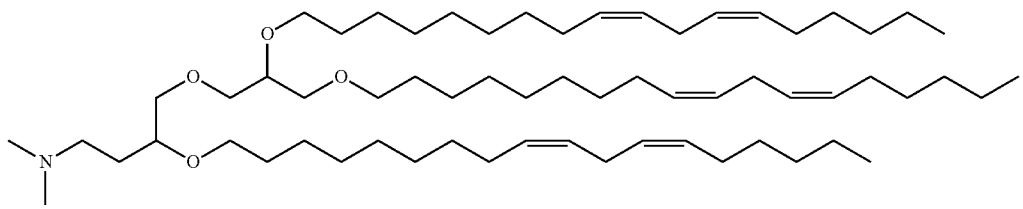

Chemical Formula: C₆₃H₁₁₇NO₄
Exact Mass: 951.9
Molecular Weight: 952.6

A 100 mL round bottom flask was charged with a stir bar, NaH (0.6 g, 24 mmol), and 25 mL benzene. Compound VI (0.37 g, 1.8 mmol) was added followed immediately by linoleyl methane sulfonate (2.8 g, 8 mmol). The reaction was refluxed overnight and progress of the reaction was monitored via t.l.c. The reaction mixture was transferred to a 250 mL separatory funnel and diluted with benzene to a final volume of 50 mL. The reaction was quenched with ethanol (30 mL) and then washed with water (50 mL). The lower aqueous phase was run off and the reaction mixture washed again with ethanol (30 mL) and water (50 mL). The organic phase was dried with MgSO₄, filtered, and solvent removed. The crude product, 2.5 g, was purified using column chromatography on silica gel (60 g), eluted with 0-3% methanol gradient in DCM.

C3-TLinDMA (Compound XI) was synthesized as follows:

Synthesis of Compound VIII

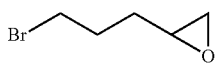

Chemical Formula: C₅H₉BrO
Exact Mass: 164.0
Molecular Weight: 165.0
Elemental Analysis: C, 36.39; H, 5.50; Br, 48.42; O, 9.69

A solution of 5-bromo-1-pentene (85 mmol) in CH₂Cl₂ (anh., 120 ml) is prepared under nitrogen in a 1000 ml RBF with a magnetic stirrer. In a separate flask, a solution of 3-chloroperbenzoic acid (77%, MW 173, 44.05 g, 196 mmol) in CH₂Cl₂ (anh., 250 ml) is prepared and added to the reaction mixture by cannula. The reaction is stirred for 3 days, and then concentrated. The product (oil/white solid mixture) is re-dissolved in THF (300 mL) and a solution of 4% sodium dithionite (180 mL) added to remove excess peracid. The mixture (now cloudy) is stirred for 20 minutes and then EtOAc (750 mL) added. The mixture is transferred to a separating funnel and the organic is washed with water (100 mL), sat. NaHCO₃ (2×300 mL, EFFERVESCENCE), water again (300 mL) and brine (300 mL). The solution is concentrated and the product purified by chromatography.

Synthesis of Compound IX

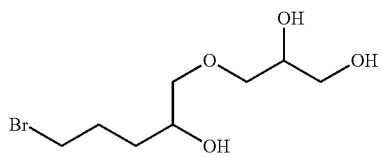

Chemical Formula: C₈H₁₇BrO₄
Exact Mass: 256.0
Molecular Weight: 257.1

A 250 ml round bottom flask is charged with Compound VIII (1.3 g, 9 mmol), glycerol (2.5 g, 27 mmol), a stir bar and then flushed with nitrogen. Anhydrous chloroform (100 mL) is added via cannula, followed by BF₃Et₂O (0.15 mL, 1.1 mmol) and refluxed for 3 hours under nitrogen. The reaction mixture is subsequently stirred at room temperature overnight.

Synthesis of Compound X

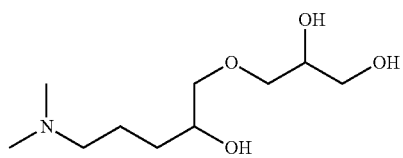

Chemical Formula: C₁₀H₂₃NO₄
Exact Mass: 221.2
Molecular Weight: 221.3

A 50 mL round bottom flask is charged with Compound IX (0.3 g, 1.2 mmol) and a stir bar. After flushing with nitrogen, dimethylamine in a 2.0 M methyl alcohol solution (25 mL) is added via syringe. The resulting mixture is stirred at room temperature for 48 hours. The progress of the reaction is monitored using t.l.c. The reaction mixture is concentrated and the crude product used without further purification.

Synthesis of C3-TLinDMA (Compound XI)

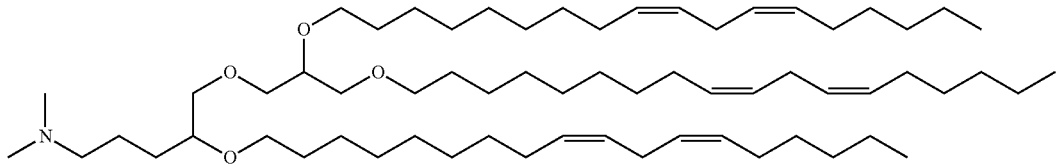

Chemical Formula: C₆₄H₁₁₉NO₄
Exact Mass: 965.9
Molecular Weight: 966.6

A 100 mL round bottom flask is charged with a stir bar, NaH (0.6 g, 24 mmol), and 25 mL benzene. Compound X (0.37 g, 1.8 mmol) is added followed immediately by linoleyl methane sulfonate (2.8 g, 8 mmol). The reaction is refluxed overnight and progress of the reaction monitored via t.l.c. The reaction mixture is transferred to a 250 mL separatory funnel and diluted with benzene to a final volume of 50 mL. The reaction is quenched with ethanol (30 mL) and then washed with water (50 mL). The lower aqueous phase is run off and the reaction mixture washed again with ethanol (30 mL) and water (50 mL). The organic phase is dried with MgSO$_4$, filtered, and solvent removed. The crude product, 2.5 g, is purified using column chromatography on silica gel (60 g), eluted with 0-3% methanol gradient in DCM.

Example 15. Synthesis of Novel C2 Lipids

Novel C2 lipids (Compounds V-VII) having the structures shown below were synthesized as shown in the following schematic diagram.

4-(2-Hydroxylethyl)-2,2-dimethyl-1,3-dioxolane (25 g, 170 mmol), triethylamine (55.9 mL, 400 mmol), and a stir bar were added to a 1000 mL round bottom flask. The flask was sealed and flushed with nitrogen. Anhydrous DCM (600 mL) was added, and the mixture cooled to approx −5° C. (ice and NaCl). Mesyl chloride (19.9 mL, 255 mmol, 1.5 eq) was added slowly via syringe over a 60 minute period, and the reaction stirred at −5° C. for a further 1.5 hours. At this point TLC showed that the starting material had been consumed. The solution was diluted with DCM (350 mL), divided into two (~500 mL) portions, and each portion worked up as follows: the solution was transferred to a 1000-mL separating funnel and washed with saturated NaHCO$_3$ (2×200 mL). The organic phase was then dried (MgSO$_4$), filtered, and concentrated (rotovap). The crude product was purified by column chromatography. Final yield: 32.0 g, 84.1%.

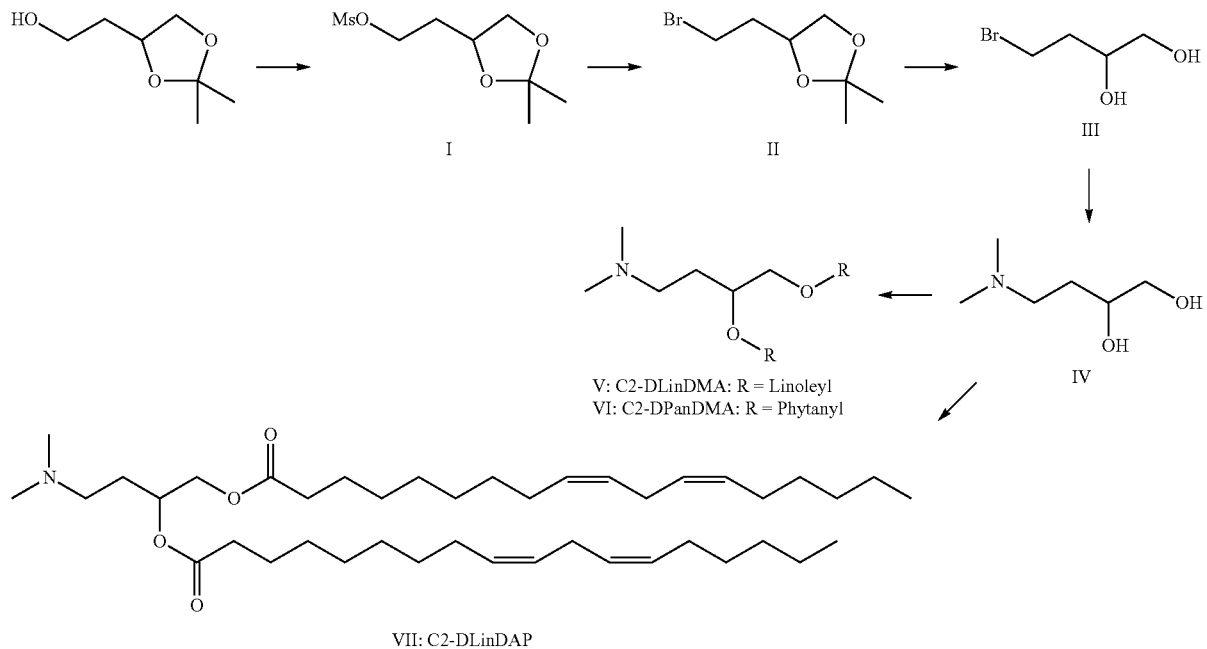

Step 1: Synthesis of 4-(2-Methanesulfonylethyl)-2,2-dimethyl-1,3-dioxolane (Compound I)

Step 2: Synthesis of 4-(2-Bromoethyl)-2,2-dimethyl-1,3-dioxolane (Compound II)

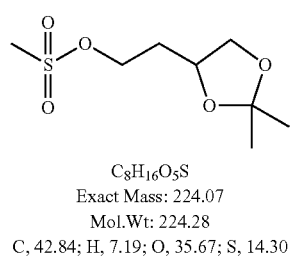

C$_8$H$_{16}$O$_5$S
Exact Mass: 224.07
Mol.Wt: 224.28
C, 42.84; H, 7.19; O, 35.67; S, 14.30

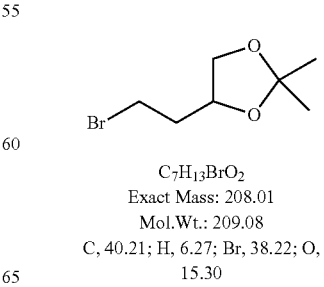

C$_7$H$_{13}$BrO$_2$
Exact Mass: 208.01
Mol.Wt.: 209.08
C, 40.21; H, 6.27; Br, 38.22; O, 15.30

Magnesium bromide etherate (40 g, 130 mmol) and a stir bar were added to a 2000 mL round bottom flask and flushed with nitrogen. A solution of 4-(2-methanesulfonylethyl)-2,2-dimethyl-1,3-dioxolane (I) (17.5 g, 78 mmol) in anhydrous diethyl ether (900 mL) was added via cannula, and the suspension stirred overnight. The ether was first decanted into a beaker. Water (200 mL) and ether (300 mL) were added to the precipitate and stirred for 5 minutes. The precipitate was dissolved, and the ether phase was then collected and added to the ether solution from the reaction. The organic phase was then washed, concentrated to about 500 mL, washed with water, dried over anhydrous $Mg_2SO_4$, filtered, and concentrated to yield a yellow oil (16.0 g). This was purified by flash chromatography to yield 10.6 g of product (50.7 mmol, 65%).

Step 3: Synthesis of 4-Bromobutane-1,2-diol (Compound III)

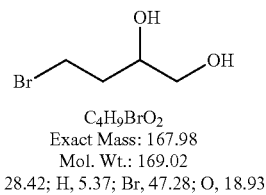

$C_4H_9BrO_2$
Exact Mass: 167.98
Mol. Wt.: 169.02
C, 28.42; H, 5.37; Br, 47.28; O, 18.93

4-(2-Bromoethyl)-2,2-dimethyl-1,3-dioxolane (II) (9 g, 43 mmol) was added to a 500 mL RBF with a stirbar. 100 mL of MeOH:$H_2$O:HCl in a ratio of (60:20:5) were added. After 30 minutes, sat. $NaHCO_3$ (~75 mL) was added (effervescence), until pH paper indicated solution was basic. At this point the mixture was slightly cloudy. Ether (300 mL) was added (while stirring) and the cloudiness disappeared. The reaction mixture was transferred to a 1000 mL sep funnel and the 2 phases separated. The extraction of the aqueous phase was repeated two more times (2×300 mL ether). Organics were combined, dried over $MgSO_4$ and concentrated to yield a colorless oil (7.0 g), which was purified by column chromatography.

Step 4: Synthesis of 4-(Dimethylamino)-1,2-butanediol (Compound IV)

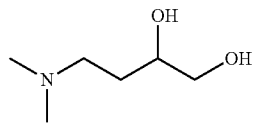

Chemical Formula: $C_6H_{15}NO_2$
Exact Mass: 133.1
Molecular Weight: 133.2
Elemental Analysis: C, 54.11; H, 11.35; N, 10.52; O, 24.03

4-Bromobutane-1,2-diol (III) (1 g, 6.0 mmol) was added to a 50 mL RBF with a stir bar, sealed, and flushed with nitrogen. 30 mL of Dimethylamine (2.0M solution in MeOH) was delivered by cannula and the reaction stirred overnight. TLC indicated all the starting material had disappeared. The solvent (and DMA) were removed by evaporation and the crude product used without further purification.

Synthesis of 1,2-Dilinoleyloxy-(N,N-dimethyl)-butyl-4-amine (C2-DLinDMA) (Compound V)

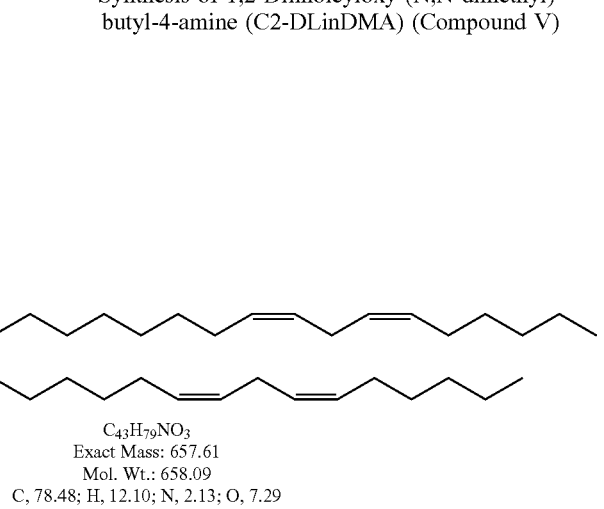

$C_{43}H_{79}NO_3$
Exact Mass: 657.61
Mol. Wt.: 658.09
C, 78.48; H, 12.10; N, 2.13; O, 7.29

4-(Dimethylamino)-1,2-butanediol (IV) (1.3 g, 3.4 mmol), linoleyl mesylate (2.0 g, 5.8 mmol), tetrabutylammonium hydrogen sulphate (0.5 g, 1.5 mmol), toluene (30 mL), and a stir bar were added to a 100 mL RBF. 30 mL of 40% NaOH was made and added to the reaction mixture. The resulting mixture was stirred at room temperature, under nitrogen for 60 hours. Deionized water (50 mL) and isopropyl acetate (50 mL) were added and the mixture stirred vigorously for a further 10-15 min. The mixture was transferred to a 250 mL separating funnel and allowed to separate and the aqueous phase removed. The organic phase was washed twice with water (2×30 mL) using MeOH to aid the separation, and the organic phase was dried (MgSO$_4$), filtered, and concentrated to obtain a dark yellow oil. The oil was purified by column chromatography.

Synthesis of 1,2-Diphytanyloxy-(N,N-dimethyl)-butyl-4-amine (C2-DPanDMA) (Compound VI)

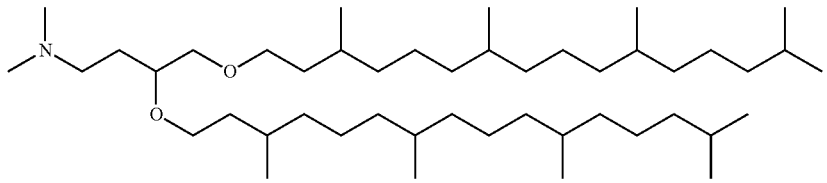

Chemical Formula: C$_{46}$H$_{95}$NO$_2$
Exact Mass: 693.7
Molecular Weight: 694.3
Elemental Analysis: C, 79.58; H, 13.79; N, 2.02; O, 4.61

Sodium hydride (360 mg, 15 mmol), benzene (40 mL), and a stir bar were added to a 50 mL round bottom flask. 4-(Dimethylamino)-1,2-butanediol (IV) (200 mg, 1.5 mmol) was added and the reaction stirred for 10 minutes (effervescence). Phytanyl Mesylate (1.07 g, 2.92 mmol) was then added and the flask fitted with a condenser, flushed with nitrogen, and heated to reflux. After 18 hours, the flask was allowed to cool to room temperature. The volume was made up to 40 mL with benzene. EtOH was added slowly to quench unreacted sodium hydride. Once quenching was complete, the reaction mixture was washed twice with an EtOH/H$_2$O, in a ratio to the benzene of 1:1:0.6 benzene:water:ethanol. The aqueous washes were combined and extracted with CHCl$_3$ (2×20 mL). Finally, the organics were combined, dried (MgSO$_4$), filtered, and concentrated (rotovap). Purification by column chromatography yielded a pale yellow oil (250 mg, 0.145 mmol, 25%).

Synthesis of 1,2-Dilinoleoyloxy-(N,N-dimethyl)-butyl-4-amine (C2-DLinDAP) (Compound VII)

solution stirred overnight. The solution was rinsed into a 250 mL separatory funnel with DCM (— 70 mL) and washed with water (2×50 mL). The organic was dried (MgSO$_4$), concentrated, and purified by chromatography.

Example 16. Synthesis of Novel Phytanyl Cationic Lipids

DPan-C2K-DMA, DPan-C1K6-DMA, and DPan-C3K-DMA having the structures shown below were synthesized as shown in the following schematic diagram.

Synthesis of Phytanol

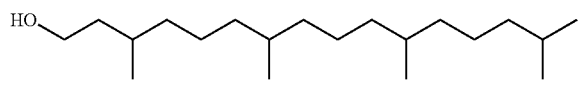

C$_{20}$H$_{42}$O
Exact Mass: 298.32
Mol. Wt.: 298.55
C, 80.46; H, 14.18; O, 5.36

Phytol (21.0 g, 70.8 mmol), ethanol (180 mL) and a stir bar were added to a 500 mL round bottom flask. Raney Nickel 2800 (as purchased, a 50% by weight solution in water if used as purchased, Nickel >89% metal present) (6.8 g, 51.5 mmol) was added, and the flask sealed and flushed with hydrogen. A 12" needle was used to bubble hydrogen through the solution for 10 minutes. The reaction was stirred for 5 days, using a balloon as a hydrogen reservoir. Hydro-

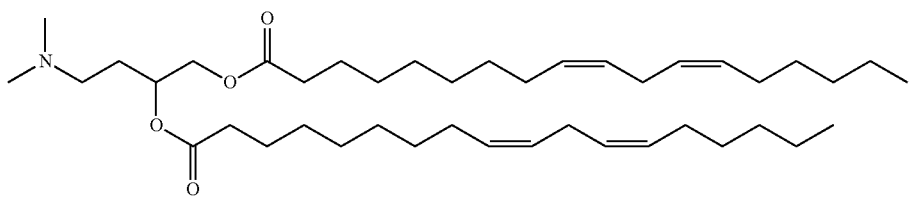

Chemical Formula: C$_{42}$H$_{75}$NO$_4$
Exact Mass: 657.6
Molecular Weight: 658.0
Elemental Analysis: C, 76.66; H, 11.49; N, 2.13; O, 9.73

A flask containing 4-(Dimethylamino)-1,2-butanediol (IV) (crude, 266 mg, 2 mmol (max)), TEA (0.84 mL, 6 mmol), and DMAP (24 mg, 0.2 mmol) was flushed with nitrogen before the addition of anhydrous CH$_2$Cl$_2$ (50 ml). Linoleoyl chloride (1.2 g, 4 mmol) was added and the gen was also bubbled through the reaction mixture at 24 h and 48 h, 5 minutes each time. The metal catalyst was then removed by filtering through Celite. The ethanolic solution was concentrated, and 200 mL of DCM added to the resulting oil. The solution was washed with water (2×100 mL), dried over MgSO$_4$, and concentrated. TLC indicated formation of the phytanol product, yield 20.0 g.

Synthesis of Phytanyl Mesylate

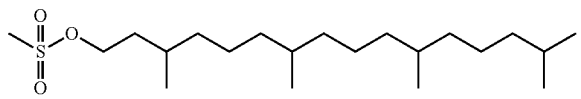

C$_{21}$H$_{44}$O$_3$S
Exact Mass: 376.30
Mol. Wt.: 376.64
C, 66.97; H, 11.78; O, 12.74; S, 8.51

Phytanol (20.0 g, 66.7 mmol), triethylamine (18.6 mL, 133 mmol) and a stir bar were added to a 1000 mL round bottom flask. The flask was sealed and flushed with nitrogen. Anhydrous DCM (250 mL) was added, and the mixture cooled to −15° C. (Ice and NaCl). Mesyl Chloride (10.4 mL, 133 mmol) was added slowly via syringe over a 30 minute period, and the reaction stirred at −15° C. for a further 1.5 hours. At this point TLC showed that the starting material had been used up. The solution was diluted with DCM (250 mL) and washed with saturated NaHCO$_3$ (2×200 mL). The organic phase was then dried (MgSO$_4$), filtered and concentrated (rotovap). The crude product was purified by column chromatography. Yield 21.5 g, 85.7%.

Synthesis of Phytanyl Bromide

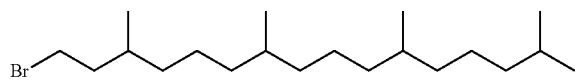

Chemical Formula: C$_{20}$H$_{41}$Br
Exact Mass: 360.2
Molecular Weight: 381.4
Elemental Analysis: C, 66.46; H, 11.43; Br, 22.11

Magnesium bromide etherate (17 g, 55 mmol) and a stir bar were added to a 500 mL round bottom flask. The flask was sealed and flushed with nitrogen and anhydrous diethyl ether (200 mL) added via cannula. A solution of phytanyl mesylate (10.9 g, 28.9 mmol (FW=377)) in anhydrous ether (50 mL) was also added via cannula, and the suspension stirred overnight. The following morning a precipitate had formed on the side of the flask. Chilled water (200 mL) was added (ppte dissolved) and the mixture transferred to a 1000-mL separating funnel. After shaking, the organic phase was separated. The aqueous phase was then extracted with ether (2×150 mL) and all ether phases combined. The ether phase was washed with water (2×150 mL), brine (150 mL) and dried over anhydrous Mg$_2$SO$_4$. The solution was filtered, concentrated, and purified by flash chromatography. Final yield 9.5 g (26.3 mmol, 91.1%).

Synthesis of Compound A

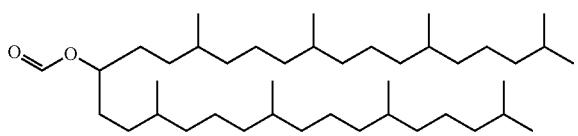

Chemical Formula: C$_{42}$H$_{84}$O$_2$
Exact Mass: 620.65
Molecular Weight: 621.12
Elemental Analysis: C, 81.22; H, 13.63; O, 5.15

Magnesium turnings (720 mg, 30 mmol), a crystal of iodine, and a stirbar were added to a 500 mL round-bottom flask. The flask was flushed with nitrogen and anhydrous diethyl ether (200 mL) added via cannula. A solution of phytanyl bromide (9.5 g, 26.3 mmol) in anhydrous ether (20 mL) was added and the resulting cloudy mixture refluxed overnight. The mixture was cooled to RT and, without removing the subaseal or condenser, ethyl formate (2.2 g, 2.41 mL, 30 mmol) added via syringe and 12" needle. The addition was made dropwise, directly into the reaction mixture, and the cloudy suspension again stirred overnight. R.M. was transferred to a 500-mL sep. funnel with ether (50 mL), and washed with 10% H$_2$SO$_4$ (100 mL—the cloudy R.M. now clarified upon shaking), water (2×100 mL) and brine. The organic was dried over anhydrous Mg$_2$SO$_4$, filtered, and concentrated. Yield (crude) was 8 g. TLC indicated that the majority of product was the diphytanylmethyl formate, which was purified by chromatography (0-6% ether in hexane).

Synthesis of Compound B

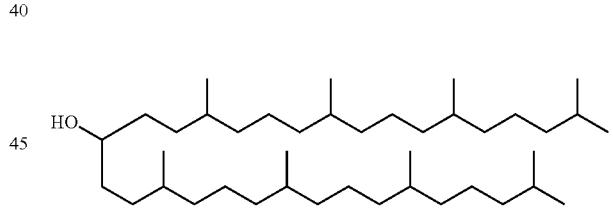

Chemical Formula: C$_{41}$H$_{84}$O
Exact Mass: 592.65
Molecular Weight: 593.11
Elemental Analysis: C, 83.03; H, 14.28; O, 2.70

The purified formate (A) (5.5 g, 8.86 mmol) was then transferred to a 1000 mL round bottom flask with stirbar and 90% EtOH (500 mL) and KOH (2.0 g, 35.7 mmol) added. The reaction mixture was clear, and was stirred overnight. The following day the mixture was concentrated by rotovap to 50% of its volume and then poured into 200 mL of 5% HCl. The aqueous phase was extracted with ether (3×100 mL). The combined ether extracts were washed with water (3×200 mL), dried (MgSO$_4$), and concentrated. TLC (DCM) revealed reaction to have gone cleanly to completion, and the product (5.5 g, 100%) was used without further purification.

Synthesis of Compound C

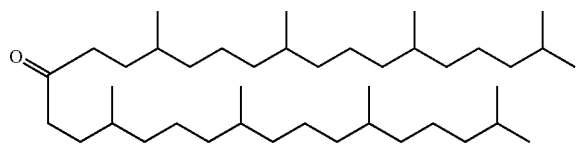

Chemical Formula: $C_{41}H_{82}O$
Exact Mass: 590.6
Molecular Weight: 591.1
Elemental Analysis: C, 83.31; H, 13.98; O, 2.71

To a mixture of Compound B (5.5 g, 9.3 mmol), pyridinium chlorochromate (PCC) (5.5 g, 25.5 mmol) and anhydrous sodium carbonate (0.6 g, 5.66 mmol) in DCM were added. The resulting suspension was stirred for 1 h, but TLC indicated still some starting material (SM) remaining. The suspension was stirred another hour, and appeared to have progressed slightly, but not to completion. Further PCC (1.0 g) and sodium carbonate (0.2 g) were added and the reaction stirred overnight. Reaction had now gone to completion. Ether (300 mL) was then added to the mixture and the resulting brown suspension filtered through a pad of silica (300 mL), washing the pad with ether (3×100 mL). The ether phases were combined, concentrated, and purified to yield 5.0 g (90%) of ketone.

Synthesis of Compound D

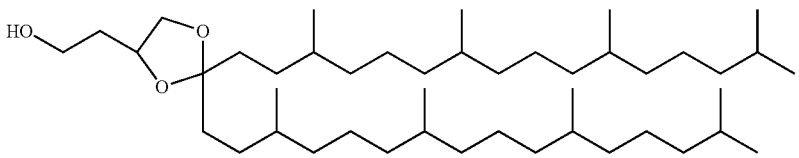

Chemical Formula: $C_{45}H_{90}O_3$
Exact Mass: 678.69
Molecular Weight: 679.19
Elemental Analysis: C, 79.58; H, 13.36; O, 7.07

A 100 mL round bottom flask was charged with Compound C (1.4 g, 2.4 mmol), 1, 2, 4-butanetriol (0.51 g, 4.8 mmol), pyridinium p-toluenesulfonate (0.06 g, 0.24 mmol), and a stir bar. The reaction vessel was flushed with nitrogen and anhydrous toluene (30 mL) added via cannula. The flask was equipped with a Dean-Stark tube and condenser and flushed with nitrogen. The reaction was refluxed under nitrogen overnight and progress of the reaction monitored via TLC. After refluxing for three hours, reaction solution deposited in the Dean-Stark tube was removed via syringe (20 mL) and the reaction vessel immediately replenished with fresh toluene (20 mL). This was repeated every hour, for a total of three times, and then left to reflux mildly overnight. After cooling to room temperature, the reaction mixture was transferred to a 250 mL separatory funnel with toluene (2×5 mL), washed with 5% aqueous $Na_2CO_3$ (2×50 mL), water (50 mL), and dried over $MgSO_4$. Evaporation of the solvent gave 1.67 g of crude product which was purified via column chromatography on silica gel (50 g) using dichloromethane as eluent. Yield: 1.4 g, 2.06 mmol, 86%.

Synthesis of Compound E

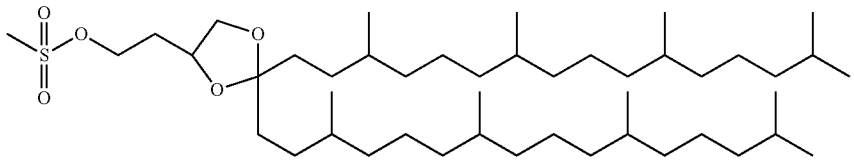

Chemical Formula: $C_{46}H_{92}O_5S$
Exact Mass: 756.67
Molecular Weight: 757.28
Elemental Analysis: C, 72.96; H, 12.25; O, 10.56; S, 4.23

A 100 mL round bottom flask was charged with Compound D (1.4 g, 2.06 mmol) and a stir bar. The vessel was flushed with nitrogen and DCM (25 mL) added. Subsequently, triethylamine (0.72 g, 7.1 mmol, 0.99 mL) was added via syringe and the resulting solution cooled to −15° C. (NaCl, ice). In a separate 50 mL round bottom flask, a solution of methanesulfonic anhydride (0.74 g, 4.1 mmol) and DCM (20 mL) was prepared. This solution was added drop wise to the above solution over a 30 minute period. The reaction vessel was maintained at −15° C. The reaction mixture was stirred at room temperature overnight and monitored via TLC. The reaction mixture was then diluted with DCM (25 mL), and washed with NaHCO$_3$ (2×30 mL), then dried over anhydrous MgSO$_4$. The crude product (1.7 g) was used in the next step without further purification.

with nitrogen and anhydrous toluene (45 mL) subsequently added via cannula. The flask was equipped with a Dean-Stark tube and condenser and flushed with nitrogen. The reaction was refluxed under nitrogen overnight and progress of the reaction monitored via TLC. After refluxing for three hours, reaction solution deposited in the Dean-Stark tube was removed via syringe (20 mL) and the reaction vessel immediately replenished with fresh toluene (20 mL). This was repeated every hour, for a total of three times, and then left to reflux mildly overnight. After cooling to room temperature, the reaction mixture was transferred to a 250 mL separatory funnel with toluene (2×5 mL), washed with 5% aqueous Na$_2$CO$_3$ (2×50 mL), water (50 mL), and dried over MgSO$_4$. Evaporation of the solvent gave 1.44 g of crude product which was then purified via column chromatography on silica gel (35 g) with 0-3% methanol gradient in dichloromethane.

Synthesis of DPan-C2K-DMA

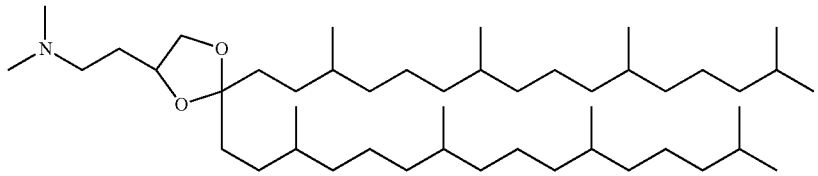

Chemical Formula: C$_{47}$H$_{95}$NO$_2$
Exact Mass: 705.74
Molecular Weight: 706.26
Elemental Analysis: C, 79.93; H, 13.56; N, 1.98; O, 4.53

A 500 mL round bottom flask was charged with crude Compound E (1.7 g, 2.5 mmol) and a stir bar. The reaction vessel was flushed with nitrogen and dimethylamine in THF (2.0 M, 65 mL) subsequently added via syringe. The resulting mixture was stirred for three days at room temperature. The reaction was concentrated and the crude product purified by column chromatography using silica gel (40 g) with a gradient of 0-5% methanol in dichloromethane.

Synthesis of Compound F

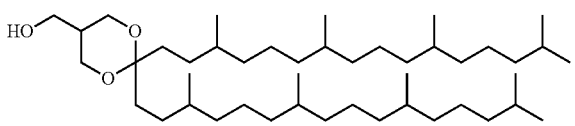

Chemical Formula: C$_{45}$H$_{90}$O$_3$
Exact Mass: 678.69
Molecular Weight: 679.19
Elemental Analysis: C, 79.58; H, 13.36; O, 7.07

A 100 mL round bottom flask was charged with Compound C (1.2 g, 2.1 mmol), 2-hydroxymethyl-1, 3-propanediol (0.45 g, 4.2 mmol), pyridinium p-toluenesulfonate (0.05 g, 0.21 mmol), and a stir bar. The reaction vessel was flushed Synthesis of Compound G

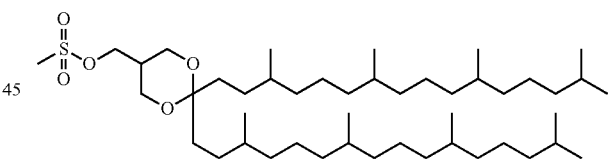

Chemical Formula: C$_{46}$H$_{92}$O$_5$S
Exact Mass: 756.67
Molecular Weight: 757.28
Elemental Analysis: C, 72.96; H, 12.25; O, 10.56; S, 4.23

A 250 mL round bottom flask was charged with Compound F (1.2 g, 1.8 mmol) and a stir bar. The vessel was flushed with nitrogen and DCM (25 mL) added. Subsequently, triethylamine (0.62 g, 6.1 mmol, 0.85 mL) was added via syringe and the resulting solution cooled to −15° C. (NaCl, ice). In a separate 50 mL round bottom flask, a solution of methanesulfonic anhydride (0.67 g, 3.7 mmol) and DCM (20 mL) was prepared. This solution was added drop wise to the above solution over a 30 minute period. The reaction vessel was maintained at −15° C. during the addition. The reaction mixture was stirred at room temperature overnight and monitored via TLC. The reaction mixture was then diluted with DCM (25 mL) and washed with NaHCO$_3$ (2×30 mL), then dried over anhydrous MgSO₄. The crude product (1.6 g) was used in the following step without further purification.

Synthesis of DPan-C1K6-DMA

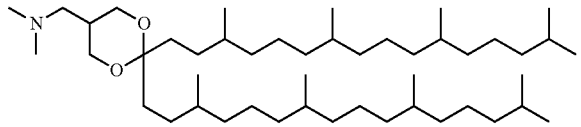

Chemical Formula: C₄₇H₉₅NO₂
Exact Mass: 705.74
Molecular Weight: 706.26
Elemental Analysis: C, 79.93; H, 13.56; N, 1.98; O, 4.53

A 250 mL round bottom flask was charged with crude Compound G (1.6 g, 2.1 mmol) and a stir bar. The reaction vessel was flushed with nitrogen and dimethylamine in THF (2.0 M, 60 mL) subsequently added via syringe. The resulting mixture was stirred for six days at room temperature. After solvent was evaporated, the crude product was purified using column chromatography on silica gel (30 g) with 0-30% ethyl acetate gradient in hexanes.

Synthesis of Compound H

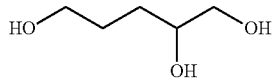

Chemical Formula: C₅H₁₂O₃
Exact Mass: 120.08
Molecular Weight: 120.15
Elemental Analysis: C, 49.98; H, 10.07; O, 39.95

A 50 mL round bottom flask was charged with (R)-γ-hydroxymethyl-γ-butyrolactone (1.0 g, 8.6 mmol), flushed with nitrogen, and sealed with a rubber septum. Anhydrous THF (40 mL) was subsequently added via syringe. The (R)-γ-hydroxymethyl-γ-butyrolactone solution was then added drop wise under nitrogen to a prepared solution containing LiAlH₄ (3.5 g, 92 mmol) in 160 mL anhydrous THF. During the addition, the reaction vessel was maintained at 0° C. The resulting suspension was stirred at room temperature overnight. The reaction mixture was cooled to 0° C. and brine (10-22 mL) added very slowly using a Pasteur pipette. The mixture was stirred under nitrogen at room temperature overnight. The white solid was filtered and washed with THF (3×25 mL). The organics were combined and concentrated. After solvent was removed, the crude product seemed to contain water along with an oily residue; therefore, the crude product was azeotroped within ethanol (100 mL) resulting in a yellow oil. The crude product (0.45 g) was used in the next step without further purification.

Synthesis of Compound I

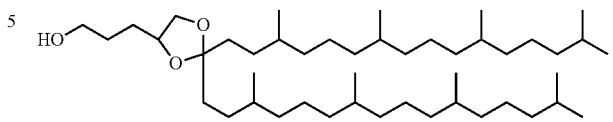

Chemical Formula: C₄₆H₉₂O₃
Exact Mass: 692.70
Molecular Weight: 693.22
Elemental Analysis: C, 79.70; H, 13.38; O, 6.92

A 100 mL round bottom flask was charged with Compound C (1.0 g, 1.8 mmol), Compound H (crude, 0.450 g, 3.6 mmol), pyridinium p-toluenesulfonate (0.05 g, 0.24 mmol), and a stir bar. The reaction vessel was flushed with nitrogen and anhydrous toluene (45 mL) subsequently added via cannula. The flask was equipped with a Dean-Stark tube and condenser and flushed with nitrogen. The reaction was refluxed under nitrogen overnight and progress of reaction monitored via TLC. After refluxing for three hours, reaction solution deposited in the Dean-Stark tube was removed via syringe (20 mL) and the reaction vessel immediately replenished with fresh toluene (20 mL). This was repeated every hour, for a total of five times, and then left to reflux mildly overnight. After cooling to room temperature, the reaction mixture was transferred to a 250 mL separatory funnel with toluene (2×5 mL), washed with 5% aqueous Na₂CO₃ (2×50 mL), water (50 mL), and dried over MgSO₄. Evaporation of the solvent gave 1.13 g of crude product which was then purified via column chromatography on silica gel (30 g) using dichloromethane as eluent. Yield, 1.0 g.

Synthesis of Compound J

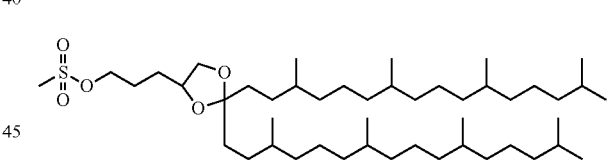

Chemical Formula: C₄₇H₉₄O₅S
Exact Mass: 770.68
Molecular Weight: 771.31
Elemental Analysis: C, 73.19; H, 12.28; O, 10.37; S, 4.16

A 250 mL round bottom flask was charged with Compound I (1.0 g, 1.44 mmol) and a stir bar. The vessel was flushed with nitrogen and DCM (25 mL) added. Subsequently, triethylamine (0.51 g, 5 mmol, and 0.7 mL) was added via syringe and the resulting solution cooled to −15° C. (NaCl, ice). In a separate 50 mL round bottom flask, a solution of methanesulfonic anhydride (0.54 g, 3.0 mmol) and anhydrous DCM (20 mL) was prepared. This solution was added drop wise to the above solution over a 30 minute period. The reaction vessel was maintained at −15° C. The reaction mixture was stirred at room temperature overnight and monitored via TLC. The reaction mixture was then diluted with DCM (25 mL) and washed with NaHCO₃ (2×30 mL), then dried over anhydrous MgSO₄. The crude product (1.2 g) was used in the next step without further purification.

Synthesis of DPan-C3K-DMA

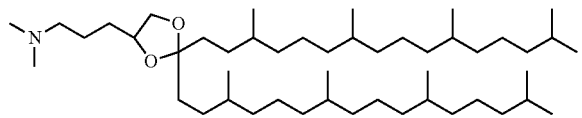

Chemical Formula: $C_{48}H_{97}NO_2$
Exact Mass: 719.75
Molecular Weight: 720.29
Elemental Analysis: C, 80.04; H, 13.57; N, 1.94; O, 4.44

A 100 mL round bottom flask was charged with crude Compound J (1.2 g, 1.6 mmol) and a stir bar. The reaction vessel was flushed with nitrogen and dimethylamine in THF (2.0 M, 45 mL) subsequently added via syringe. The resulting mixture was stirred for four days at room temperature. After solvent was evaporated, the crude product was purified using column chromatography on silica gel (30 g) with 0-30% ethyl acetate gradient in hexanes.

Example 17. Synthesis of DLen-C2K-DMA

DLen-C2K-DMA having the structure shown below was synthesized as shown in the following schematic diagram.

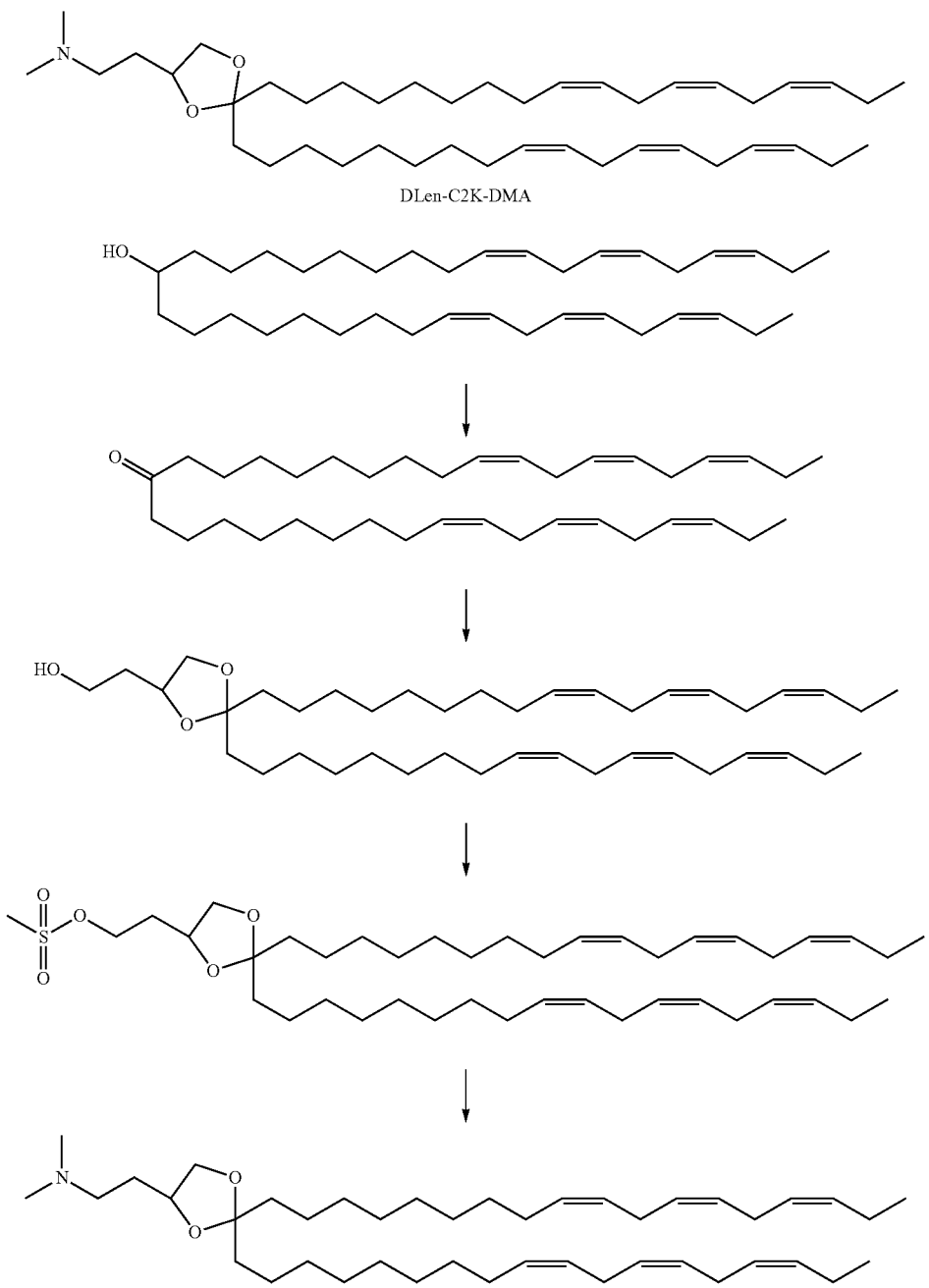

DLen-C2K-DMA

Synthesis of Dilinolenyl Ketone

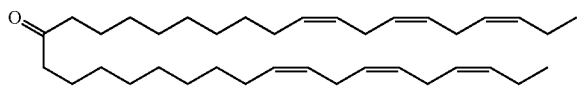 [SMILES: CC/C=C\C/C=C\C/C=C\CCCCCCCCC(=O)CCCCCCCC/C=C\C/C=C\C/C=C\CC]

To a 1000 mL RBF containing a solution of dilinolenyl methanol (6.0 g, 11.4 mmol) in anh. DCM (200 mL) was added pyridinium chlorochromate (7.39 g, 34.2 mmol), anh. sodium carbonate (1.0 g, 5.66 mmol) and a stirbar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 4.2 g (8.0 mmol, 70%) of the ketone.

Synthesis of Linolenyl Ketal

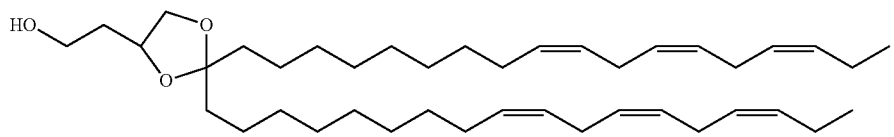 [SMILES: CC/C=C\C/C=C\C/C=C\CCCCCCCCC1(CCCCCCCC/C=C\C/C=C\C/C=C\CC)OCC(CCO)O1]

A 100 mL RBF was charged with dilinolenyl ketone (4.2 g, 8.2 mmol), 1,2,4-butanetriol (3.4 g, 32 mmol), PPTS (200 mg, 0.8 mmol) and a stir bar. The flask was flushed with nitrogen and anhydrous toluene (60 mL) added. The reaction vessel was fitted with a Dean Stark tube and condenser and brought to reflux and the reaction was left overnight. After cooling to room temperature, the reaction mixture diluted with toluene (50 mL), and washed with 5% aq. $Na_2CO_3$ (2×50 mL), water (50 mL), dried ($MgSO_4$) and purified by chromatography to yield 3.0 g (4.9 mmol, 59%) of the ketal.

Mesylate Formation:

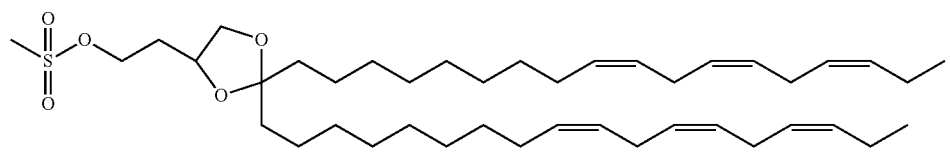 [SMILES: CC/C=C\C/C=C\C/C=C\CCCCCCCCC1(CCCCCCCC/C=C\C/C=C\C/C=C\CC)OCC(CCOS(C)(=O)=O)O1]

A 250 mL RBF was charged with the linolenyl ketal (3.0 g, 4.9 mmol), TEA (2.2 mL, 15.6 mmol) and a stir bar. The flask was flushed with nitrogen, anh. DCM (20 mL) added, and the solution cooled to −15° C. In a separate 50 mL flask, a solution of MsCl (9.7 mmol, 2 eqv.) in anhydrous DCM (30 mL) was prepared, then transferred to the reaction vessel by syringe over 20 minutes. The reaction was stirred for 90 minutes at −15° C., at which point starting material had been consumed. The reaction mixture was diluted with a further 50 mL of DCM, washed with $NaHCO_3$ (2×50 mL), dried ($MgSO_4$) and purified by chromatography. Final yield 3.1 g, 4.5 mmol, 92%.

Synthesis of DLen-C2K-DMA

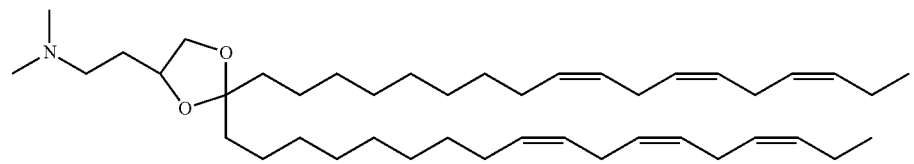 [SMILES: CC/C=C\C/C=C\C/C=C\CCCCCCCCC1(CCCCCCCC/C=C\C/C=C\C/C=C\CC)OCC(CCN(C)C)O1]

A 250 mL RBF was charged with the mesylate (3.0 g, 4.35 mmol), isopropanol (25 mL) and a stir bar. The flask was flushed with nitrogen, sealed, and a 2.0 M solution of dimethylamine in methanol (120 mL) added via cannula. The reaction was stirred at room temperature for 3 days. The solution was concentrated and purified by chromatography. Final yield 2.49 g, 3.9 mmol, 90%.

Example 18. Synthesis of γ-DLen-C2K-DMA

γ-DLen-C2K-DMA having the structure shown below was synthesized as shown in the following schematic diagram.

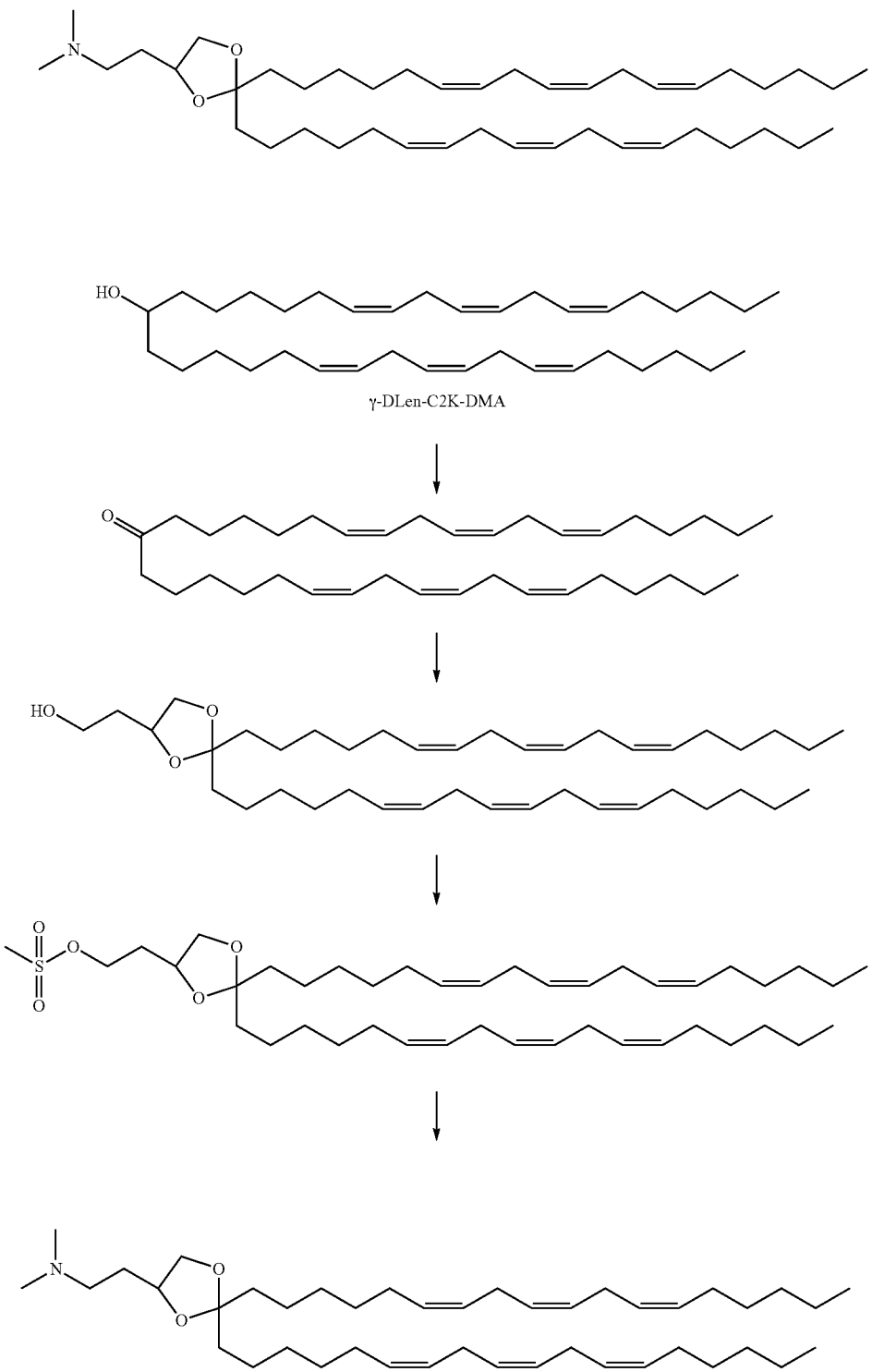

γ-DLen-C2K-DMA

Synthesis of Di-γ-Linolenyl Ketone

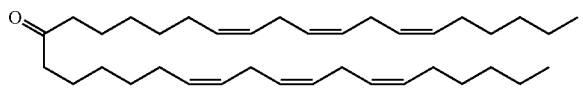 [SMILES: CCCCC/C=C\C/C=C\C/C=C\CCCCCC(=O)CCCCC/C=C\C/C=C\C/C=C\CCCCC]

To a 1000 mL RBF containing a solution of di-γ-linolenyl methanol (6.0 g, 11.4 mmol) in anh. DCM (200 mL) was added pyridinium chlorochromate (7.39 g, 34.2 mmol), anh. sodium carbonate (1.0 g, 5.66 mmol) and a stirbar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 5.5 g (10.5 mmol, 92%) of ketone.

Synthesis of γ-Linolenyl Ketal

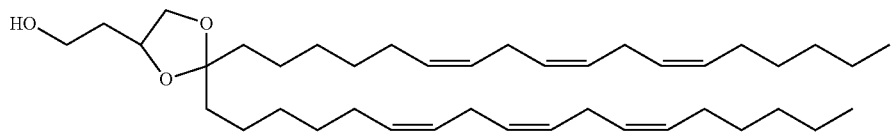

A 100 mL RBF was charged with di-γ-linolenyl ketone (2.14 g, 4.1 mmol), 1,2,4-butanetriol (1.7 g, 16.0 mmol), PPTS (100 mg, 0.4 mmol) and a stir bar. The flask was flushed with nitrogen and anhydrous toluene (30 mL) added. The reaction vessel was fitted with a Dean Stark tube and condenser and brought to reflux and the reaction was left overnight. After cooling to room temperature, the reaction mixture was washed with 5% aq. $Na_2CO_3$ (2×50 mL), water (50 mL), dried ($MgSO_4$) and purified by chromatography to yield 1.34 g (2.2 mmol, 53%) of the ketal.

Mesylate Formation:

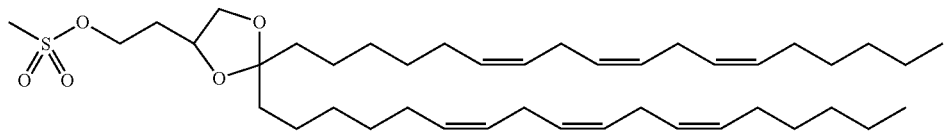 [SMILES: CCCCC/C=C\C/C=C\C/C=C\CCCCCC1(CCCCC/C=C\C/C=C\C/C=C\CCCCC)OCC(CCOS(C)(=O)=O)O1]

A 250 mL RBF was charged with the γ-linolenyl ketal (1.34 g, 2.19 mmol), TEA (1 mL, 7.1 mmol) and a stir bar. The flask was flushed with nitrogen, anh. DCM (10 mL) added, and the solution cooled to −15° C. In a separate 50 mL flask, a solution of MsCl (342 μL, 4.4 mmol, 2 eqv.) in anhydrous DCM (15 mL) was prepared, then transferred to the reaction vessel by syringe over 20 minutes. The reaction was stirred for 90 minutes at −15° C., at which point starting material had been consumed. The reaction mixture was diluted with a further 50 mL of DCM, washed with $NaHCO_3$ (2×50 mL), dried ($MgSO_4$) and purified by chromatography. Final yield 1.31 g, 1.90 mmol, 87%.

Synthesis of γ-DLen-C2K-DMA

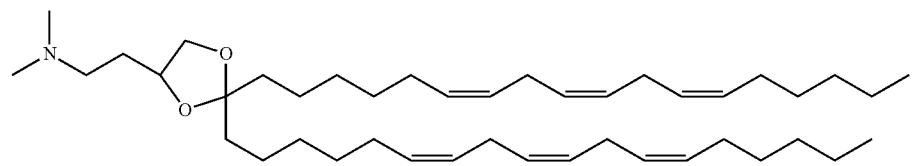 [SMILES: CCCCC/C=C\C/C=C\C/C=C\CCCCCC1(CCCCC/C=C\C/C=C\C/C=C\CCCCC)OCC(CCN(C)C)O1]

A 250 mL RBF was charged with the mesylate (1.31 g, 1.9 mmol), isopropanol (10 mL) and a stir bar. The flask was flushed with nitrogen, sealed, and a 2.0 M solution of dimethylamine in methanol (60 mL) added via cannula. The reaction was stirred at room temperature for 3 days. The solution was concentrated and purified by chromatography. Final yield 1.1 g, 1.72 mmol, 91%.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A nucleic acid-lipid particle comprising:
   (a) a nucleic acid;
   (b) a cationic lipid comprising from about 45 mol % to 65 mol % of the total lipid present in the particle;
   (c) a non-cationic lipid comprising from 20 mol % to 55 mol % of the total lipid present in the particle, wherein the non-cationic lipid comprises a mixture of a phospholipid and cholesterol or a derivative thereof; and
   (d) a conjugated lipid that inhibits aggregation of particles comprising from 2 mol % to 15 mol % of the total lipid present in the particle, wherein the conjugated lipid comprises a polyethyleneglycol (PEG)-lipid conjugate.

2. The nucleic acid-lipid particle of claim 1, wherein the nucleic acid comprises an RNA.

3. The nucleic acid-lipid particle of claim 2, wherein the RNA comprises an mRNA.

4. The nucleic acid-lipid particle of claim 1, wherein the cationic lipid comprises from 45 mol % to 60 mol % of the total lipid present in the particle.

5. The nucleic acid-lipid particle of claim 1, wherein the cationic lipid comprises from 45 mol % to 55 mol % of the total lipid present in the particle.

6. The nucleic acid-lipid particle of claim 1, wherein the cationic lipid is protonated at a pH below the pKa of the cationic lipid.

7. The nucleic acid-lipid particle of claim 1, wherein the mixture of the phospholipid and cholesterol or derivative thereof comprises from 30 mol % to 50 mol % of the total lipid present in the particle.

8. The nucleic acid-lipid particle of claim 1, wherein the phospholipid comprises from 2 mol % to 15 mol % of the total lipid present in the particle.

9. The nucleic acid-lipid particle of claim 1, wherein the PEG-lipid conjugate comprises from 2 mol % to 12 mol % of the total lipid present in the particle.

10. The nucleic acid-lipid particle of claim 1, wherein the PEG-lipid conjugate comprises from 3 mol % to 10 mol % of the total lipid present in the particle.

11. The nucleic acid-lipid particle of claim 1, wherein the PEG has an average molecular weight of from about 1,000 daltons to about 5,000 daltons.

12. The nucleic acid-lipid particle of claim 1, wherein the PEG has an average molecular weight of about 2,000 daltons.

13. The nucleic acid-lipid particle of claim 1, wherein the PEG-lipid conjugate comprises a PEG-diacylglycerol (PEG-DAG) conjugate or a PEG-dialkyloxypropyl (PEG-DAA) conjugate.

14. A pharmaceutical composition comprising a nucleic acid-lipid particle of claim 1 and a pharmaceutically acceptable carrier.

15. The pharmaceutical composition of claim 14, wherein the nucleic acid is fully encapsulated in the nucleic acid-lipid particle.

16. A method for introducing a nucleic acid into a cell, the method comprising:
    contacting the cell with a nucleic acid-lipid particle of claim 1.

17. A method for the in vivo delivery of a nucleic acid, the method comprising:
    administering to a mammal a nucleic acid-lipid particle of claim 1.

* * * * *